US011833221B2

(12) United States Patent
Rigo et al.

(10) Patent No.: US 11,833,221 B2
(45) Date of Patent: Dec. 5, 2023

(54) OLIGOMERIC COMPOUNDS FOR REDUCING DMPK EXPRESSION

(71) Applicant: Ionis Pharmaceuticals, Inc., Carlsbad, CA (US)

(72) Inventors: Frank Rigo, Carlsbad, CA (US); Chrissa A. Dwyer, Collegeville, PA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 17/823,854

(22) Filed: Aug. 31, 2022

(65) Prior Publication Data

US 2023/0114429 A1    Apr. 13, 2023

Related U.S. Application Data

(60) Provisional application No. 63/239,765, filed on Sep. 1, 2021.

(51) Int. Cl.
*A61K 47/68* (2017.01)
*A61K 47/54* (2017.01)
*C12N 15/113* (2010.01)

(52) U.S. Cl.
CPC ........ *A61K 47/6849* (2017.08); *A61K 47/549* (2017.08); *A61K 47/6807* (2017.08); *C12N 15/1137* (2013.01); *C12N 2310/315* (2013.01); *C12N 2310/3231* (2013.01)

(58) Field of Classification Search
CPC .............. A61K 47/549; A61K 47/6807; A61K 47/6849; C12N 15/1137; C12N 2310/315; C12N 2310/3231
See application file for complete search history.

(56) References Cited

U.S. PATENT DOCUMENTS

| | | |
|---|---|---|
| 3,687,808 A | 8/1972 | Merigan et al. |
| 4,845,205 A | 7/1989 | Huynh Dinh et al. |
| 5,034,506 A | 7/1991 | Summerton et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,185,444 A | 2/1993 | Summerton et al. |
| 5,367,066 A | 11/1994 | Urdea et al. |
| 5,432,272 A | 7/1995 | Benner |
| 5,434,257 A | 7/1995 | Matteucci |
| 5,457,187 A | 10/1995 | Gmelner et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,552,282 A | 9/1996 | Caskey et al. |
| 5,552,540 A | 9/1996 | Haralambidis |
| 5,587,469 A | 12/1996 | Cook et al. |
| 5,594,121 A | 1/1997 | Froehler et al. |
| 5,596,091 A | 1/1997 | Switzer |
| 5,614,617 A | 3/1997 | Cook et al. |
| 5,645,985 A | 7/1997 | Froehler et al. |
| 5,646,269 A | 7/1997 | Matteucci |
| 5,681,941 A | 10/1997 | Cook et al. |
| 5,698,685 A | 12/1997 | Summerton et al. |
| 5,750,692 A | 5/1998 | Cook et al. |
| 5,763,588 A | 6/1998 | Matteucci et al. |
| 5,801,154 A | 9/1998 | Baracchini et al. |
| 5,830,653 A | 11/1998 | Froehler et al. |
| 5,955,265 A | 9/1999 | Brook et al. |
| 6,005,096 A | 12/1999 | Matteucci et al. |
| 6,007,992 A | 12/1999 | Lin et al. |
| 6,028,183 A | 2/2000 | Lin et al. |
| 6,268,490 B1 | 7/2001 | Imanishi et al. |
| 6,329,501 B1 | 12/2001 | Smith |
| 6,525,191 B1 | 2/2003 | Ramasamy |
| 6,582,908 B2 | 6/2003 | Fodor et al. |
| 6,670,461 B1 | 12/2003 | Wengel et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel |
| 7,208,174 B2 | 4/2007 | Huwyler et al. |
| 7,374,927 B2 | 5/2008 | Palma et al. |
| 7,399,845 B2 | 7/2008 | Seth et al. |
| 7,427,672 B2 | 9/2008 | Imanishi et al. |

(Continued)

FOREIGN PATENT DOCUMENTS

| | | |
|---|---|---|
| WO | WO 1991/004753 | 4/1991 |
| WO | WO 1999/014226 | 3/1999 |

(Continued)

OTHER PUBLICATIONS https://www.sigmaaldrich.com/US/en/technical-documents/technical-article/genomics/gene-expression-and-silencing/phosphorothioates (retrieved from the internet Mar. 23, 2023; Google date of Dec. 6, 2016).*
Henry S, et al. (Feb. 2000) JPET. 292(2):468-479 (abailable online at http://www.jpet.org).*
Song X, et al. (Dec. 15, 2017) Mol Ther Nucleic Acids. 9:242-250. (doi: 10.1016/j.omtn.2017.10.003. Epub Oct. 7, 2017).*
GenBank Accession No. NT_011109.16.
International Search Report for application PCT/US22/075768 dated Jan. 17, 2023.

(Continued)

*Primary Examiner* — Robert S Landsman

(74) *Attorney, Agent, or Firm* — McNeill Baur PLLC

(57) ABSTRACT

Provided are oligomeric compounds, methods, and pharmaceutical compositions for DMPK the amount or activity of DMPK RNA in a cell or animal, and in certain instances reducing the amount of DMPK protein in a cell or animal. Such oligomeric compounds, methods, and pharmaceutical compositions are useful to treat type 1 myotonic dystrophy.

30 Claims, No Drawings

Specification includes a Sequence Listing.

(56) References Cited

U.S. PATENT DOCUMENTS

| | | | |
|---|---|---|---|
| 7,709,616 B2 | 5/2010 | Bentwich et al. | |
| 7,901,882 B2 | 3/2011 | Cao et al. | |
| 7,973,019 B1 | 7/2011 | Chatterton et al. | |
| 8,158,354 B2 | 4/2012 | Sarkar | |
| RE44,779 E | 2/2014 | Imanishi et al. | |
| 9,012,421 B2 | 4/2015 | Migawa et al. | |
| 9,592,250 B2 | 3/2017 | Woolf et al. | |
| 9,765,338 B2 | 9/2017 | Bennett et al. | |
| 10,954,519 B2 * | 3/2021 | Swayze .................. | A61P 21/02 |
| 2001/0053519 A1 | 12/2001 | Fodor et al. | |
| 2003/0158403 A1 | 8/2003 | Manoharan et al. | |
| 2003/0207804 A1 | 11/2003 | Manoharan et al. | |
| 2003/0228597 A1 | 12/2003 | Cowsert et al. | |
| 2004/0147023 A1 | 7/2004 | Crooke et al. | |
| 2004/0171570 A1 | 9/2004 | Allerson et al. | |
| 2004/0241651 A1 | 12/2004 | Olek et al. | |
| 2005/0019746 A1 | 1/2005 | Seery et al. | |
| 2005/0075306 A1 | 4/2005 | Schreiber et al. | |
| 2005/0130923 A1 | 6/2005 | Bhat et al. | |
| 2007/0031844 A1 | 2/2007 | Khvorova et al. | |
| 2007/0031940 A1 | 2/2007 | Van Rompaey et al. | |
| 2007/0134697 A1 | 6/2007 | Khvorova et al. | |
| 2007/0243546 A1 | 10/2007 | Cao et al. | |
| 2007/0287831 A1 | 12/2007 | Seth et al. | |
| 2008/0015158 A1 | 1/2008 | Ichiro et al. | |
| 2008/0039618 A1 | 2/2008 | Allerson et al. | |
| 2008/0242629 A1 | 10/2008 | Crooke et al. | |
| 2009/0081675 A1 | 3/2009 | Colston et al. | |
| 2010/0016215 A1 | 1/2010 | Moulton et al. | |
| 2010/0047289 A1 | 2/2010 | Fakhari et al. | |
| 2010/0190837 A1 | 7/2010 | Migawa et al. | |
| 2011/0178283 A1 | 7/2011 | Rigoutsos et al. | |
| 2011/0229880 A1 | 9/2011 | Wood et al. | |
| 2013/0059902 A1 | 3/2013 | Corey et al. | |
| 2013/0225659 A1 | 8/2013 | Bennett | |
| 2013/0237585 A1 | 9/2013 | Bennett et al. | |
| 2015/0099791 A1 | 4/2015 | Krieg et al. | |
| 2015/0191727 A1 | 7/2015 | Migawa et al. | |
| 2016/0068845 A1 | 3/2016 | Bennett et al. | |
| 2016/0304877 A1 | 10/2016 | Swayze et al. | |
| 2019/0276832 A1 | 9/2019 | Swayze et al. | |
| 2021/0052631 A1 | 2/2021 | Prakash et al. | |
| 2021/0403916 A1 | 12/2021 | Swayze et al. | |
| 2023/0174987 A1 | 6/2023 | Bennett et al. | |

FOREIGN PATENT DOCUMENTS

| | | |
|---|---|---|
| WO | WO 2000/058332 | 10/2000 |
| WO | WO 2001/019161 | 3/2001 |
| WO | WO 2002/001953 | 1/2002 |
| WO | WO 2002/090514 | 11/2002 |
| WO | WO 2003/013437 | 2/2003 |
| WO | WO 2004/028458 | 4/2004 |
| WO | WO 2004/093783 | 11/2004 |
| WO | WO 2004/106356 | 12/2004 |
| WO | WO 2005/116204 | 12/2005 |
| WO | WO 2005/121368 | 12/2005 |
| WO | WO 2006/034348 | 3/2006 |
| WO | WO 2007/089584 | 8/2007 |
| WO | WO 2007/089611 | 8/2007 |
| WO | WO 2007/121272 | 10/2007 |
| WO | WO 2007/134181 | 11/2007 |
| WO | WO 2008/018795 | 2/2008 |
| WO | WO 2008/036406 | 3/2008 |
| WO | WO 2008/039071 | 4/2008 |
| WO | WO 2008/049085 | 4/2008 |
| WO | WO 2008/150729 | 12/2008 |
| WO | WO 2008/154401 | 12/2008 |
| WO | WO 2009/006478 | 1/2009 |
| WO | WO 2009/098197 | 8/2009 |
| WO | WO 2009/099326 | 8/2009 |
| WO | WO 2010/014592 | 2/2010 |
| WO | WO 2010/029303 | 3/2010 |
| WO | WO 2010/115993 | 10/2010 |
| WO | WO 2011/097388 | 8/2011 |
| WO | WO 2011/097641 | 8/2011 |
| WO | WO 2011/113889 | 9/2011 |
| WO | WO 2012/012443 | 1/2012 |
| WO | WO 2012/012467 | 1/2012 |
| WO | WO 2013/173637 | 11/2013 |
| WO | WO 2014/120861 | 8/2014 |
| WO | WO 2015/021457 | 2/2015 |
| WO | WO 2017/053995 | 3/2017 |
| WO | WO 2017/221883 | 12/2017 |
| WO | WO 2018/002812 | 1/2018 |
| WO | WO 2018/078131 | 5/2018 |
| WO | WO 2018/078134 | 5/2018 |
| WO | WO 2019/222354 | 11/2019 |
| WO | WO 2020/028861 | 2/2020 |
| WO | WO 2020/113393 | 6/2020 |
| WO | WO 2020/247782 | 12/2020 |
| WO | WO 2020/247818 | 12/2020 |
| WO | WO 2021/076856 | 4/2021 |
| WO | WO 2021/142234 | 7/2021 |
| WO | 2023034868 A1 | 3/2023 |
| WO | 2023034870 A2 | 3/2023 |

OTHER PUBLICATIONS

Albaek et al., "Bi- and Tricyclic Nucleoside Derivatives Restricted in S-Type Conformations and Obtained by RCM-Reactions" Nucleosides, Nucleotides & Nucleic Acids (2003) 22(5-8):723-725.

Altmann et al., "Second Generation of Antisense Oligonucleotides: From Nuclease Resistance to Biological Efficacy in Animals" Chimia (1996) 50:168-176.

Altmann et al., "Second-generation antisense oligonucleotides: structure-activity relationships and the design of improved signal-transduction inhibitors" Biochem. Soc. Trans. (1996) 24:630-637.

Altmann et al., "Second Generation Antisense Oligonucleotides—Inhibition of PKC-a and c-RAF Kinase Expression by Chimeric Oligonucleotides Incorporating 6'-Substituted Carbocyclic Nucleosides and 2'-O-Ethylene Glycol Substituted Ribonucleosides" Nucleosides & Nucleotides (1997) 16(7-9):917-926.

Aronin et al., "Expanded CAG repeats in the crosshairs" Nature Biotechnology (2009) 27(5): 451-452.

Ascoli et al., "Identification of a novel nuclear domain" J. Cell Biol. (1991) 112(5):785-795.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272(18):11944-12000.

Ballantyne et al., "Locked nucleic acids in PCR primers increase sensitivity and performance" Genomics (2008) 91: 301-305.

Braasch et al., "Locked nucleic acid (LNA): fine-tuning the recognition of DNA and RNA" Chem. Biol. (2001) 8:1-7.

Branch et al., "A good antisense molecule is hard to find," TIBS (1998) 23:45-50.

Brook et al., "Molecular basis of myotonic dystrophy: Expansion of a trinucleotide (CTG) repeat at the 3' end of a transcript encoding a protein kinase family member" Cell (1992) 68(4):799-808.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Cho et al., "Myotonic dystrophy: Emerging mechanisms for DM1 and DM2" Biochemica et Biophysica Acta (2007) 1772: 195-204.

Cleary et al., "The contribution of cis-elements to disease-associated repeat instability: clinical and experimental evidence" Cytogenet. Genome Res. (2003) 100:25-55.

Clemson et al., "An Architectural Role for a Nuclear Noncoding RNA: NEAT1 RNA Is Essential for the Structure of Paraspeckles" Mol. Cell (2009) 33:717-726.

Conte et al., "Conformational properties and thermodynamics of the RNA duplex r(CGCAAAUUUGCG)2: comparison with the DNA analogue d(CGCAAATTTGCG)2" Nucleic Acids Res. (1997) 25(13):2627-2634.

Cooper, "RNA and Disease" Cell (2009) 136:777-793.

Costa, "Non-coding RNAs and new opportunities for the private secotr" Drug Discovery today (2009) 14:446-452.

(56) References Cited

OTHER PUBLICATIONS

Cremer et al., "Chromosome Territories, Interchromatin Domain Compartment, and Nuclear Matrix: An Integrated View of the Functional Nuclear Architecture" Crit. Rev. Eukaroytic Gene Expr. (2000) 10:179-212.

Crooke et al., "Basic Principles of Antisense Therapeutics" Antisense Research and Application (1998) Chapter 1:1-50.

Davis et al., "Expansion of a CUG trinucleotide repeat in the 3* untranslated region of myotonic dystrophy protein kinase transcripts results in nuclear retention of transcripts" PNAS (1997) 94:7388-7393.

De Die-Smulders et al., "Age and causes of death in adult-onset myotonic dystrophy." *Brain* (1998) 121:1557-1563.

Denegri et al., "Human Chromosomes 9, 12, and 15 Contain the Nucleation Sites of Stress-Induced Nuclear Bodies" Mol. Biol. Cell (2002) 13:2069-2079.

Dong et al., "Implication of snoRNA U50 in human breast cancer" Journal of Genetics and Genomics (2009) 36(8): 447-454.

Doucas et al., "The PML nuclear compartment and cancer" Biochem. Biophys. Acta (1996) 1288(3):M25-M29.

Elayadi et al., "Application of PNA and LNA oligomers to chemotherapy" Curr. Opinion Invens. Drugs (2001) 2:558-561.

Englisch et al., "Chemically Modified Oligonucleotides as Probes and Inhibitors" Agnew Chem. Int. Ed. Engl. (1991) 30:613-629.

Fakan et al., "Ultrastructural Distribution of Nuclear Ribonucleoproteins as Visualized by Immunocytochemistry on Thin Sections" J. Cell Biol. (1984) 98:358-363.

Flanagan et al., "A cytosine analog that confers enhanced potency to antisense oligonucleotides" PNAS (1999) 96:3513-3518.

Fox et al., "P54nrb Forms a Heterodimer with PSP1 That Localizes to Paraspeckles in an RNA-dependent Manner" Mol. Biol. Cell (2005) 16:5304-5315.

Freier et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21):6365-6372.

Fu et al., "Factor required for mammalian spliceosome assembly is localized to discrete regions in the nucleus" Nature (1990) 343:437-441.

Galderisi et al., "Myotonic dystrophy: antisense oligonucleotide inhibition of DMPK gene expression in vitro" Biochem. Biophys. Res. Commun. (1996) 221(3):750-754.

Gautschi et al., "Activity of a Novel bcl-2/bcl-xL-Bispecific Antisense Oligonucleotide Against Tumors of Diverse Histologic Origins" J. Natl. Cancer Inst. (2001) 93:463-471.

Guo et al., "Inhibition of metastasis-associated lung adenocarcinoma transcript 1 in CaSki human cervical cancer cells suppresses cell proliferation and invasion" Acta Biochimica et Biophysica Sinica (2010) 42(3): 224-229.

Guttman et al., "Chromatin signature reveals over a thousand highly conserved large non-coding RNAs in mammals" Nature (2009) 458:223-227.

Hu et al., "Allele-specific silencing of mutant huntingtin and ataxin-3 genes by targeting expanded CAG repeats in mRNAs" Nature Biotechnology (2009) 27(5): 478-484.

Hu et al., "Allele-selective inhibition of mutant huntingtin by peptide nucleic acid-peptide conjugates, locked nucleic acid, and small interfering RNA" Annals of the New York Academy of Sciences (2009) 1175: 24-31.

Huang, "Review: Perinucleolar Structures" J. Struct. Biol. (2000) 129:233-240.

Ichikawa et al. "The genomic structure and expression of MJD, the Machado-Joseph disease gene" J Hum Genet (2001) 46: 413-422.

Ideue et al., "Efficient oligonucleotide-mediated degradation of nuclear noncoding RNAs in mammalian cultured cells" RNA (2009) 15(8): 1578-1587.

Ionis Pharmaceuticals, Inc. Press Release, Recently Published Preclinical Data Show Significant and Sustained Reduction of Muscle DMPK RNA with a Generation 2.5 Antisense Compound, Sep. 1, 2015, 1 Page.

Ji et al., "MALAT-1, a novel noncoding RNA, and thymosin b4 predict metastasis and survival in early-stage non-small cell lung cancer" Oncogene (2003) 22:8031-8041.

Jolly et al., "In vivo binding of active heat shock transcription factor 1 to human chromosome 9 heterochromatin during stress" J. Cell Biol. (2002) 156:775-781.

Kanadia et al., "Reversal of RNA missplicing and myotonia after muscleblind overexpression in a mouse poly (CUG) model for myotonic dystrophy" PNAS (2006) 103(31):11748-11753.

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

Krol et al., "Ribonuclease dicer cleaves triplet repeat hairpins into shorter repeats that silence specific targets" Molecular Cell (2007) 25:575-586.

Kroschwitz, "Polynucleotides" Concise Encyclopedia of Polymer Science and Engineering (1990) John Wiley & Sons, NY pp. 858-859.

Kumar et al., "The first analogues of LNA (locked nucleic acids): phosphorothioate-LNA and 2'-thio-LNA" Bioorg Med Chem Lett. (1998) 8:2219-2222.

Kurchavov et al., "A New Phosphoramidite Reagent for the Incorporation of Diazaphenoxazinone Nucleoside with Enhanced Base-Pairing Properties into Oligodeoxynucleotides" Nucleosides and Nucleotides (1997) 16)10 & 11):1837-1846.

Lavorgna et al., "In search of antisense" Trends Biochem. Sci. (2004) 29:88-94.

Lebedev at el., "Oligonucleotides containing 2-aminoadenine and 5-methylcytosine are more effective as primers for PCR amplification than their nonmodified counterparts," Genetic Analysis: Biomolecular Engineering (1996) 13:15-21.

Lee et al., "Targeted Degradation of Toxic RNA in Myotonic Dystrophy" p. 35, Abstracts of papers presented at the 2010 meeting on RNA & oligonucleotide therapeutics. Apr. 7-10, 2010.

Lehner et al., "Antisense transcripts in the human genome" Trends. Genet. (2002) 18:63-65.

Lesnik et al., "Relative Thermodynamic Stability of DNA, RNA, and DNA:RNA Hybried Duplexes: Relationship with Base Composition and Structure" Biochemistry (1995) 34:10807-10815.

Leumann, "DNA Analogues: From Supramolecular Principles to Biological Properties" Bioorg. & Med. Chem. (2002) 10:841-854.

Liang et al., "Efficient and specific knockdown of small non-coding RNAs in mammalian cells and in mice" Nucleic Acids Research (2010) 39(3): E13.

Lin et al., "Tricyclic 2'-Deoxycytidine Analogs: Synthesis and Incorporation into Oligodeoxynucleotides Which Have Enhanced Binding to Complementary RNA" J. Am. Chem. Soc. (1995) 117:3873-3874.

Lin et al., "A Cytosine Analogue Capable of Clamp-Like Binding to a Guanine in Helical Nucleic Acids" J. Am. Chem. Soc. (1998) 120:8531-8532.

Lin et al., "Failure of MBNL1-dependent post-natal splicing transitions in myotonic dystrophy" Human Mol. Genet. (2006) 15(13):2087-2097.

Liquori et al., "Myotonic Dystrophy Type 2 Caused by a CCTG Expansion in Intron 1 of ZNF9" Science (2001) 293:864-867.

Lolle, "Genome-wide non-mendelian inheritance of extra-genomic information in *Arabidopsis*" Nature (2005) 434:505-509.

Maher e tal., "Comparative hybrid arrest by tandem antisense oligodeoxyribonucleotides or oligodeoxyribonucleoside methylphosphonates in a cell-free system" Nuc. Acid. Res. (1988) 16:3341-3358.

Mankodi et al., "Expanding CUG Repeats Trigger Aberrant Splicing of CIC-1 Chloride Channel Pre-mRNA and Hyperexcitability of Skeletal Muscle in Myotonic Dystrophy" Mol. Cell. (2002) 10:35-44.

(56) References Cited

OTHER PUBLICATIONS

Manning et al., "BNANC Gapmers Revert Splicing and Reduce RNA Foci with Low Toxicity in Myotonic Dystrophy Cells" ACS Chem Biol (2017) 12: 2503-2509.
Martin, "Ein neuer Zugang zu 2'-O-Alkylribonucleosiden und Eigenschaften deren Oligonucleotide" Helv. Chim. Acta. (1995) 78:486-504.
Melone et al., "Antisense Oligonucleotides and Myotonin Gene Expression in C2 Mouse Cells" Antisense & Nucleic Acid Drug Development (1998) 8: 25-33.
Mercer et al., "Specific expression of long noncoding RNAs in the mouse brain" PNAS (2008) 105(2):716-721.
Miller et al., "Recruitment of human muscleblind proteins to (CUG)(n) expansions associated with myotonic dystrophy." EMBO J. (2000) 19:4439-4448.
Mouritzen et al., "ProbeLibrary: A new method for faster design and execution of quantitative real-time PCR" Nature Methods (2005) 2:313-317.
Mulders et al., "Triplet-repeat oligonucleotide-mediated reversal of RNA toxicity in myotonic dystrophy" Proceedings of the National Academy of Sciences (2009) 106: 13915-13928.
New England Biolabs 1998/99 Catalog (cover page and pp. 121 and 284).
Noronha et al., "Amplimers with 1-15 3'-terminal phosphorothioate linkages resist degradation by Vent polymersase and reduce Taq polymerase mispriming," PCR Methods & Applicatio, Cold Spring Harbor Laboratory Press (1992) 2: 131-136.
Orum et al., "Locked nucleic acids: A promising molecular family for gene-function analysis and antisense drug development" Curr. Opinion Mol. Ther. (2001) 3:239-243.
O'Rourke, "Mechanisms of RNA-mediated Disease" J. Biol. Chem. (2009) 284(12):7419-7423.
Osborne et al., "RNA-dominant diseases." Hum Mol Genet. (2006) 15:R162-9.
Pandey et al., "Identification and Characterization of Modified Antisense Oligonucleotides Targeting DMPK in Mice and Nonhuman Primates for the Treatment of Myotonic Dystrophy Type 1," J Pharmacol Exp Ther (2015) 355: 329-340.
Peng et al., "The poly(A)-limiting element enhances mRNA accumulation by increasing the efficiency of pre-mRNA 3' processing" RNA (2005) 11:958-965.
Ploner et al., "Methodological obstacles in knocking down small noncoding RNAs" RNA (2009) 15(10): 1797-1804.
Prasanth et al., "Regulating Gene Expression through RNA Nuclear Retention" Celll (2005) 123(2): 249-263.
Ranum et al., "RNA-mediated neuromuscular disorders." Annu Rev Neurosci (2006) 29:259-277.
Rassoulzadegan et al., "RNA-mediated non-mendelian inheritance of an epigenetic change in the mouse" Nature (2006) 441:469-474.
Reynolds et al., "Rational siRNA design for RNA interference" Nature Biotechnology (2004) 22(3):326-330.
Sanghvi et al., "Heterocyclic Base Modifications in Nucleic Acids and Their Applications in Antisense Oligonucleotides" Antisense Research and Applications (1993) pp. 273-288.
Sasaki et al., "MENε/β noncoding RNAs are essential for structural integrity of nuclear paraspeckles" PNAS (2009) 106(8):2525-2530.
Sato et al., "In vivo gene delivery to tumor cells by transferrin-streptavidin-DNA conjugate" FASEB J (2000) 14: 2108-2118.
Scholefield et al., "Therapeutic gene silencing strategies for polyglutamine disorders" Trends in Genetics (2010) 26(1): 29-38.
Searle et al., "On the stability of nucleic acid structures in solution: enthalpy-entropy compensations, internal rotations and reversibility" Nucleic Acids Res. (1993) 21:2051-2056.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.

Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
*Sun Pharmaceutical Industries, Ltd.* vs. *Eli Lilly & Co* (2010) 1-16.
Sunwoo et al., "MEN e/b nuclear-retained non-coding RNAs are up-regulated upon muscle differentiation and are essential components of paraspeckles" Genome Res. (2009) 19:347-359.
Swayze et al., "The Medicinal Chemistry of Oligonucleotides" in Antisense Drug Technology, 2nd Edition, Chapter 6, pp. 143-182, Crooke ed., 2008.
Thiry, "Birth of a nucleolus: the evolution of nucleolar compartments " Trends. Cell Biol. (2005) 15:194-199.
Van Der Burg et al., "Beyond the brain: widespread pathology in Huntington's disease", Lancet Neurology (2009) 8(8): 765-774.
Viegas et al., "Regulating the regulators: How ribonucleases dictate the rules in the control of small non-coding RNAs" RNA Biol. (2008) 5:230-243.
Wahlestedt et al., "Potent and nontoxic antisense oligonucleotide containing locked nucleic acids" Proc. Natl. Acad. Sci. USA (2000) 97: 5633-5638.
Wang et al., "Synthesis and binding property of an oligonucleotide containing tetraflurophenoxazine" Tetrahedron Lett. (1998) 39:8385-8388.
Watts e tal., "Chemically modified siRNAs: tools and applications" Drug Discovery Today (2008) 13(19-20): 842-855.
Wheeler et al., "Reversal of RNA dominance by displacement of protein sequestered on triplet repeat RNA" Science (2009) 325:336-339.
Wheeler et al., "Myotonic dystrophy: RNA-mediated muscle disease." Curr Opin Neurol (2007) 20:572-576.
Wheeler et al., "Targeting Nuclear RNA for in vivo Correstoin of Myotonic Dystrophy," Nature (2012) 488:111-117.
Wilusz et al., "3' End Processing of a Long Nuclear-Retained Noncoding RNA Yields a tRNA-like Cytoplasmic RNA" Cell (2008) 135:919-932.
Woolf et al., "Specificity of antisense oligonucleotides in vivo" PNAS (1992) 89:7305-7309.
Yelin et al., "Widespread occurrence of antisense transcription in the human genome" Nat. Biotechnol. (2003) 21(4):379-386.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
European Seach Report for Application EP 16153949.9 dated May 11, 2016.
European Search Report for application EP 11740540.7 dated Aug. 19, 2014.
European Search Report for application EP 11810309.2 dated Aug. 19, 2014.
European Search Report for application EP 11810291.2 dated Feb. 4, 2014.
European Search Report for application EP 14834532.5 dated Feb. 20, 2017.
Partial Search Report for application EP 18199910.3 dated Apr. 11, 2019.
European Search Report for application EP 19191940.6 dated Jun. 26, 2020.
European Search Report for application EP 21187583.6 dated Jun. 22, 2022.
Partial Search Report for application EP 21187583.6 dated Mar. 21, 2022.
International Search Report for application PCT/US11/24099 dated Jun. 22, 2011.
International Search Report for application PCT/US11/44583 dated Mar. 1, 2012.
International Search Report for application PCT/US11/44555 dated Apr. 11, 2012.
International Search Report for application PCT/US14/050481 dated Feb. 2, 2015.
Bennett et al., "RNA Targeting Therapeutics: Molecular Mechanisms of Antisense Oligonucleotides as a Therapeutic Platform" Ann Rev Pharmacol Toxicol (2010) 50: 259-293.

(56) References Cited

OTHER PUBLICATIONS

Benichou et al., "Antisense oligonucleotides as a potential treatment for brain deficits observed in myotonic dystrophy type 1" Gene Ther (2022) 1-12.
Cenik et al., "Argonaute proteins" Current Biology (2011) 21: R446-R449.
Doucet et al., "RNA-based gene therapy for myotonic dystrophy type 1 (DM1)" Abstract 150 for the Ottawa Conference on New Directions in Biology & Disease of Skeleta (May 5-8, 2010) Ottawa, Canada.
Furling et al., "Viral vector producing antisense RNA restores myotonic dystrophy myoblast functions" Gene Ther (2003) 10: 795-802.
Furling et al., "Therapeutic RNA strategies for myotonic dystrophy with CTG repeats" Abstract for Nucleotide Repeat Expansion Disorders I: Poster Presentations (2004) Neuromuscular Disorders 14.
Gagnon et al., "RNAi Factors are Present and Active in Human Cell Nuclei" Cell Rep (2014) 6: 211-221.
Jauvin et al., "Targeting DMPK with Antisense Oligonucleotide Improves Muscle Strength in Myotonic Dystrophy Type 1 Mice" Mol Ther: Nucl Acids (2017) 7: 465-474.
Koshelev et al., "Therapeutic application for a cell culture model of myotonic dystrophy" Abstract 130 for New Directions in Biology & Disease of Skeletal Muscle (Apr. 27-30, 2008) New Orleans.
Kurreck et al., "Antisense technologies" Eur J Biochem (2003) 270: 1628-1644.
Langlois et al., "Cytoplasmic and Nuclear Retained DMPK mRNAs Are Targets for RNA Interference in Myotonic Dystrophy Cells" J Biol Chem (2005) 280: 16949-16954.
Langlois et al., "Hammerhead Ribozyme-Mediated Destruction of Nuclear Foci in Myotonic Dystrophy Myoblasts" Mol Ther (2003) 7: 670-680.
Langlois et al., "Ribozyme and Antisense RNA-Based Gene Therapies for Myotonic Dystrophy" Mol Ther (2003) 7: S320.
Liang et al., "Rnase H1-Dependent Antisense Oligonucleotides Are Robustly Active in Directing RNA Cleavage in Both the Cytoplasm and the Nucleus" Mol Ther (2017) 25: 2075-2092.
Mignon et al., "Update on IONIS-DMPKRx Program" MDF Annual Conference (Sep. 14-15, 2018) Nashville, TN.
Monia et al., "Evaluation of 2'-Modified Oligonucleotides Containing 2'-Deoxy Gaps as Antisense Inhibitors of Gene Expression" J of Biol Chem (1993) 268: 14514-14522.
Mulders et al., "Molecular therapy in myotonic dystrophy: focus on RNA gain-of-function" Human Mol Genetics (2010) 19: R90-R97.
Ostergaard et al., "Conjugation of hydrophobic moieties enhances potency of antisense oligonucleotides in the muscle of rodents and non-human primates" Nucl Acid Res (2019) 47: 6045-6058.
Prakash et al., "Fatty acid conjugation enhances potency of antisense oligonucleotides in muscle" Nucl Acid Res (2019) 47: 6029-6044.
Scanlon et al., "Anti-Genes: siRNA, Ribozymes and Antisense" Curr Pharma Biotech (2004) 56: 415-420.
Scherr et al., "Detection of Antisense and Ribozyme Accessible Sites on Native mRNAs: Application to NCOA3 mRNA" Mol Ther (2001) 4: 454-460.
Stein "The experimental use of antisense oligonucleotides: a guide for the perplexed" J Clin Invest (2001) 108: 641-644.
Vickers et al., "Efficient Reduction of Target RNAs by Small Interfering RNA and Rnase H-dependent Antisense Agents" J Biol Chem (2003) 278: 7108-7118.
Wheeler et al., "Myotonic Dystrophy : Therapeutic Strategies for the Future" Neurotherapeutics: J Am Soc Exp Neurotherapeutics (2008) 5: 592-600.
Seth et al., "Targeted delivery of nucleic acid therapeutics" Presentation for TIDES 2020 (Sep. 15-18, 2020) virtual.
Seth et al., "Traversing protected tissue barriers for oligonucleotide delivery" Presentation for TIDES USA 2021 (Sep. 20-23, 2021) Boston, MA.
GenBank NCBI Ref. No. XM_035463770.1, 2 pages.
GenBank NCBI Ref. No. XM_051814311.1, 2 pages.
International Search Report for PCT/US22/075772 dated Feb. 23, 2023, 13 pages.

* cited by examiner

OLIGOMERIC COMPOUNDS FOR REDUCING DMPK EXPRESSION

SEQUENCE LISTING

The present application is being filed along with a Sequence Listing in electronic format. The Sequence Listing is provided as a file entitled BIOL0441USSEQ.xml, created on Aug. 23, 2022 which is 241 KB in size. The information in the electronic format of the sequence listing is incorporated herein by reference in its entirety.

FIELD

Provided are oligomeric compounds, methods, and pharmaceutical compositions for reducing the amount or activity of DMPK RNA in a cell or animal, and in certain instances reducing the amount of DMPK protein in a cell or animal. Such oligomeric compounds, methods, and pharmaceutical compositions are useful to treat type 1 myotonic dystrophy (DM1) in an animal.

BACKGROUND

Myotonic dystrophy type 1 (DM1) is the most common form of muscular dystrophy in adults with an estimated frequency of 1 in 7,500 (Harper P S., Myotonic Dystrophy. London: W.B. Saunders Company; 2001). DM1 is an autosomal dominant disorder caused by expansion of a non-coding CTG repeat in DMPK1. DMPK1 is a gene encoding a cytosolic serine/threonine kinase (Brook J D, et al., *Cell.,* 1992, 68(4):799-808). The physiologic functions and substrates of this kinase have not been fully determined. The expanded CTG repeat is located in the 3' untranslated region (UTR) of DMPK1. This mutation leads to RNA dominance, a process in which expression of RNA containing an expanded CUG repeat (CUGexp) induces cell dysfunction (Osborne R J and Thornton C A., *Human Molecular Genetics.,* 2006, 15(2): R162-R169).

The DMPK gene normally has 5-37 CTG repeats in the 3' untranslated region. In myotonic dystrophy type 1, this number is significantly expanded and is, for example, in the range of 50 to greater than 3,500 (Harper, Myotonic Dystrophy (Saunders, London, ed. 3, 2001); Annu. Rev. Neurosci. 29: 259, 2006; EMBO J. 19: 4439, 2000; Curr Opin Neurol. 20: 572, 2007).

The CUGexp tract interacts with RNA binding proteins including muscleblind-like (MBNL) protein, a splicing factor, and causes the mutant transcript to be retained in nuclear foci. The toxicity of this RNA stems from sequestration of RNA binding proteins and activation of signaling pathways. Studies in animal models have shown that phenotypes of DM1 can be reversed if toxicity of CUGexp RNA is reduced (Wheeler™, et al., *Science.,* 2009, 325(5938):336-339; Mulders S A, et al., *Proc Natl Acad Sci USA.,* 2009, 106(33): 13915-13920).

In DM1, skeletal muscle is the most severely affected tissue, but the disease also has important effects on cardiac and smooth muscle, ocular lens, and brain. The cranial, distal limb, and diaphragm muscles are preferentially affected. Manual dexterity is compromised early, which causes several decades of severe disability. The median age at death is 55 years, usually from respiratory failure (de Die-Smulders C E, et al., *Brain.,* 1998, 121(Pt 8):1557-1563).

Antisense technology is emerging as an effective means for modulating expression of certain gene products and may therefore prove to be uniquely useful in a number of therapeutic, diagnostic, and research applications for the modulation of DMPK1.

Presently there is no treatment that can modify the course of DM1. The burden of disease, therefore, is significant. It is, therefore, an object herein to provide compounds, compositions, and methods for treating DM1.

SUMMARY

Oligomeric compounds, methods, and pharmaceutical compositions of certain embodiments described herein are useful for reducing or inhibiting DMPK expression in a cell or animal. In certain embodiments, DMPK RNA or protein levels can be reduced in a cell or animal. In certain embodiments, the subject has type 1 myotonic dystrophy (DM1). In certain embodiments, the subject has a disease or disorder associated with a mutation in DMPK.

Also provided are methods of treating an animal having type 1 myotonic dystrophy.

DETAILED DESCRIPTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well-known and commonly used in the art. Where permitted, all patents, applications, published applications and other publications and other data referred to throughout in the disclosure are incorporated by reference herein in their entirety.

Unless otherwise indicated, the following terms have the following meanings:

As used herein, "2'-deoxynucleoside" means a nucleoside comprising a 2'-H(H) deoxyfuranosyl sugar moiety. In certain embodiments, a 2'-deoxynucleoside is a 2'-β-D-deoxynucleoside and comprises a 2'-β-D-deoxyribosyl sugar moiety, which has the β-D ribosyl configuration as found in naturally occurring deoxyribonucleic acids (DNA). In certain embodiments, a 2'-deoxynucleoside may comprise a modified nucleobase or may comprise an RNA nucleobase (uracil).

As used herein, "2'-MOE" means a 2'-OCH$_2$CH$_2$OCH$_3$ group in place of the 2'-OH group of a furanosyl sugar moiety. A "2'-MOE sugar moiety" means a sugar moiety with a 2'-OCH$_2$CH$_2$OCH$_3$ group in place of the 2'-OH group of a furanosyl sugar moiety. Unless otherwise indicated, a 2'-MOE sugar moiety is in the β-D-ribosyl configuration. "MOE" means O-methoxyethyl.

As used herein, "2'-MOE nucleoside" means a nucleoside comprising a 2'-MOE sugar moiety.

As used herein, "2'-OMe" means a 2'-OCH$_3$ group in place of the 2'-OH group of a furanosyl sugar moiety. A "2'-O-methyl sugar moiety" or "2'-OMe sugar moiety" means a sugar moiety with a 2'-OCH$_3$ group in place of the 2'-OH group of a furanosyl sugar moiety. Unless otherwise indicated, a 2'-OMe sugar moiety is in the β-D-ribosyl configuration.

As used herein, "2'-OMe nucleoside" means a nucleoside comprising a 2'-OMe sugar moiety.

As used herein, "5-methylcytosine" means a cytosine modified with a methyl group attached to the 5 position.

A 5-methylcytosine is a modified nucleobase.

As used herein, "ameliorate" in reference to a treatment means improvement in at least one symptom or hallmark relative to the same symptom or hallmark in the absence of the treatment. In certain embodiments, amelioration is the reduction in the severity or frequency of a symptom or hallmark or the delayed onset or slowing of progression in the severity or frequency of a symptom or hallmark. In certain embodiments, the symptom or hallmark is one or more of muscle stiffness, myotonia, disabling distal weakness, weakness in face and jaw muscles, difficulty in swallowing, drooping of the eyelids (ptosis), weakness of neck muscles, weakness in arm and leg muscles, persistent muscle pain, hypersomnia, muscle wasting, dysphagia, respiratory insufficiency, irregular heartbeat, heart muscle damage, apathy, insulin resistance, and cataracts.

As used herein, "antisense agent" means an antisense compound and optionally one or more additional features, such as a sense compound.

As used herein, "cerebrospinal fluid" or "CSF" means the fluid filling the space around the brain and spinal cord. "Artificial cerebrospinal fluid" or "aCSF" means a prepared or manufactured fluid that has certain properties (e.g., osmolarity, pH, and/or electrolytes) of cerebrospinal fluid and is biocompatible with CSF.

As used herein, "conjugate group" means a group of atoms that is directly attached to an oligonucleotide.

Conjugate groups include a conjugate moiety and a conjugate linker that attaches the conjugate moiety to the oligonucleotide.

As used herein, "conjugate linker" means a single bond or a group of atoms comprising at least one bond that connects a conjugate moiety to an oligonucleotide.

As used herein, "conjugate moiety" means a group of atoms that modifies one or more properties of a molecule compared to the identical molecule lacking the conjugate moiety, including but not limited to pharmacodynamics, pharmacokinetics, stability, binding, absorption, tissue distribution, cellular distribution, cellular uptake, charge and clearance.

As used herein, "constrained ethyl" or "cEt" or "cEt sugar moiety" means a β-D ribosyl bicyclic sugar moiety wherein the second ring of the bicyclic sugar is formed via a bridge connecting the 4'-carbon and the 2'-carbon of the β-D ribosyl sugar moiety, wherein the bridge has the formula 4'-CH(CH$_3$)—O-2', and wherein the methyl group of the bridge is in the S configuration.

As used herein, "cEt nucleoside" means a nucleoside comprising a cEt sugar moiety.

As used herein, "deoxy region" means a region of 5-12 contiguous nucleotides, wherein at least 70% of the nucleosides comprise a β-D-2'-deoxyribosyl sugar moiety. In certain embodiments, a deoxy region is the gap of a gapmer.

As used herein, "internucleoside linkage" is the covalent linkage between adjacent nucleosides in an oligonucleotide. As used herein "modified internucleoside linkage" means any internucleoside linkage other than a phosphodiester internucleoside linkage.

As used herein, "linked nucleosides" are nucleosides that are connected in a contiguous sequence (i.e., no additional nucleosides are presented between those that are linked).

As used herein, "motif" means the pattern of unmodified and/or modified sugar moieties, nucleobases, and/or internucleoside linkages, in an oligonucleotide.

As used herein, "modified nucleoside" means a nucleoside comprising a modified nucleobase and/or a modified sugar moiety.

As used herein, "non-bicyclic modified sugar moiety" means a modified sugar moiety that comprises a modification, such as a substituent, that does not form a bridge between two atoms of the sugar to form a second ring.

As used herein, "nucleobase" means an unmodified nucleobase or a modified nucleobase. A nucleobase is a heterocyclic moiety. As used herein an "unmodified nucleobase" is adenine (A), thymine (T), cytosine (C), uracil (U), or guanine (G). As used herein, a "modified nucleobase" is a group of atoms other than unmodified A, T, C, U, or G capable of pairing with at least one other nucleobase. A "5-methylcytosine" is a modified nucleobase. A universal base is a modified nucleobase that can pair with any one of the five unmodified nucleobases.

As used herein, "nucleobase sequence" means the order of contiguous nucleobases in a nucleic acid or oligonucleotide independent of any sugar or internucleoside linkage modification.

As used herein, "nucleoside" means a compound or fragment of a compound comprising a nucleobase and a sugar moiety. The nucleobase and sugar moiety are each, independently, unmodified or modified.

As used herein, "oligomeric compound" means an oligonucleotide and optionally one or more additional features, such as a conjugate group or terminal group. An oligomeric compound may be paired with a second oligomeric compound that is complementary to the first oligomeric compound or may be unpaired. A "singled-stranded oligomeric compound" is an unpaired oligomeric compound.

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "pharmaceutically acceptable carrier or diluent" means any substance suitable for use in administering to an animal. Certain such carriers enable pharmaceutical compositions to be formulated as, for example, tablets, pills, dragees, capsules, liquids, gels, syrups, slurries, suspension and lozenges for the oral ingestion by a subject. In certain embodiments, a pharmaceutically acceptable carrier or diluent is sterile water, sterile saline, sterile buffer solution, or sterile artificial cerebrospinal fluid.

As used herein "pharmaceutically acceptable salts" means physiologically and pharmaceutically acceptable salts of compounds. Pharmaceutically acceptable salts retain the desired biological activity of the parent compound and do not impart undesired toxicological effects thereto.

As used herein "pharmaceutical composition" means a mixture of substances suitable for administering to a subject. For example, a pharmaceutical composition may comprise an oligomeric compound and a sterile aqueous solution. In certain embodiments, a pharmaceutical composition shows activity in free uptake assay in certain cell lines.

As used herein, "prodrug" means an inactive or less active form of a compound which, when administered to a subject, is metabolized to form the active, or more active, compound. In certain embodiments, a prodrug comprises a cell-targeting moiety and at least one active compound.

As used herein, "stereorandom" or "stereorandom chiral center" in the context of a population of molecules of identical molecular formula means a chiral center that is not controlled during synthesis, or enriched following synthesis, for a particular absolute stereochemical configuration. The stereochemical configuration of a chiral center is random when it is the result of a synthetic method that is not designed to control the stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center ("racemic"). In certain embodiments, the stereorandom chiral center is not racemic because one absolute configuration predominates following synthesis, e.g., due to the action of non-chiral reagents near the enriched stereochemistry of an adjacent sugar moiety. In certain embodiments, the stereorandom chiral center is at the phosphorous atom of a stereorandom phosphorothioate internucleoside linkage.

As used herein, "sugar moiety" means an unmodified sugar moiety or a modified sugar moiety. As used herein, "unmodified sugar moiety" means a 2'-OH(H) ribosyl moiety, as found in RNA (an "unmodified RNA sugar moiety"), or a 2'-H(H) deoxyribosyl sugar moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate.

As used herein, "symptom or hallmark" means any physical feature or test result that indicates the existence or extent of a disease or disorder. In certain embodiments, a symptom is apparent to a subject or to a medical professional examining or testing said subject. In certain embodiments, a hallmark is apparent upon invasive diagnostic testing, including, but not limited to, post-mortem tests.

As used herein, "target nucleic acid" and "target RNA" mean a nucleic acid that an oligomeric compound is designed to affect. Target RNA means an RNA transcript and includes pre-mRNA and mRNA unless otherwise specified.

As used herein, "target region" means a portion of a target nucleic acid to which an oligomeric compound is designed to hybridize.

As used herein, "terminal group" means a chemical group or group of atoms that is covalently linked to a terminus of an oligonucleotide.

As used herein, "antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound.

As used herein, "gapmer" means a modified oligonucleotide comprising an internal region positioned between external regions having one or more nucleosides, wherein the nucleosides comprising the internal region are chemically distinct from the nucleoside or nucleosides comprising the external regions, and wherein the modified oligonucleotide supports RNAse H cleavage. The internal region may be referred to as the "gap" and the external regions may be referred to as the "wings." In certain embodiments, the internal region is a deoxy region. The positions of the internal region or gap refer to the order of the nucleosides of the internal region and are counted starting from the 5'-end of the internal region. Unless otherwise indicated, "gapmer" refers to a sugar motif. In certain embodiments, each nucleoside of the gap is a 2'-β-D-deoxynucleoside. As used herein, the term "MOE gapmer" indicates a gapmer having a gap comprising 2'-β-D-deoxynucleosides and wings comprising 2'-MOE nucleosides. Unless otherwise indicated, a gapmer may comprise one or more modified internucleoside linkages and/or modified nucleobases and such modifications do not necessarily follow the gapmer pattern of the sugar modifications.

As used herein, "hybridization" means the annealing of oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases. In certain embodiments, complementary nucleic acid molecules include, but are not limited to, an antisense compound and a nucleic acid target. In certain embodiments, complementary nucleic acid molecules include, but are not limited to, an oligonucleotide and a nucleic acid target.

As used herein, "RNAi agent" means an antisense agent that acts, at least in part, through RISC or Ago2 to modulate a target nucleic acid and/or protein encoded by a target nucleic acid. RNAi agents include, but are not limited to double-stranded siRNA, single-stranded RNAi (ssRNAi), and microRNA, including microRNA mimics. RNAi agents may comprise conjugate groups and/or terminal groups. In certain embodiments, an RNAi agent modulates the amount and/or activity, of a target nucleic acid. The term RNAi agent excludes antisense agents that act through RNase H.

As used herein, "RNase H agent" means an antisense agent that acts through RNase H to modulate a target nucleic acid and/or protein encoded by a target nucleic acid. In certain embodiments, RNase H agents are single-stranded. In certain embodiments, RNase H agents are double-stranded. RNase H compounds may comprise conjugate groups and/or terminal groups. In certain embodiments, an RNase H agent modulates the amount and/or activity of a target nucleic acid. The term RNase H agent excludes antisense agents that act principally through RISC/Ago2.

As used herein, "treating" means improving a subject's disease or condition by administering an oligomeric compound described herein. In certain embodiments, treating a subject improves a symptom relative to the same symptom in the absence of the treatment. In certain embodiments, treatment reduces in the severity or frequency of a symptom, or delays the onset of a symptom, slows the progression of a symptom, or slows the severity or frequency of a symptom.

As used herein, "therapeutically effective amount" means an amount of a pharmaceutical agent or composition that provides a therapeutic benefit to an animal. For example, a therapeutically effective amount improves a symptom of a disease.

CERTAIN EMBODIMENTS

Embodiment 1. An oligomeric compound comprising a modified oligonucleotide according to the following chemical notation: $T_{ks}T_{ko}{}^mC_{ko}{}^mC_{ds}C_{ys}G_{ds}A_{ds}A_{ds}T_{ds}G_{ds}T_{ds}{}^mC_{ds}{}^mC_{ds}G_{ko}A_{ks}{}^mC_k$ (SEQ ID NO: 13), wherein:
- A=an adenine nucleobase,
- $^mC$=a 5-methylcytosine nucleobase,
- C=a cytosine nucleobase,
- G=a guanine nucleobase,
- T=a thymine nucleobase,
- y=a 2'-OMe sugar moiety,
- k=a cEt sugar moiety,
- d=a 2'-β-D-deoxyribosyl sugar moiety,
- s=a phosphorothioate internucleoside linkage, and
- o=a phosphodiester internucleoside linkage.

Embodiment 2. The oligomeric compound of embodiment 1 comprising a conjugate group.

Embodiment 3. The oligomeric compound of embodiment 2, wherein the conjugate group comprises a conjugate moiety and a conjugate linker.

Embodiment 4. The oligomeric compound of embodiment 2, wherein the conjugate group comprises $C_{10}$-$C_{24}$ alkyl.

Embodiment 5. The oligomeric compound of embodiment 2, wherein the conjugate group comprises $C_{16}$ alkyl.

Embodiment 6. The oligomeric compound of embodiment 3, wherein the conjugate moiety is a cell-targeting moiety.

Embodiment 7. The oligomeric compound of embodiment 3, wherein the cell-targeting moiety is selected from a carbohydrate, an antibody, and an antibody fragment.

Embodiment 8. The oligomeric compound of any of embodiments 6-7, wherein the cell-targeting moiety binds a cell surface receptor on a skeletal muscle cell.

Embodiment 9. The oligomeric compound of any of embodiments 6-8, wherein the cell-targeting moiety is an antibody or an antibody fragment that binds a transferrin receptor.

Embodiment 10. A modified oligonucleotide according to the following chemical structure:

(SEQ ID NO: 13)

or a salt thereof.

Embodiment 11. The modified oligo nucleotide of embodiment 10, which is a sodium salt or a potassium salt.
Embodiment 12. A modified oligonucleotide according to the following chemical structure:
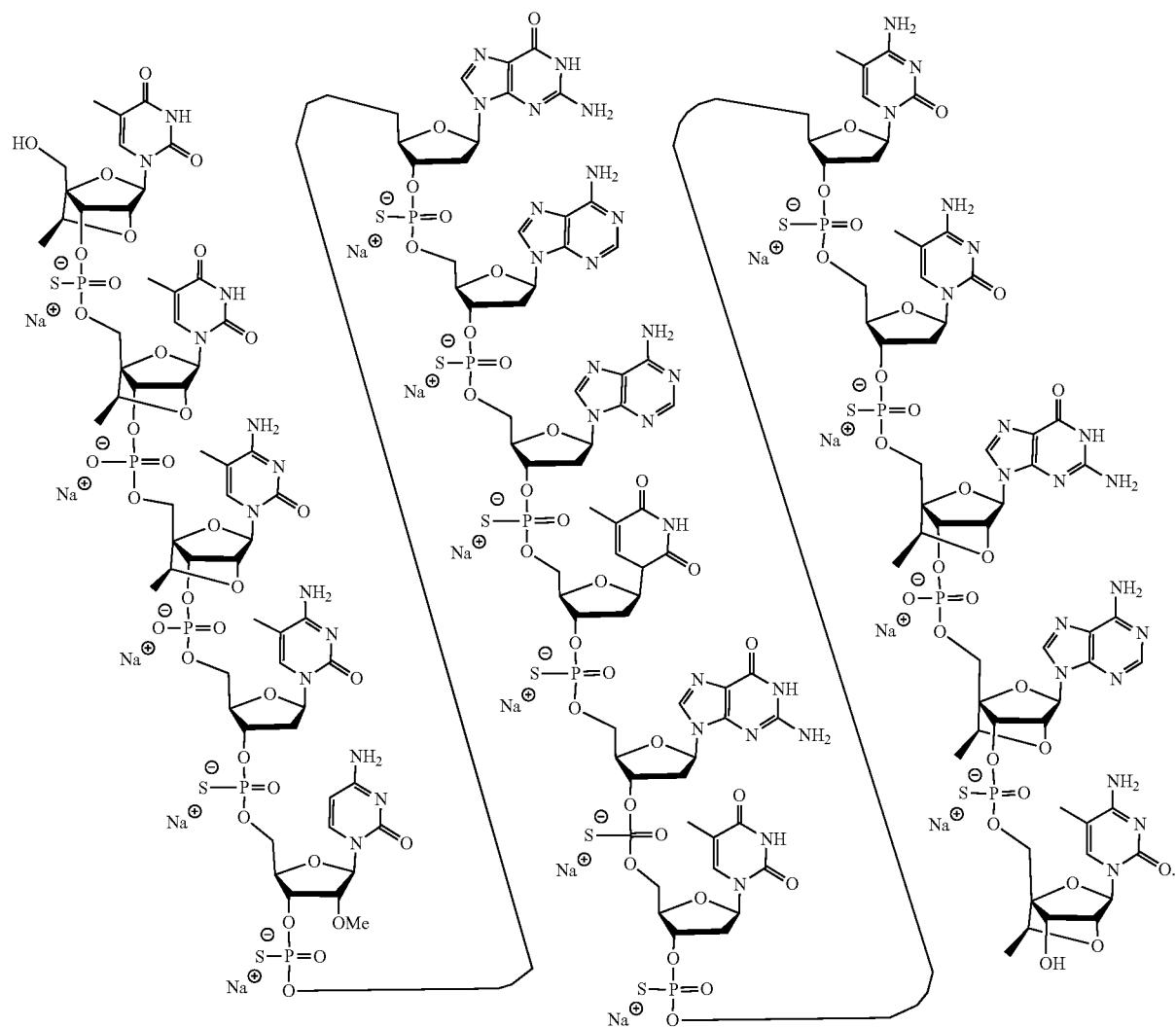
(SEQ ID NO: 13)

Embodiment 13. An oligomeric compound according to the following chemical structure:
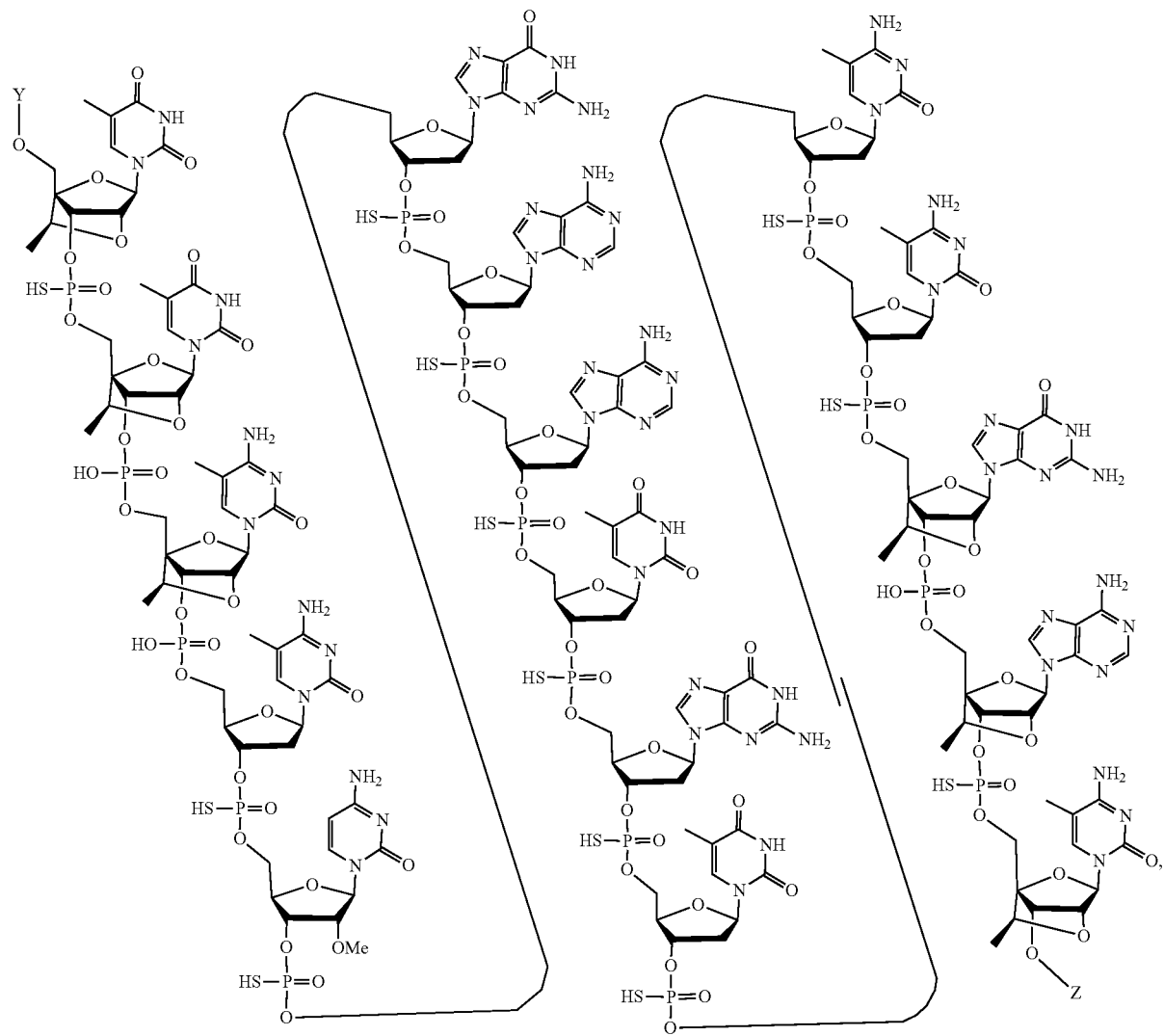
(SEQ ID NO: 30)

or a salt thereof, wherein Y and Z are selected from H and a conjugate group, wherein at least one of Y and Z is a conjugate group.

Embodiment 14. The oligomeric compound of embodiment 13, which is a sodium salt or a potassium salt.

Embodiment 15. An oligomeric compound according to the following chemical structure:

(SEQ ID NO: 30)

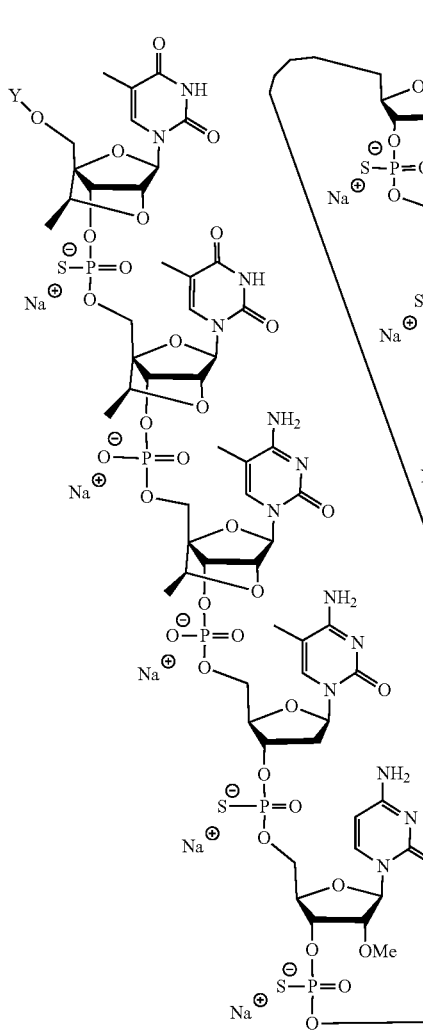
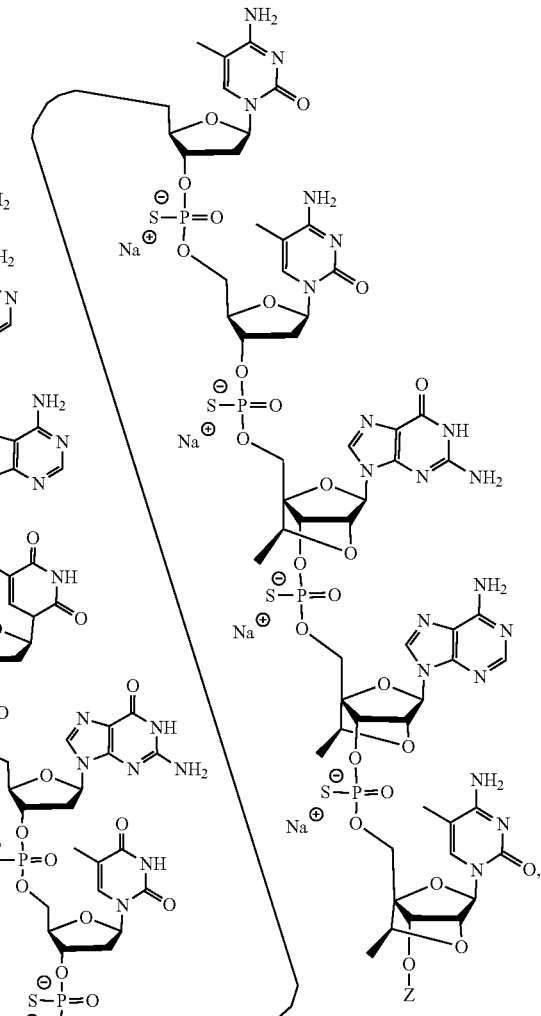

wherein Y and Z are selected from H and a conjugate group, wherein at least one of Y and Z is a conjugate group.

Embodiment 16. The oligomeric compound of any of embodiments 13-15, wherein the conjugate group comprises a conjugate moiety and a conjugate linker.

Embodiment 17. The oligomeric compound of any of embodiments 13-15, wherein the conjugate group comprises $C_{10}$-$C_{24}$ alkyl.

Embodiment 18. The oligomeric compound of any of embodiments 13-15, wherein the conjugate group comprises $C_{16}$.

Embodiment 19. The oligomeric compound of embodiment 16, wherein the conjugate moiety is a cell-targeting moiety.

Embodiment 20. The oligomeric compound of embodiment 19, wherein the cell-targeting moiety binds a cell surface receptor on a skeletal muscle cell.

Embodiment 21. The oligomeric compound of embodiment 19 or embodiment 20, wherein the cell-targeting moiety is selected from a carbohydrate and an antibody.

Embodiment 22. The oligomeric compound of embodiment 19 or embodiment 20, wherein the cell-targeting moiety is an antibody or an antibody fragment that binds a transferrin receptor.

Embodiment 23. The oligomeric compound of embodiment 19, wherein the cell-targeting moiety comprises a GalNAc.

Embodiment 24. The oligomeric compound of any of embodiments 13-15, wherein Y is:

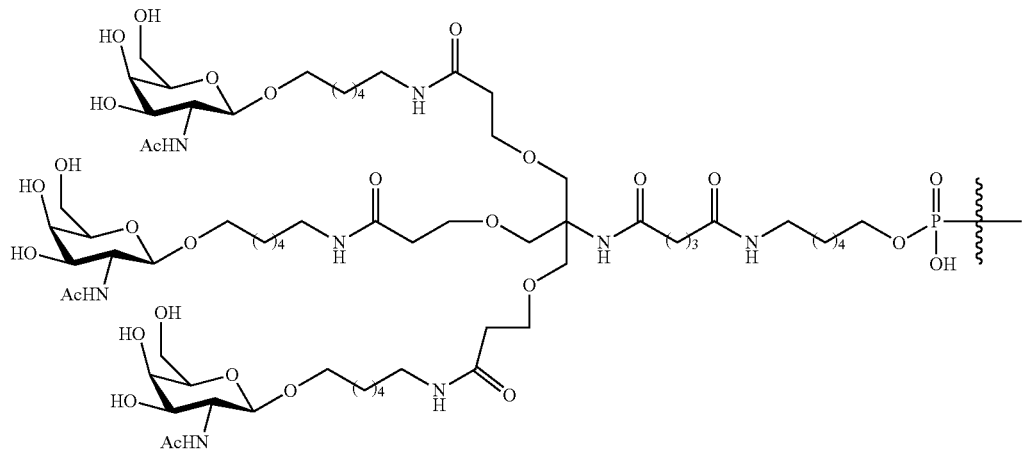

Embodiment 25. A prodrug of the oligomeric compound of any of embodiments 1-9 and 13-24 or the modified oligonucleotide of any of embodiments 10-12.

Embodiment 26. The oligomeric compound of any of embodiments 1-9 and 13-24, wherein the oligomeric compound is a prodrug.

Embodiment 27. A population of oligomeric compounds of any of embodiments 1-9 and 13-24, or modified oligonucleotides of any of embodiments 10-12, wherein all of the phosphorothioate internucleoside linkages of the modified oligonucleotide are stereorandom.

Embodiment 28. An oligomeric compound comprising a modified oligonucleotide according to the following chemical notation: $T_{ks}T_{ks}{}^{m}C_{ks}{}^{m}C_{ds}C_{ys}G_{ds}A_{ds}A_{ds}T_{ds}G_{ds}T_{ds}{}^{m}C_{ds}{}^{m}C_{ds}G_{ks}A_{ks}{}^{m}C_{k}$ (SEQ ID NO: 20), wherein:
A=an adenine nucleobase,
$^{m}$C=a 5-methylcytosine nucleobase,
C=a cytosine nucleobase,
G=a guanine nucleobase,
T=a thymine nucleobase,
y=a 2'-OMe sugar moiety,
k=a cEt sugar moiety,
d=a 2'-β-D-deoxyribosyl sugar moiety, and
s=a phosphorothioate internucleoside linkage.

Embodiment 29. The oligomeric compound of embodiment 28 comprising a conjugate group.

Embodiment 30. The oligomeric compound of embodiment 29, wherein the conjugate group comprises a conjugate moiety and a conjugate linker.

Embodiment 31. The oligomeric compound of embodiment 29, wherein the conjugate group comprises $C_{10}$-$C_{24}$ alkyl.

Embodiment 32. The oligomeric compound of embodiment 29, wherein the conjugate group comprises $C_{16}$ alkyl.

Embodiment 33. The oligomeric compound of embodiment 30, wherein the conjugate moiety is a cell-targeting moiety.

Embodiment 34. The oligomeric compound of embodiment 30, wherein the cell-targeting moiety is selected from a carbohydrate, an antibody, and an antibody fragment.

Embodiment 35. The oligomeric compound of any of embodiments 33-34, wherein the cell-targeting moiety binds a cell surface receptor on a skeletal muscle cell.

Embodiment 36. The oligomeric compound of any of embodiments 33-35, wherein the cell-targeting moiety is an antibody or an antibody fragment that binds a transferrin receptor.

Embodiment 37. A modified oligonucleotide according to the following chemical structure:
(SEQ ID NO: 20)
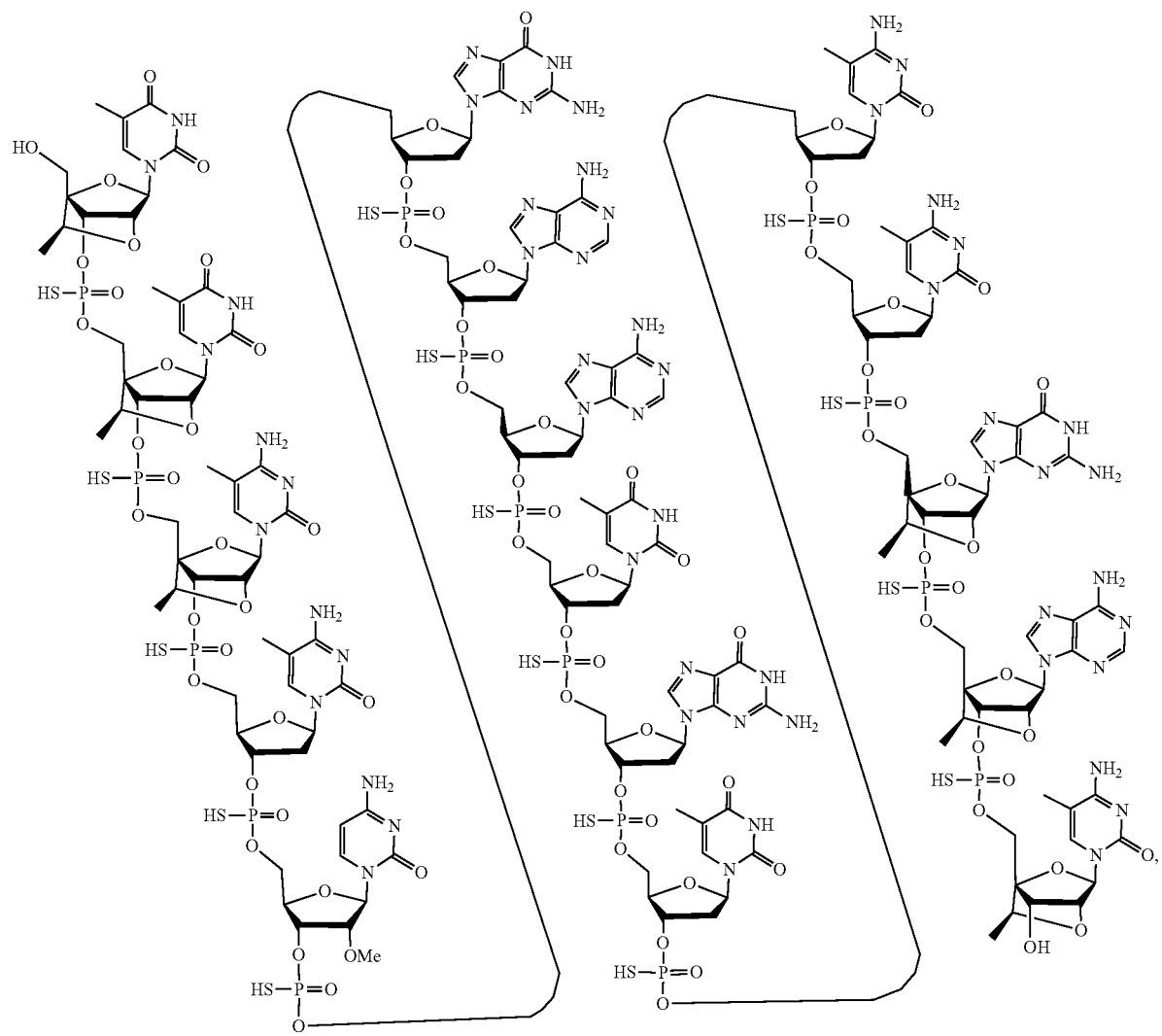
or a salt thereof.

Embodiment 38. The modified oligonucleotide of embodiment 37, which is a sodium salt or a potassium salt.
Embodiment 39. A modified oligonucleotide according to the following chemical structure:
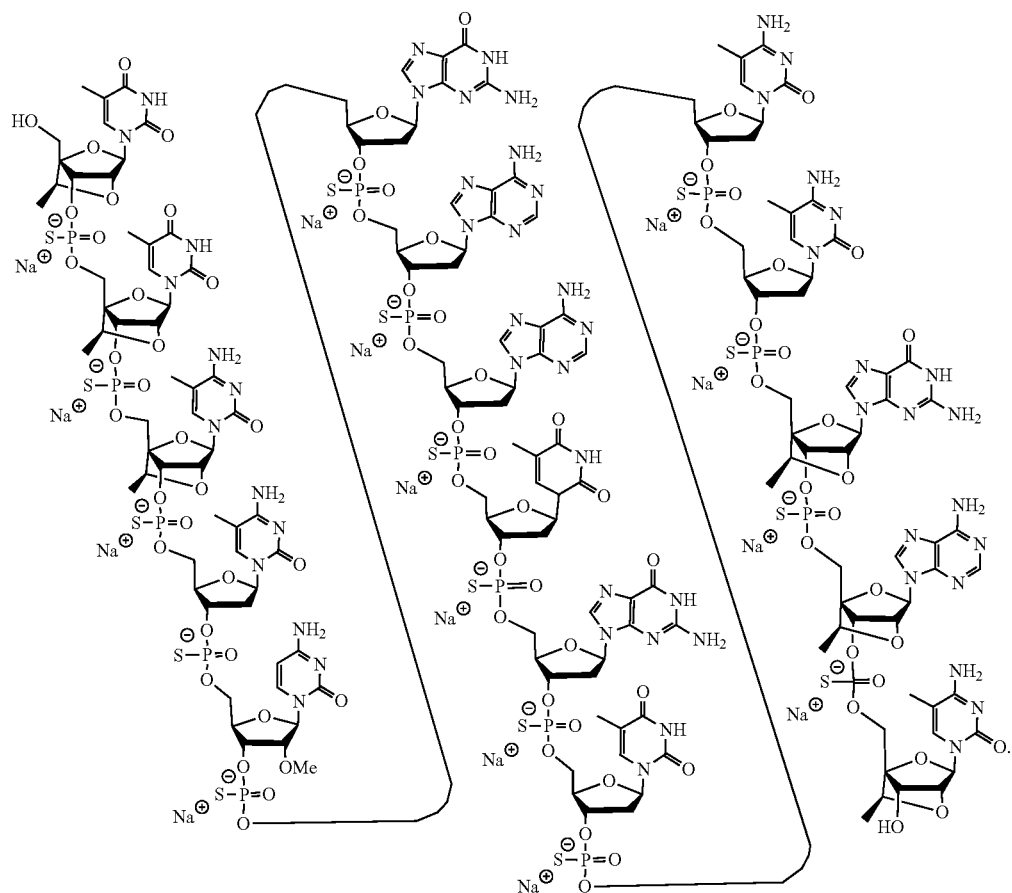
(SEQ ID NO: 20)

Embodiment 40. An oligomeric compound according to the following chemical structure:
(SEQ ID NO: 28)
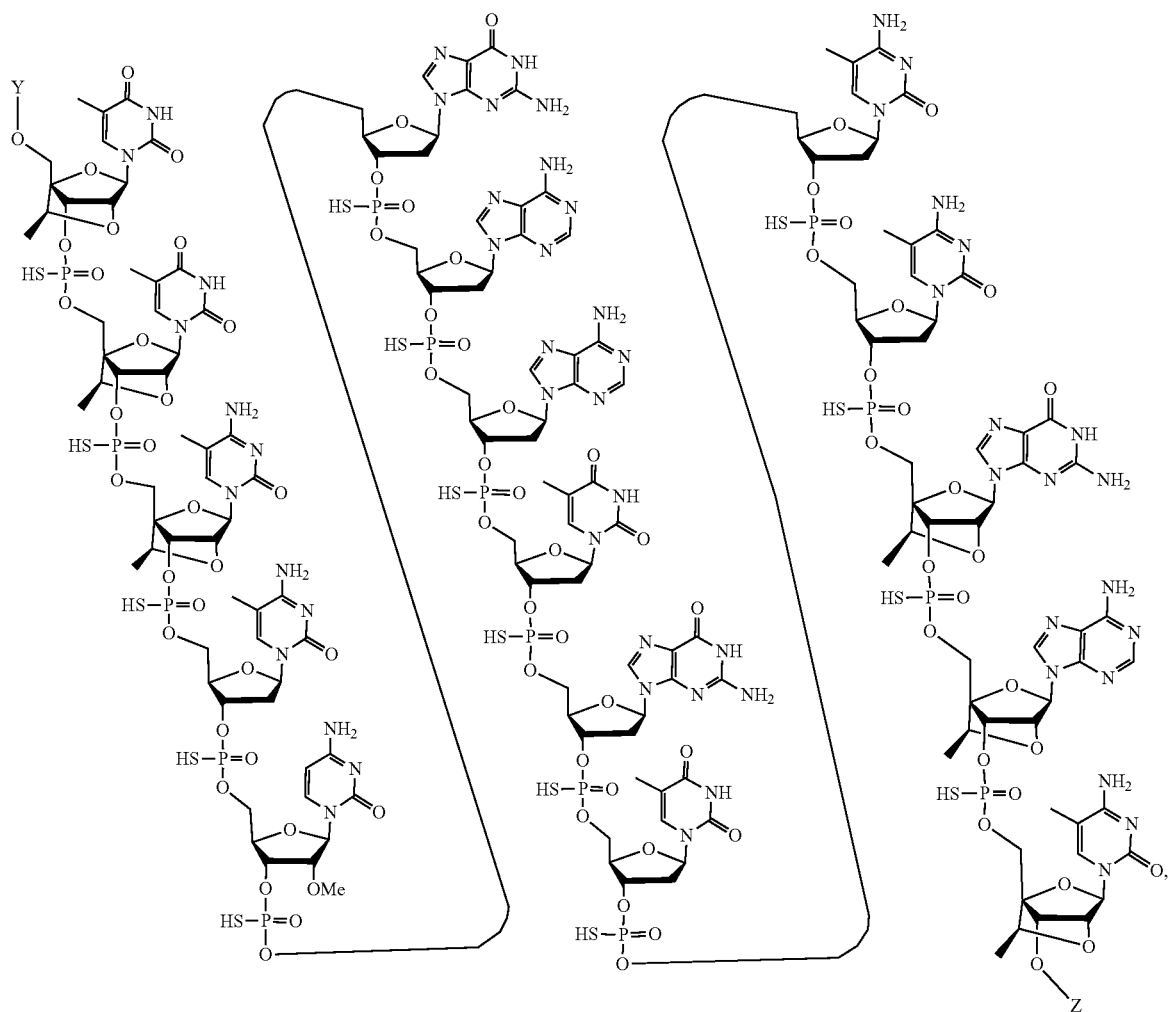
or a salt thereof, wherein Y and Z are selected from H and a conjugate group, wherein at least one of Y and Z is a conjugate group.

Embodiment 41. The oligomeric compound of embodiment 40, which is a sodium salt or a potassium salt.

Embodiment 42. An oligomeric compound according to the following chemical structure:

(SEQ ID NO: 28)

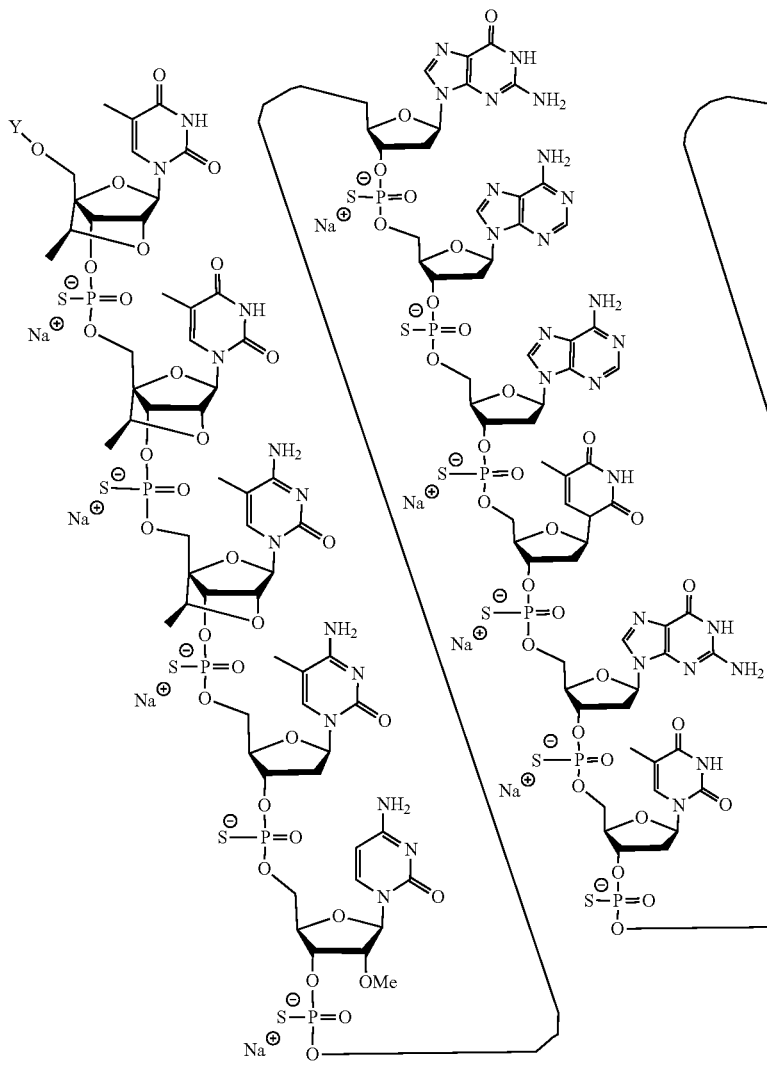
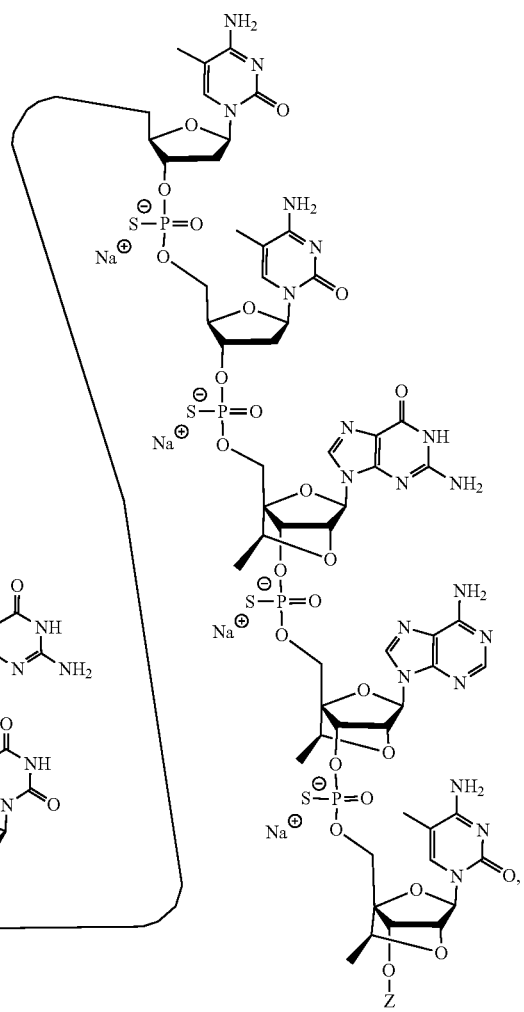

wherein Y and Z are selected from H and a conjugate group, wherein at least one of Y and Z is a conjugate group.

Embodiment 43. The oligomeric compound of any of embodiments 40-42, wherein the conjugate group comprises a conjugate moiety and a conjugate linker.

Embodiment 44. The oligomeric compound of any of embodiments 40-42, wherein the conjugate group comprises $C_{10}$-$C_{24}$ alkyl.

Embodiment 45. The oligomeric compound of any of embodiments 40-42, wherein the conjugate group comprises $C_{16}$.

Embodiment 46. The oligomeric compound of embodiment 43, wherein the conjugate moiety is a cell-targeting moiety.

Embodiment 47. The oligomeric compound of embodiment 46, wherein the cell-targeting moiety binds a cell surface receptor on a skeletal muscle cell.

Embodiment 48. The oligomeric compound of embodiment 46 or embodiment 47, wherein the cell-targeting moiety is selected from a carbohydrate and an antibody.

Embodiment 49. The oligomeric compound of embodiment 46 or embodiment 47, wherein the cell-targeting moiety is an antibody or an antibody fragment that binds a transferrin receptor.

Embodiment 50. The oligomeric compound of embodiment 46, wherein the cell-targeting moiety comprises a GalNAc.

Embodiment 51. The oligomeric compound of any of embodiments 40-42, wherein Y is:

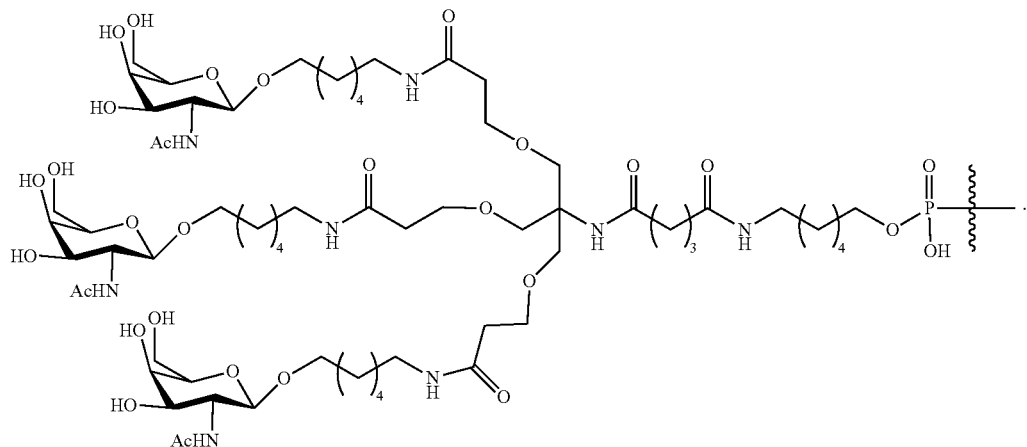

Embodiment 52. A prodrug of the oligomeric compound of any of embodiments 28-36 and 40-51 or the modified oligonucleotide of any of embodiments 37-39.
Embodiment 53. The oligomeric compound any of embodiments 28-36 and 40-51, wherein the oligomeric compound is a prodrug.
Embodiment 54. A population of oligomeric compounds of any of embodiments 28-36 and 40-51 or modified oligonucleotides of any of embodiments 37-39, wherein all of the phosphorothioate internucleoside linkages of the modified oligonucleotide are stereorandom.
Embodiment 55. An oligomeric compound comprising a modified oligonucleotide according to the following chemical notation: $^{m}C_{ks}G_{ko}A_{ko}A_{ds}U_{ys}G_{ds}T_{ds}{}^{m}C_{ds}{}^{m}C_{ds}G_{ds}A_{ds}{}^{m}C_{ds}A_{ds}G_{ko}T_{ks}G_{k}$ (SEQ ID NO: 14), wherein:
A=an adenine nucleobase,
$^{m}$C=a 5-methylcytosine nucleobase,
G=a guanine nucleobase,
T=a thymine nucleobase,
U=a uracil nucleobase,
y=a 2'-OMe sugar moiety,
k=a cEt sugar moiety,
d=a 2'-β-D-deoxyribosyl sugar moiety,
s=a phosphorothioate internucleoside linkage, and
o=a phosphodiester internucleoside linkage.

Embodiment 56. The oligomeric compound of embodiment 55 comprising a conjugate group.
Embodiment 57. The oligomeric compound of embodiment 56, wherein the conjugate group comprises a conjugate moiety and a conjugate linker.
Embodiment 58. The oligomeric compound of embodiment 56, wherein the conjugate group comprises $C_{10}$-$C_{24}$ alkyl.
Embodiment 59. The oligomeric compound of embodiment 56, wherein the conjugate group comprises $C_{16}$ alkyl.
Embodiment 60. The oligomeric compound of embodiment 57, wherein the conjugate moiety is a cell-targeting moiety.
Embodiment 61. The oligomeric compound of embodiment 60, wherein the cell-targeting moiety is selected from a carbohydrate, an antibody, and an antibody fragment.
Embodiment 62. The oligomeric compound of any of embodiments 60-61, wherein the cell-targeting moiety binds a cell surface receptor on a skeletal muscle cell.
Embodiment 63. The oligomeric compound of any of embodiments 60-62, wherein the cell-targeting moiety is an antibody or an antibody fragment that binds a transferrin receptor.

Embodiment 64. A modified oligonucleotide according to the following chemical structure:
(SEQ ID NO: 14)
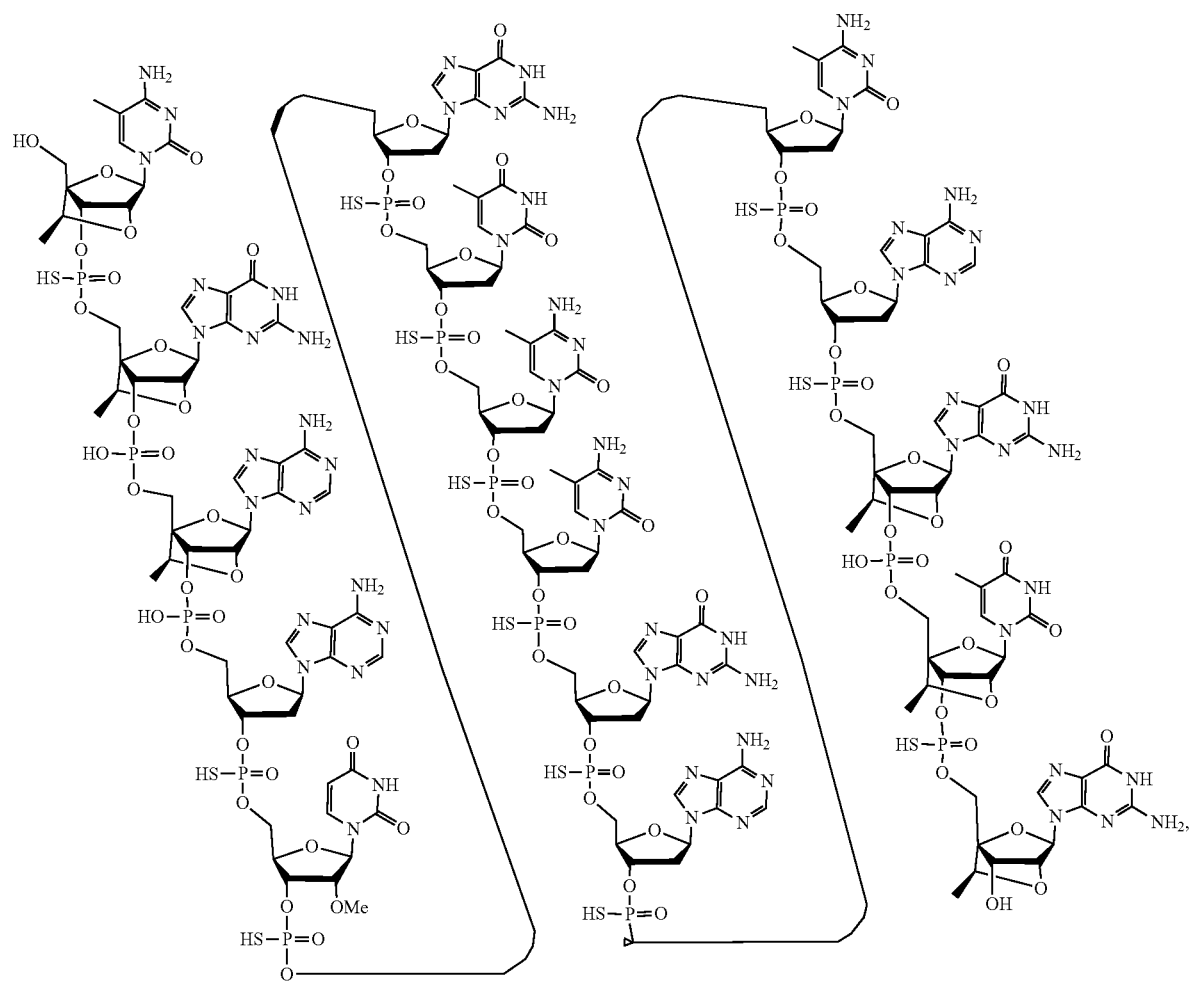
or a salt thereof.

Embodiment 65. The modified oligonucleotide of embodiment 64, which is a sodium salt or a potassium salt.
Embodiment 66. A modified oligonucleotide according to the following chemical structure:
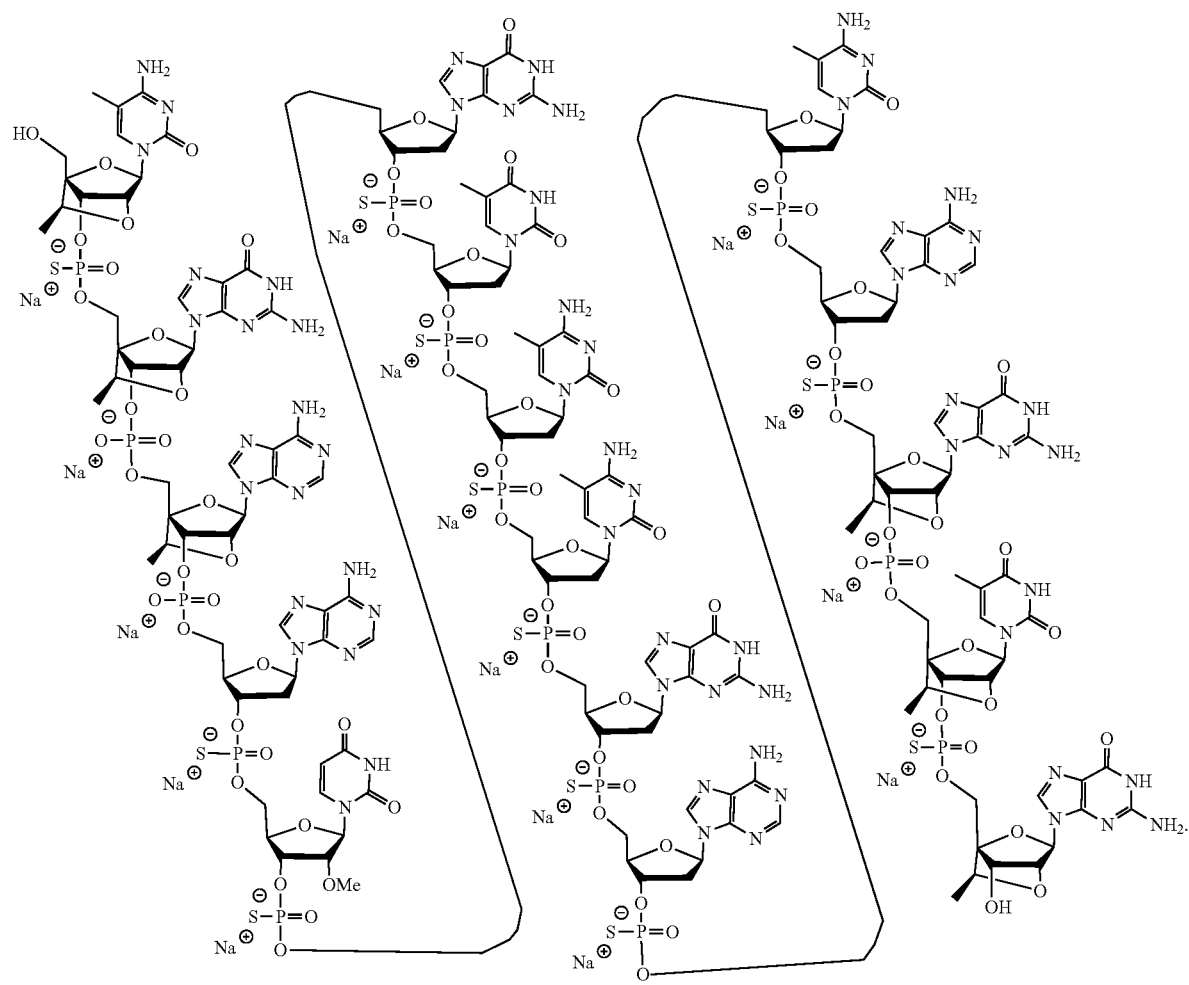
(SEQ ID NO: 14)

Embodiment 67. An oligomeric compound according to the following chemical structure:
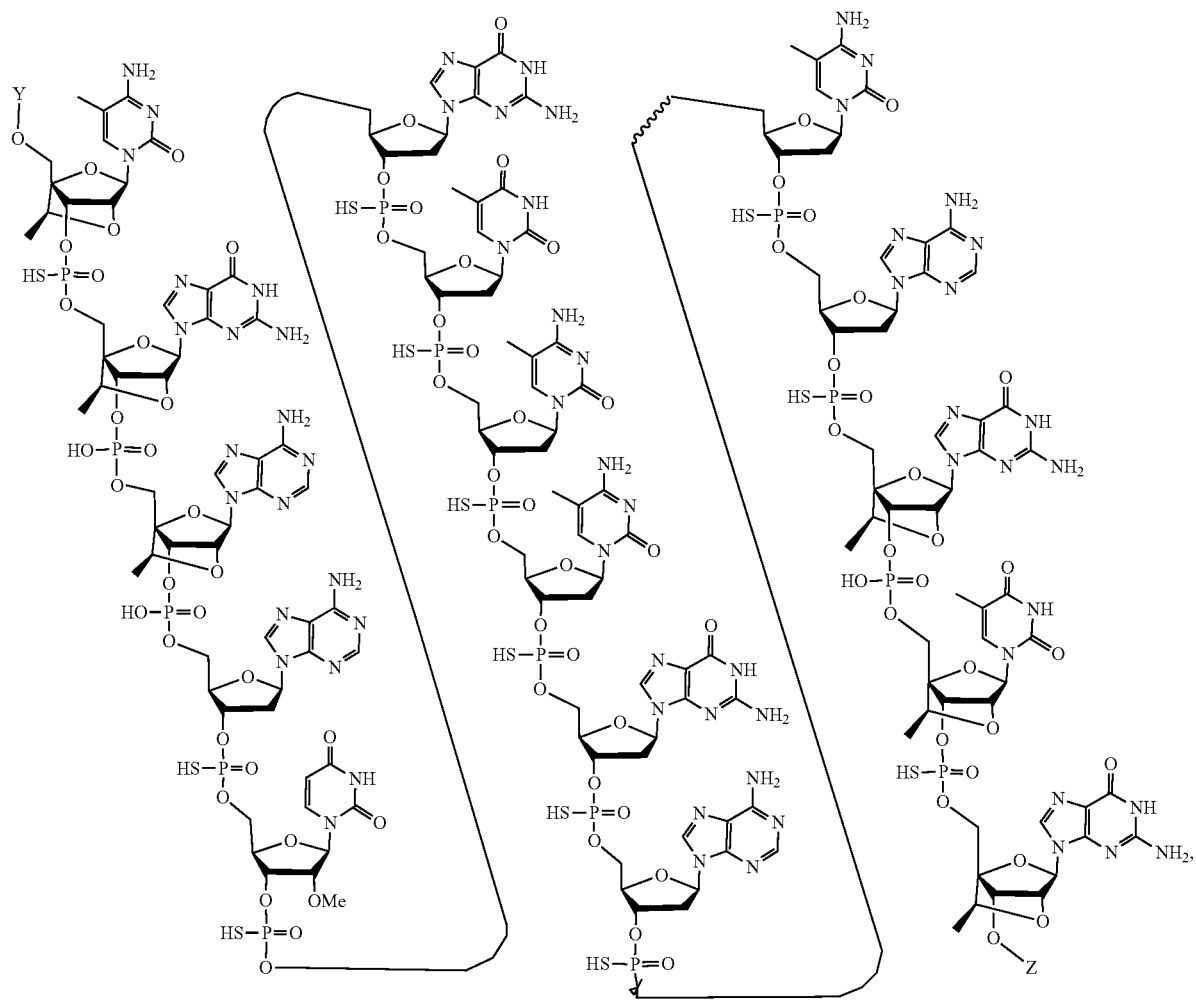
(SEQ ID NO: 29)
or a salt thereof, wherein Y and Z are selected from H and a conjugate group, wherein at least one of Y and Z is a conjugate group.

Embodiment 68. The oligomeric compound of embodiment 67, which is a sodium salt or a potassium salt.

Embodiment 69. An oligomeric compound according to the following chemical structure:

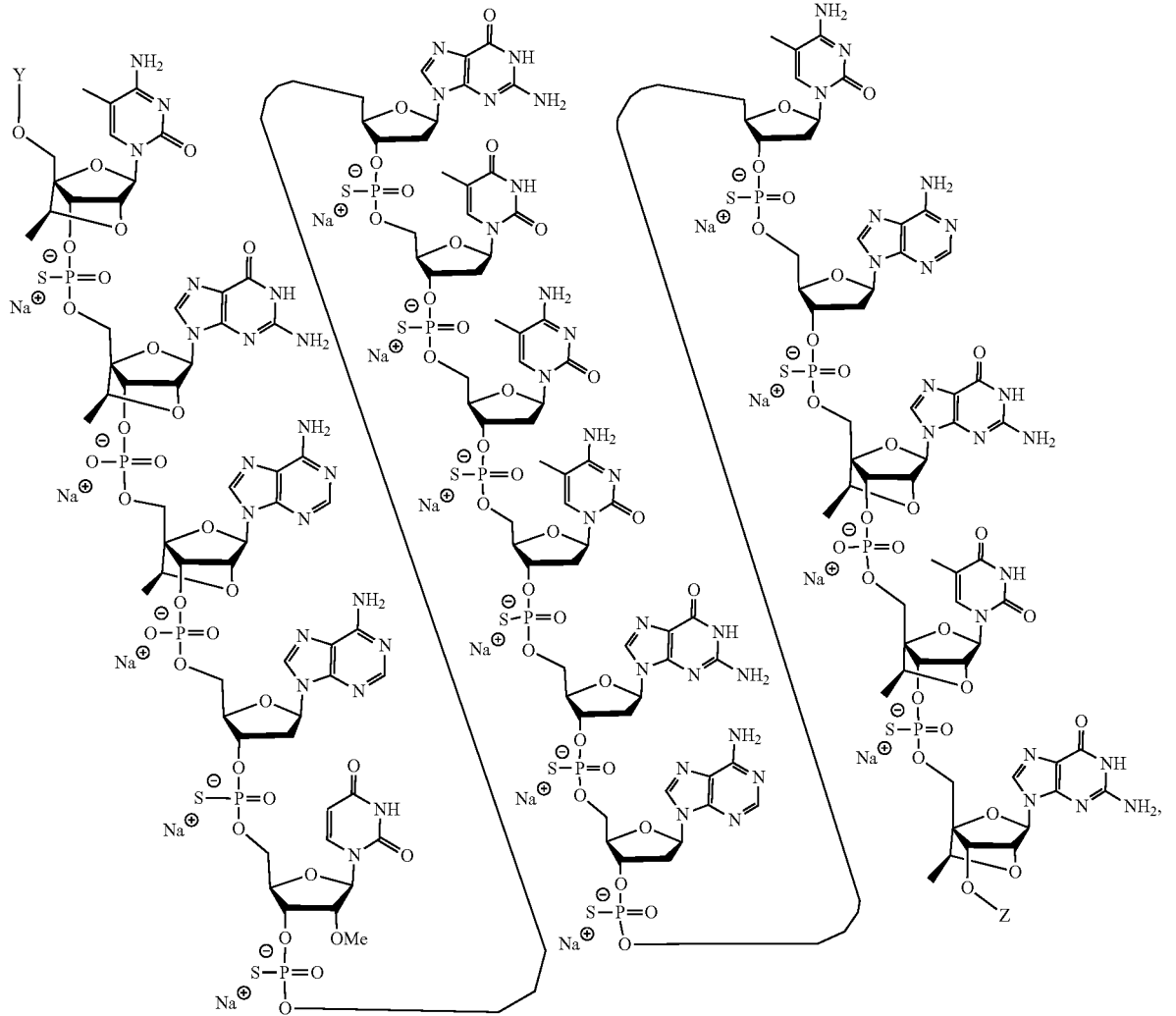

(SEQ ID NO: 29)

wherein Y and Z are selected from H and a conjugate group, wherein at least one of Y and Z is a conjugate group.

Embodiment 70. The oligomeric compound of any of embodiments 67-69, wherein the conjugate group comprises a conjugate moiety and a conjugate linker.

Embodiment 71. The oligomeric compound of any of embodiments 67-69, wherein the conjugate moiety is $C_{10}$-$C_{24}$ alkyl.

Embodiment 72. The oligomeric compound of any of embodiments 67-69, wherein the conjugate moiety is $C_{16}$.

Embodiment 73. The oligomeric compound of embodiment 70, wherein the conjugate moiety is a cell-targeting moiety.

Embodiment 74. The oligomeric compound of embodiment 73, wherein the cell-targeting moiety binds a cell surface receptor on a skeletal muscle cell.

Embodiment 75. The oligomeric compound of any of embodiments 73-74, wherein the cell-targeting moiety is selected from a carbohydrate and an antibody.

Embodiment 76. The oligomeric compound of any of embodiments 73-74, wherein the cell-targeting moiety is an antibody or an antibody fragment that binds a transferrin receptor.

Embodiment 77. The oligomeric compound of embodiment 73, wherein the cell-targeting moiety comprises a GalNAc.

Embodiment 78. The oligomeric compound of any of embodiments 67-69, wherein Y is:

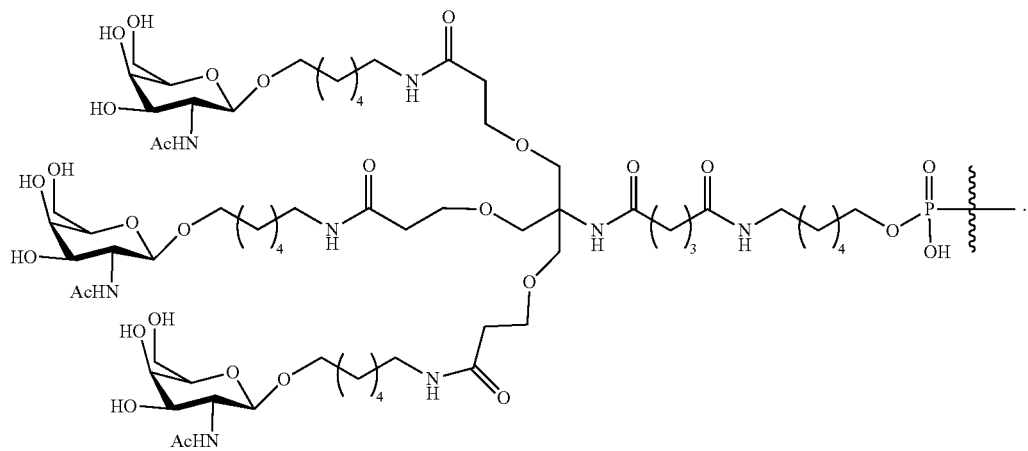

Embodiment 79. A prodrug of the oligomeric compound of any of embodiments 55-63 and 67-78 or the modified oligonucleotide of any of embodiments 64-66.

Embodiment 80. The oligomeric compound of any of embodiments 55-63 and 67-78, wherein the oligomeric compound is a prodrug.

Embodiment 81. A population of oligomeric compounds of any of embodiments 55-63 and 67-78 or modified oligonucleotides of any of embodiments 64-66, wherein all of the phosphorothioate internucleoside linkages of the modified oligonucleotide are stereorandom.

Embodiment 82. An oligomeric compound comprising a modified oligonucleotide according to the following chemical notation: $^{m}C_{ks}T_{ko}T_{eo}T_{ds}T_{ds}A_{ds}T_{ds}T_{ds}{}^{m}C_{ds}G_{ds}{}^{m}C_{ds}G_{ds}A_{ds}G_{ko}G_{ks}G_{k}$ (SEQ ID NO: 15), wherein:
A=an adenine nucleobase,
$^{m}C$=a 5-methylcytosine nucleobase,
G=a guanine nucleobase,
T=a thymine nucleobase,
k=a cEt sugar moiety,
e=a 2'-MOE sugar moiety,
d=a 2'-β-D-deoxyribosyl sugar moiety,
s=a phosphorothioate internucleoside linkage, and
o=a phosphodiester internucleoside linkage.

Embodiment 83. The oligomeric compound of embodiment 82 comprising a conjugate group.

Embodiment 84. The oligomeric compound of embodiment 83, wherein the conjugate group comprises a conjugate moiety and a conjugate linker.

Embodiment 85. The oligomeric compound of embodiment 83, wherein the conjugate group comprises $C_{10}$-$C_{24}$ alkyl.

Embodiment 86. The oligomeric compound of embodiment 83, wherein the conjugate group comprises $C_{16}$ alkyl.

Embodiment 87. The oligomeric compound of embodiment 84, wherein the conjugate moiety is a cell-targeting moiety.

Embodiment 88. The oligomeric compound of embodiment 87, wherein the cell-targeting moiety is selected from a carbohydrate, an antibody, and an antibody fragment.

Embodiment 89. The oligomeric compound of any of embodiments 87-88, wherein the cell-targeting moiety binds a cell surface receptor on a skeletal muscle cell.

Embodiment 90. The oligomeric compound of any of embodiments 87-89, wherein the cell-targeting moiety is an antibody or an antibody fragment that binds a transferrin receptor.

Embodiment 91. A modified oligo nucleotide according to the following chemical structure:
(SEQ ID NO: 15)
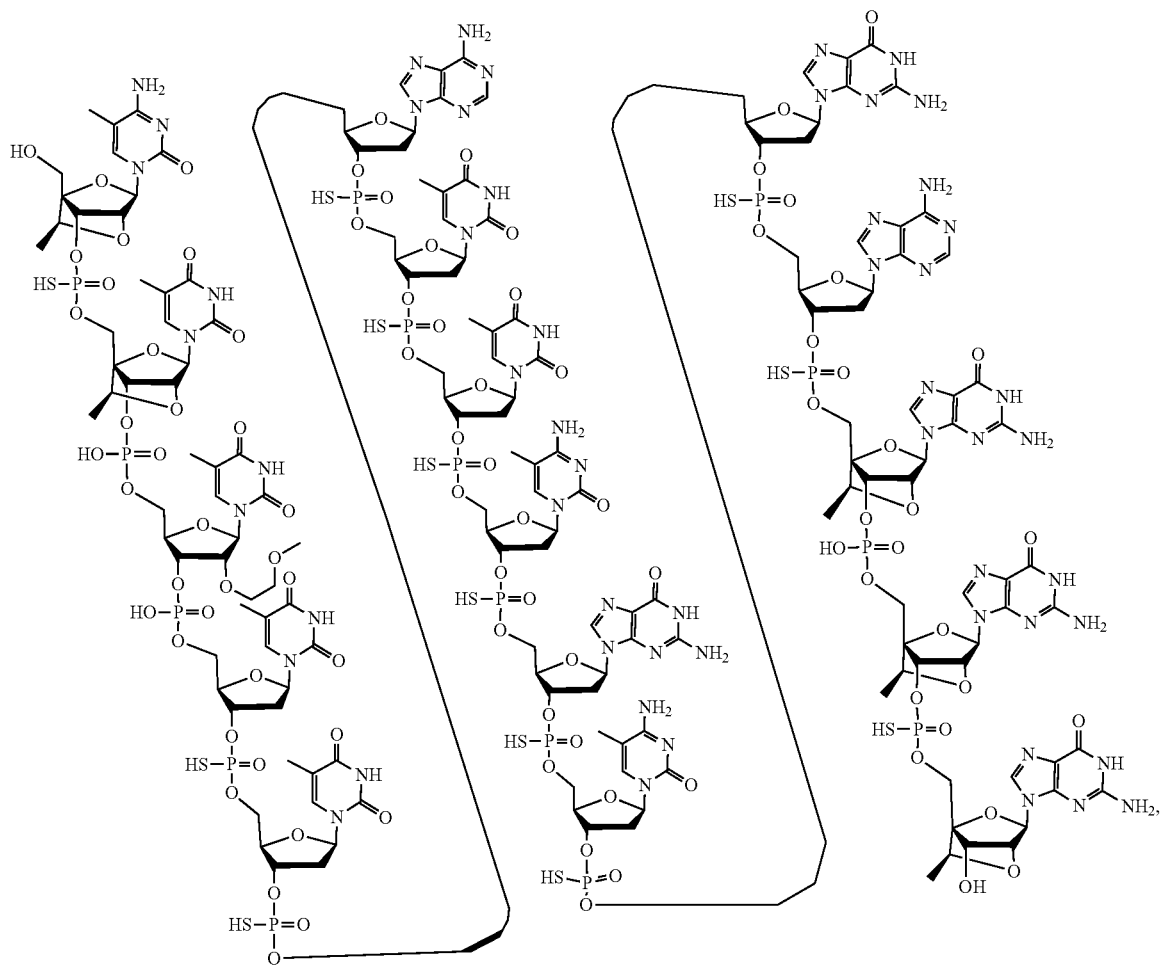
or a salt thereof.
Embodiment 92. The modified oligonucleotide of embodiment 91, which is a sodium salt or a potassium salt.

Embodiment 93. A modified oligonucleotide according to the following chemical structure:
(SEQ ID NO: 15)
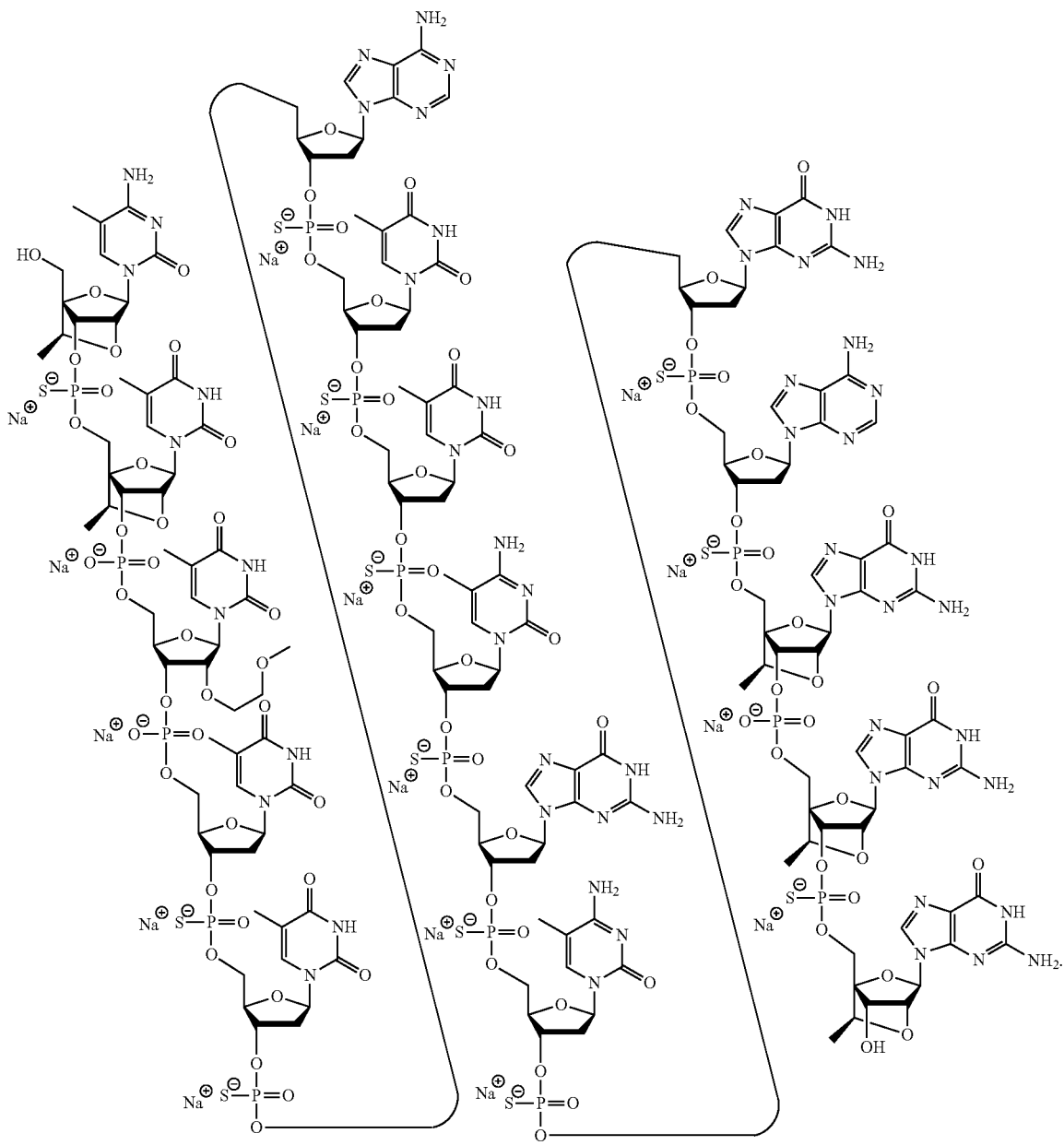

Embodiment 94. An oligomeric compound according to the following chemical structure:
(SEQ ID NO: 31)
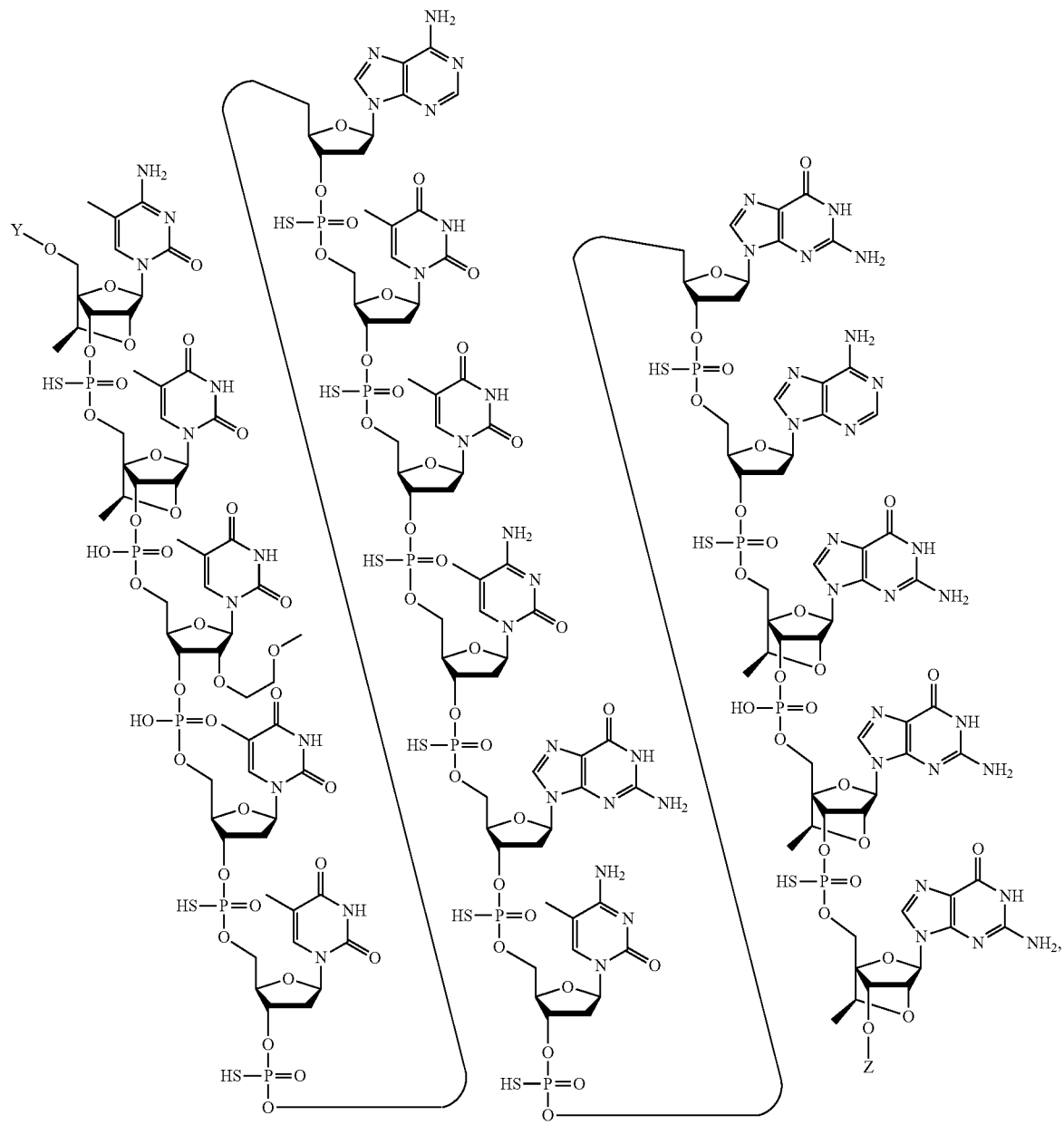
or a salt thereof, wherein Y and Z are selected from H and a conjugate group, wherein at least one of Y and Z is a conjugate group.

Embodiment 95. The oligomeric compound of embodiment 94, which is a sodium salt or a potassium salt.

Embodiment 96. An oligomeric compound according to the following chemical structure:

Embodiment 100. The oligomeric compound of embodiment 97, wherein the conjugate moiety is a cell-targeting moiety.

(SEQ ID NO: 31)

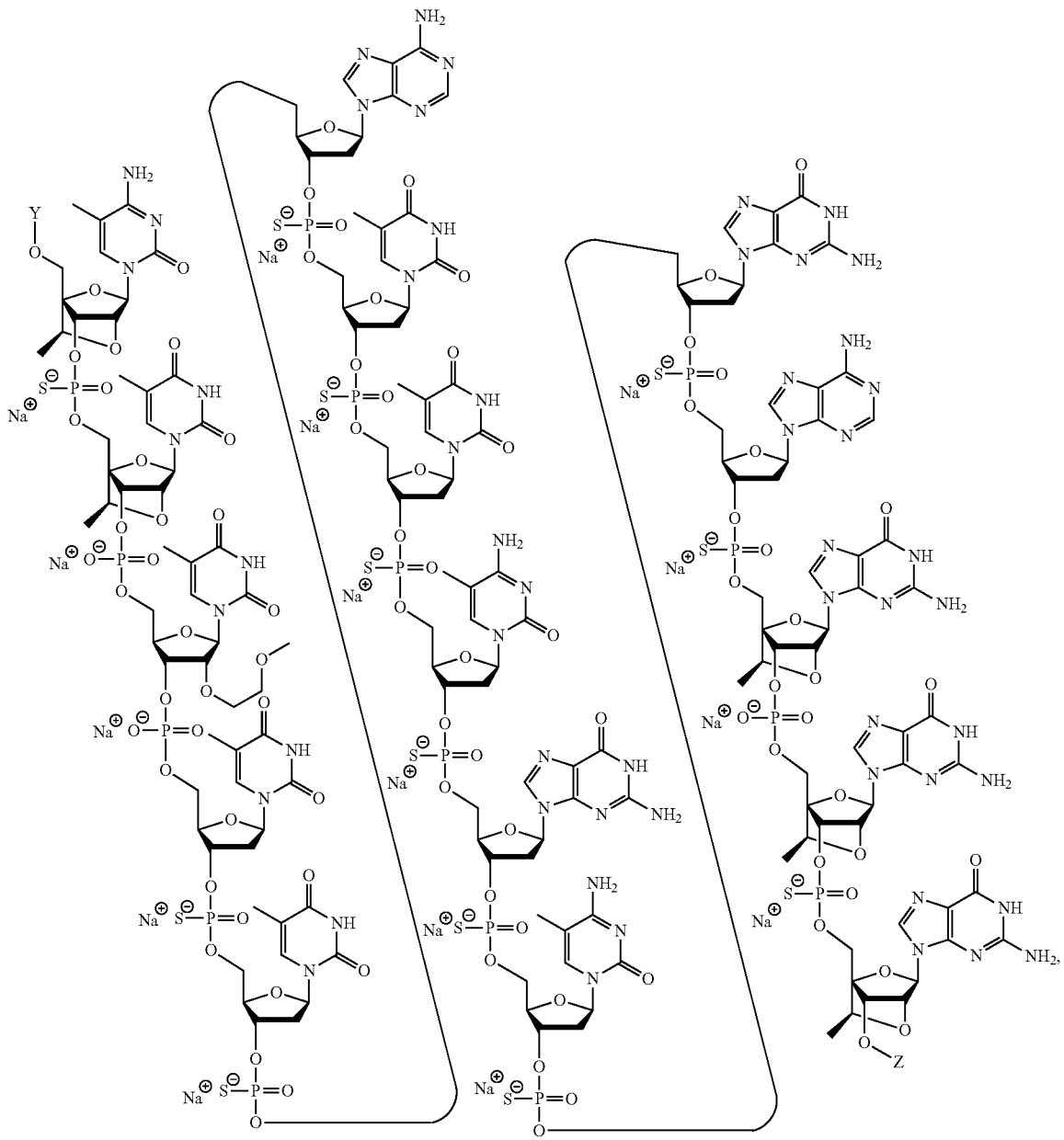

wherein Y and Z are selected from H and a conjugate group, wherein at least one of Y and Z is a conjugate group.

Embodiment 97. The oligomeric compound of any of embodiments 94-96, wherein the conjugate group comprises a conjugate moiety and a conjugate linker.

Embodiment 98. The oligomeric compound of any of embodiments 94-96, wherein the conjugate group comprises $C_{10}$-$C_{24}$ alkyl.

Embodiment 99. The oligomeric compound of any of embodiments 94-96, wherein the conjugate group comprises $C_{16}$.

Embodiment 101. The oligomeric compound of embodiment 100, wherein the cell-targeting moiety binds a cell surface receptor on a skeletal muscle cell.

Embodiment 102. The oligomeric compound of any of embodiments 100-101, wherein the cell-targeting moiety is selected from a carbohydrate and an antibody.

Embodiment 103. The oligomeric compound of any of embodiments 100-101, wherein the cell-targeting moiety is an antibody or an antibody fragment that binds a transferrin receptor.

Embodiment 104. The oligomeric compound of embodiment 100, wherein the cell-targeting moiety comprises a GalNAc.

Embodiment 105. The oligomeric compound of any of embodiments 94-96, wherein Y is:

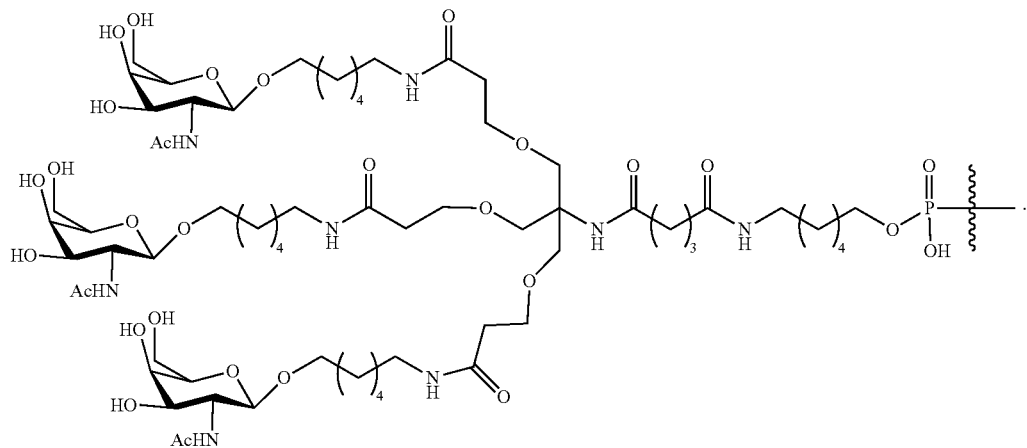

Embodiment 106. A prodrug of the oligomeric compound of any of embodiments 82-90 and 94-105 or the modified oligonucleotide of any of embodiments 91-93.

Embodiment 107. The oligomeric compound of any of embodiments 82-90 and 94-105, wherein the oligomeric compound is a prodrug.

Embodiment 108. A population of oligomeric compounds of any of embodiments 82-90 and 94-105 or modified oligonucleotides of any of embodiments 91-93, wherein all of the phosphorothioate internucleoside linkages of the modified oligonucleotide are stereorandom.

Embodiment 109. An oligomeric compound comprising a modified oligonucleotide according to the following chemical notation: $A_{ks}{}^{m}C_{ko}A_{ko}A_{ds}T_{ds}A_{ds}A_{ds}A_{ds}T_{ds}A_{ds}{}^{m}C_{ds}{}^{m}C_{ds}G_{ds}A_{ko}G_{ks}G_{k}$ (SEQ ID NO: 11), wherein:
A=an adenine nucleobase,
$^{m}$C=a 5-methylcytosine nucleobase,
G=a guanine nucleobase,
T=a thymine nucleobase,
k=a cEt sugar moiety,
d=a 2'-β-D-deoxyribosyl sugar moiety,
s=a phosphorothioate internucleoside linkage, and
o=a phosphodiester internucleoside linkage.

Embodiment 110. The oligomeric compound of embodiment 109 comprising a conjugate group.

Embodiment 111. The oligomeric compound of embodiment 110, wherein the conjugate group comprises a conjugate moiety and a conjugate linker.

Embodiment 112. The oligomeric compound of embodiment 110, wherein the conjugate group comprises $C_{10}$-$C_{24}$ alkyl.

Embodiment 113. The oligomeric compound of embodiment 110, wherein the conjugate group comprises $C_{16}$ alkyl.

Embodiment 114. The oligomeric compound of embodiment 111, wherein the conjugate moiety is a cell-targeting moiety.

Embodiment 115. The oligomeric compound of embodiment 114, wherein the cell-targeting moiety is selected from a carbohydrate, an antibody, and an antibody fragment.

Embodiment 116. The oligomeric compound of any of embodiments 114-115, wherein the cell-targeting moiety binds a cell surface receptor on a skeletal muscle cell.

Embodiment 117. The oligomeric compound of any of embodiments 114-116, wherein the cell-targeting moiety is an antibody or an antibody fragment that binds a transferrin receptor.

Embodiment 118. A modified oligonucleotide according to the following chemical structure:
(SEQ ID NO: 11)
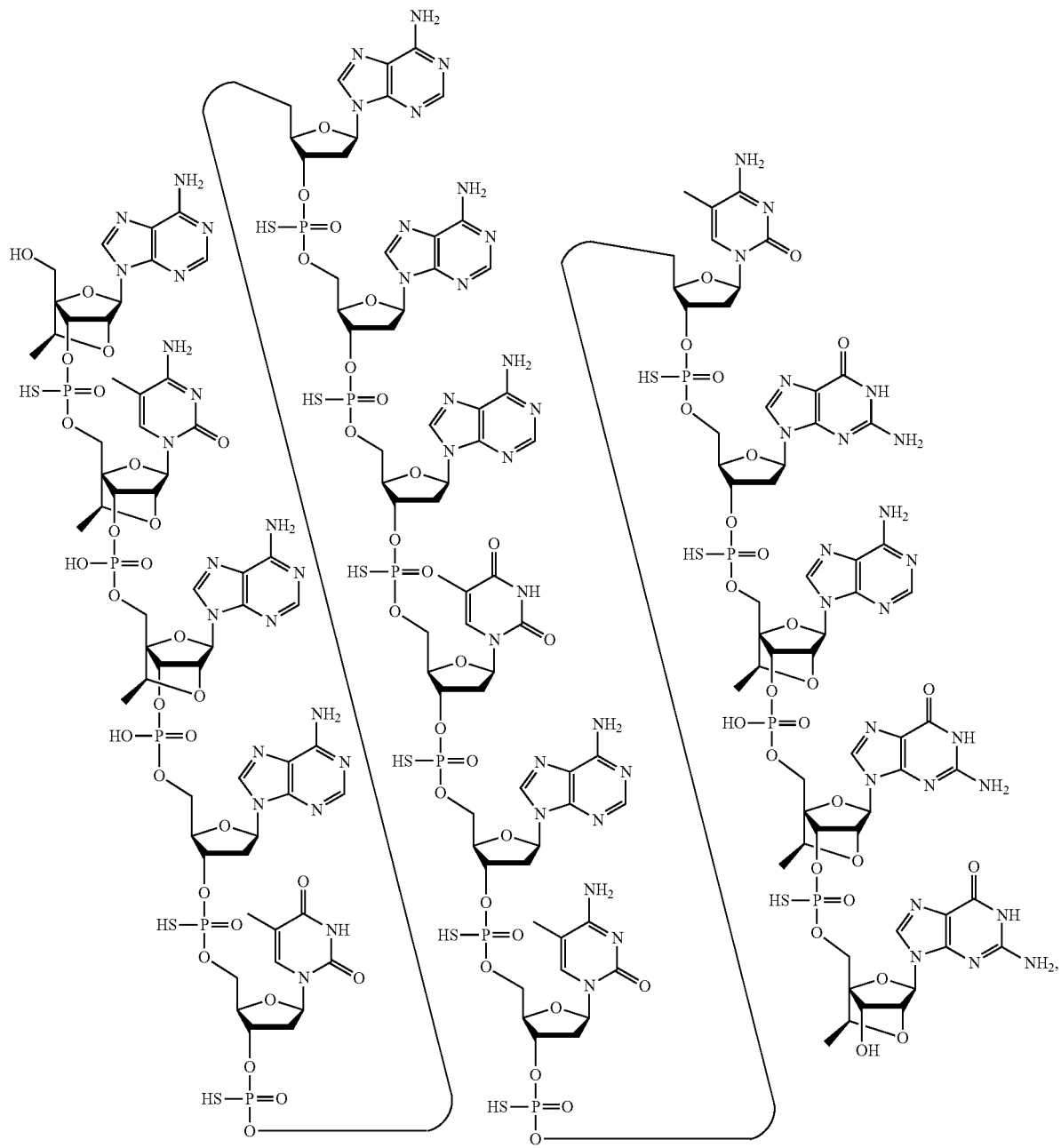
or a salt thereof.
Embodiment 119. The modified oligonucleotide of embodiment 118, which is a sodium salt or a potassium salt.

Embodiment 120. A modified oligonucleotide according to the following chemical structure:
(SEQ ID NO: 11)
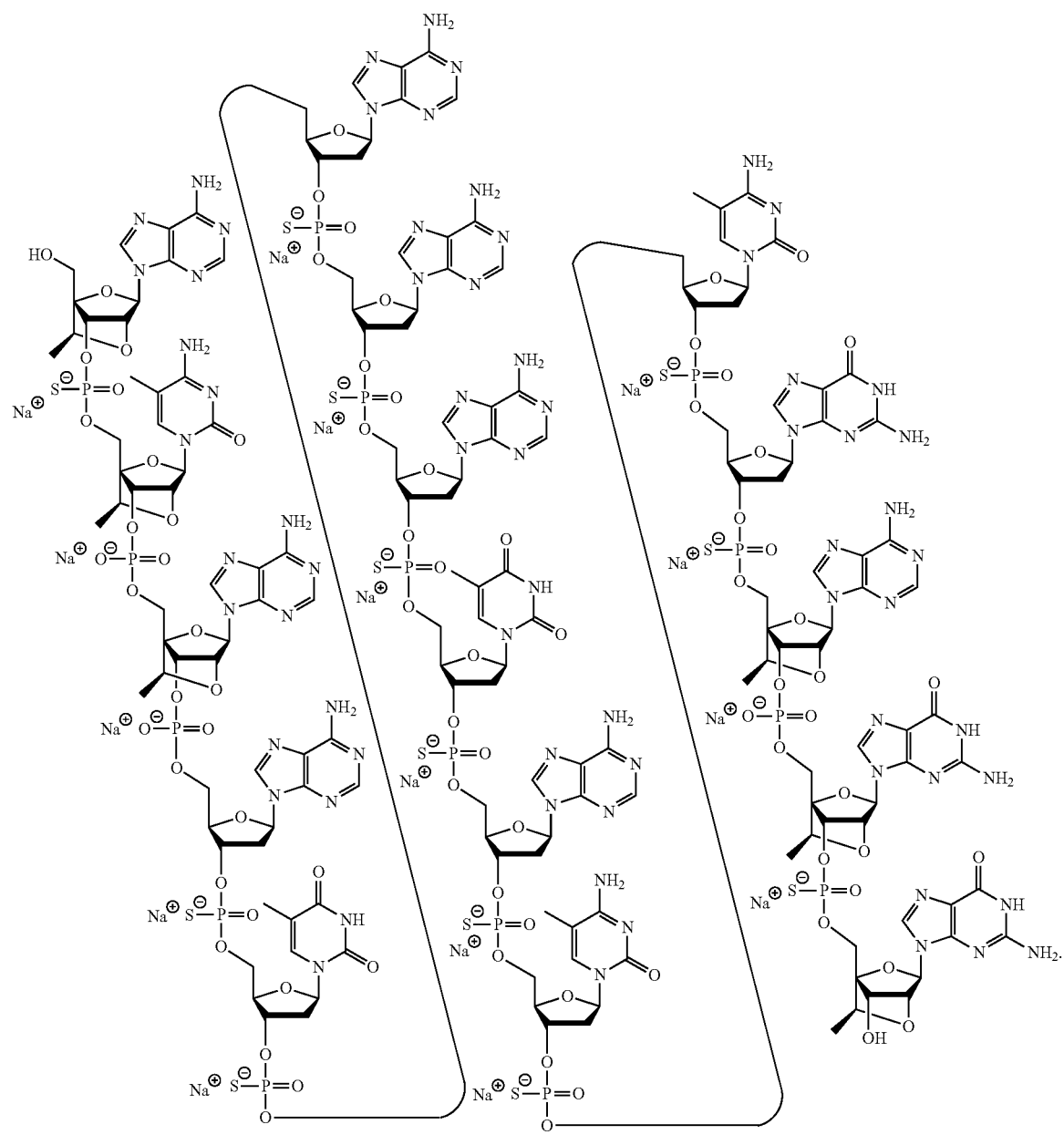

Embodiment 121. An oligomeric compound according to the following chemical structure:
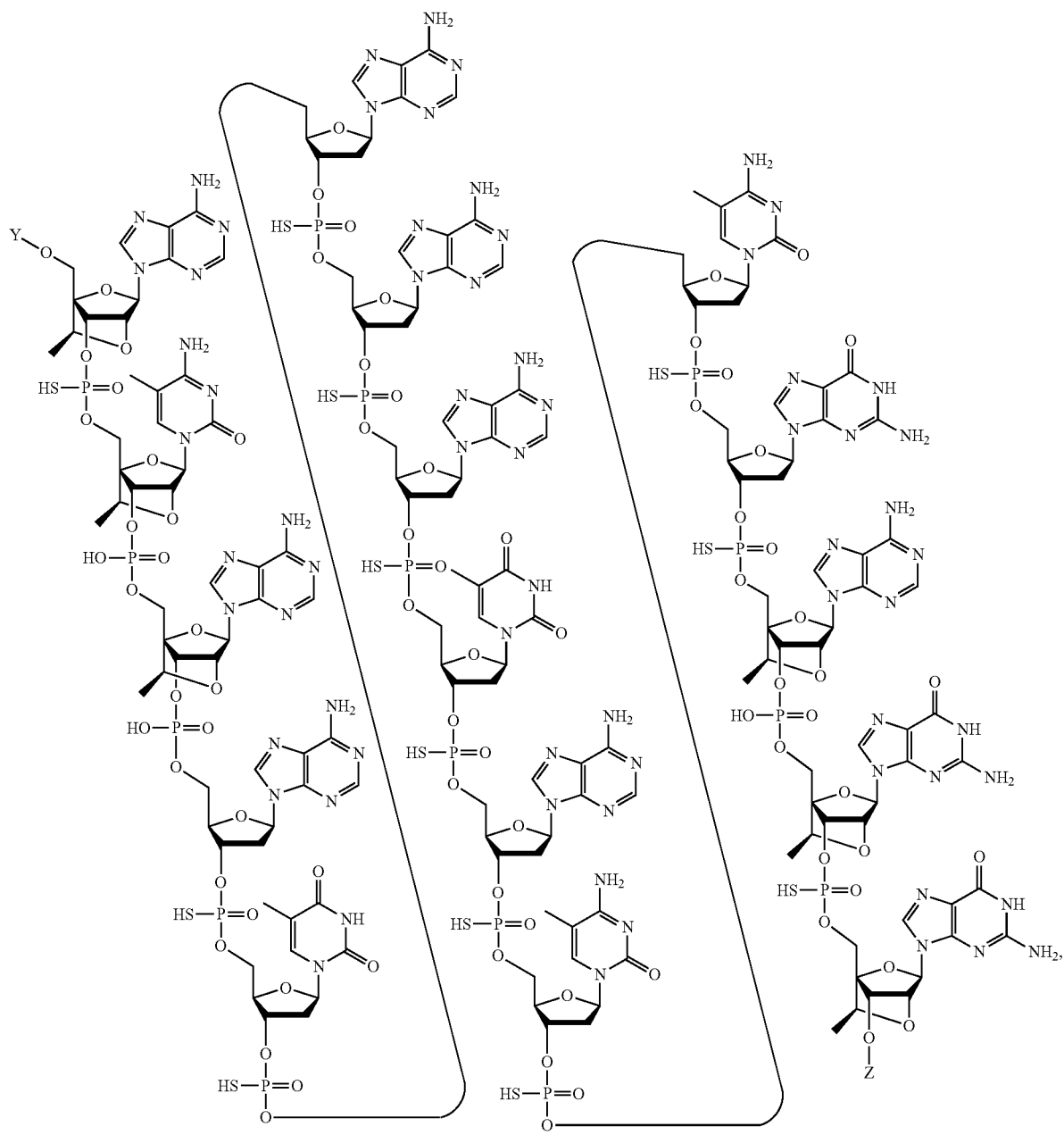
(SEQ ID NO: 32)
or a salt thereof, wherein Y and Z are selected from H and a conjugate group, wherein at least one of Y and Z is a conjugate group.
Embodiment 122. The oligomeric compound of embodiment 121, which is a sodium salt or a potassium salt.

Embodiment 123. An oligomeric compound according to the following chemical structure:

(SEQ ID NO: 11)

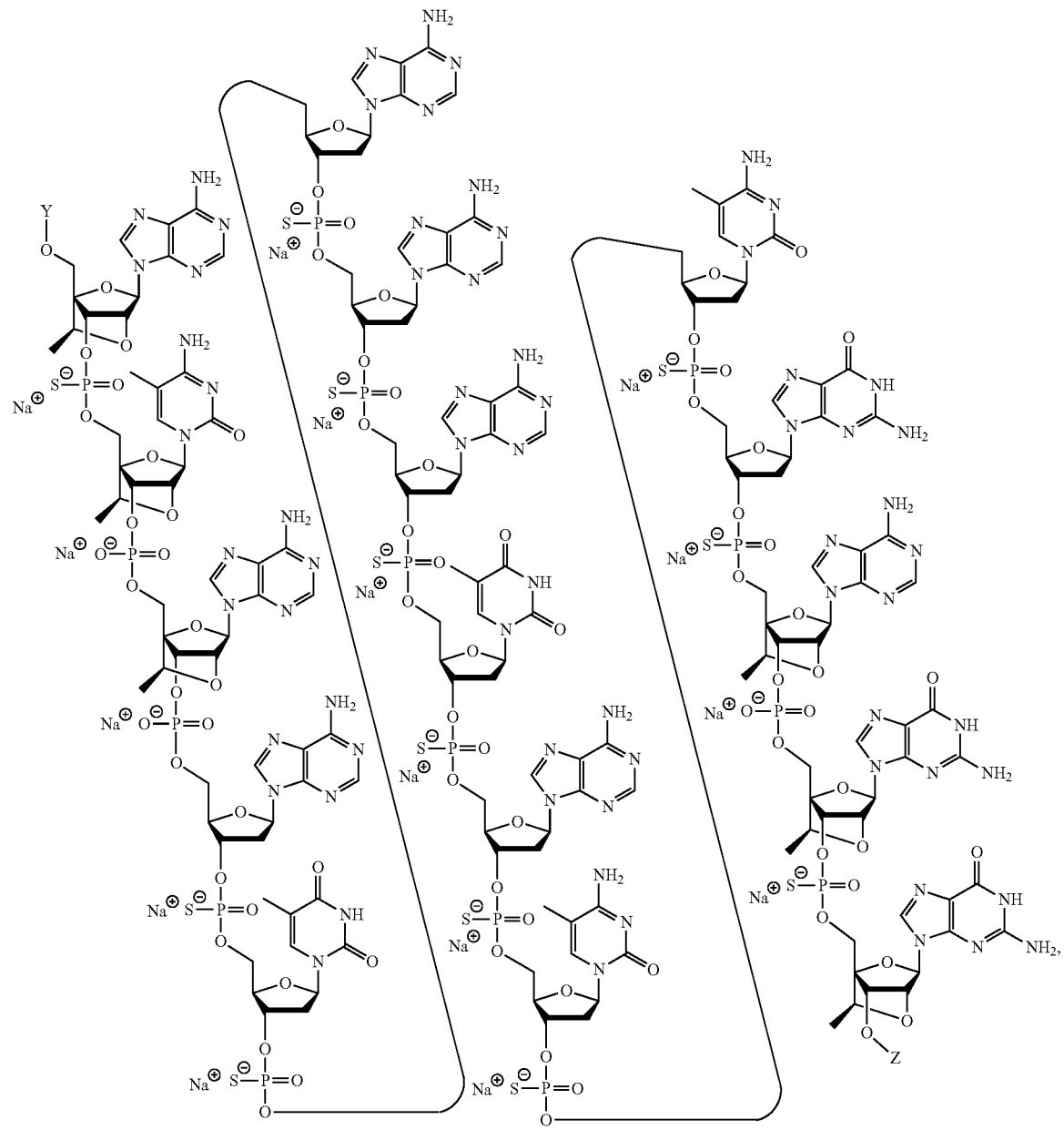

wherein Y and Z are selected from H and a conjugate group, wherein at least one of Y and Z is a conjugate group.

Embodiment 124. The oligomeric compound of any of embodiments 121-123, wherein the conjugate group comprises a conjugate moiety and a conjugate linker.

Embodiment 125. The oligomeric compound of any of embodiments 121-123, wherein the conjugate group comprises $C_{10}$-$C_{24}$ alkyl.

Embodiment 126. The oligomeric compound of any of embodiments 121-123, wherein the conjugate group comprises $C_{16}$.

Embodiment 127. The oligomeric compound of embodiment 124, wherein the conjugate moiety is a cell-targeting moiety.

Embodiment 128. The oligomeric compound of embodiment 127, wherein the cell-targeting moiety binds a cell surface receptor on a skeletal muscle cell.

Embodiment 129. The oligomeric compound of embodiment 127 or embodiment 128, wherein the cell-targeting moiety is selected from a carbohydrate and an antibody.

Embodiment 130. The oligomeric compound of embodiment 127 or embodiment 128, wherein the cell-targeting moiety is an antibody or an antibody fragment that binds a transferrin receptor.

Embodiment 131. The oligomeric compound of embodiment 127, wherein the cell-targeting moiety comprises a GalNAc.

Embodiment 132. The oligomeric compound of any of embodiments 121-123, wherein Y is:

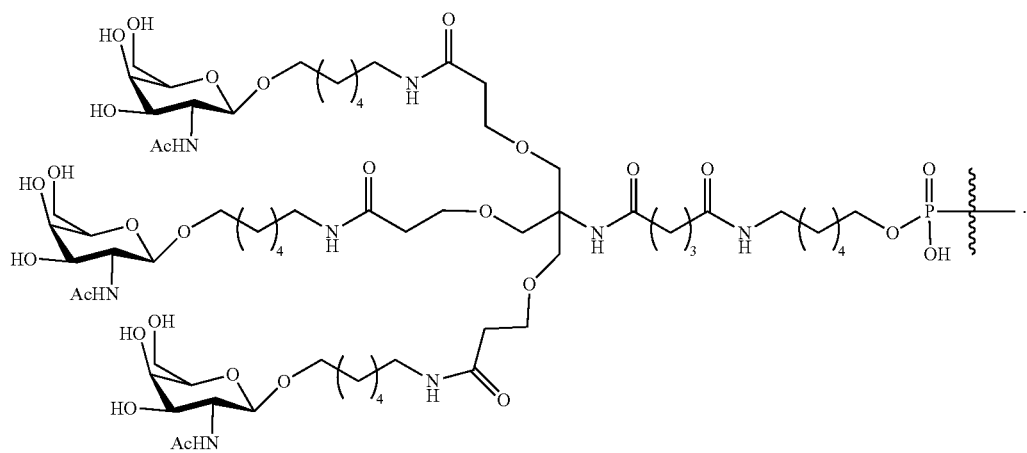

Embodiment 133. A prodrug of the oligomeric compound of any of embodiments 109-117 and 121-132 or the modified oligonucleotide of any of embodiments 118-120.

Embodiment 134. The oligomeric compound of any of embodiments 109-117 and 121-132, wherein the oligomeric compound is a prodrug.

Embodiment 135. A population of oligomeric compounds of any of embodiments 109-117 and 121-132 or modified oligonucleotides of any of embodiments 118-120, wherein all of the phosphorothioate internucleoside linkages of the modified oligonucleotide are stereorandom.

Embodiment 136. A pharmaceutical composition an oligomeric compound of any of embodiments 1-9, 13-24, 26, 28-36, 40-51, 53, 55-63, 67-78, 80, 82-90, 94-105, 107, 109-117, 121-132, or 134, a modified oligonucleotide of any of embodiments 10-12, 37-39, 64-66, 91-93, 118-120, a prodrug of any of embodiments 25, 52, 79, 106, or 133, or a population of oligomeric compounds of any of embodiments 27, 54, 81, 108, or 135, and a pharmaceutically acceptable diluent.

Embodiment 137. The pharmaceutical composition of embodiment 136, wherein the pharmaceutically acceptable diluent is water or phosphate-buffered saline.

Embodiment 138. The pharmaceutical composition of embodiment 137, wherein the pharmaceutical composition consists essentially of the oligomeric compound, the modified oligonucleotide, the prodrug, or the population, and water or phosphate-buffered saline.

Embodiment 139. A method comprising administering to a subject an oligomeric compound of any of embodiments 1-9, 13-24, 26, 28-36, 40-51, 53, 55-63, 67-78, 80, 82-90, 94-105, 107, 109-117, 121-132, or 134, a modified oligonucleotide of any of embodiments 10-12, 37-39, 64-66, 91-93, 118-120, a prodrug of any of embodiments 25, 52, 79, 106, or 133, or a population of oligomeric compounds of any of embodiments 27, 54, 81, 108, or 135, or a pharmaceutical composition of any of embodiments 136-138.

Embodiment 140. A method of treating a disease associated with DMPK, comprising administering to a subject having a disease associated with DMPK a therapeutically effective amount of an oligomeric compound of any of embodiments 1-9, 13-24, 26, 28-36, 40-51, 53, 55-63, 67-78, 80, 82-90, 94-105, 107, 109-117, 121-132, or 134, a modified oligonucleotide of any of embodiments 10-12, 37-39, 64-66, 91-93, 118-120, a prodrug of any of embodiments 25, 52, 79, 106, or 133, or a population of oligomeric compounds of any of embodiments 27, 54, 81, 108, or 135, or a pharmaceutical composition of any of embodiments 136-138; thereby treating the disease associated with DMPK.

Embodiment 141. The method of embodiment 140, wherein the disease associated with DMPK is type 1 myotonic dystrophy.

Embodiment 142. The method of any of embodiments 140-141, wherein the administering an oligomeric compound of any of embodiments 1-9, 13-24, 26, 28-36, 40-51, 53, 55-63, 67-78, 80, 82-90, 94-105, 107, 109-117, 121-132, or 134, a modified oligonucleotide of any of embodiments 10-12, 37-39, 64-66, 91-93, 118-120, a prodrug of any of embodiments 25, 52, 79, 106, or 133, or a population of oligomeric compounds of any of embodiments 27, 54, 81, 108, or 135, or a pharmaceutical composition of any of embodiments 136-138 reduces myotonia and/or spliceopathy in the subject.

Embodiment 143. The method of any of embodiments 139-142, wherein the subject is human.

Embodiment 144. A method of reducing expression of DMPK in a cell, comprising contacting the cell with an oligomeric compound of any of embodiments 1-9, 13-24, 26, 28-36, 40-51, 53, 55-63, 67-78, 80, 82-90, 94-105, 107, 109-117, 121-132, or 134, a modified oligonucleotide of any of embodiments 10-12, 37-39, 64-66, 91-93, 118-120, a prodrug of any of embodiments 25, 52, 79, 106, or 133, or a population of oligomeric compounds of any of embodiments 27, 54, 81, 108, or 135, or a pharmaceutical composition of any of embodiments 136-138.

Embodiment 145. The method of embodiment 144, wherein the cell is a muscle cell.

Embodiment 146. The method of embodiment 144 or 145, wherein the cell is a human cell.

Embodiment 147. Use of an oligomeric compound of any of embodiments 1-9, 13-24, 26, 28-36, 40-51, 53, 55-63, 67-78, 80, 82-90, 94-105, 107, 109-117, 121-132, or 134, a modified oligonucleotide of any of embodiments 10-12, 37-39, 64-66, 91-93, 118-120, a prodrug of any of embodiments 25, 52, 79, 106, or 133, or a population of oligomeric compounds of any of embodiments 27, 54, 81, 108, or 135, or a pharmaceutical composition of any of embodiments 136-138 for treating a disease associated with DMPK.

Embodiment 148. Use of an oligomeric compound of any of embodiments 1-9, 13-24, 26, 28-36, 40-51, 53, 55-63, 67-78, 80, 82-90, 94-105, 107, 109-117, 121-132, or 134, a modified oligonucleotide of any of embodiments 10-12, 37-39, 64-66, 91-93, 118-120, a prodrug of any of embodiments 25, 52, 79, 106, or 133, or a population of oligomeric compounds of any of embodiments 27, 54, 81, 108, or 135, or a pharmaceutical composition of any of embodiments 136-138 in the manufacture of a medicament for treating a disease associated with DMPK.

Embodiment 149. The use of any of embodiments 147-148, wherein the disease associated with DMPK is type 1 myotonic dystrophy.

1. Compound No. 1522461

In certain embodiments, Compound No. 1522461 is characterized as a mixed wing gapmer of linked nucleosides and having a nucleobase sequence (from 5' to 3') of TTCCCGAATGTCCGAC (SEQ ID NO 35), wherein each of nucleosides 1-3 and 14-16 (from 5' to 3') are cEt nucleosides, nucleoside 5 is a 2'-OMe nucleoside, and each of nucleosides 4 and 6-13 are 2'-β-D-deoxynucleosides, wherein the internucleoside linkages between nucleosides 2 to 3, 3 to 4 and 14 to 15 are phosphodiester internucleoside linkages, the internucleoside linkages between nucleosides 1 to 2, 4 to 5, 5 to 6, 6 to 7, 7 to 8, 8 to 9, 9 to 10, 10 to 11, 11 to 12, 12 to 13, 13 to 14, and 15 to 16 are phosphorothioate internucleoside linkages. The cytosines at positions 3, 4, 12, 13, and 16 are 5-methylcytosines, while the cytosine at position 5 is a non-methylated cytosine.

In certain embodiments, Compound No. 1522461 is represented by the following chemical notation: $T_{ks}T_{ko}{}^mC_{ko}{}^mC_{ds}C_{ys}G_{ds}A_{ds}A_{ds}T_{ds}G_{ds}T_{ds}{}^mC_{ds}{}^mC_{ds}G_{ko}A_{ks}{}^mC_k$ (SEQ ID NO: 13), wherein:

A=an adenine nucleobase, mC=a 5-methylcytosine nucleobase,

C=a cytosine nucleobase,

G=a guanine nucleobase,

T=a thymine nucleobase, y=a 2'-OMe sugar moiety, k=a cEt sugar moiety, d=a 2'-β-D-deoxyribosyl sugar moiety, s=a phosphorothioate internucleoside linkage, and o=a phosphodiester internucleoside linkage.

In certain embodiments, Compound No. 1522461 is represented by the following chemical structure:
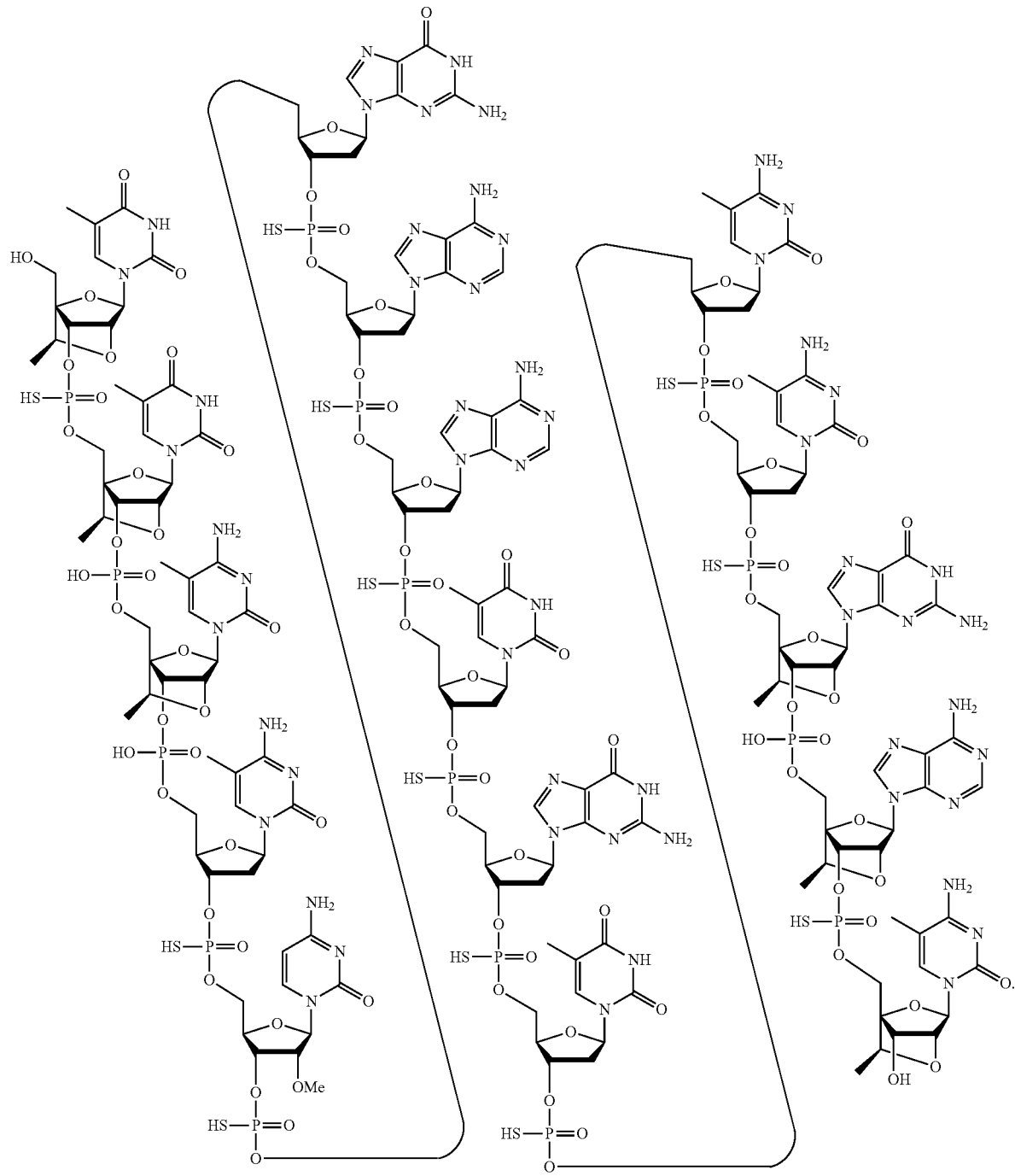
(SEQ ID NO 13)

Structure 1. Compound No. 1522461
In certain embodiments, an oligomeric compound comprises the sodium salt or the potassium salt of the modified oligonucleotide represented by Structure 1.
In certain embodiments, the sodium salt of Compound No. 1522461 is represented by the following chemical structure:
(SEQ ID NO 13)
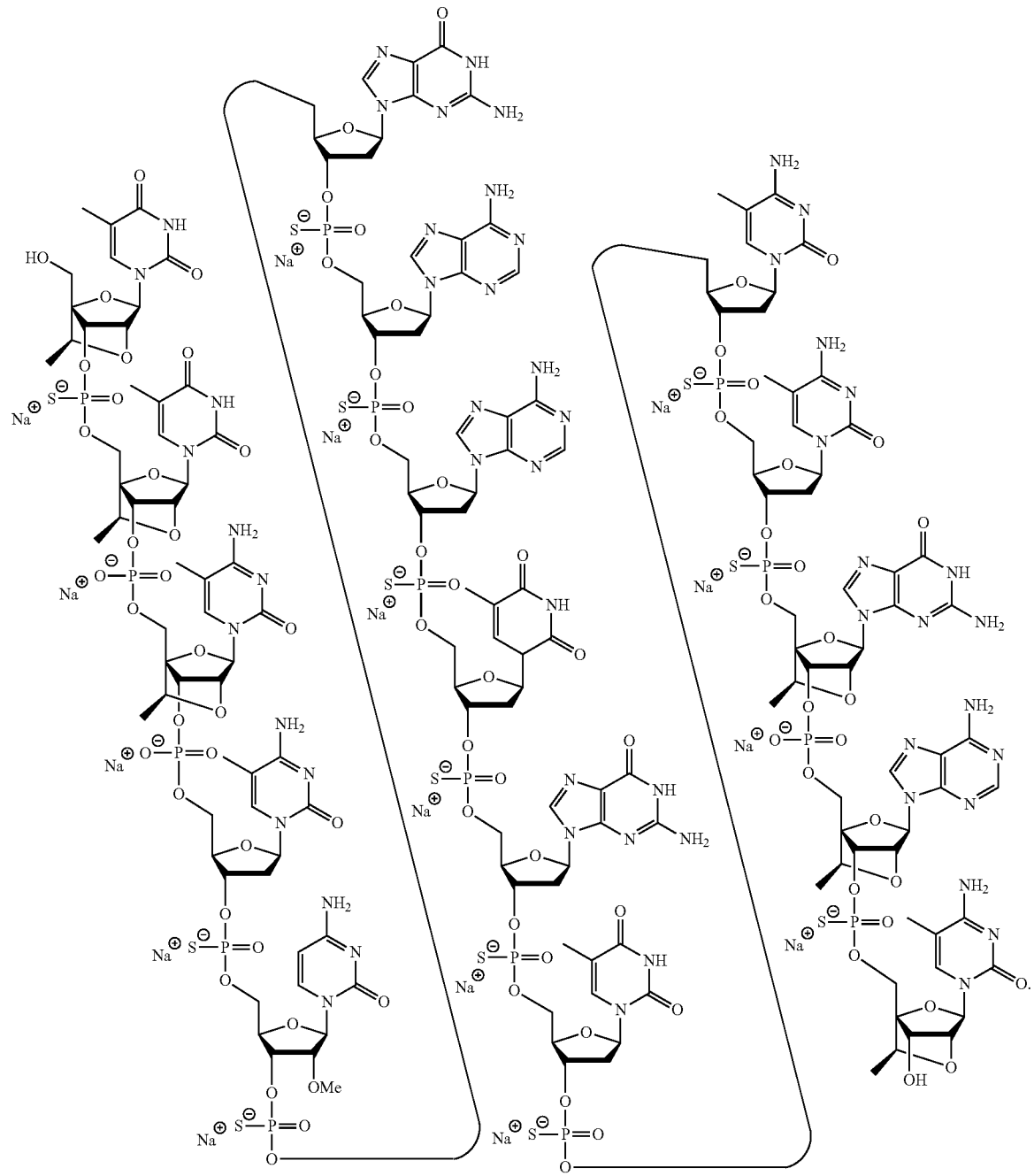

Structure 2. The Sodium Salt of Compound No. 1522461
In certain embodiments, an oligomeric compound comprises a conjugate group.
In certain embodiments, a prodrug of Compound No. 1522461 is represented by the following chemical structure:
(SEQ ID NO: 30)
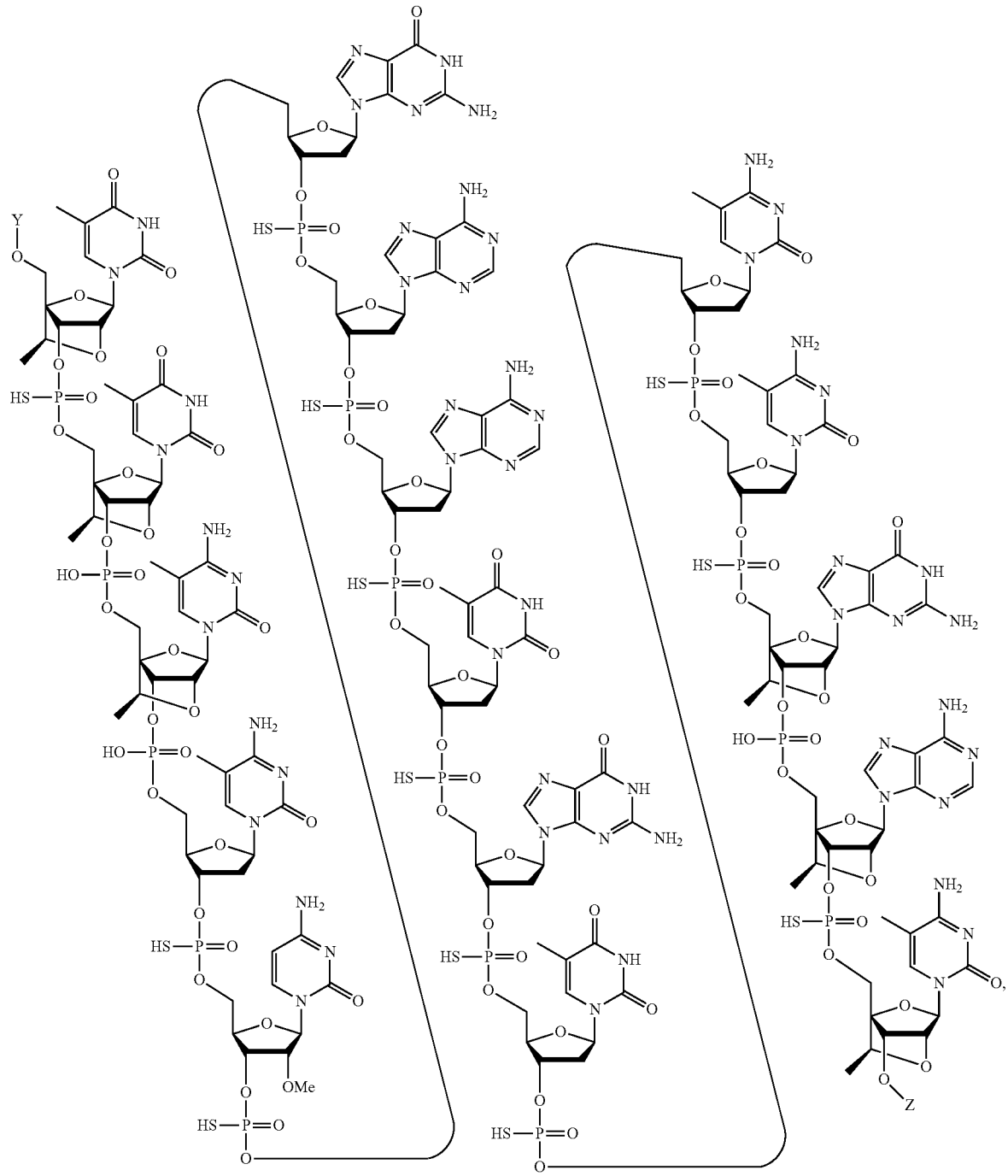
wherein Y and Z are selected from H and a conjugate group, wherein at least one of Y and Z is a conjugate group.

Structure 3. A Prodrug of Compound No. 1522461

In certain embodiments, a prodrug of Compound No. 1522461 is represented by the following chemical structure:

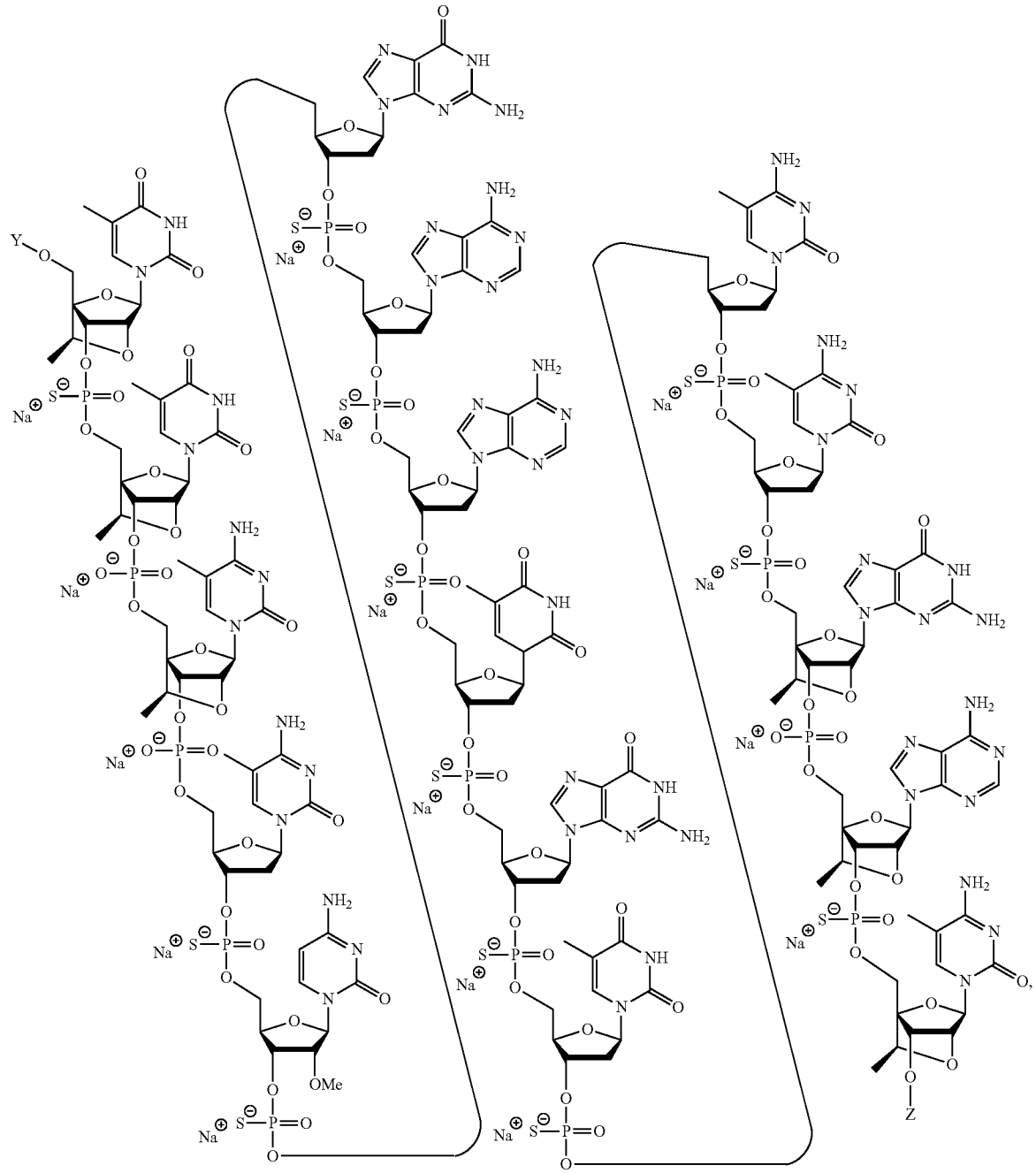

(SEQ ID NO 30)

wherein Y and Z are selected from H and a conjugate group, wherein at least one of Y and Z is a conjugate group.

Structure 4. A Prodrug of Compound No. 1522461

2. Compound No. 1400741

In certain embodiments, Compound No. 1400741 is characterized as a mixed wing gapmer of linked nucleosides and having a nucleobase sequence (from 5' to 3') of TTCCCGAATGTCCGAC (SEQ ID NO 35), wherein each of nucleosides 1-3 and 14-16 (from 5' to 3') are cEt nucleosides, nucleoside 5 is a 2'-OMe nucleoside, and each of nucleosides 4 and 6-13 are 2'-β-D-deoxynucleosides, wherein each internucleoside linkage is a phosphorothioate internucleoside linkage. The cytosines at positions 3-4, 12, 13, and 16 are 5-methylcytosines, while the cytosine at position 5 is a non-methylated cytosine.

In certain embodiments, Compound No. 1400741 is represented by the following chemical notation: $T_{ks}T_{ks}^{m}C_{ks}^{m}C_{ds}C_{ys}G_{ds}A_{ds}A_{ds}T_{ds}G_{ds}T_{ds}^{m}C_{ds}^{m}C_{ds}G_{ks}A_{ks}^{m}C_{k}$ (SEQ ID NO: 20), wherein:

A=an adenine nucleobase, mC=a 5-methylcytosine nucleobase,

C=a cytosine nucleobase,
G=a guanine nucleobase,
T=a thymine nucleobase,
y=a 2'-OMe sugar moiety,
k=a cEt sugar moiety,
d=a 2'-β-D-deoxyribosyl sugar moiety, and
s=a phosphorothioate internucleoside linkage.
In certain embodiments, Compound No. 1400741 is represented by the following chemical structure:
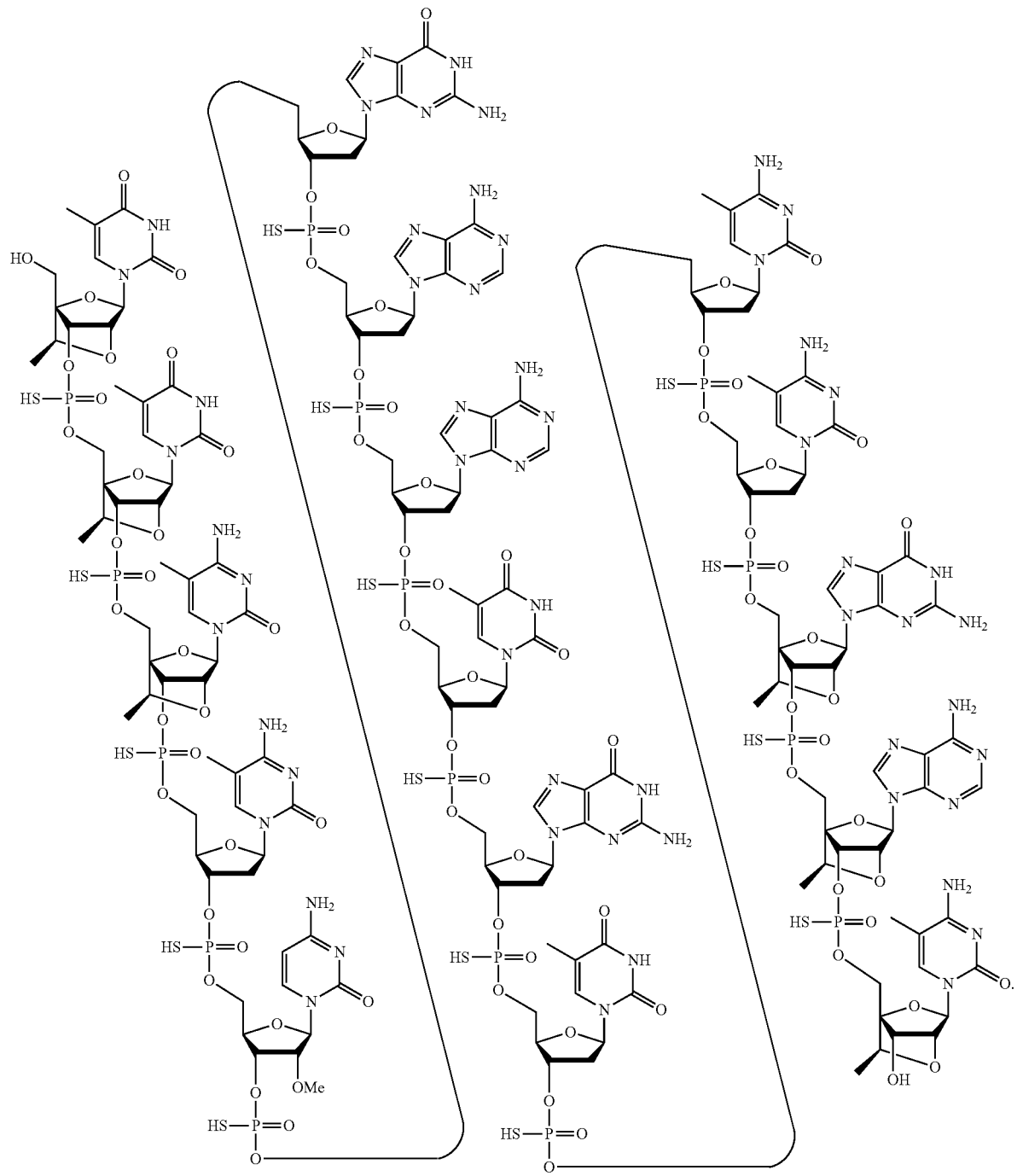
(SEQ ID NO 20)

Structure 5. Compound No. 1400741
In certain embodiments, an oligomeric compound comprises the sodium salt or the potassium salt of the modified oligonucleotide represented by Structure 5.
In certain embodiments, the sodium salt of Compound No. 1400741 is represented by the following chemical structure:
(SEQ ID NO 20)
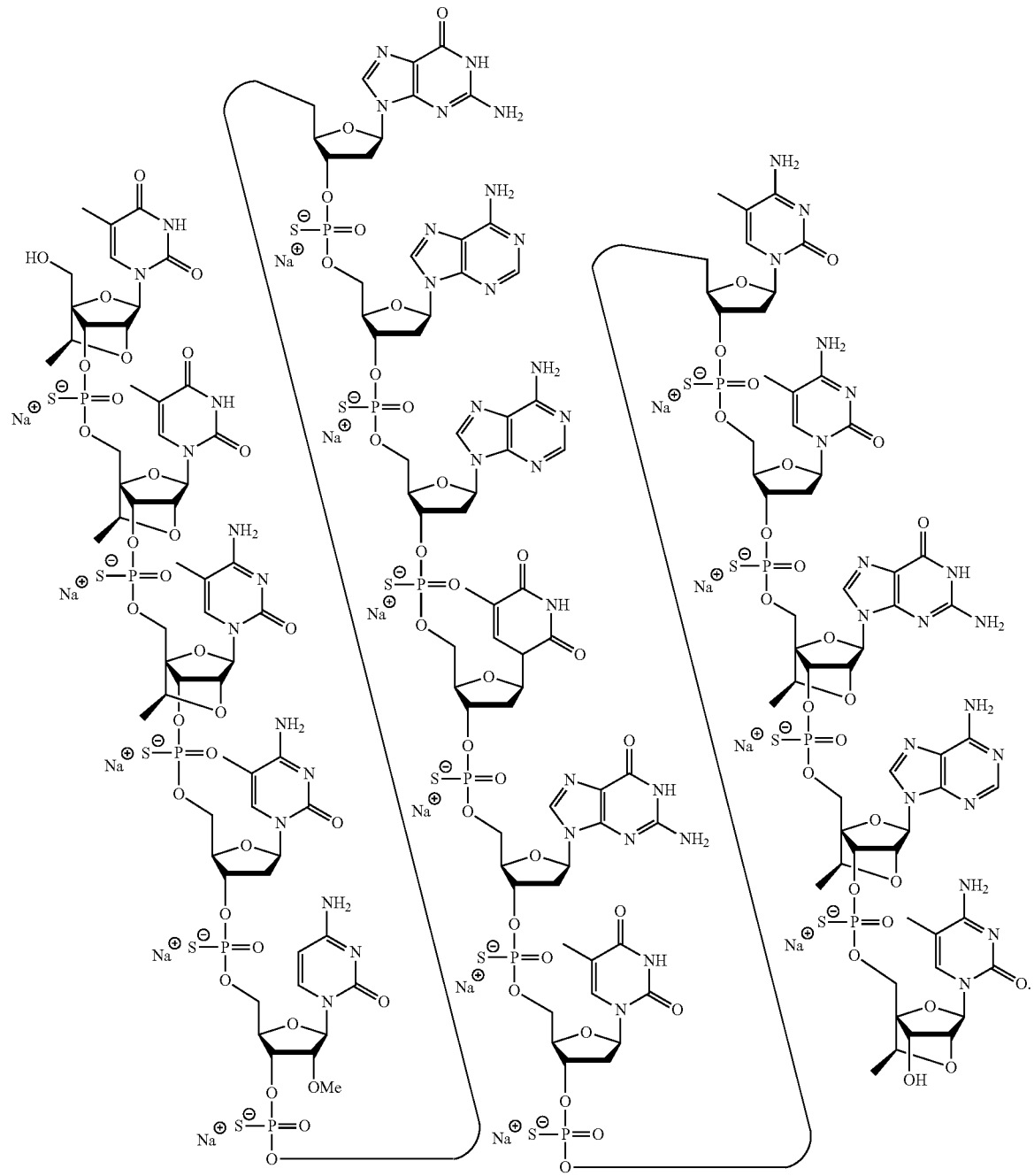

Structure 6. The Sodium Salt of Compound No. 1400741
In certain embodiments, an oligomeric compound comprises a conjugate group.
In certain embodiments, a prodrug of Compound No. 1400741 is represented by the following chemical structure:
(SEQ ID NO 28)
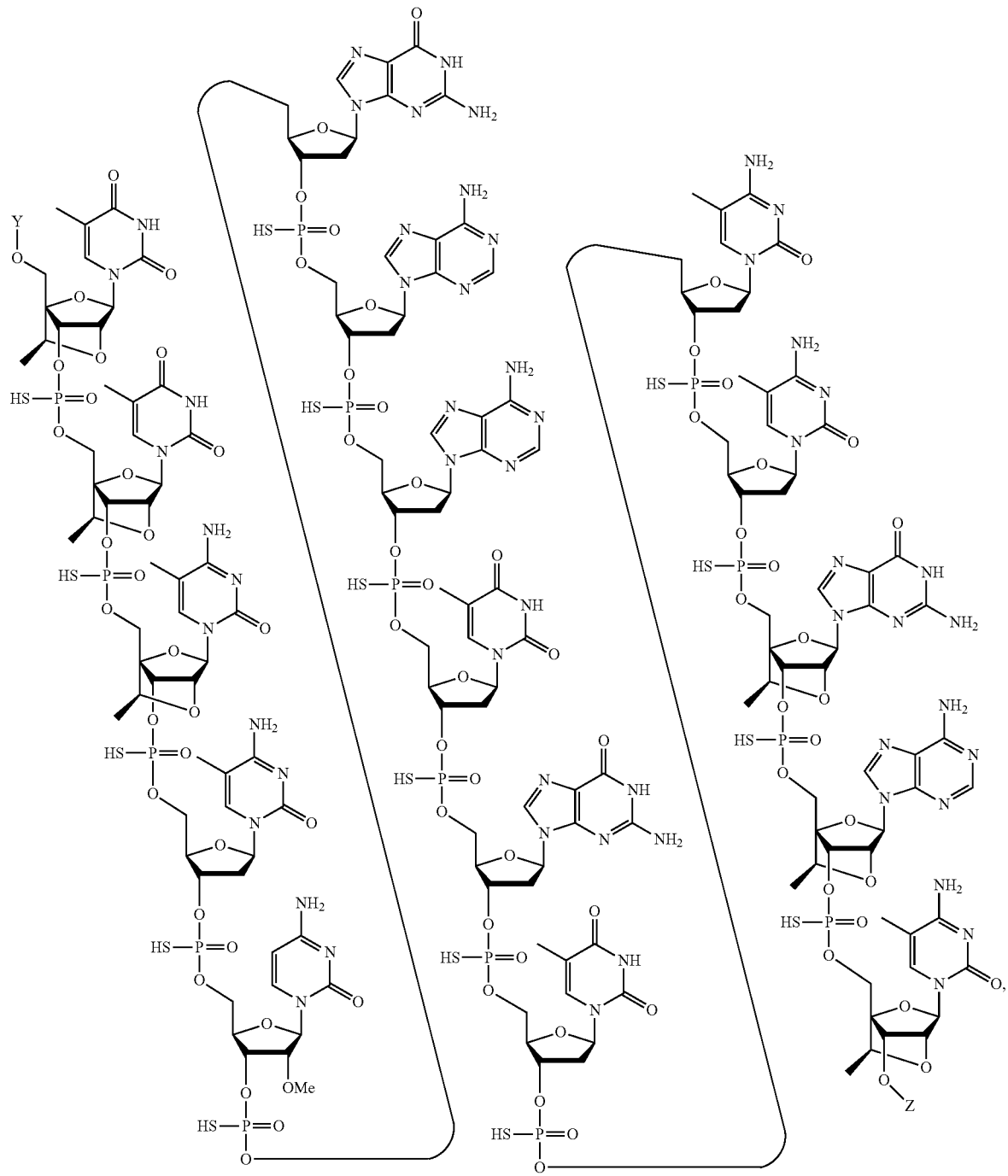
wherein Y and Z are selected from H and a conjugate group, wherein at least one of Y and Z is a conjugate group.

Structure 7. A Prodrug of Compound No. 1400741

In certain embodiments, a prodrug of Compound No. 1400741 is represented by the following chemical structure:

of nucleosides 1-3 and 14-16 (from 5' to 3') are cEt nucleosides, nucleoside 5 is a 2'-OMe nucleoside, and each of nucleosides 4 and 6-13 are 2'-β-D-deoxynucleosides, (SEQ ID NO 28)

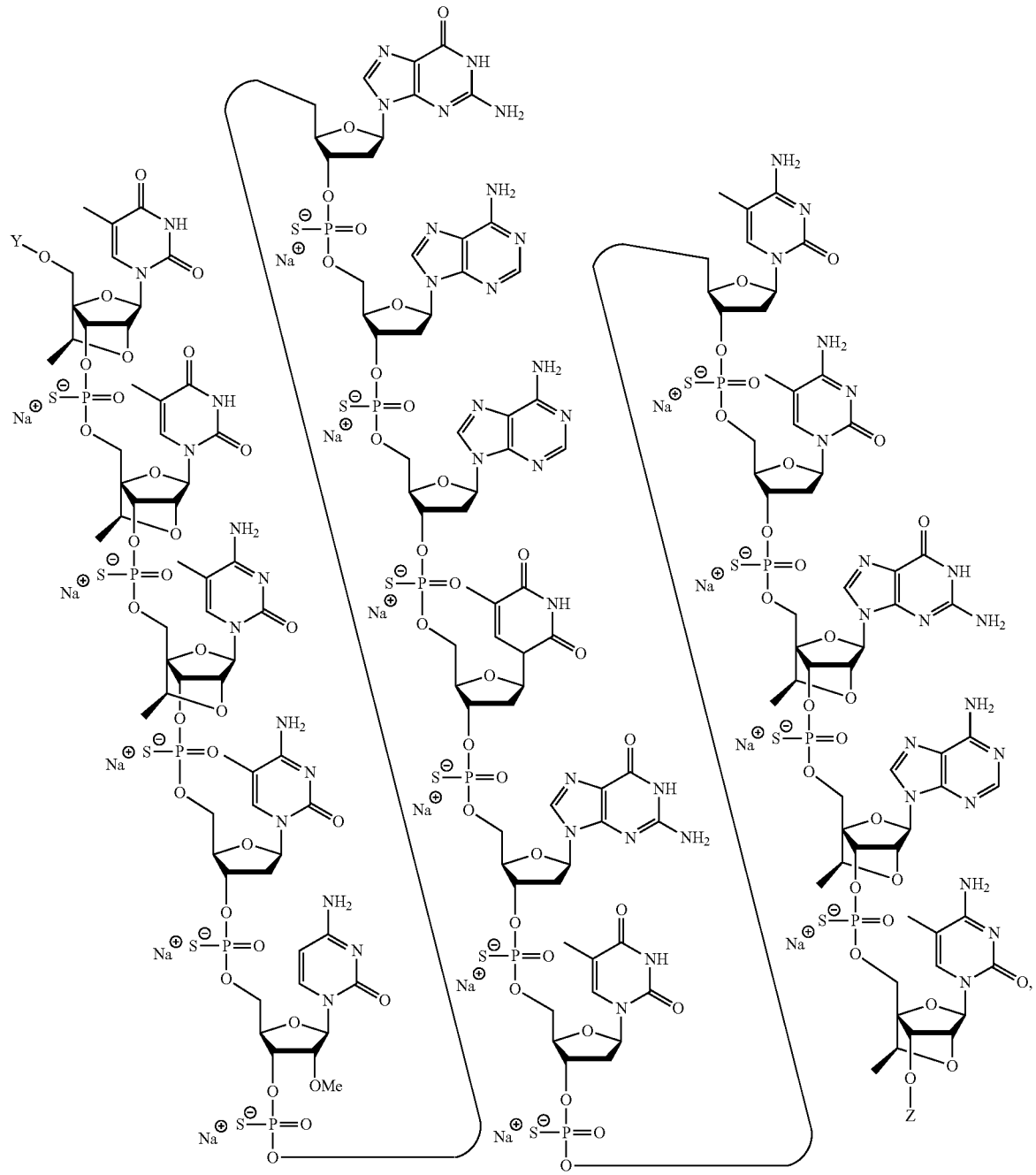

wherein Y and Z are selected from H and a conjugate group, wherein at least one of Y and Z is a conjugate group.

Structure 8. A Prodrug of Compound No. 1400741

3. Compound No. 1522459

In certain embodiments, Compound No. 1522459 is characterized as a mixed wing gapmer of linked nucleosides and having a nucleobase sequence (from 5' to 3') of CGAAUGTCCGACAGTG (SEQ ID NO 36), wherein each wherein the internucleoside linkages between nucleosides 2 to 3, 3 to 4 and 14 to 15 are phosphodiester internucleoside linkages, the internucleoside linkages between nucleosides 1 to 2, 4 to 5, 5 to 6, 6 to 7, 7 to 8, 8 to 9, 9 to 10, 10 to 11, 11 to 12, 12 to 13, 13 to 14, and 15 to 16 are phosphorothioate internucleoside linkages. Each cytosine is a 5-methylcytosine.

In certain embodiments, Compound No. 1522459 is represented by the following chemical notation: $^mC_{ks}G_{ko}A_{ko}A_{ds}U_{ys}G_{ds}T_{ds}{}^mC_{ds}{}^mC_{ds}G_{ds}A_{ds}{}^mC_{ds}A_{ds}G_{ko}T_{ks}G_k$ (SEQ ID NO: 14), wherein:
A=an adenine nucleobase,
mC=a 5-methylcytosine nucleobase,
U=a uracil nucleobase,
G=a guanine nucleobase,
T=a thymine nucleobase,
y=a 2'-OMe sugar moiety,
k=a cEt sugar moiety,
d=a 2'-β-D-deoxyribosyl sugar moiety,
s=a phosphorothioate internucleoside linkage, and
o=a phosphodiester internucleoside linkage.

In certain embodiments Compound No. 1522459 is represented by the following chemical structure:

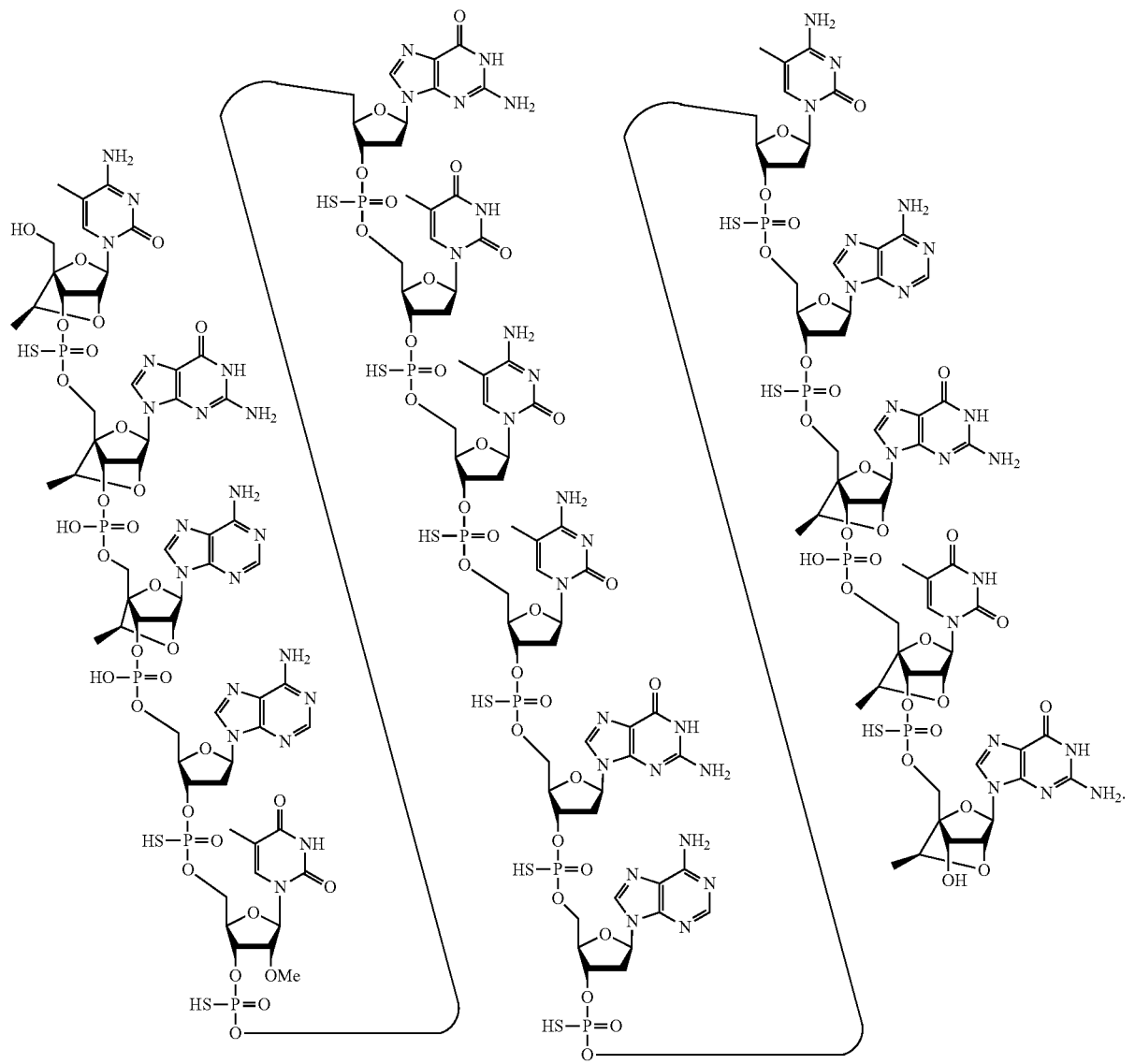

(SEQ ID NO 14)

Structure 9. Compound No. 1522459
In certain embodiments, an oligomeric compound comprises the sodium salt or the potassium salt of the modified oligonucleotide represented by Structure 9.
In certain embodiments the sodium salt of Compound No. 1522459 is represented by the following chemical structure:
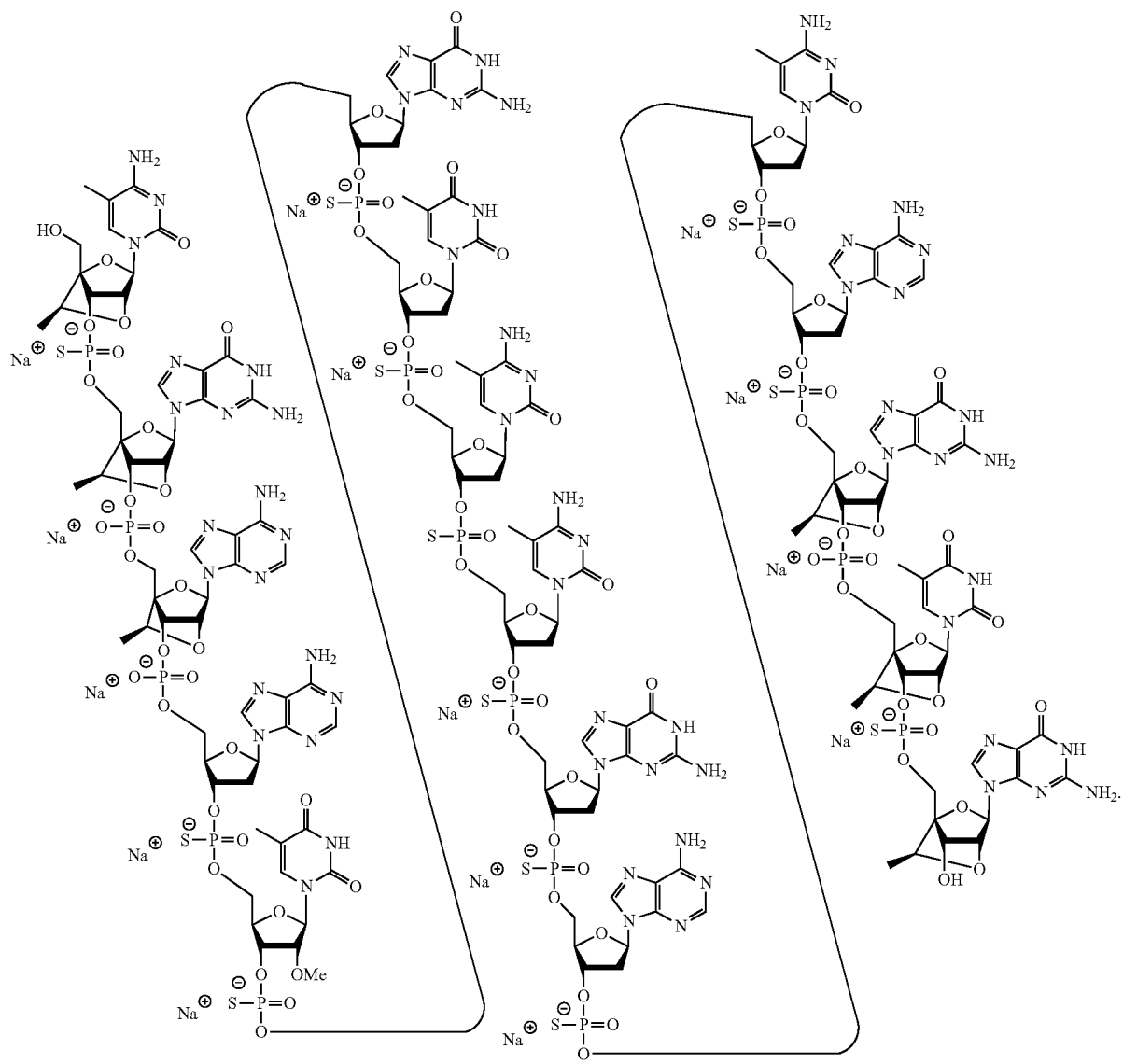
(SEQ ID NO 14)

Structure 10. The sodium salt of Compound No. 1522459
In certain embodiments, an oligomeric compound comprises a conjugate group.
In certain embodiments, a prodrug of Compound No. 1522459 is represented by the following chemical structure:
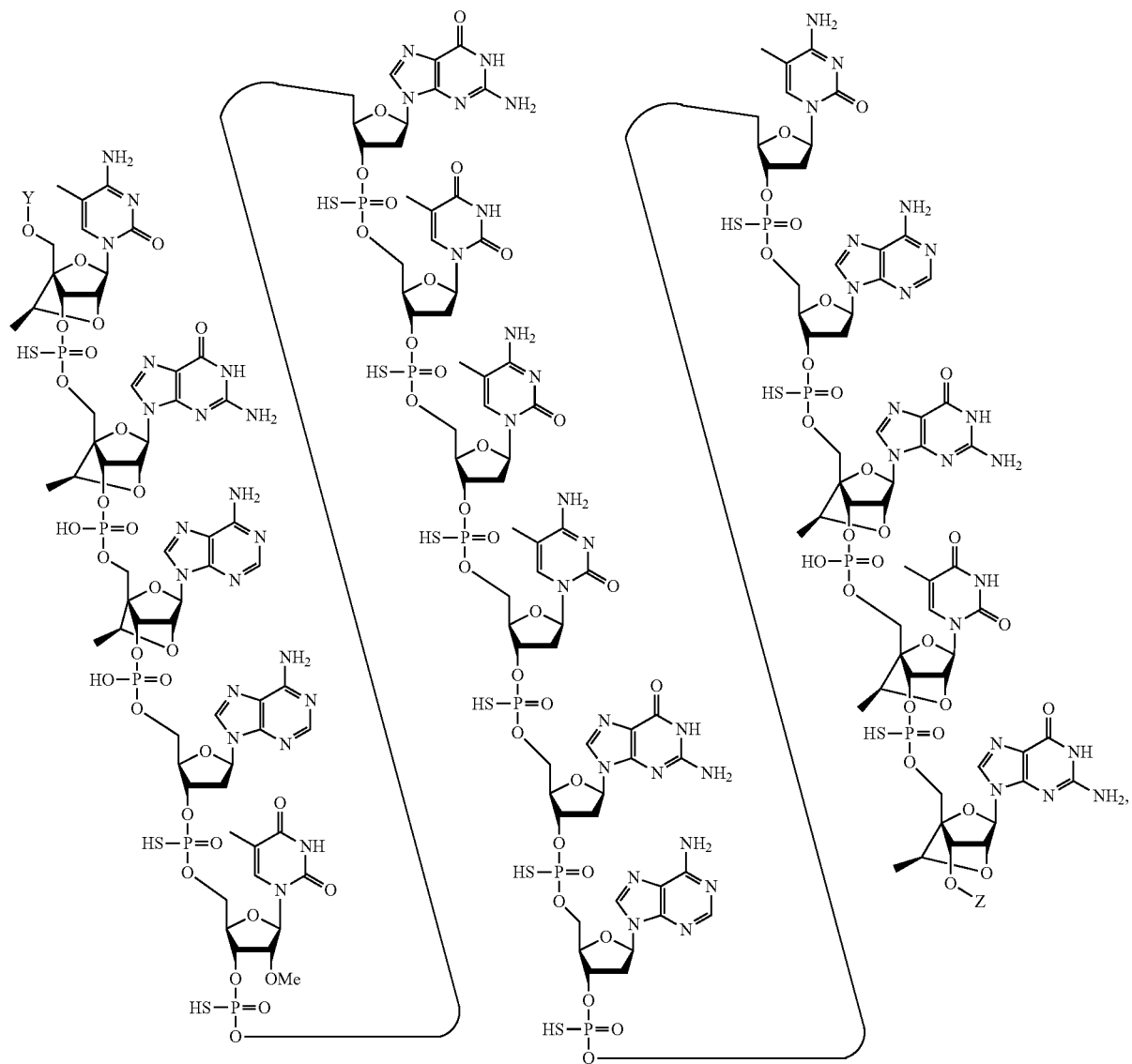
(SEQ ID NO 29)
wherein Y and Z are selected from H and a conjugate group, wherein at least one of Y and Z is a conjugate group.

Structure 11. A Prodrug of Compound No. 1522459

(SEQ ID NO 29)

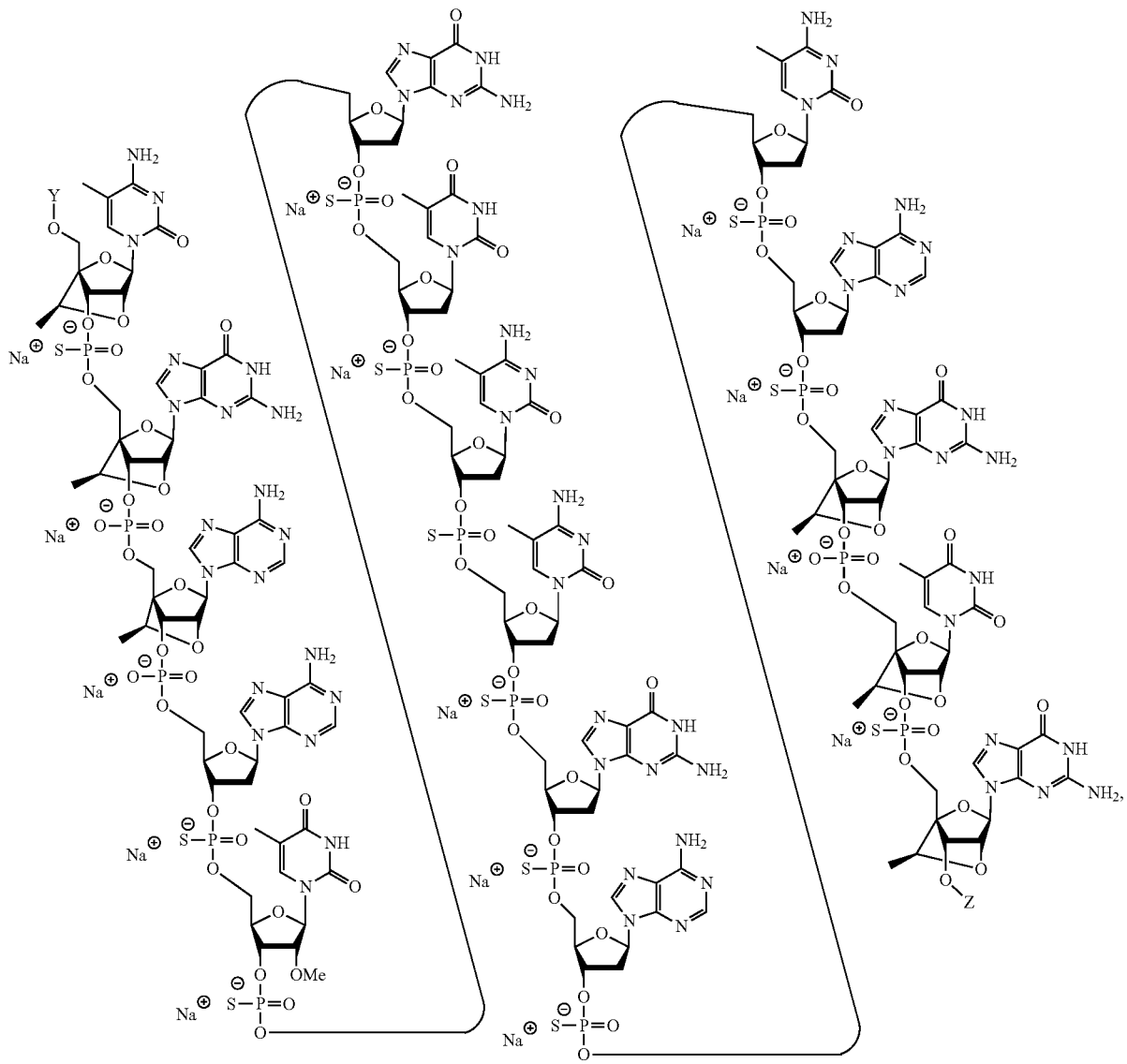

wherein Y and Z are selected from H and a conjugate group, wherein at least one of Y and Z is a conjugate group.
Structure 12. A Prodrug of Compound No. 1522459

4. Compound No. 1522464

In certain embodiments, Compound No. 1522464 is characterized as a mixed wing gapmer of linked nucleosides and having a nucleobase sequence (from 5' to 3') of CTTTTAT-TCGCGAGGG (SEQ ID NO 37), wherein each of nucleosides 1-2 and 14-16 (from 5' to 3') are cEt nucleosides, nucleoside 3 is a 2'-MOE nucleoside, and each of nucleosides 4-13 are 2'-β-D-deoxynucleosides, wherein the internucleoside linkages between nucleosides 2 to 3, 3 to 4 and 14 to 15 are phosphodiester internucleoside linkages, the internucleoside linkages between nucleosides 1 to 2, 4 to 5, 5 to 6, 6 to 7, 7 to 8, 8 to 9, 9 to 10, 10 to 11, 11 to 12, 12 to 13, 13 to 14, and 15 to 16 are phosphorothioate internucleoside linkages. Each cytosine is a 5-methylcytosine.

In certain embodiments, Compound No. 1522464 is represented by the following chemical notation: $^{m}C_{ks}T_{ko}T_{eo}T_{ds}T_{ds}A_{ds}T_{ds}T_{ds}{}^{m}C_{ds}G_{ds}{}^{m}C_{ds}G_{ds}A_{ds}G_{ko}G_{ks}G_{k}$ (SEQ ID NO: 15), wherein:

A=an adenine nucleobase,
mC=a 5-methylcytosine nucleobase,
G=a guanine nucleobase,
T=a thymine nucleobase,
e=a 2'-MOE sugar moiety,
k=a cEt sugar moiety,
d=a 2'-β-D-deoxyribosyl sugar moiety,
s=a phosphorothioate internucleoside linkage, and
o=a phosphodiester internucleoside linkage.

In certain embodiments, Compound No. 1522464 is represented by the following chemical structure:
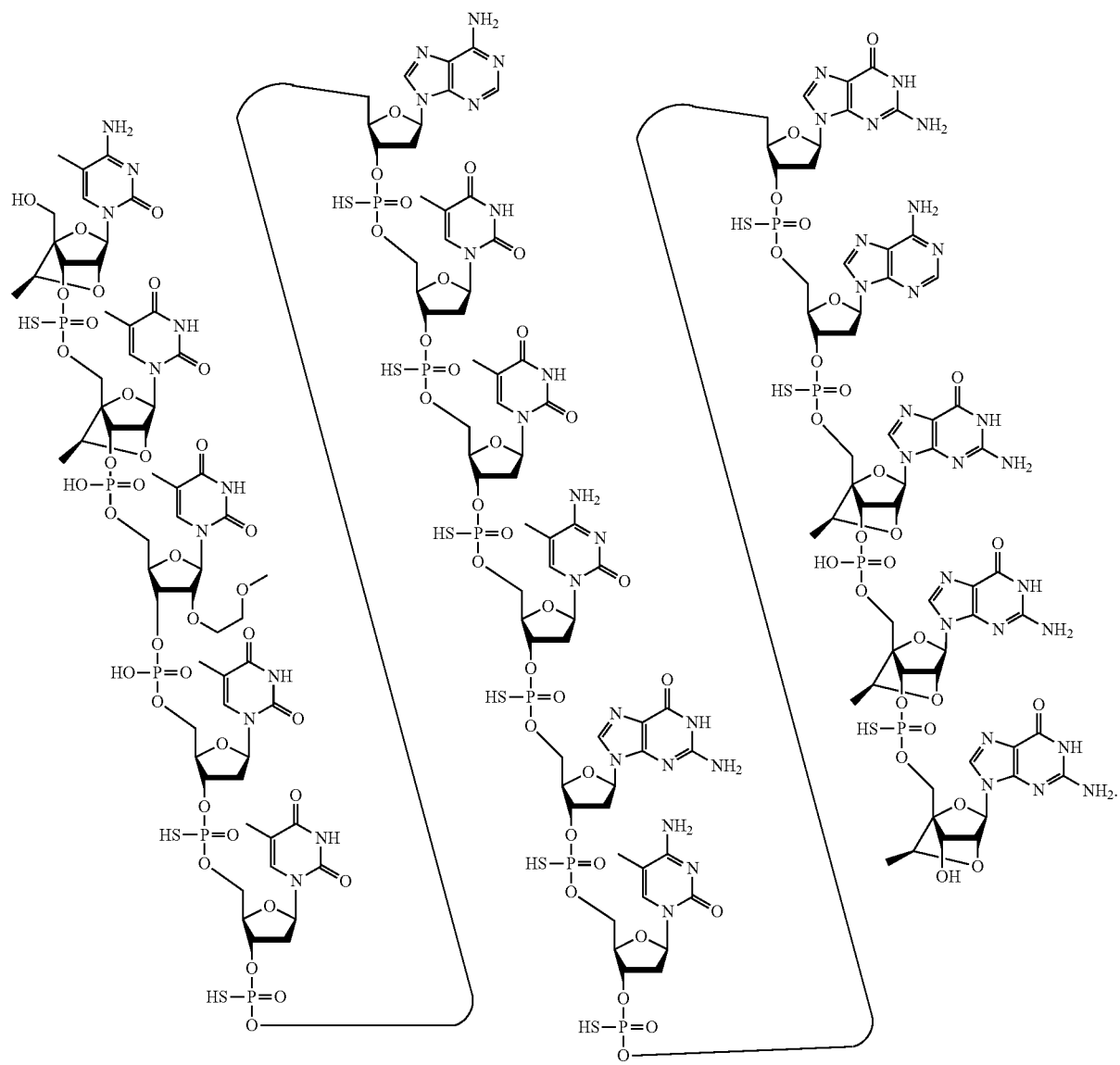
(SEQ ID NO 15)

Structure 13. Compound No. 1522464
In certain embodiments, an oligomeric compound comprises the sodium salt or the potassium salt of the modified oligonucleotide represented by Structure 13.
In certain embodiments, the sodium salt of Compound No. 1522464 is represented by the following chemical structure:
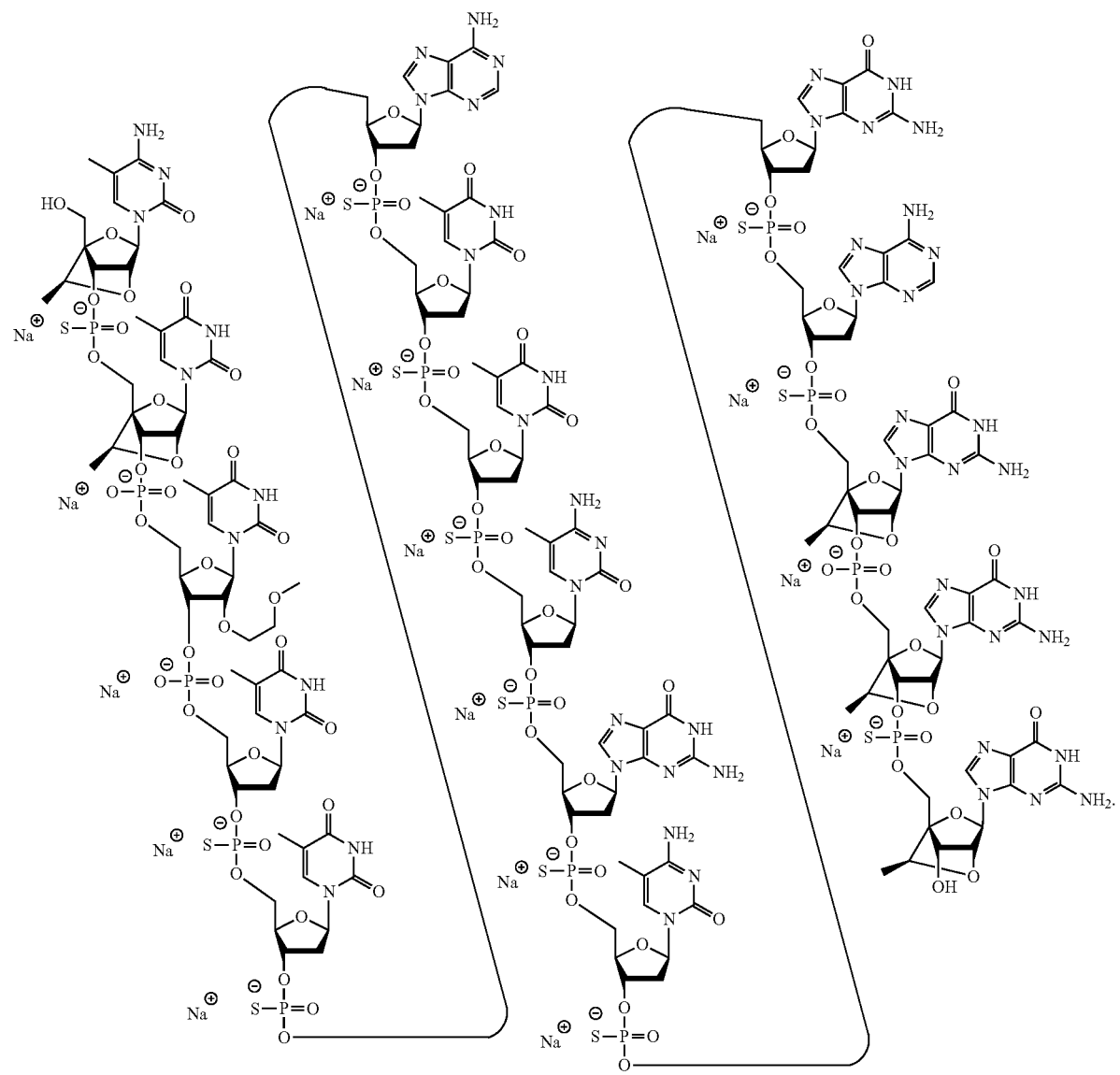
(SEQ ID NO 15)

Structure 14. The Sodium Salt of Compound No. 1522464
In certain embodiments, an oligomeric compound comprises a conjugate group.
In certain embodiments, a prodrug of Compound No. 1522464 is represented by the following chemical structure:
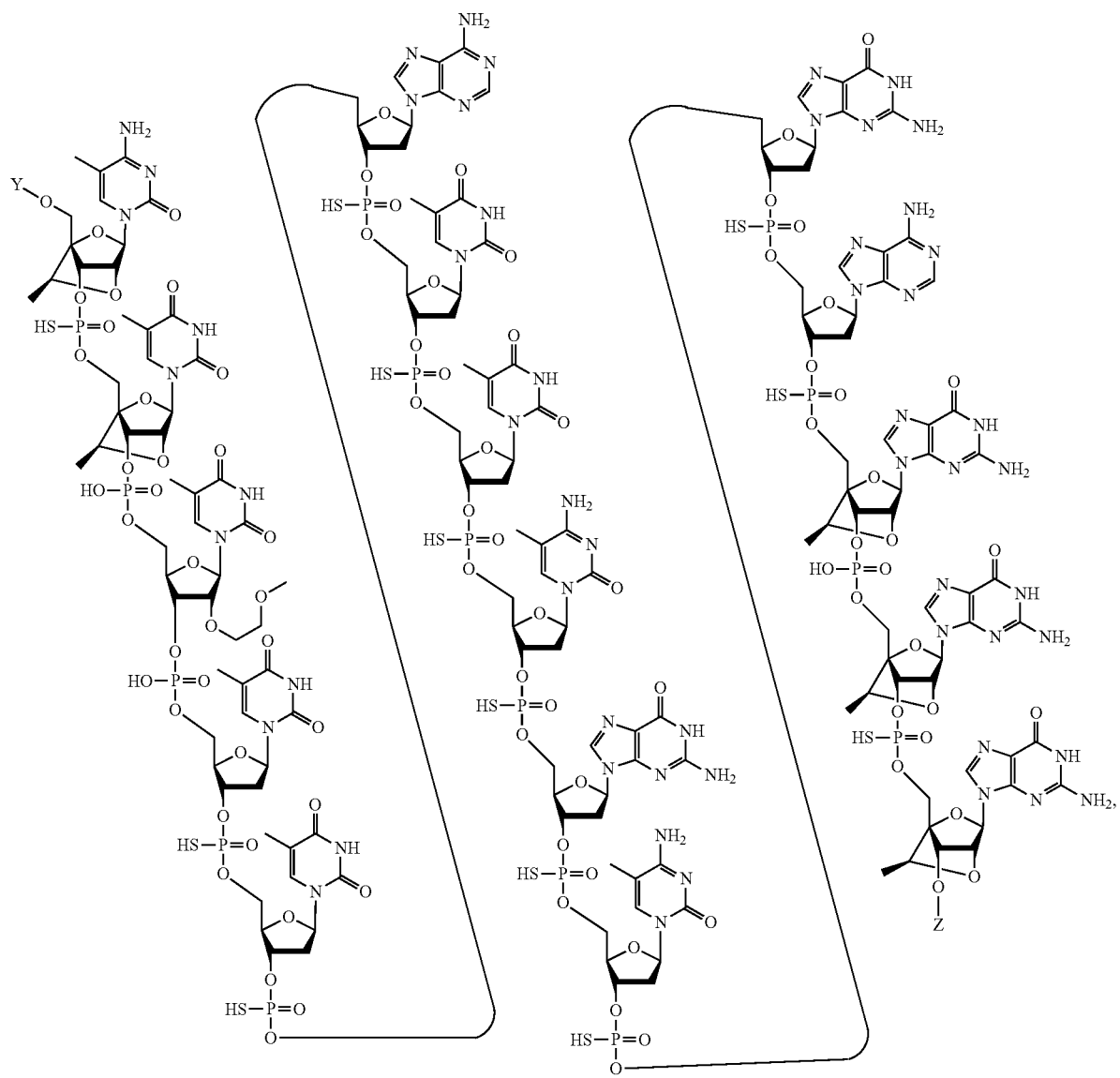
(SEQ ID NO 31)
wherein Y and Z are selected from H and a conjugate group, wherein at least one of Y and Z is a conjugate group.

Structure 15. A Prodrug of Compound No. 1522464

In certain embodiments, a prodrug of Compound No. 1522464 is represented by the following chemical structure:

(SEQ ID NO 31)

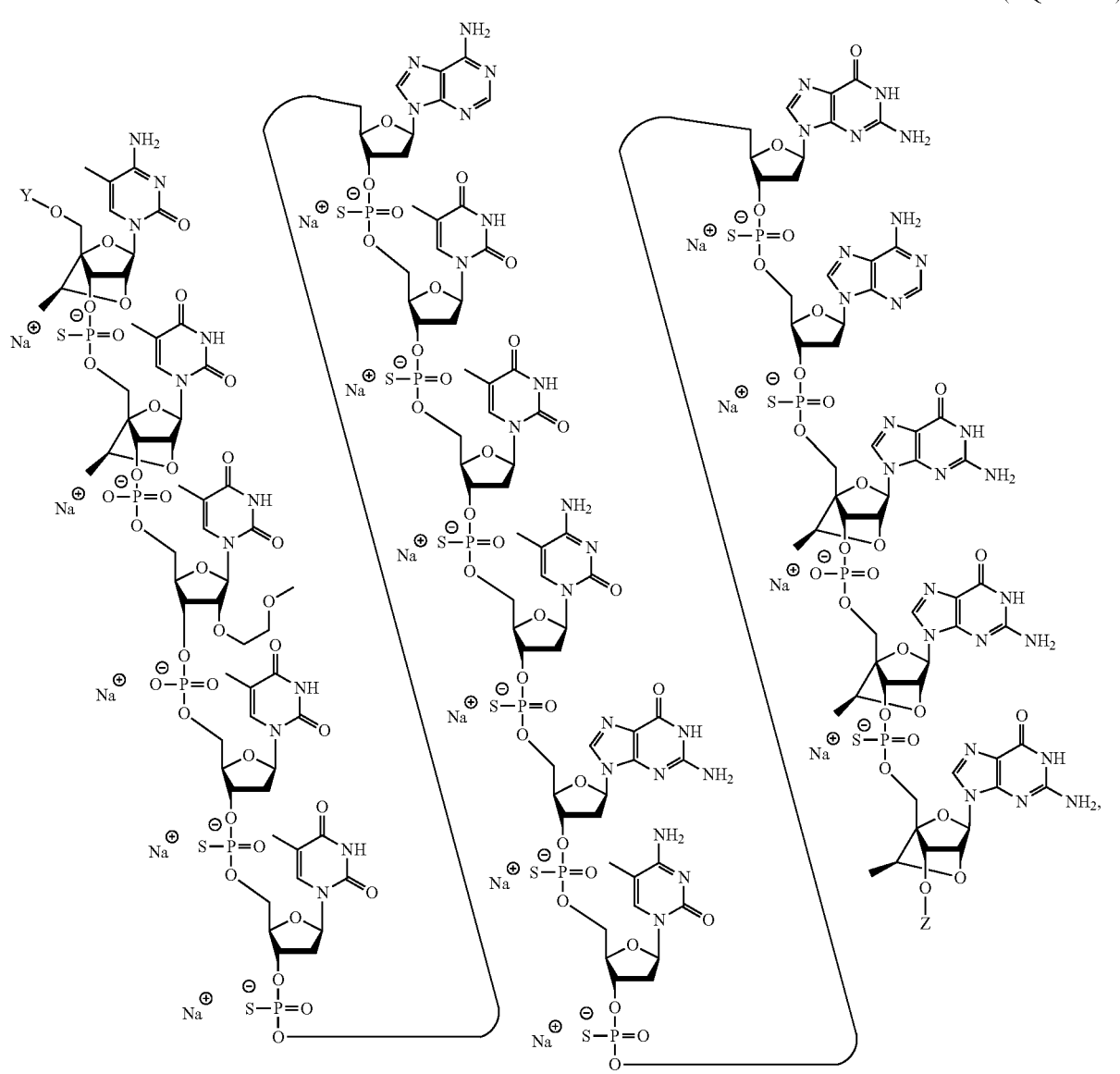

wherein Y and Z are selected from H and a conjugate group, wherein at least one of Y and Z is a conjugate group.

Structure 16. A Prodrug of Compound No. 1522464

5. Compound No. 1525073

In certain embodiments, Compound No. 1525073 is characterized as a cEt gapmer of linked nucleosides and having a nucleobase sequence (from 5' to 3') of ACAATAAATACCGAGG (SEQ ID NO 33), wherein each of nucleosides 1-3 and 14-16 (from 5' to 3') are cEt nucleosides, and each of nucleosides 4-13 are 2'-β-D-deoxynucleosides, wherein the internucleoside linkages between nucleosides 2 to 3, 3 to 4 and 14 to 15 are phosphodiester internucleoside linkages, the internucleoside linkages between nucleosides 1 to 2, 4 to 5, 5 to 6, 6 to 7, 7 to 8, 8 to 9, 9 to 10, 10 to 11, 11 to 12, 12 to 13, 13 to 14, and 15 to 16 are phosphorothioate internucleoside linkages. Each cytosine is a 5-methylcytosine.

In certain embodiments, Compound No. 1525073 is represented by the following chemical notation: $A_{ks}{}^mC_{ko}A_{ko}A_{ds}T_{ds}A_{ds}A_{ds}A_{ds}T_{ds}A_{ds}{}^mC_{ds}{}^mC_{ds}G_{ds}A_{ko}G_{ks}G_k$ (SEQ ID NO: 11), wherein:

A=an adenine nucleobase,
mC=a 5-methylcytosine nucleobase,
G=a guanine nucleobase,
T=a thymine nucleobase,
k=a cEt sugar moiety,
d=a 2'-β-D-deoxyribosyl sugar moiety,
s=a phosphorothioate internucleoside linkage, and
o=a phosphodiester internucleoside linkage.

In certain embodiments, Compound No. 1525073 is represented by the following chemical structure:
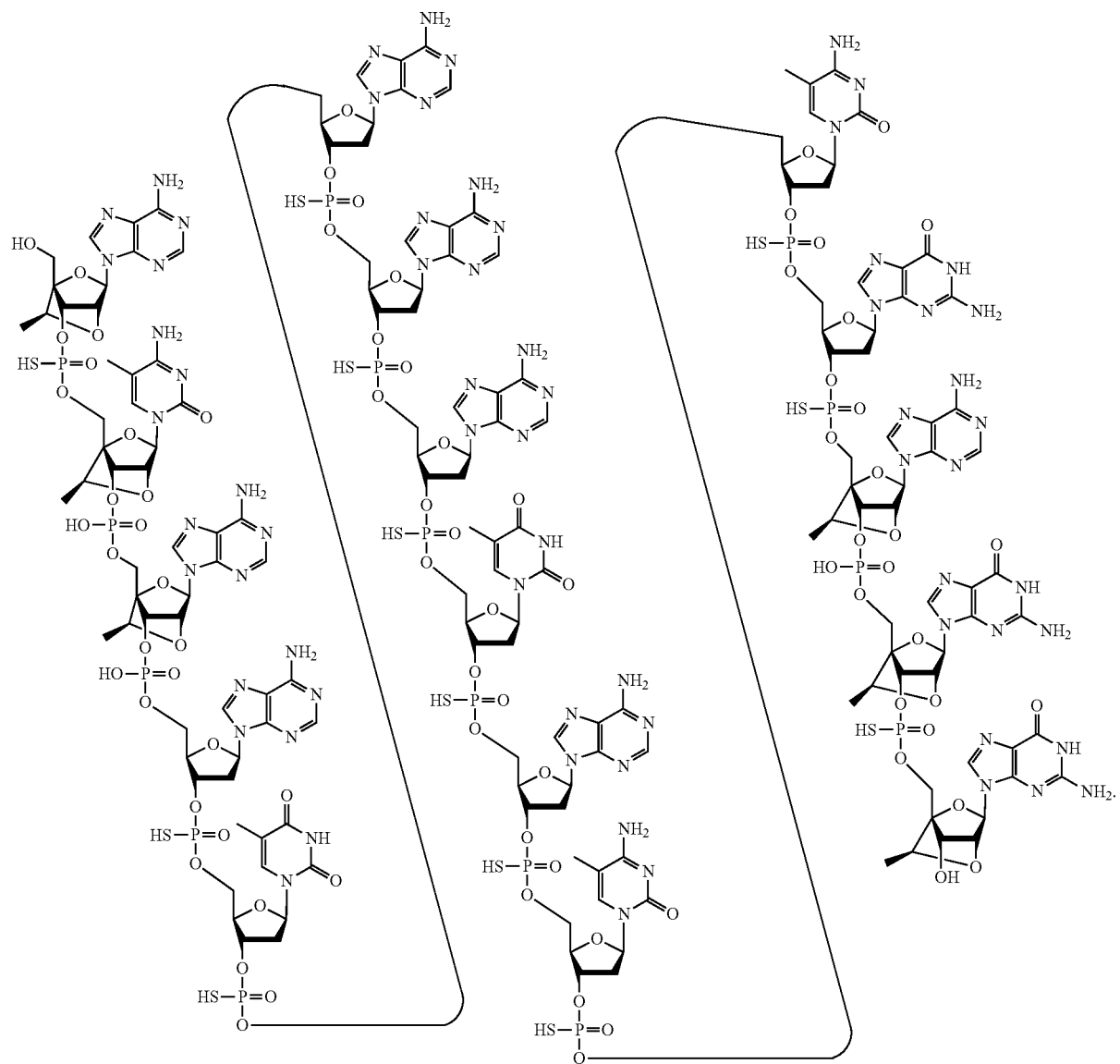
(SEQ ID NO 11)

Structure 17. Compound No. 1525073
In certain embodiments, an oligomeric compound comprises the sodium salt or the potassium salt of the modified oligonucleotide represented by Structure 17.
In certain embodiments, the sodium salt of Compound No. 1525073 is represented by the following chemical structure:
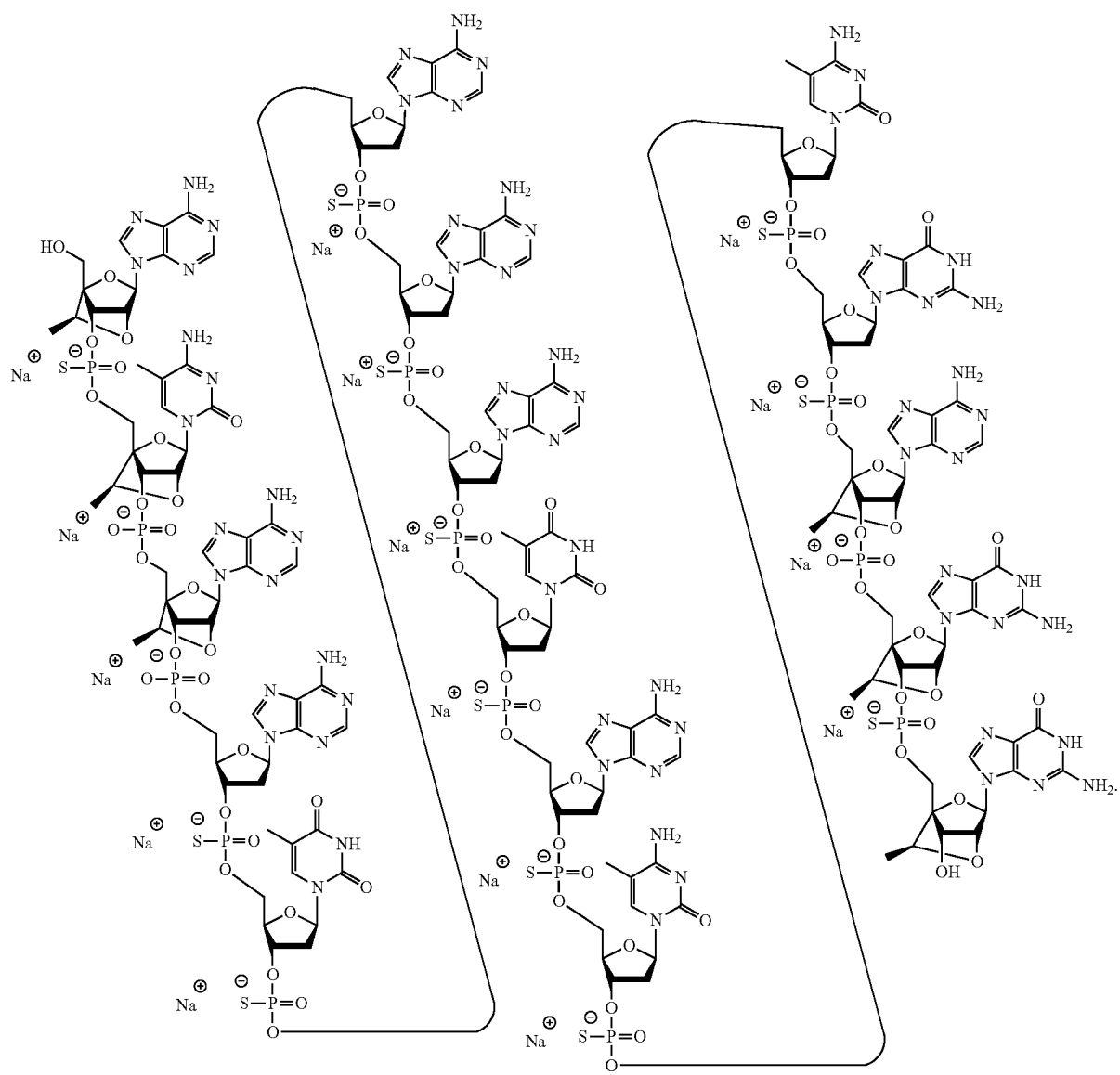
(SEQ ID NO 11)

Structure 18. The Sodium Salt of Compound No. 1525073
In certain embodiments, an oligomeric compound comprises a conjugate group.
In certain embodiments, a prodrug of Compound No. 1525073 is represented by the following chemical structure:
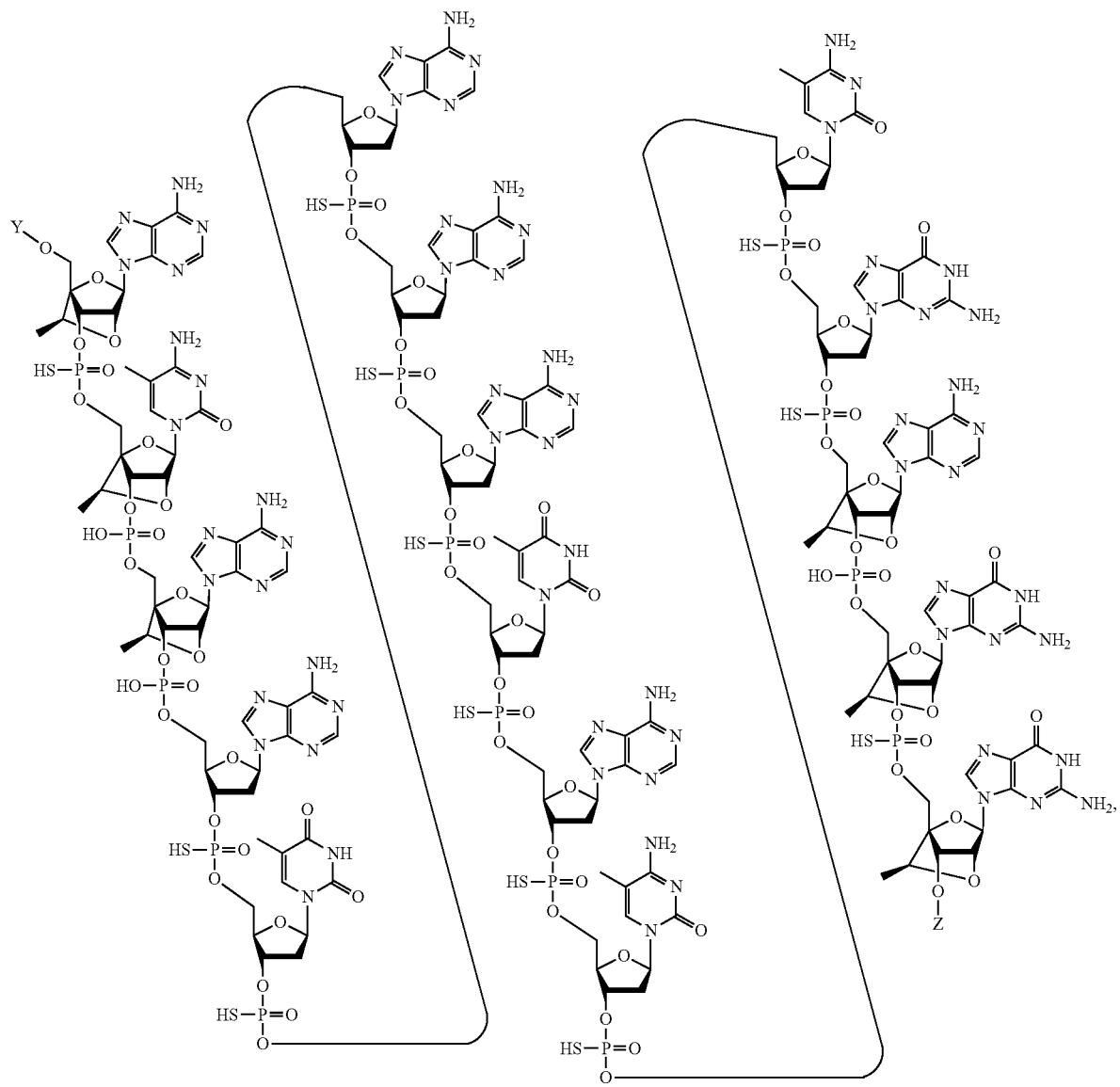
(SEQ ID NO 32)
wherein Y and Z are selected from H and a conjugate group, wherein at least one of Y and Z is a conjugate group.

Structure 19. A Conjugate of Compound No. 1525073

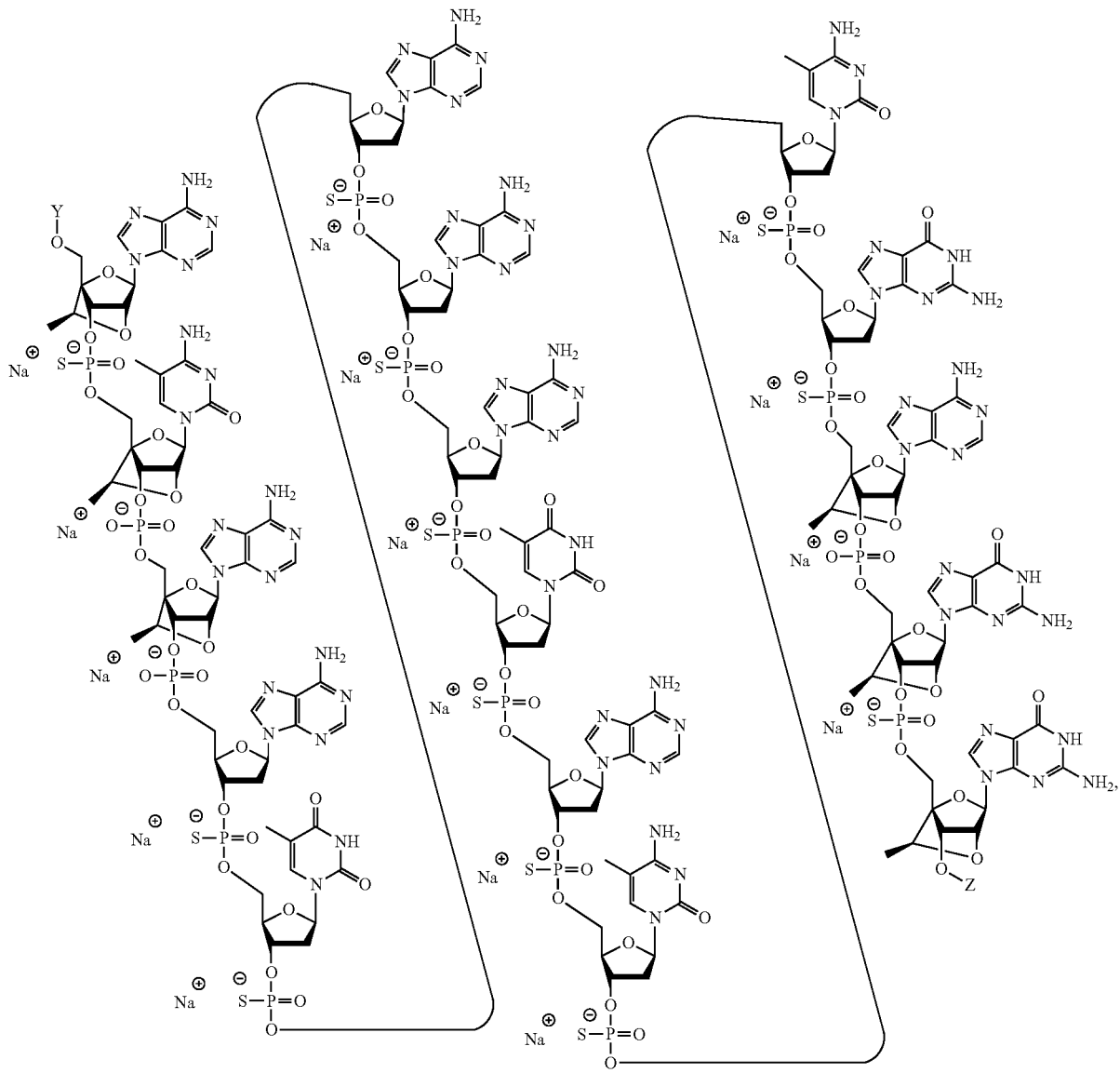

(SEQ ID NO 32)

wherein Y and Z are selected from H and a conjugate group, wherein at least one of Y and Z is a conjugate group.
Structure 20. A Prodrug of Compound No. 1525073

I. Certain Oligonucleotides

In certain embodiments, provided herein are oligomeric compounds comprising oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA. That is, modified oligonucleotides comprise at least one modified nucleoside (comprising a modified sugar moiety and/or a modified nucleobase) and/or at least one modified internucleoside linkage.

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties comprising a furanosyl ring with one or more substituent groups none of which bridges two atoms of the furanosyl ring to form a bicyclic structure. Such non bridging substituents may be at any position of the furanosyl, including but not limited to substituents at the 2', 3', 4', and/or 5' positions. Examples of 2'-substituent groups suitable for non-bicyclic modified sugar moieties include but are not limited to 2'-O(CH$_2$)$_2$OCH$_3$ ("MOE" or "O-methoxyethyl").

In certain embodiments, modified furanosyl sugar moieties and nucleosides incorporating such modified furanosyl sugar moieties are further defined by isomeric configuration. For example, a 2'-deoxyfuranosyl sugar moiety may be in seven isomeric configurations other than the naturally occurring β-D-deoxyribosyl configuration. Such modified sugar moieties are described in, e.g., WO 2019/157531, incorporated by reference herein. A 2'-modified sugar moiety has an additional stereocenter at the 2'-position relative to a 2'-deoxyfuranosyl sugar moiety; therefore, such sugar moieties have a total of sixteen possible isomeric configurations. 2'-modified sugar moieties described herein are in the β-D-ribosyl isomeric configuration unless otherwise specified.

2. Certain Modified Nucleobases

In certain embodiments, modified oligonucleotides comprise one or more nucleosides comprising an unmodified nucleobase. In certain embodiments, modified oligonucleotides comprise one or more nucleosides comprising a modified nucleobase. Examples of modified nucleobases include 5-methylcytosine.

Publications that teach the preparation of certain modified nucleobases include without limitation, Manoharan et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

3. Certain Modified Internucleoside Linkages

The naturally occurring internucleoside linkage of RNA and DNA is a 3' to 5' phosphodiester linkage. In certain embodiments, nucleosides of modified oligonucleotides may be linked together using one or more modified internucleoside linkages. The two main classes of internucleoside linking groups are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS—P=S"). Representative non-phosphorus containing internucleoside linking groups include but are not limited to methylenemethylimino (—CH$_2$—N(CH$_3$)—O—CH$_2$—), thiodiester, thionocarbamate (—O—C(=O)(NH)—S—); siloxane (—O—SiH$_2$—O—); and N,N'-dimethylhydrazine (—CH$_2$—N(CH$_3$)—N(CH$_3$)—). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Methods of preparation of phosphorous-containing and non-phosphorous-containing internucleoside linkages are well known to those skilled in the art.

In certain embodiments, a modified internucleoside linkage is any of those described in WO/2021/030778, incorporated by reference herein. In certain embodiments, a modified internucleoside linkage comprises the formula:

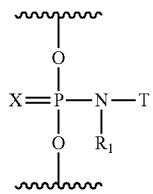

wherein independently for each internucleoside linking group of the modified oligonucleotide:

X is selected from O or S;

R$_1$ is selected from H, C$_1$-C$_6$ alkyl, and substituted C$_1$-C$_6$ alkyl; and T is selected from SO$_2$R$_2$, C(=O)R$_3$, and P(=O)R$_4$R$_5$, wherein:

R$_2$ is selected from an aryl, a substituted aryl, a heterocycle, a substituted heterocycle, an aromatic heterocycle, a substituted aromatic heterocycle, a diazole, a substituted diazole, a C$_1$-C$_6$ alkoxy, C$_1$-C$_6$ alkyl, C$_1$-C$_6$ alkenyl, C$_1$-C$_6$ alkynyl, substituted C$_1$-C$_6$ alkyl, substituted C$_1$-C$_6$ alkenyl substituted C$_1$-C$_6$ alkynyl, and a conjugate group;

R$_3$ is selected from an aryl, a substituted aryl, CH$_3$, N(CH$_3$)$_2$, OCH$_3$ and a conjugate group;

R$_4$ is selected from OCH$_3$, OH, C$_1$-C$_6$ alkyl, substituted C$_1$-C$_6$ alkyl and a conjugate group; and R$_5$ is selected from OCH$_3$, OH, C$_1$-C$_6$ alkyl, and substituted C$_1$-C$_6$ alkyl.

In certain embodiments, a modified internucleoside linkage comprises a mesyl phosphoramidate linking group having a formula:

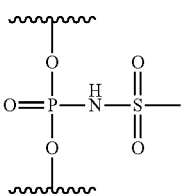

In certain embodiments, a mesyl phosphoramidate internucleoside linkage may comprise a chiral center. In certain embodiments, modified oligonucleotides comprising (Rp) and/or (Sp) mesyl phosphoramidates comprise one or more of the following formulas, respectively, wherein "B" indicates a nucleobase:

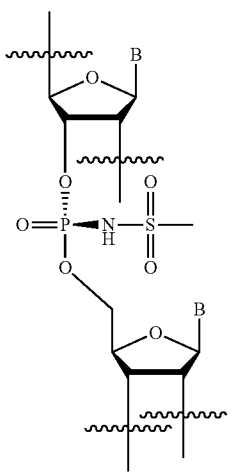

(S$_p$)

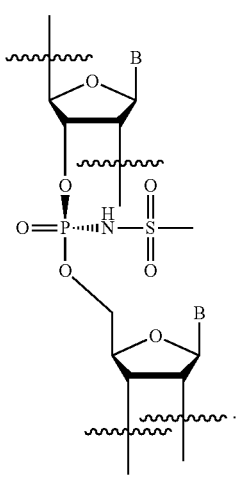

(R$_p$)

Representative internucleoside linkages having a chiral center include but are not limited to alkylphosphonates, mesyl phosphoramidates, and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate or other linkages containing chiral centers in particular stereochemical configurations. In certain embodiments, populations of modified oligonucleotides comprise phosphorothioate internucleoside linkages wherein all of the phosphorothioate internucleoside linkages are stereorandom. In certain embodiments, populations of modified oligonucleotides comprise mesyl phosphoramidate internucleoside linkages wherein all of the mesyl phosphoramidate internucleoside linkages are stereorandom. Such modified oligonucleotides can be generated using synthetic methods that result in random selection of the stereochemical configuration of each phosphorothioate or mesyl phosphoramidate linkage. Nonetheless, each individual phosphorothioate or mesyl phosphoramidate of each individual oligonucleotide molecule has a defined stereoconfiguration. In certain embodiments, populations of modified oligonucleotides are enriched for modified oligonucleotides comprising one or more particular phosphorothioate or mesyl phosphoramidate internucleoside linkages in a particular, independently selected stereochemical configuration. In certain embodiments, the particular configuration of the particular phosphorothioate or mesyl phosphoramidate linkage is present in at least 65% of the molecules in the population. In certain embodiments, the particular configuration of the particular phosphorothioate or mesyl phosphoramidate linkage is present in at least 70% of the molecules in the population. In certain embodiments, the particular configuration of the particular phosphorothioate or mesyl phosphoramidate linkage is present in at least 80% of the molecules in the population. In certain embodiments, the particular configuration of the particular phosphorothioate or mesyl phosphoramidate linkage is present in at least 90% of the molecules in the population. In certain embodiments, the particular configuration of the particular phosphorothioate or mesyl phosphoramidate linkage is present in at least 99% of the molecules in the population. Such chirally enriched populations of modified oligonucleotides can be generated using synthetic methods known in the art, e.g., methods described in Oka et al., JACS 125, 8307 (2003), Wan et al. Nuc. Acid. Res. 42, 13456 (2014), and WO 2017/015555. In certain embodiments, a population of modified oligonucleotides is enriched for modified oligonucleotides having at least one indicated phosphorothioate or mesyl phosphoramidate in the (Sp) configuration. In certain embodiments, a population of modified oligonucleotides is enriched for modified oligonucleotides having at least one phosphorothioate or mesyl phosphoramidate in the (Rp) configuration. In certain embodiments, modified oligonucleotides comprising (Rp) and/or (Sp) phosphorothioates comprise one or more of the following formulas, respectively, wherein "B" indicates a nucleobase:

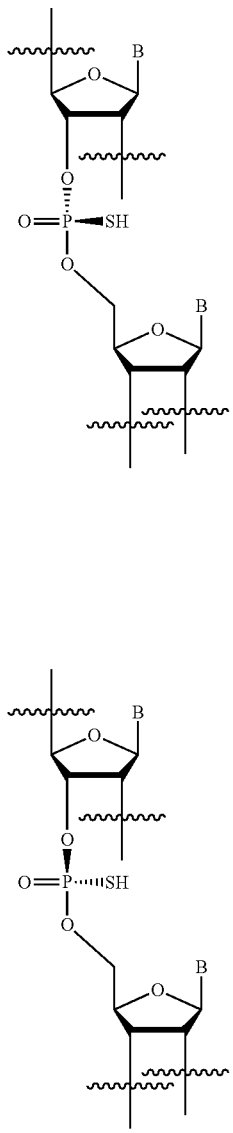

($R_p$)

($S_p$)

Unless otherwise indicated, chiral internucleoside linkages of modified oligonucleotides described herein can be stereorandom or in a particular stereochemical configuration.

Neutral internucleoside linkages include, without limitation, phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O—$CH_2$—O-5'), methoxypropyl (MOP), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

In certain embodiments, modified oligonucleotides comprise one or more inverted nucleoside, as shown below:

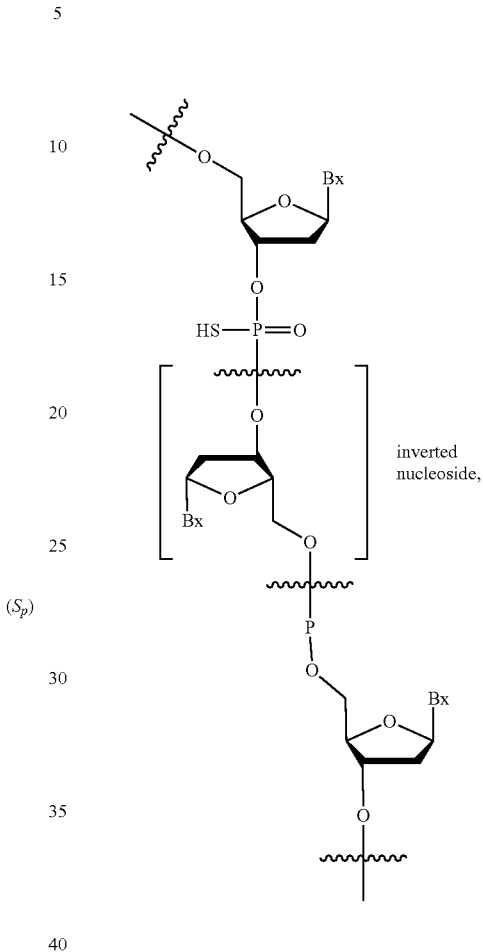

inverted nucleoside, wherein each Bx independently represents any nucleobase.

In certain embodiments, an inverted nucleoside is terminal (i.e., the last nucleoside on one end of an oligonucleotide) and so only one internucleoside linkage depicted above will be present. In certain such embodiments, additional features (such as a conjugate group) may be attached to the inverted nucleoside. Such terminal inverted nucleosides can be attached to either or both ends of an oligonucleotide.

In certain embodiments, such groups lack a nucleobase and are referred to herein as inverted sugar moieties. In certain embodiments, an inverted sugar moiety is terminal (i.e., attached to the last nucleoside on one end of an oligonucleotide) and so only one internucleoside linkage above will be present. In certain such embodiments, additional features (such as a conjugate group) may be attached to the inverted sugar moiety. Such terminal inverted sugar moieties can be attached to either or both ends of an oligonucleotide.

In certain embodiments, nucleic acids can be linked 2' to 5' rather than the standard 3' to 5' linkage. Such a linkage is illustrated below.

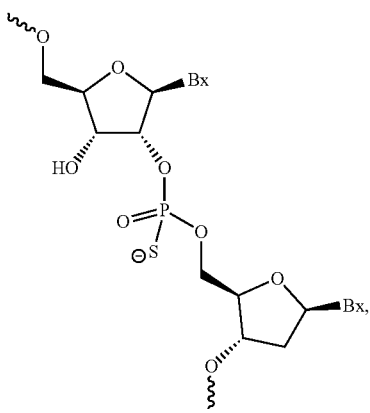

wherein each Bx represents any nucleobase.

B. Certain Motifs

In certain embodiments, modified oligonucleotides comprise one or more modified nucleosides comprising a modified sugar moiety. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

Gapmer Oligonucleotides

In certain embodiments, modified oligonucleotides comprise or consist of a region having a gapmer motif, which is defined by two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-6 nucleosides. In certain embodiments, each nucleoside of each wing of a gapmer comprises a modified sugar moiety. In certain embodiments, at least one nucleoside of each wing of a gapmer comprises a modified sugar moiety. In certain embodiments, at least two nucleosides of each wing of a gapmer comprises a modified sugar moiety. In certain embodiments, at least three nucleosides of each wing of a gapmer comprises a modified sugar moiety. In certain embodiments, at least four nucleosides of each wing of a gapmer comprises a modified sugar moiety.

In certain embodiments, the gap of a gapmer comprises 7-12 nucleosides. In certain embodiments, each nucleoside of the gap of a gapmer comprises a 2'-β-D-deoxyribosyl sugar moiety. In certain embodiments, at least one nucleoside of the gap of a gapmer comprises a modified sugar moiety.

In certain embodiments, the gapmer is a deoxy gapmer. In certain embodiments, the nucleosides on the gap side of each wing/gap junction comprise 2'-deoxyribosyl sugar moieties and the nucleosides on the wing sides of each wing/gap junction comprise modified sugar moieties. In certain embodiments, each nucleoside of the gap comprises a 2'-β-D-deoxyribosyl sugar moiety. In certain embodiments, each nucleoside of each wing of a gapmer comprises a modified sugar moiety. In certain embodiments, at least one nucleoside of the gap of a gapmer comprises a modified sugar moiety. In certain embodiments, one nucleoside of the gap comprises a modified sugar moiety and each remaining nucleoside of the gap comprises a 2'-deoxyribosyl sugar moiety. In certain embodiments, at least one nucleoside of the gap of a gapmer comprises a 2'-OMe sugar moiety.

Herein, the lengths (number of nucleosides) of the three regions of a gapmer may be provided using the notation [# of nucleosides in the 5'-wing]—[# of nucleosides in the gap]—[# of nucleosides in the 3'-wing]. Thus, a 3-10-3 gapmer consists of 3 linked nucleosides in each wing and 10 linked nucleosides in the gap. Where such nomenclature is followed by a specific modification, that modification is the modification in each sugar moiety of each wing and the gap nucleosides comprise 2'-β-D-deoxyribosyl sugar moieties. Thus, a 5-10-5 MOE gapmer consists of 5 linked 2'-MOE nucleosides in the 5'-wing, 10 linked 2'-β-D-deoxynucleosides in the gap, and 5 linked 2'-MOE nucleosides in the 3'-wing. A 6-10-4 MOE gapmer consists of 6 linked 2'-MOE nucleosides in the 5'-wing, 10 linked 2'-β-D-deoxynucleosides in the gap, and 4 linked 2'-MOE nucleosides in the 3'-wing. A 3-10-3 cEt gapmer consists of 3 linked cEt nucleosides in the 5'-wing, 10 linked 2'-β-D-deoxynucleosides in the gap, and 3 linked cEt nucleosides in the 3'-wing.

In certain embodiments, modified oligonucleotides are 5-10-5 MOE gapmers. In certain embodiments, modified oligonucleotides are 6-10-4 MOE gapmers.

In certain embodiments, modified oligonucleotides have a sugar motif selected from 5' to 3': eeeeedddddddddeeeee; wherein each "d" represents a 2'-β-D-deoxyribosyl sugar moiety, and each "e" represents a 2'-MOE sugar moiety.

In certain embodiments, modified oligonucleotides have a sugar motif selected from 5' to 3': eeeeeedddddddddeeee; wherein each "d" represents a 2'-β-D-deoxyribosyl sugar moiety, and each "e" represents a 2'-MOE sugar moiety.

In certain embodiments, modified oligonucleotides are 5-10-5 cEt gapmers.

In certain embodiments, modified oligonucleotides have the sugar motif from 5' to 3': kkkdddddddddddkkk; wherein each "d" represents a 2'-β-D-deoxyribosyl sugar moiety, and each "k" represents a cEt sugar moiety.

In certain embodiments, modified oligonucleotides have the sugar motif from 5' to 3': kkkdyddddddddkkk; wherein each "d" represents a 2'-β-D-deoxyribosyl sugar moiety, each "y" represents a 2'-OMe sugar moiety, and each "k" represents a cEt sugar moiety.

In certain embodiments, modified oligonucleotides have the sugar motif from 5' to 3': kkedddddddddkkk; wherein each "d" represents a 2'-β-D-deoxyribosyl sugar moiety, each "e" represents a 2'-MOE sugar moiety, and each "k" represents a cEt sugar moiety.

2. Certain Nucleobase Motifs

In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each cytosine is modified. In certain embodiments, some or all of the cytosine nucleobases in a modified oligonucleotide are 5-methylcytosines. In certain embodiments, all of the cytosine nucleobases are 5-methylcytosines and all of the other nucleobases of the modified oligonucleotide are unmodified nucleobases.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl sugar moiety.

3. Certain Internucleoside Linkage Motifs

In certain embodiments, oligonucleotides comprise modified and/or unmodified internucleoside linkages arranged along the oligonucleotide or region thereof in a defined pattern or motif. In certain embodiments, each internucleoside linking group is a phosphodiester internucleoside linkage (P=O). In certain embodiments, each internucleoside linking group of a modified oligonucleotide is a phosphorothioate internucleoside linkage (P=S). In certain embodiments, each internucleoside linkage of a modified oligonucleotide is independently selected from a phosphorothioate internucleoside linkage and phosphodiester internucleoside linkage. In certain embodiments, each phosphorothioate internucleoside linkage is independently selected from a stereorandom phosphorothioate, a (Sp) phosphorothioate, and a (Rp) phosphorothioate.

In certain embodiments, the sugar motif of a modified oligonucleotide is a gapmer and the internucleoside linkages within the gap are all modified. In certain such embodiments, some, or all of the internucleoside linkages in the wings are unmodified phosphodiester internucleoside linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester linkage is not a terminal internucleoside linkage, and the remaining internucleoside linkages are phosphorothioate internucleoside linkages. In certain such embodiments, all of the phosphorothioate linkages are stereorandom. In certain embodiments, all of the phosphorothioate linkages in the wings are (Sp) phosphorothioates, and the gap comprises at least one Sp, Sp, Rp motif. In certain embodiments, populations of modified oligonucleotides are enriched for modified oligonucleotides comprising such internucleoside linkage motifs.

In certain embodiments, modified oligonucleotides have an internucleoside linkage motif of (5' to 3'): sooosssssssssssooss wherein each "s" represents a phosphorothioate internucleoside linkage and each "o" represents a phosphodiester internucleoside linkage. In certain embodiments, modified oligonucleotides have an internucleoside linkage motif of (5' to 3'): sooooossssssssssoss, wherein each "s" represents a phosphorothioate internucleoside linkage and each "o" represents a phosphodiester internucleoside linkage. In certain embodiments, modified oligonucleotides have an internucleoside linkage motif of (5' to 3'): soossssssssssos, wherein each "s" represents a phosphorothioate internucleoside linkage and each "o" represents a phosphodiester internucleoside linkage.

Certain Oligomeric Compounds

In certain embodiments, provided herein are oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance.

In certain embodiments, conjugation of one or more carbohydrate moieties to a modified oligonucleotide can optimize one or more properties of the modified oligonucleotide. In certain embodiments, the carbohydrate moiety is attached to a modified subunit of the modified oligonucleotide. For example, the ribose sugar of one or more ribonucleotide subunits of a modified oligonucleotide can be replaced with another moiety, e.g. a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS), which is a modified sugar moiety. A cyclic carrier may be a carbocyclic ring system, i.e., one or more ring atoms may be a heteroatom, e.g., nitrogen, oxygen, sulphur. The cyclic carrier may be a monocyclic ring system, or may contain two or more rings, e.g. fused rings. The cyclic carrier may be a fully saturated ring system, or it may contain one or more double bonds. In certain embodiments, the modified oligonucleotide is a gapmer.

In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., *Proc. Natl. Acad. Sci. USA*, 1989, 86, 6553-6556), cholic acid (Manoharan et al., *Bioorg. Med. Chem. Lett.*, 1994, 4, 1053-1060), a thioether, e.g., hexyl-S-tritylthiol (Manoharan et al., *Ann. N. Y. Acad. Sci.*, 1992, 660, 306-309; Manoharan et al., *Bioorg. Med. Chem. Lett.*, 1993, 3, 2765-2770), a thiocholesterol (Oberhauser et al., *Nucl. Acids Res.*, 1992, 20, 533-538), an aliphatic chain, e.g., do-decan-diol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid a palmityl moiety (Mishra et al., *Biochim. Biophys. Acta*, 1995, 1264, 229-237), an octadecylamine or hexylamino-carbonyl-oxycholesterol moiety (Crooke et al., *J. Pharmacol. Exp. Ther.*, 1996, 277, 923-937), a tocopherol group (Nishina et al., *Molecular Therapy Nucleic Acids*, 2015, 4, e220; and Nishina et al., *Molecular Therapy*, 2008, 16, 734-740), or a GalNAc cluster (e.g., WO2014/179620).

In certain embodiments, the conjugate group may comprise a conjugate moiety selected from any of a C22 alkyl, C20 alkyl, C16 alkyl, C10 alkyl, C21 alkyl, C19 alkyl, C18 alkyl, C15 alkyl, C14 alkyl, C13 alkyl, C12 alkyl, C11 alkyl, C9 alkyl, C8 alkyl, C7 alkyl, C6 alkyl, C5 alkyl, C22 alkenyl, C20 alkenyl, C16 alkenyl, C10 alkenyl, C21 alkenyl, C19 alkenyl, C18 alkenyl, C15 alkenyl, C14 alkenyl, C13 alkenyl, C12 alkenyl, C11 alkenyl, C9 alkenyl, C8 alkenyl, C7 alkenyl, C6 alkenyl, or C5 alkenyl.

In certain embodiments, the conjugate group may comprise a conjugate moiety selected from any of a C22 alkyl, C20 alkyl, C16 alkyl, C10 alkyl, C21 alkyl, C19 alkyl, C18 alkyl, C15 alkyl, C14 alkyl, C13 alkyl, C12 alkyl, C11 alkyl, C9 alkyl, C8 alkyl, C7 alkyl, C6 alkyl, or C5 alkyl, where the alkyl chain has one or more unsaturated bonds.

In certain embodiments, a conjugate group is a lipid having the following structure:

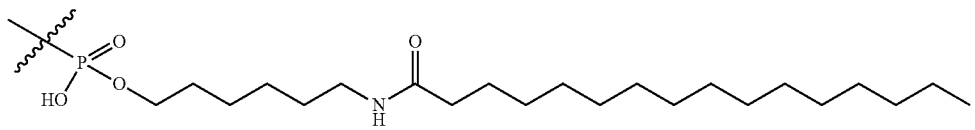 [SMILES: *P(=O)(O)OCCCCCCNC(=O)CCCCCCCCCCCCCCC]

1. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises pyrrolidine.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate moieties to compounds, such as the oligonucleotides provided herein. In general, a bifunctional linking moiety comprises at least two functional groups. One of the functional groups is selected to react with a particular site on a compound and the other is selected to react with a conjugate moiety. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxynucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

3. Cell-Targeting Moieties

In certain embodiments, a conjugate group comprises a cell-targeting moiety. In certain embodiments, a conjugate group has the general formula:

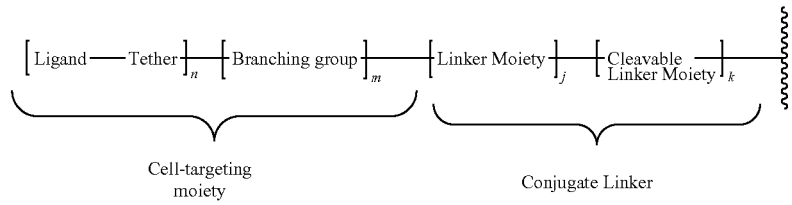

wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group.

In certain embodiments, each ligand of a cell-targeting moiety has an affinity for at least one type of receptor on a target cell. In certain embodiments, each ligand has an affinity for at least one type of receptor on the surface of a mammalian liver cell. In certain embodiments, each ligand has an affinity for the hepatic asialoglycoprotein receptor (ASGP-R). In certain embodiments, each ligand is a carbohydrate.

In certain embodiments, a conjugate group comprises a cell-targeting conjugate moiety. In certain embodiments, a conjugate group has the general formula:

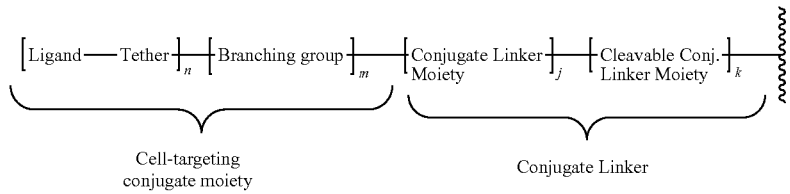

wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group. In certain embodiments, cell-targeting moieties comprise three tethered ligands covalently attached to a branching group.

In certain embodiments, the cell-targeting moiety binds a cell surface receptor on a muscle cell. In certain embodiments, the cell-targeting moiety binds a cell surface receptor on a muscle cell. In certain embodiments, the cell-targeting moiety binds a cell surface receptor on a skeletal muscle cell. In some embodiments, the cell-targeting moiety binds a transferrin receptor. In certain embodiments, the cell-targeting moiety is an antibody that binds a transferrin receptor (e.g., Sugo et al., Development of an antibody-siRNA conjugate targeted to cardiac and skeletal muscles, J Controlled Release 237:1-13 (2016)). In some embodiments, the antibody that binds a transferrin receptor is a humanized antibody, a chimeric antibody, a monoclonal antibody, or a recombinant or engineered version thereof. In certain embodiments, the cell-targeting moiety is an antibody fragment that binds a transferrin receptor. In some embodiments, the antibody fragment that binds a transferrin receptor is a F(ab')$_2$, a Fab, a Fab', a Fv, recombinant or engineered versions thereof, or engineered peptides.

B. Certain Terminal Groups

In certain embodiments, oligomeric compounds comprise one or more terminal groups. In certain such embodiments, oligomeric compounds comprise a stabilized 5'-phosphate. Stabilized 5'-phosphates include, but are not limited to 5'-phosphonates, including, but not limited to 5'-vinylphosphonates. In certain embodiments, terminal groups comprise one or more abasic sugar moieties and/or inverted nucleosides. In certain embodiments, terminal groups comprise one or more 2'-linked nucleosides or sugar moieties. In certain such embodiments, the 2'-linked group is an abasic sugar moiety.

II. Antisense Activity

In certain embodiments, oligomeric compounds and oligomeric duplexes are capable of hybridizing to a target nucleic acid, resulting in at least one antisense activity; such oligomeric compounds and oligomeric duplexes are antisense compounds. In certain embodiments, antisense compounds have antisense activity when they reduce or inhibit the amount or activity of a target nucleic acid by 25% or more in the standard cell assay. In certain embodiments, antisense compounds selectively affect one or more target nucleic acid. Such antisense compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, described herein are antisense compounds that are sufficiently "DNA-like" to elicit RNase H activity. In certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute. Antisense compounds that are loaded into RISC are RNAi compounds. RNAi compounds may be double-stranded (siRNA or dsRNAi) or single-stranded (ssRNA).

In certain embodiments, hybridization of an antisense compound to a target nucleic acid does not result in recruitment of a protein that cleaves that target nucleic acid. In certain embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein and/or a phenotypic change in a cell or animal.

III. Certain Target Nucleic Acids

In certain embodiments, oligomeric compounds comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: a mature mRNA and a pre-mRNA, including intronic, exonic and untranslated regions. In certain embodiments, the target RNA is a mature mRNA. In certain embodiments, the target nucleic acid is a pre-mRNA. In certain embodiments, the target region is entirely within an intron. In certain embodiments, the target region spans an intron/exon junction. In certain embodiments, the target region is at least 50% within an intron.

A. DMPK

In certain embodiments, oligomeric compounds comprise or consist of an oligonucleotide comprising a region that is complementary to a target nucleic acid, wherein the target nucleic acid is a DMPK nucleic acid. In certain embodiments, a DMPK nucleic acid has the sequence set forth in SEQ ID NO: 1 (the complement of GENBANK Accession No. NT_011109.16, truncated from nucleotides 18539000 to 18566000), SEQ ID NO: 2 (GENBANK Accession No. NM_004409.4). In certain embodiments, a DMPK nucleic acid has the sequence set forth in SEQ ID NO: 3 (the complement of GENBANK Accession No. NC_000019.10, truncated from nucleotides 45767001 to 45786000), SEQ ID NO: 4 (GENBANK Accession No. NM_001288764.1), and/or SEQ ID NO: 5 (GENBANK Accession No. NM_001081560.2).

In certain embodiments, contacting a cell with an oligomeric compound complementary to SEQ ID NO: 1 or SEQ ID NO: 2 reduces the amount of DMPK RNA, and in certain embodiments reduces the amount of DMPK protein. In certain embodiments, contacting a cell with an oligomeric compound complementary to SEQ ID NO: 3, SEQ ID NO: 4, and/or SEQ ID NO: 5 reduces the amount of DMPK RNA, and in certain embodiments reduces the amount of DMPK protein. In certain embodiments, the oligomeric compound consists of a modified oligonucleotide. In certain embodiments, the oligomeric compound consists of a modified oligonucleotide and a conjugate group.

B. Certain Target Nucleic Acids in Certain Tissues

In certain embodiments, oligomeric compounds comprise or consist of an oligonucleotide comprising a region that is complementary to a target nucleic acid, wherein the target nucleic acid is expressed in a pharmacologically relevant tissue. In certain embodiments, the pharmacologically relevant tissues are muscle tissues, such as tibialis anterior, gastrocnemius, and quadriceps muscles. In certain embodiments, the pharmacologically relevant tissue is heart muscle tissue. In certain embodiments, the target nucleic acid is expressed in a pharmacologically relevant cell. In certain embodiments the pharmacologically relevant cell is a muscle cell. In certain embodiments the pharmacologically relevant cell is a skeletal muscle cell.

IV. Certain Pharmaceutical Compositions

In certain embodiments, described herein are pharmaceutical compositions comprising one or more oligomeric compounds. In certain embodiments, the one or more oligomeric compounds each consists of a modified oligonucleotide. In certain embodiments, the pharmaceutical composition comprises a pharmaceutically acceptable diluent or carrier. In certain embodiments, a pharmaceutical composition comprises or consists of a sterile saline solution and one or more oligomeric compound. In certain embodiments, the sterile saline is pharmaceutical grade saline. In certain embodiments, a pharmaceutical composition comprises or consists of one or more oligomeric compound and sterile water. In certain embodiments, the sterile water is pharmaceutical grade water. In certain embodiments, a pharmaceutical composition comprises or consists of one or more oligomeric compound and phosphate-buffered saline (PBS). In certain embodiments, the sterile PBS is pharmaceutical grade PBS. In certain embodiments, a pharmaceutical composition comprises or consists of one or more oligomeric compound and artificial cerebrospinal fluid. In certain embodiments, the artificial cerebrospinal fluid is pharmaceutical grade artificial cerebrospinal fluid.

In certain embodiments, a pharmaceutical composition comprises a modified oligonucleotide and PBS. In certain embodiments, a pharmaceutical composition consists of a modified oligonucleotide and PBS. In certain embodiments, a pharmaceutical composition consists essentially of a modified oligonucleotide and PBS. In certain embodiments, the PBS is pharmaceutical grade.

In certain embodiments, a pharmaceutical composition comprises a modified oligonucleotide and artificial cerebrospinal fluid. In certain embodiments, a pharmaceutical composition consists of a modified oligonucleotide and artificial cerebrospinal fluid. In certain embodiments, a pharmaceutical composition consists essentially of a modified oligonucleotide and artificial cerebrospinal fluid. In certain embodiments, the artificial cerebrospinal fluid is pharmaceutical grade.

In certain embodiments, pharmaceutical compositions comprise one or more oligomeric compound and one or more excipients. In certain embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, oligomeric compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an oligomeric compound encompass any pharmaceutically acceptable salts of the oligomeric compound, esters of the oligomeric compound, or salts of such esters. In certain embodiments, pharmaceutical compositions comprising oligomeric compounds comprising one or more oligonucleotide, upon administration to an animal, including a human, are capable of providing (directly or indirectly) the biologically active metabolite or residue thereof. Accordingly, for example, the disclosure is also drawn to pharmaceutically acceptable salts of oligomeric compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an oligomeric compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, intrathecal (IT), intracerebroventricular (ICV), etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes.

Under certain conditions, certain compounds disclosed herein act as acids. Although such compounds may be drawn or described in protonated (free acid) form, or ionized and in association with a cation (salt) form, aqueous solutions of such compounds exist in equilibrium among such forms. For example, a phosphate linkage of an oligonucleotide in aqueous solution exists in equilibrium among free acid, anion and salt forms. Unless otherwise indicated, compounds described herein are intended to include all such forms. Moreover, certain oligonucleotides have several such linkages, each of which is in equilibrium. Thus, oligonucleotides in solution exist in an ensemble of forms at multiple positions all at equilibrium. The term "oligonucleotide" is intended to include all such forms. Drawn structures necessarily depict a single form. Nevertheless, unless otherwise indicated, such drawings are likewise intended to include corresponding forms. Herein, a structure depicting the free acid of a compound followed by the term "or a salt thereof" expressly includes all such forms that may be fully or partially protonated/de-protonated/in association with a cation. In certain instances, one or more specific cation is identified.

In certain embodiments, modified oligonucleotides or oligomeric compounds are in aqueous solution with sodium. In certain embodiments, modified oligonucleotides or oligomeric compounds are in aqueous solution with potassium. In certain embodiments, modified oligonucleotides or oligomeric compounds are in PBS. In certain embodiments, modified oligonucleotides or oligomeric compounds are in water. In certain such embodiments, the pH of the solution is adjusted with NaOH and/or HCl to achieve a desired pH.

Herein, certain specific doses are described. A dose may be in the form of a dosage unit. For clarity, a dose (or dosage unit) of a modified oligonucleotide or an oligomeric compound in milligrams indicates the mass of the free acid form of the modified oligonucleotide or oligomeric compound. As described above, in aqueous solution, the free acid is in equilibrium with anionic and salt forms. However, for the purpose of calculating dose, it is assumed that the modified oligonucleotide or oligomeric compound exists as a solvent-free, sodium-acetate free, anhydrous, free acid. For example, where a modified oligonucleotide or an oligomeric compound is in solution comprising sodium (e.g., saline), the modified oligonucleotide or oligomeric compound may be partially or fully de-protonated and in association with $Na^+$ ions. However, the mass of the protons is nevertheless counted toward the weight of the dose, and the mass of the $Na^+$ ions is not counted toward the weight of the dose. Thus, for example, a dose, or dosage unit, of 10 mg of Compound No. 1522461, equals the number of fully protonated molecules that weighs 10 mg. This would be equivalent to 10.62 mg of solvent-free, sodium acetate-free, anhydrous sodiated Compound No. 1522461. When an oligomeric compound comprises a conjugate group, the mass of the conjugate group is included in calculating the dose of such oligomeric compound. If the conjugate group also has an acid, the conjugate group is likewise assumed to be fully protonated for the purpose of calculating dose.

Certain Comparator Compositions

In certain embodiments, ISIS-DMPK$_{Rx}$ (generic name baliforsen; Compound No. 598769), entered into clinical trials for treatment of DM1, is a comparator compound (see, e.g., Thorton, et al., Neurology, 86(16 supplement): P3.163, 2016). ISIS-DMPK$_{Rx}$, 598769 was previously described in WO2015/021457, incorporated herein by reference, and has a nucleobase sequence (from 5' to 3') of TCCCGAATGTCCGACA (SEQ ID NO: 34). The sugar motif for Compound No. 598769 is (from 5' to 3'): eekkddddddddkkee; wherein each "e" represents a 2'-MOE sugar moiety, each "d" represents a 2'-β-D-deoxyribosyl sugar moiety, and each "k" represents a cEt sugar moiety. The internucleoside linkage motif for Compound No. 598769 is (from 5' to 3'): ssssssssssssss; wherein each "s" represents a phosphorothioate internucleoside linkage. Each cytosine nucleobase in Compound No. 598769 is a 5-methylcytosine.

In certain embodiments, Compound No. 486178, although not entered into clinical trials, is a comparator compound (see, e.g., Yadava, et al., Hum. Mol. Genetics, 29(9): 1440-1453, 2020; Pandey, et al., J. Pharamacol. Expt. Therapy, 355(2):329-340, 2015). Compound No. 486178 was previously described in WO 2015/021457 A2, WO 2017/053995 A1, and WO 2019/118916 A1, each of which is incorporated herein by reference, and consists of the nucleobase sequence (from 5' to 3'): ACAATAAATACCGAGG (SEQ ID NO: 33). The sugar motif for Compound No. 486178 is (from 5' to 3'): kkkddddddddddkkk; wherein each "d" represents a 2'-β-D-deoxyribosyl sugar moiety, and each "k" represents a cEt sugar moiety. The internucleoside linkage motif for Compound No. 486178 is (from 5' to 3'): ssssssssssssss; wherein each "s" represents a phosphorothioate internucleoside linkage. Each cytosine nucleobase in Compound No. 486178 is a 5-methylcytosine.

In certain embodiments, compounds described herein are superior relative to compounds described WO2015/021457, because they demonstrate one or more improved properties, such as activity, potency, and/or tolerability.

For example, Compound No. 1400741, Compound No. 1522459, and Compound No. 1522461, Compound No. 1522464, and Compound No. 1525073 each demonstrated improved potency in vitro as compared to Compound No. 486178.

As shown in Example 2, Compound No. 1400741, Compound No. 1522459, and Compound No. 1522461, Compound No. 1522464, and Compound No. 1525073 achieved an in vitro IC$_{50}$ of 0.04 μM, 0.03 μM, 0.09 μM, 0.21 μM, and 0.18 μM, respectively. In comparison, Compound No. 486178 achieved an in vitro IC$_{50}$ of >2 μM. Therefore, each of Compound No. 1400741, Compound No. 1522459, and Compound No. 1522461, Compound No. 1522464, and Compound No. 1525073 are more potent than Compound No. 486178 in this assay.

For example, Compound No. 1400741, Compound No. 1522459, and Compound No. 1522461, Compound No. 1522464, and Compound No. 1525073 each demonstrated reduced liver toxicity compared to compound No. 598769. In order to assess liver toxicity in a short time frame, each compound was conjugated to a triantennary THA-GalNAc moiety, shown below. This ensures delivery of the modified oligonucleotide to the liver, and shows liver toxicity that otherwise might not be detected outside of longer term, repeat-dosing studies.

For example, at 96 hours after dosing, as shown in the table below, Compound No. 1400741 conjugated to THA-GalNAc, Compound. No. 1525079, achieves an ALT value of 54 (U/L), and an AST value of 62 (U/L). Compound No. 1522459 conjugated to THA-GalNAc, Compound. No. 1522487, achieves an ALT value of 30 (U/L), and an AST value of 49 (U/L). Compound No. 1522461 conjugated to THA-GalNAc, Compound. No. 1522489, achieves an ALT value of 46 (U/L), and an AST value of 76 (U/L). Compound No. 1522464 conjugated to THA-GalNAc, Compound. No. 1522492, achieves an ALT value of 65 (U/L), and an AST value of 81 (U/L). Compound No. 1525073 conjugated to THA-GalNAc, Compound. No. 1525089, achieves an ALT value of 67(U/L), and an AST value of 70 (U/L). In comparison, Compound No. 1525074, Compound No. 598769 conjugated to THA-GalNAcc, achieved an ALT value of 848 (U/L) and an AST value of 600 (U/L). Therefore, each of Compound No. 1400741, Compound No. 1522459, and Compound No. 1522461, Compound No. 1522464, and Compound No. 1525073 are more tolerable than Compound No. 598769 in this assay.

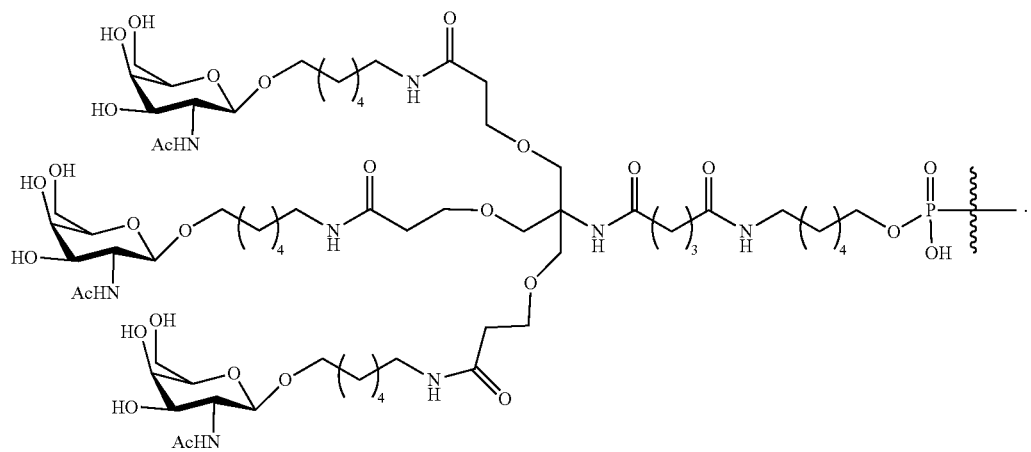

THA-GalNAc

TABLE 1

Plasma chemistry markers in BALB/c mice for GalNAc-conjugated oligomeric compounds

| Compound No. | Unconjugated Parent Compound No. | ALT (U/L) | AST(U/L) |
|---|---|---|---|
| PBS | N/A | 61 | 149 |
| 1525074 | 598769 | 848 | 600 |
| 1525079 | 1400741 | 54 | 62 |
| 1522487 | 1522459 | 30 | 49 |
| 1522489 | 1522461 | 46 | 76 |
| 1522492 | 1522464 | 65 | 81 |
| 1525089 | 1525073 | 67 | 70 |

NONLIMITING DISCLOSURE AND INCORPORATION BY REFERENCE

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references, GenBank accession numbers, ENSEMBL identifiers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of an uracil of RNA). Accordingly, nucleic acid sequences provided herein, including, but not limited to those in the sequence listing, are intended to encompass nucleic acids containing any combination of natural or modified RNA and/or DNA, unless otherwise stated, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^m$CGAUCG," wherein $^m$C indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms, unless specified otherwise. Likewise, tautomeric forms of the compounds herein are also included unless otherwise indicated. Unless otherwise indicated, compounds described herein are intended to include corresponding salt forms.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^1H$ hydrogen atoms. Isotopic substitutions encompassed by the compounds herein include but are not limited to: $^2H$ or $^3H$ in place of $^1H$, $^{13}C$ or $^{14}C$ in place of $^{12}C$, $^{15}N$ in place of $^{14}N$, $^{17}O$ or $^{18}O$ in place of $^{16}O$ and $^{33}S$, $^{34}S$, $^{35}S$, or $^{36}S$ in place of $^{32}S$. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1: Design of Modified Oligonucleotides Complementary to Human DMPK Nucleic Acid Modified oligonucleotides complementary to a human DMPK nucleic acid were designed, as described in the tables below. "Start site" indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence. Each modified oligonucleotide listed in the tables below is 100% complementary to SEQ ID NO: 1 (the complement of GENBANK Accession No. NT_011109.16, truncated from nucleotides 18539000 to 18566000), or to SEQ ID NO: 2 (GENBANK Accession No. NM_004409.4), or to both.

Compound 598769 (ISIS DMPK-Rx) and Compound No. 486178 were previously described in WO2015/021457.

Design of Modified Oligonucleotides Complementary to Human DMPK

| Compound Number | Chemistry Notation (5'-3') | Start Site SEQ ID NO: 1 | Stop Site SEQ ID NO: 1 | Start Site SEQ ID NO: 2 | Start Site SEQ ID NO: 2 | SEQ ID NO. |
|---|---|---|---|---|---|---|
| 486178 | $A_{ks}{}^mC_{ks}A_{ks}A_{ds}T_{ds}A_{ds}A_{ds}A_{ds}T_{ds}A_{ds}{}^mC_{ds}{}^mC_{ds}G_{ds}A_{ks}G_{ks}G_k$ | 24730 | 24745 | 2788 | 2803 | 19 |
| 598769 | $T_{es}{}^mC_{es}{}^mC_{ks}{}^mC_{ks}G_{ds}A_{ds}A_{ds}T_{ds}G_{ds}T_{ds}{}^mC_{ds}{}^mC_{ds}G_{ks}A_{ks}{}^mC_{es}A_e$ | 19498 | 19513 | 1359 | 1374 | 12 |
| 1400741 | $T_{ks}T_{ks}{}^mC_{ks}{}^mC_{ds}\underline{\mathit{C}}_{ys}G_{ds}A_{ds}A_{ds}T_{ds}G_{ds}T_s{}^mC_{ds}{}^mC_{ds}G_{ks}A_{ks}{}^mC_k$ | 19499 | 19514 | 1360 | 1375 | 20 |
| 1522459 | ${}^mC_{ks}G_{ko}A_{ko}A_{ds}U_{ys}G_{ds}T_{ds}{}^mC_{ds}{}^mC_{ds}G_{ds}A_{ds}{}^mC_{ds}A_{ds}G_{ko}T_{ks}G_k$ | 19495 | 19510 | 1356 | 1371 | 14 |
| 1522461 | $T_{ks}T_{ko}{}^mC_{ko}{}^mC_{ds}\underline{\mathit{C}}_{ys}G_{ds}A_{ds}A_{ds}T_{ds}G_{ds}T_{ds}{}^mC_{ds}{}^mC_{ds}G_{ko}A_{ks}{}^mC_k$ | 19499 | 19514 | 1360 | 1375 | 13 |
| 1522464 | ${}^mC_{ks}T_{ko}T_{eo}T_{ds}T_{ds}A_{ds}T_{ds}T_{ds}{}^mC_{ds}G_{ds}{}^mC_{ds}G_{ds}A_{ds}G_{ko}G_{ks}G_k$ | 24775 | 24790 | 2833 | 2848 | 15 |
| 1525073 | $A_{ks}{}^mC_{ko}A_{ko}A_{ds}T_{ds}A_{ds}A_{ds}A_{ds}T_{ds}A_{ds}{}^mC_{ds}{}^mC_{ds}G_{ds}A_{ko}G_{ks}G_k$ | 24730 | 24745 | 2788 | 2803 | 11 |

A subscript "k" represents a cEt sugar moiety, a subscript "y" represents a 2'-OMe sugar moiety, a subscript "e" represents a 2'-MOE sugar moiety, a subscript "d" represents a 2'-β-D-deoxyribosyl sugar moiety, a subscript "s" indicates a phosphorothioate internucleoside linkage, a subscript "o" represents a phosphodiester internucleoside linkage, and superscript "m" before a C represents a 5-methylcytosine, while a bold, underlined, italicized "*C*" without a superscript "m" is a non-methylated cytosine.

Example 2: Dose-Dependent Inhibition of Human DMPK in A431 Cells by Modified Oligonucleotides Modified oligonucleotides were tested at various doses in A431 cells. Cells were plated at a density of 11,000 cells per well and were treated using free uptake with modified oligonucleotides at various doses, as specified in the table below. After a treatment period of approximately 48 hours, DMPK RNA levels were measured by quantitative real-time RTPCR using the human DMPK primer-probe set RTS38095 (forward sequence CTGAGCCGG-GAGATGGA, designated herein as SEQ ID NO: 6; reverse sequence GGACGTGTGCCTCTAGGT, designated herein as SEQ ID NO: 7; probe sequence TGACTGGCGAAGTTCTGGTTGTCC, designated herein as SEQ ID NO: 8). DMPK RNA levels were normalized to total RNA, as measured by human GAPDH. Human GAPDH was amplified using the human primer probe set RTS104 (forward sequence GAAGGTGAAGGTCG-GAGTC, designated herein as SEQ ID NO: 16; reverse sequence GAAGATGGTGATGGGATTTC, designated herein as SEQ ID NO: 17; probe sequence CAAGCTTCCCGTTCTCAGCC, designated herein as SEQ ID NO: 18). Results are presented as percent DMPK RNA, relative to the amount in untreated control cells (% UTC).

The half maximal inhibitory concentration ($IC_{50}$) of each modified oligonucleotide was calculated using the log (inhibitor) vs. normalized response—variable slope in GraphPad Prism and is also presented in the tables below.

TABLE 2

Dose-dependent reduction of human DMPK RNA in A431 cells by modified oligonucleotides

| Compound No. | DMPK RNA (% UTC) | | | | $IC_{50}$ (µM) |
|---|---|---|---|---|---|
| | 31 nM | 125 nM | 500 nM | 2000 nM | |
| 486178 | 108 | 83 | 78 | 54 | >2.0 |

TABLE 3

Dose-dependent reduction of human DMPK RNA in A431 cells by modified oligonucleotides

| Compound No. | DMPK RNA (% UTC) | | | | | | | | $IC_{50}$ (µM) |
|---|---|---|---|---|---|---|---|---|---|
| | 3 nM | 9 nM | 27 nM | 82 nM | 247 nM | 741 nM | 2222 nM | 6667 nM | 20000 nM | |
| 598769 | 88 | 85 | 58 | 38 | 21 | 8 | 5 | 5 | 2 | 0.05 |
| 1400741 | 90 | 75 | 62 | 36 | 17 | 14 | 9 | 5 | 5 | 0.04 |
| 1522459 | 87 | 80 | 55 | 31 | 9 | 5 | 3 | 2 | 2 | 0.03 |
| 1522461 | 84 | 76 | 75 | 53 | 31 | 17 | 15 | 9 | 8 | 0.09 |
| 1522464 | 78 | 78 | 76 | 71 | 50 | 30 | 21 | 15 | 10 | 0.21 |
| 1525073 | 85 | 89 | 80 | 64 | 44 | 28 | 14 | 7 | 4 | 0.18 |

Example 3: Dose-Dependent Inhibition of Human DMPK in SH-SY5Y Cells by Modified Oligonucleotides Modified oligonucleotides were tested at various doses in SH-SY5Y cells. Cells were plated at a density of 35,000 cells per well and were treated using electroporation with modified oligonucleotides at various doses, as specified in the table below. After a treatment period of approximately 24 hours, DMPK RNA levels were measured by quantitative real-time RTPCR using the human DMPK primer-probe set RTS38095 (described herein above). DMPK RNA levels were normalized to total RNA, as measured by human GAPDH. Human GAPDH was amplified using the human primer probe set RTS104 (described herein above). Results are presented as percent of DMPK RNA, relative to the amount in untreated control cells (% UTC).

The half maximal inhibitory concentration ($IC_{50}$) of each modified oligonucleotide was calculated using the log (inhibitor) vs. normalized response—variable slope in GraphPad Prism and is also presented in the tables below.

oligonucleotide listed in the tables below is 100% complementary to SEQ ID NO: 1 (the complement of GENBANK Accession No. NT_011109.16, truncated from nucleotides 18539000 to 18566000), or to SEQ ID NO: 2 (GENBANK Accession No. NM_004409.4), or to both.

The modified oligonucleotides in the table below are 16 nucleosides in length. The sugar motifs for the modified oligonucleotides are described in the column labeled "Sugar Motif (5' to 3')" in the table below, wherein each "k" represents a cEt sugar moiety, each "e" represents a 2'-MOE sugar moiety, each "d" represents a 2'-β-D-deoxyribosyl sugar moiety, and each "y" represents a 2'-O-methylribosyl sugar moiety. The internucleoside linkage motif for the modified oligonucleotides is (from 5' to 3'): soosssssssssos, wherein each "s" represents a phosphorothioate internucleoside linkage and each "o" represents a phosphodiester inter-

TABLE 4

Dose-dependent reduction of human DMPK RNA in SH-SY5Y cells by modified oligonucleotides

| Compound | DMPK RNA (% UTC) | | | | | | | | | $IC_{50}$ |
|---|---|---|---|---|---|---|---|---|---|---|
| No. | 3 nM | 9 nM | 27 nM | 82 nM | 247 nM | 741 nM | 2222 nM | 6667 nM | 20000 nM | (µM) |
| 598769 | 91 | 61 | 50 | 27 | 25 | 27 | 10 | 6 | 4 | 0.03 |
| 1400741 | 68 | 49 | 44 | 20 | 28 | 16 | 9 | 8 | 1 | 0.01 |
| 1522459 | 60 | 39 | 13 | 10 | 9 | 5 | 5 | 1 | 0.2 | 0.005 |
| 1522461 | 83 | 54 | 36 | 21 | 19 | 13 | 13 | 3 | 2 | 0.02 |
| 1522464 | 91 | 91 | 98 | 63 | 51 | 33 | 16 | 17 | 5 | 0.28 |
| 1525073 | 121 | 94 | 79 | 73 | 59 | 48 | 10 | 4 | 4 | 0.37 |

Example 4: Design of Modified Oligonucleotides Complementary to Human DMPK RNA Modified oligonucleotides complementary to a human DMPK RNA were designed as described in the table below. "Start site" indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence. Each modified nucleoside linkage. Each cytosine residue is a 5-methylcytosine unless otherwise indicated. Non-methylated cytosines are represented in bold underlined italicized font as "_C_".

The modified oligonucleotides in the table below are all conjugated to a THA-C6-GalNAc$_3$ conjugate (designated as [THA-GalNAc-]) at the 5' end of the modified oligonucleotide. THA-GalNAc is represented by the structure below, wherein the phosphate group is attached to the 5'-oxygen atom of the 5'-nucleoside:

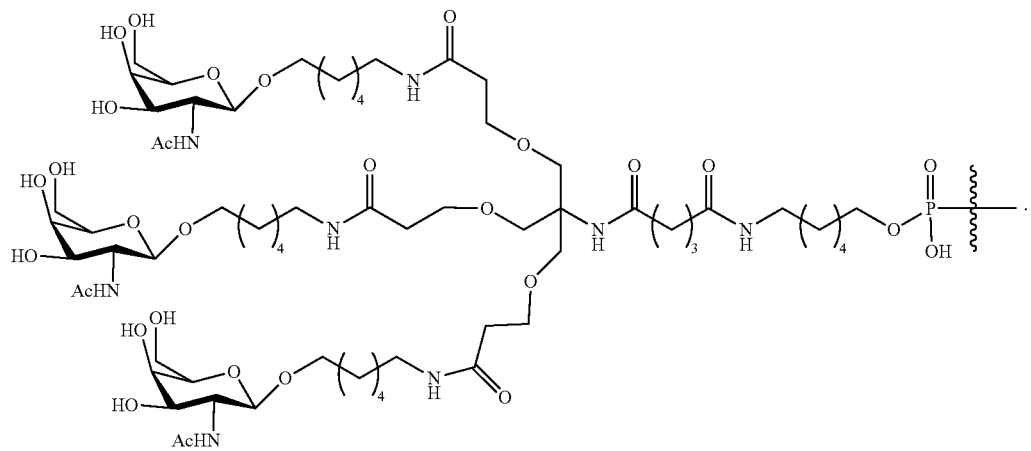

TABLE 5

THA-C6-GalNAc$_3$ conjugated mixed sugar modified oligonucleotides with mixed PS/PO internucleoside linkages complementary to human DMPK

| Compound Number | SEQ ID No: 1 Start Site | SEQ ID No: 1 Stop Site | SEQ ID No: 2 Start Site | SEQ ID No: 2 Stop Site | Chemistry Notation (5'-3') | SEQ ID NO |
|---|---|---|---|---|---|---|
| 1522484 | 19498 | 19513 | 1359 | 1374 | THA-GalNAc-$T_{es}{}^mC_{eo}{}^mC_{ko}{}^mC_{ks}$ $G_{ds}A_{ds}A_{ds}T_{ds}G_{ds}$ $T_{ds}{}^mC_{ds}{}^mC_{ds}G_{ks}$ $A_{ko}{}^mC_{es}A_e$ | 21 |
| 1522487 | 19495 | 19510 | 1356 | 1371 | THA-GalNAc-${}^mC_{ks}G_{ko}A_{ko}A_{ds}$ $U_{ys}G_{ds}T_{ds}{}^mC_{ds}$ ${}^mC_{ds}G_{ds}A_{ds}{}^mC_{ds}$ $A_{ds}G_{ko}T_{ks}G_k$ | 22 |
| 1522489 | 19499 | 19514 | 1360 | 1375 | THA-GalNAc-$T_{ks}T_{ko}{}^mC_{ko}$ ${}^mC_{ds}C_{ys}G_{ds}A_{ds}$ $A_{ds}ST_{ds}G_{ds}T_{ds}$ ${}^mC_{ds}{}^mC_{ds}G_{ko}A_{ks}$ ${}^mC_k$ | 23 |
| 1522492 | 24775 | 24790 | 2833 | 2848 | THA-GalNAc-${}^mC_{ks}T_{ko}T_{ep}T_{ds}$ $T_{ds}A_{ds}T_{ds}T_{ds}$ ${}^mG_{ds}G_{ds}{}^mC_{ds}$ $G_{ds}A_{ds}G_{ko}G_{ks}$ $G_k$ | 24 |
| 1525089 | 24730 | 24745 | 2788 | 2803 | THA-GalNAc-$A_{ks}{}^mC_{ko}A_{kp}A_{ds}$ $T_{ds}A_{ds}A_{ds}A_{ds}$ $T_{ds}A_{ds}{}^mC_{ds}{}^mC_{ds}$ $G_{ds}A_{ko}G_{ks}G_k$ | 27 |
| 1525074 | 19498 | 19513 | 1359 | 1374 | THA-GalNAc-$T_{es}{}^mC_{es}{}^mC_{ks}{}^mC_{ks}$ $G_{ds}A_{ds}A_{ds}T_{ds}G_{ds}$ $T_{ds}{}^mC_{ds}{}^mC_{ds}G_{ks}$ $A_{ks}{}^mC_{es}A_e$ | 25 |
| 1525079 | 19499 | 19514 | 1360 | 1375 | THA-GalNAc-$T_{ks}T_{ks}{}^mC_{ks}$ ${}^mC_{ds}C_{ys}G_{ds}A_{ds}$ $A_{ds}T_{ds}G_{ds}T_{ds}$ ${}^mC_{ds}{}^mC_{ds}G_{ks}A_{ks}$ ${}^mC_k$ | 26 |

Example 5: Tolerability of Modified Oligonucleotides Complementary to Human DMPK in Wildtype Mice Wildtype BALB/c mice (Charles River Laboratory) were treated with modified oligonucleotides selected from studies described above and evaluated for changes in the levels of various plasma chemistry markers.

Treatment

Groups of four BALB/c mice each received a single subcutaneous injection with 50 mg/kg of modified oligonucleotides. One group of four BALB/c mice received a single subcutaneous injection of PBS for each experiment. Each experiment is identified in separate tables below.

Plasma Chemistry Markers 96 hours post treatment, mice were sacrificed. To evaluate the effect of modified oligonucleotides on liver and kidney function, plasma levels of alanine aminotransferase (ALT) and aspartate aminotransferase (AST) were measured on the day the mice were sacrificed using an automated clinical chemistry analyzer (Hitachi Olympus AU400c, Melville, NY). The results for each group of mice are presented in the tables below.

TABLE 6

Plasma chemistry markers in BALB/c mice

| Compound No. | ALT (U/L) | AST (U/L) |
|---|---|---|
| PBS | 61 | 149 |
| 1525074 | 848 | 600 |
| 1525079 | 54 | 62 |
| 1525089 | 67 | 70 |

TABLE 7

Plasma chemistry markers in BALB/c mice

| Compound No. | ALT (U/L) | AST (U/L) |
|---|---|---|
| PBS | 22 | 64 |
| 1522484 | 301 | 244 |
| 1522487 | 30 | 49 |
| 1522489 | 46 | 76 |
| 1522492 | 65 | 81 |

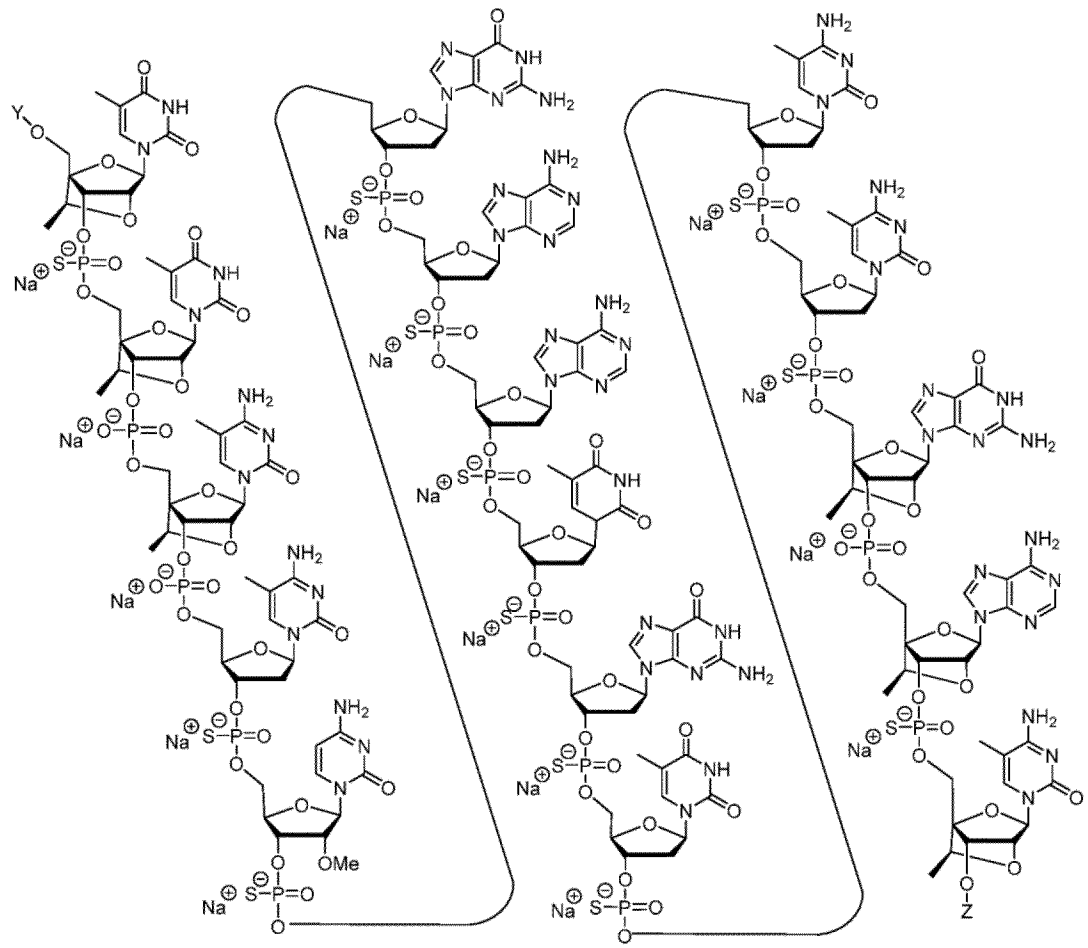

The invention claimed is:
1. A modified oligonucleotide according to the following chemical structure:
(SEQ ID NO: 13)
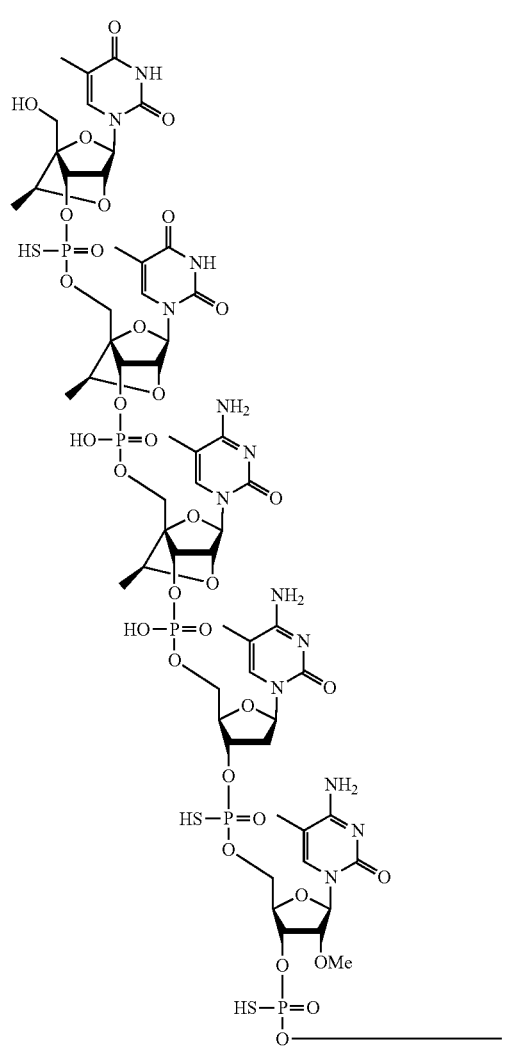
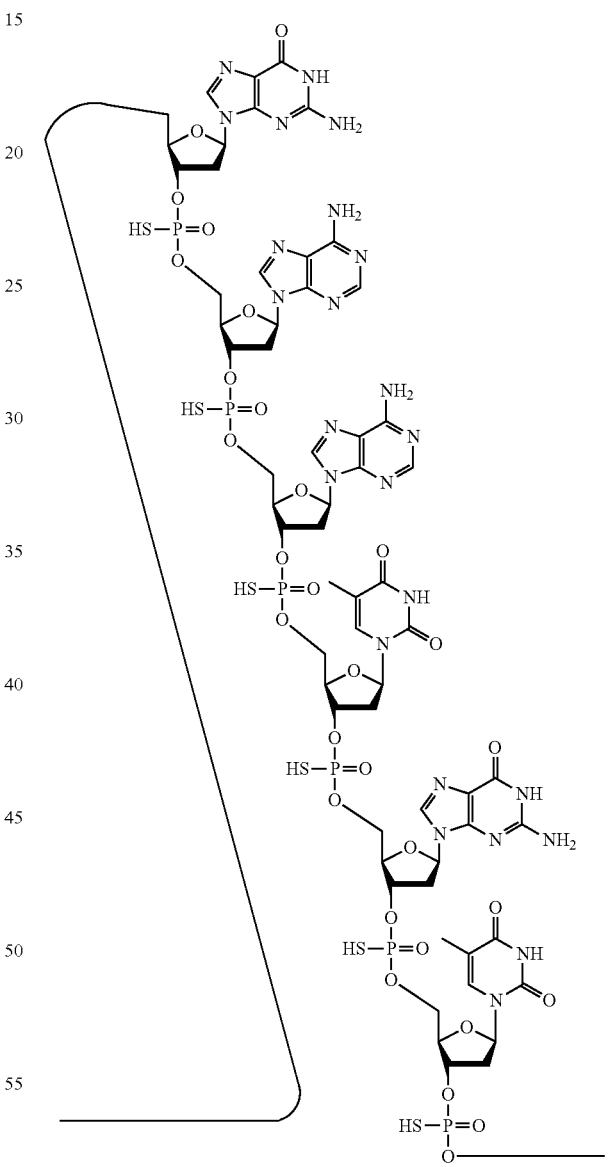

-continued

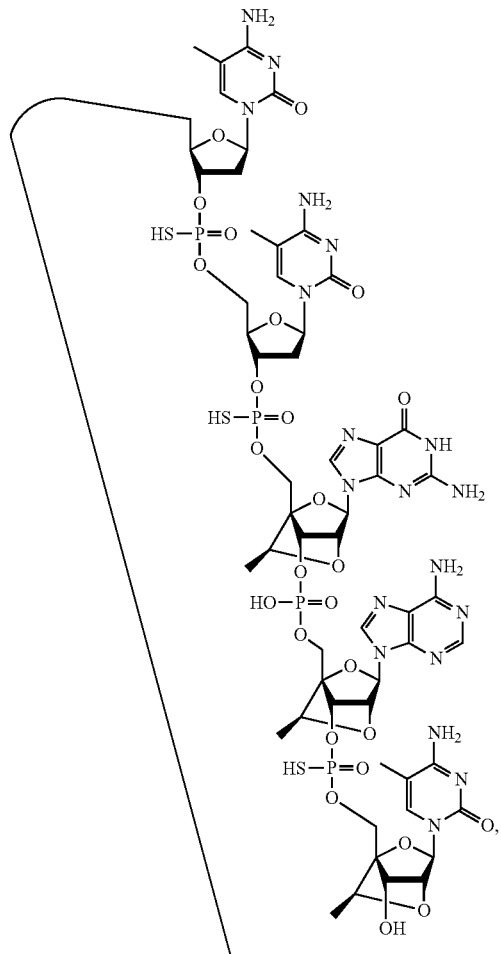

or a salt thereof.

2. An oligomeric compound comprising a modified oligonucleotide according to the following chemical notation: $T_{ks}T_{ko}{}^mC_{ko}{}^mC_{ds}C_{ys}G_{ds}A_{ds}A_{ds}T_{ds}G_{ds}T_{ds}{}^mC_{ds}{}^mC_{ds}G_{ko}A_{ks}{}^mC_k$ (SEQ ID NO: 13), wherein:

A=an adenine nucleobase, $^mC$=a 5-methylcytosine nucleobase,

C=a cytosine nucleobase,

G=a guanine nucleobase,

T=a thymine nucleobase, y=a 2'-OMe sugar moiety, k=a cEt sugar moiety, d=a 2'-β-D-deoxyribosyl sugar moiety, s=a phosphorothioate internucleoside linkage, and o=a phosphodiester internucleoside linkage.

3. The oligomeric compound of claim 2 comprising a conjugate group.

4. The oligomeric compound of claim 3, wherein the conjugate group comprises a conjugate moiety and a conjugate linker.

5. The oligomeric compound of claim 4, wherein the conjugate moiety is a cell-targeting moiety.

6. The oligomeric compound of claim 5, wherein the cell-targeting moiety binds a cell surface receptor on a skeletal muscle cell.

7. The oligomeric compound of claim 6, wherein the cell-targeting moiety is selected from a carbohydrate, an antibody, and an antibody fragment.

8. A population of oligomeric compounds of claim 2, wherein all of the phosphorothioate internucleoside linkages of the modified oligonucleotide are stereorandom.

9. A pharmaceutical composition of an oligomeric compound of claim 2 and a pharmaceutically acceptable diluent.

10. The pharmaceutical composition of claim 9, wherein the pharmaceutically acceptable diluent is water or phosphate-buffered saline.

11. An oligomeric compound according to the following chemical structure:

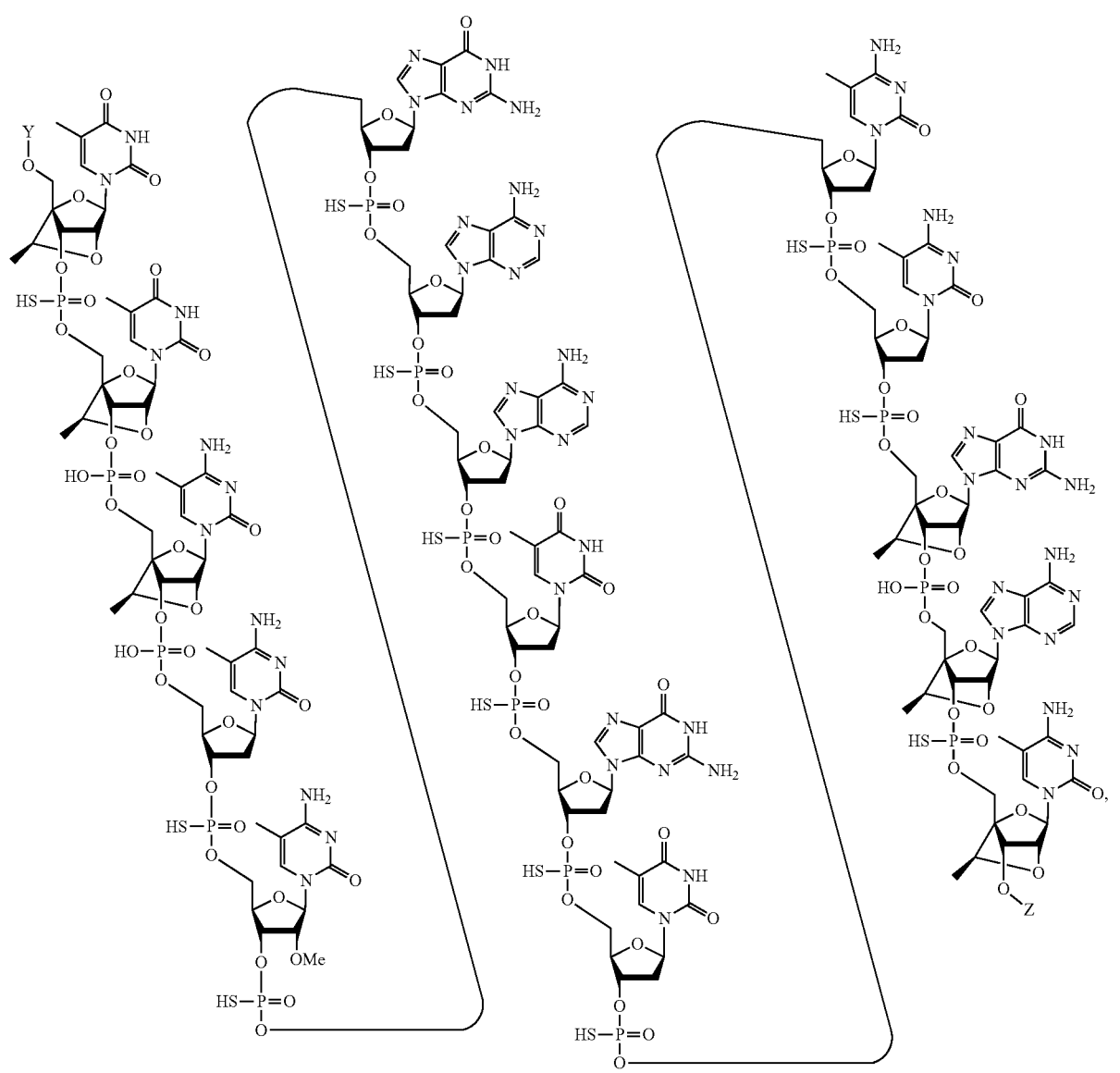

(SEQ ID NO: 30)

or a salt thereof wherein Y and Z are from H and a conjugate group, wherein at least one of Y and Z is a conjugate group.

12. The oligomeric compound of claim 11, wherein the conjugate group comprises a conjugate moiety and a conjugate linker.

13. The oligomeric compound of claim 11, wherein the conjugate group comprises $C_{10}$-$C_{24}$alkyl.

14. The oligomeric compound of claim 12, wherein the conjugate moiety is a cell-targeting moiety.

15. The oligomeric compound of claim 14, wherein the cell-targeting moiety binds a cell surface receptor on a skeletal muscle cell.

16. The oligomeric compound of claim 14, wherein the cell-targeting moiety is selected from a carbohydrate and an antibody.

17. The oligomeric compound of claim 14, wherein the cell-targeting moiety is an antibody or an antibody fragment that binds a transferrin receptor.

18. A population of oligomeric compounds of claim 11, wherein all of the phosphorothioate internucleoside linkages of the oligomeric compound are stereorandom.

19. A pharmaceutical composition of an oligomeric compound of claim 11 and a pharmaceutically acceptable diluent.

20. The pharmaceutical composition of claim 19, wherein the pharmaceutically acceptable diluent is water or phosphate-buffered saline.

21. An oligomeric compound according to the following chemical structure:

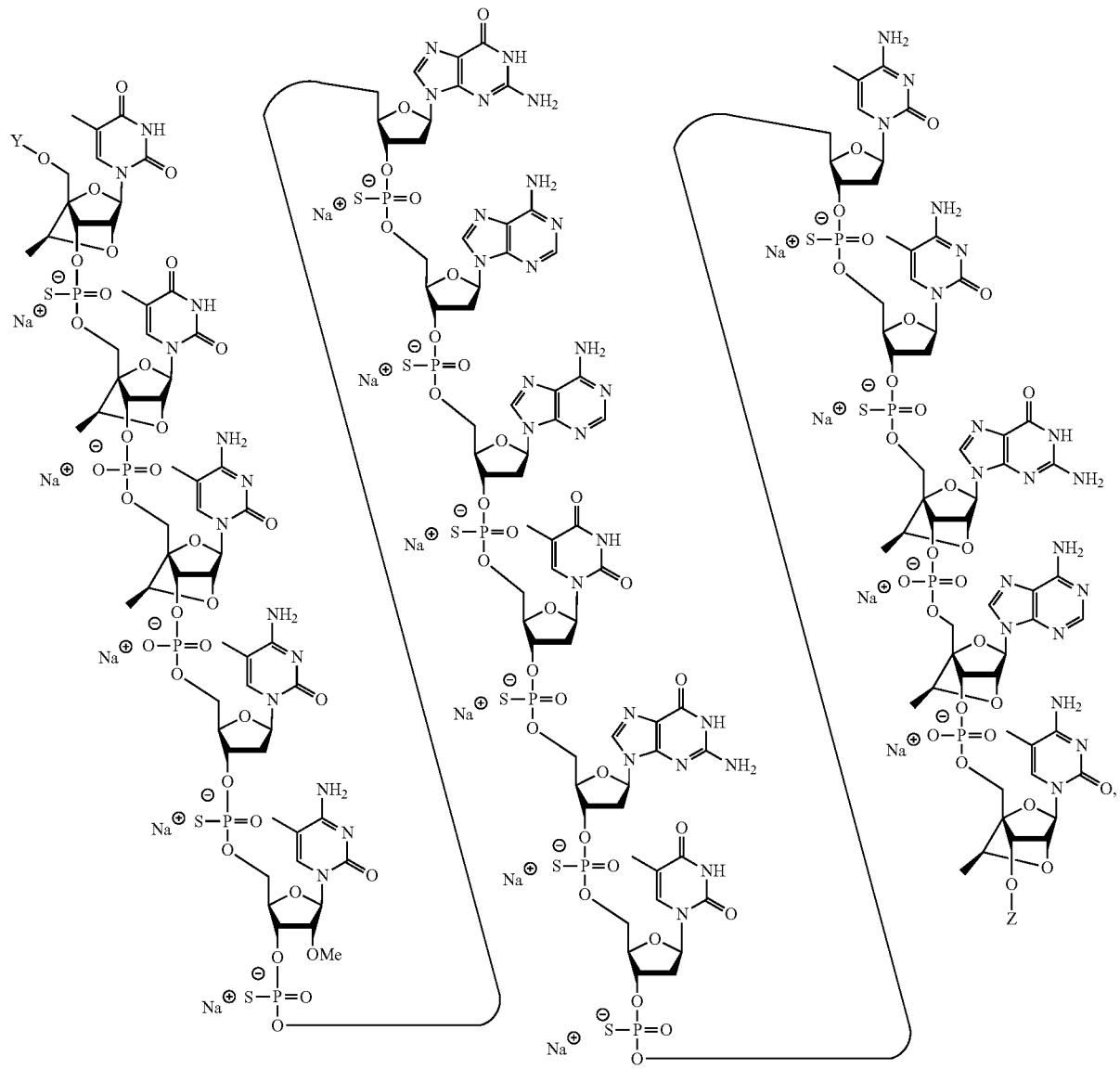

(SEQ ID NO: 30)

wherein Y and Z are selected from H and a conjugate group, wherein at least one of Y and Z is a conjugate group.

22. The oligomeric compound of claim 21, wherein the conjugate group comprises a conjugate moiety and a conjugate linker.

23. The oligomeric compound of claim 21, wherein the conjugate group comprises $C_{10}$-$C_{24}$ alkyl.

24. The oligomeric compound of claim 22, wherein the conjugate moiety is a cell-targeting moiety.

25. The oligomeric compound of claim 24, wherein the cell-targeting moiety binds a cell surface receptor on a skeletal muscle cell.

26. The oligomeric compound of claim 24, wherein the cell-targeting moiety is selected from a carbohydrate and an antibody.

27. The oligomeric compound of claim 24, wherein the cell-targeting moiety is an antibody or an antibody fragment that binds a transferrin receptor.

28. A population of oligomeric compounds of claim 21, wherein all of the phosphorothioate internucleoside linkages of the oligomeric compound are stereorandom.

29. A pharmaceutical composition of an oligomeric compound of claim 21 and a pharmaceutically acceptable diluent.

30. The pharmaceutical composition of claim 29, wherein the pharmaceutically acceptable diluent is water or phosphate-buffered saline.

\* \* \* \* \*

UNITED STATES PATENT AND TRADEMARK OFFICE
CERTIFICATE OF CORRECTION

PATENT NO. : 11,833,221 B2
APPLICATION NO. : 17/823854
DATED : December 5, 2023
INVENTOR(S) : Frank Rigo et al.

It is certified that error appears in the above-identified patent and that said Letters Patent is hereby corrected as shown below:

In the Specification

In Columns 7 and 8, the structure should read:

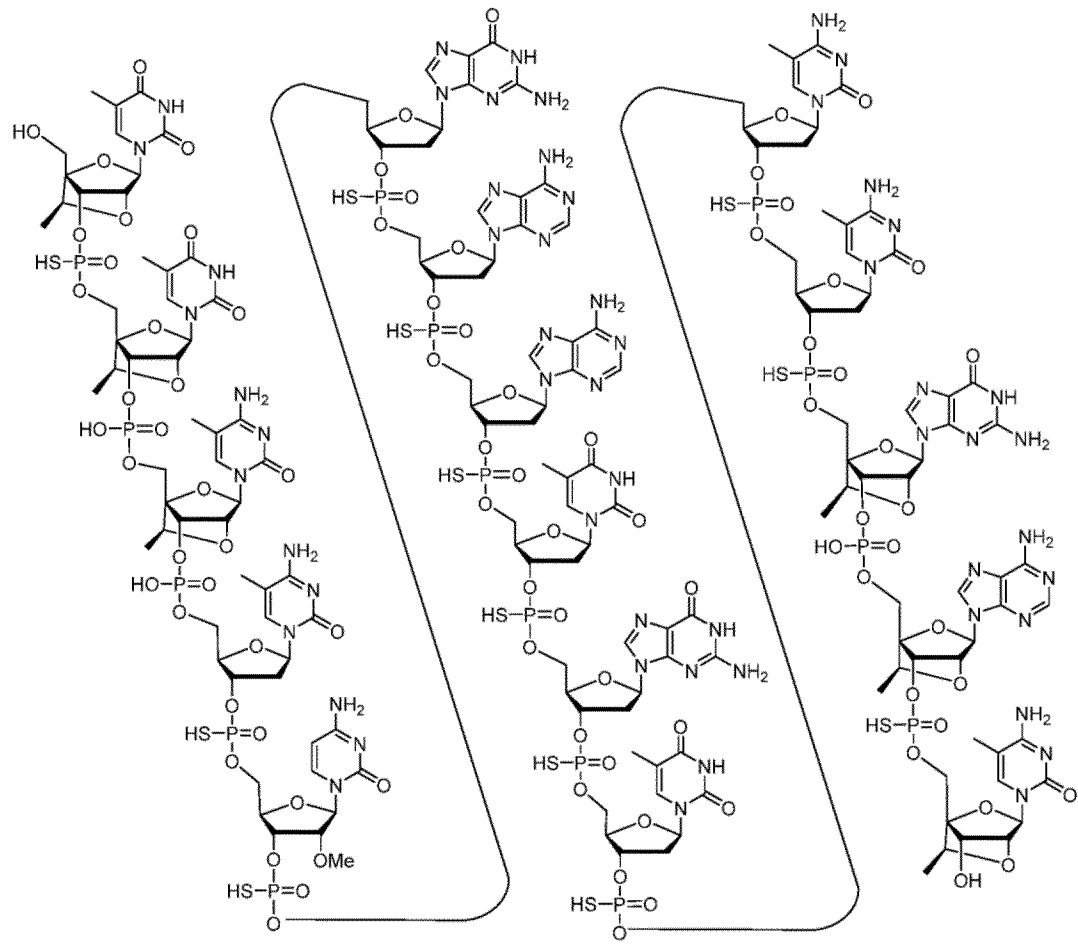

Signed and Sealed this
Fourth Day of June, 2024

Katherine Kelly Vidal
*Director of the United States Patent and Trademark Office*

CERTIFICATE OF CORRECTION (continued)
U.S. Pat. No. 11,833,221 B2

In Columns 9 and 10, the structure should read:

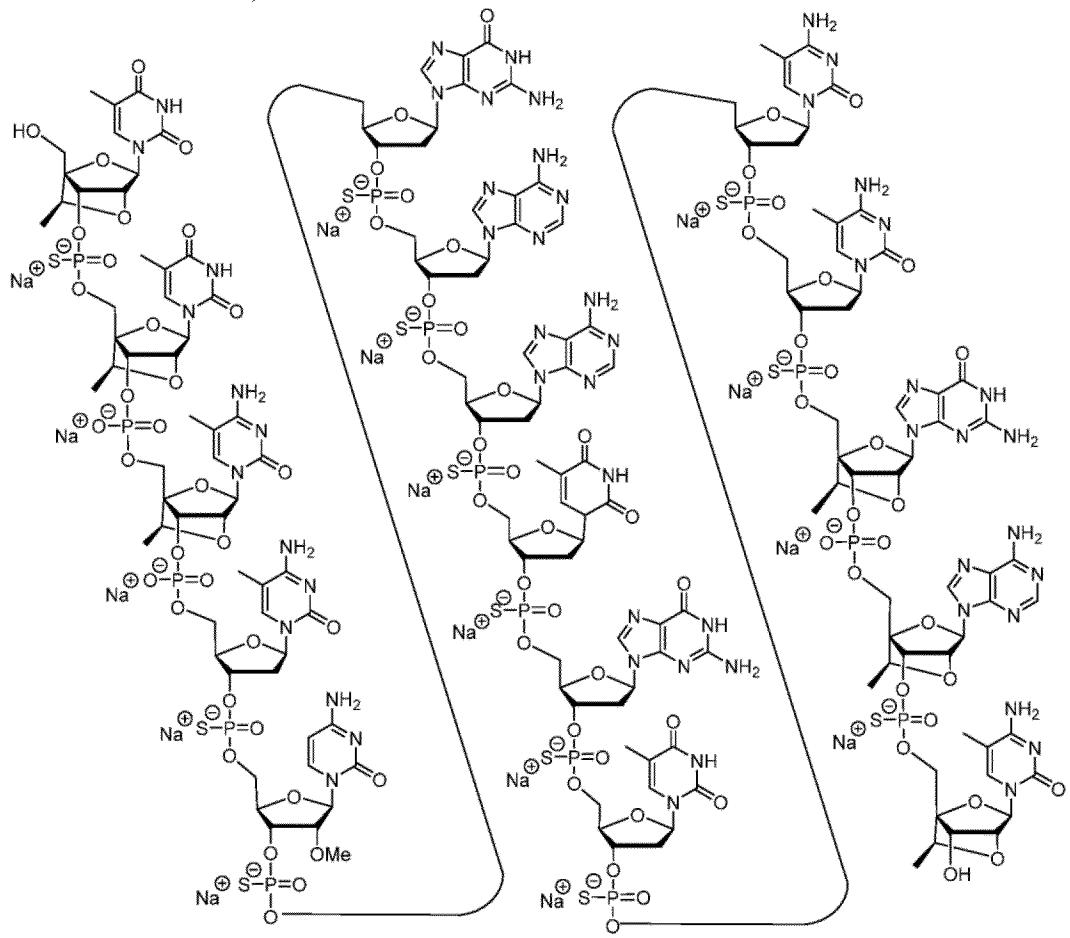

CERTIFICATE OF CORRECTION (continued)
U.S. Pat. No. 11,833,221 B2

In Columns 11 and 12, the structure should read:

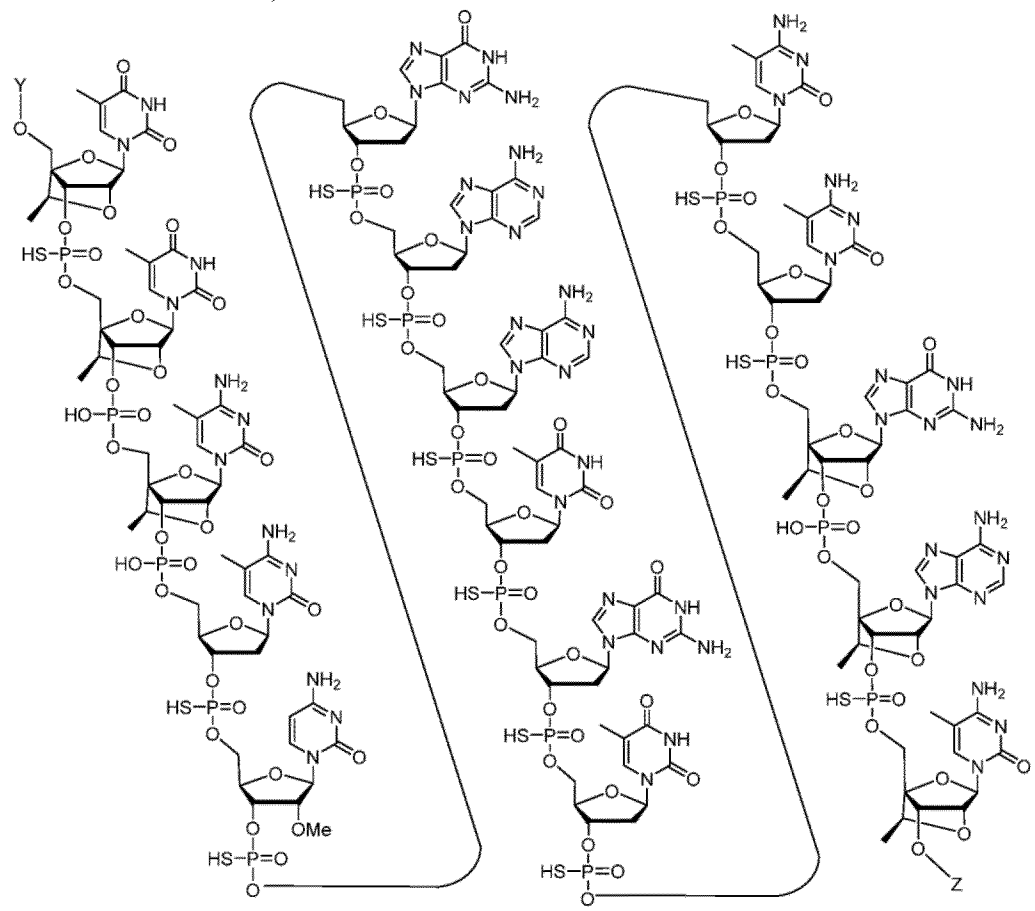

CERTIFICATE OF CORRECTION (continued)
U.S. Pat. No. 11,833,221 B2

In Columns 13 and 14, the structure should read:

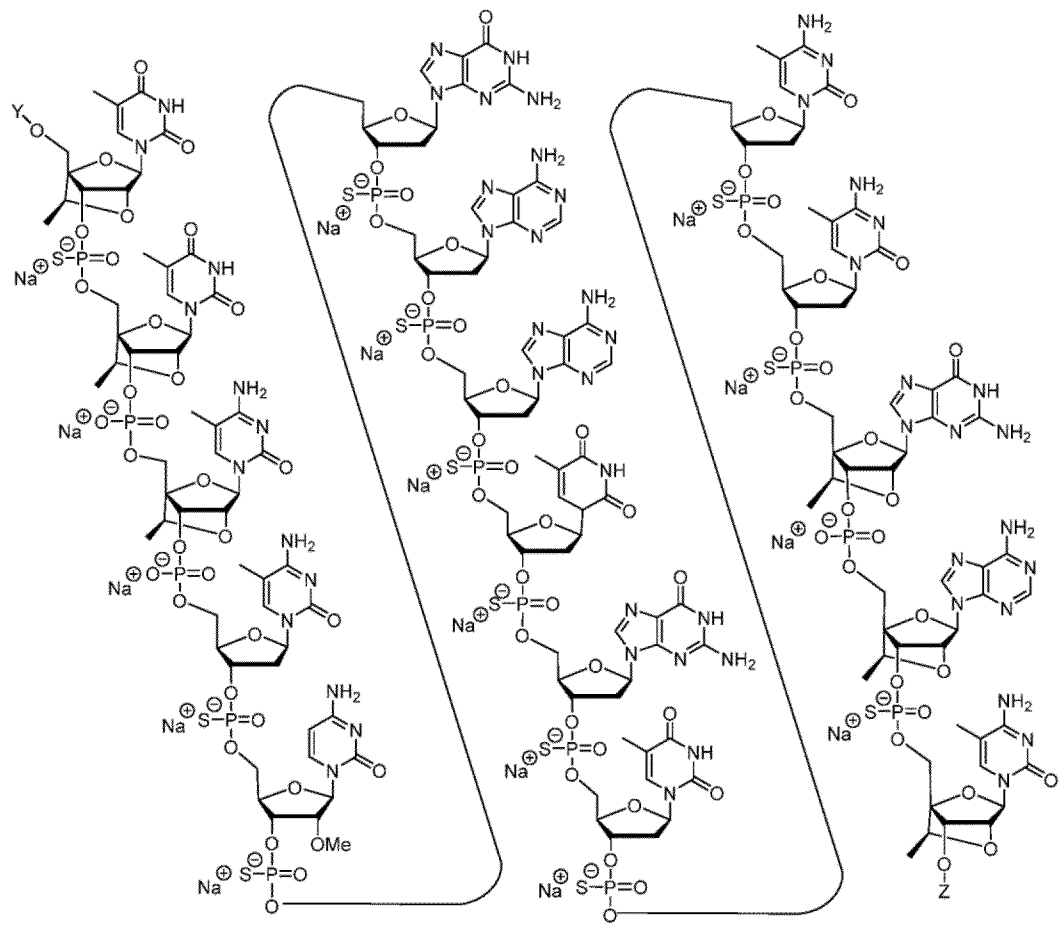

CERTIFICATE OF CORRECTION (continued)
U.S. Pat. No. 11,833,221 B2

In Columns 17 and 18, the structure should read:

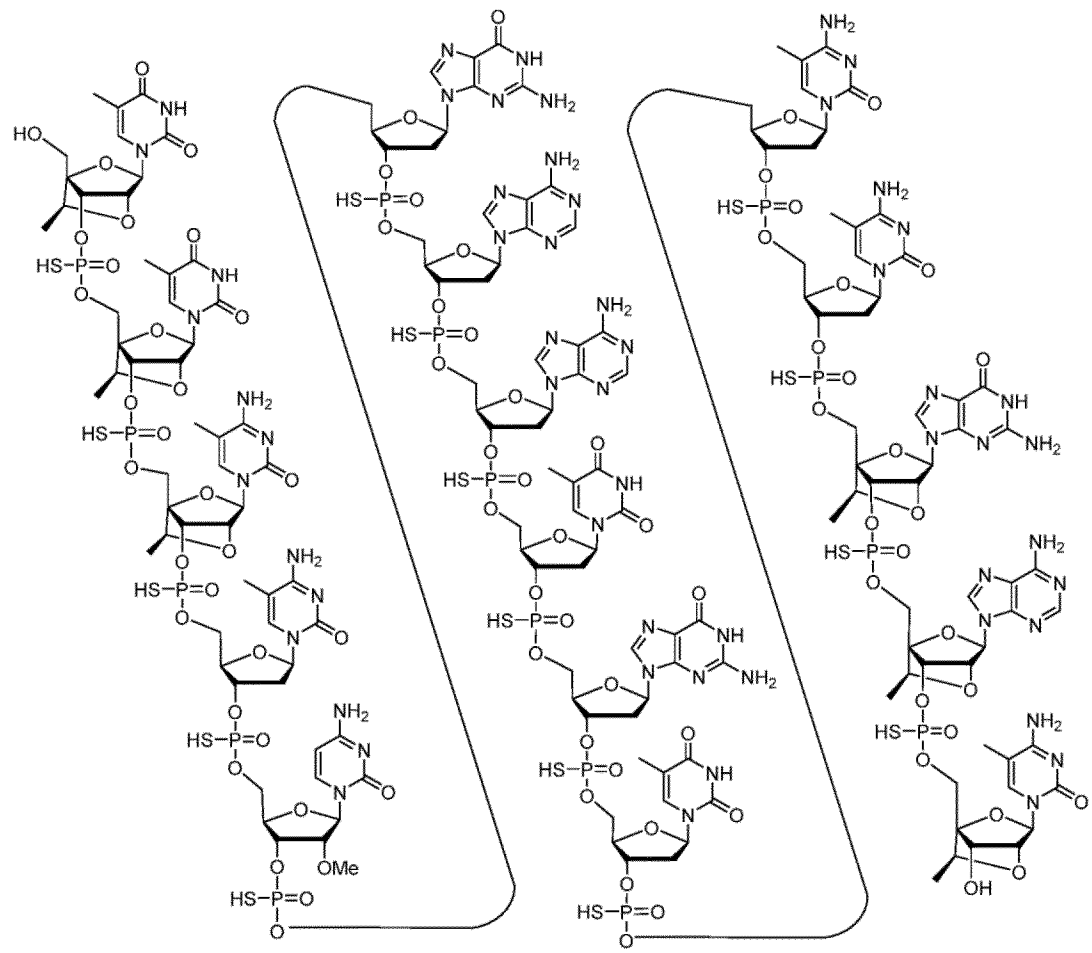

CERTIFICATE OF CORRECTION (continued)
U.S. Pat. No. 11,833,221 B2

In Columns 19 and 20, the structure should read:

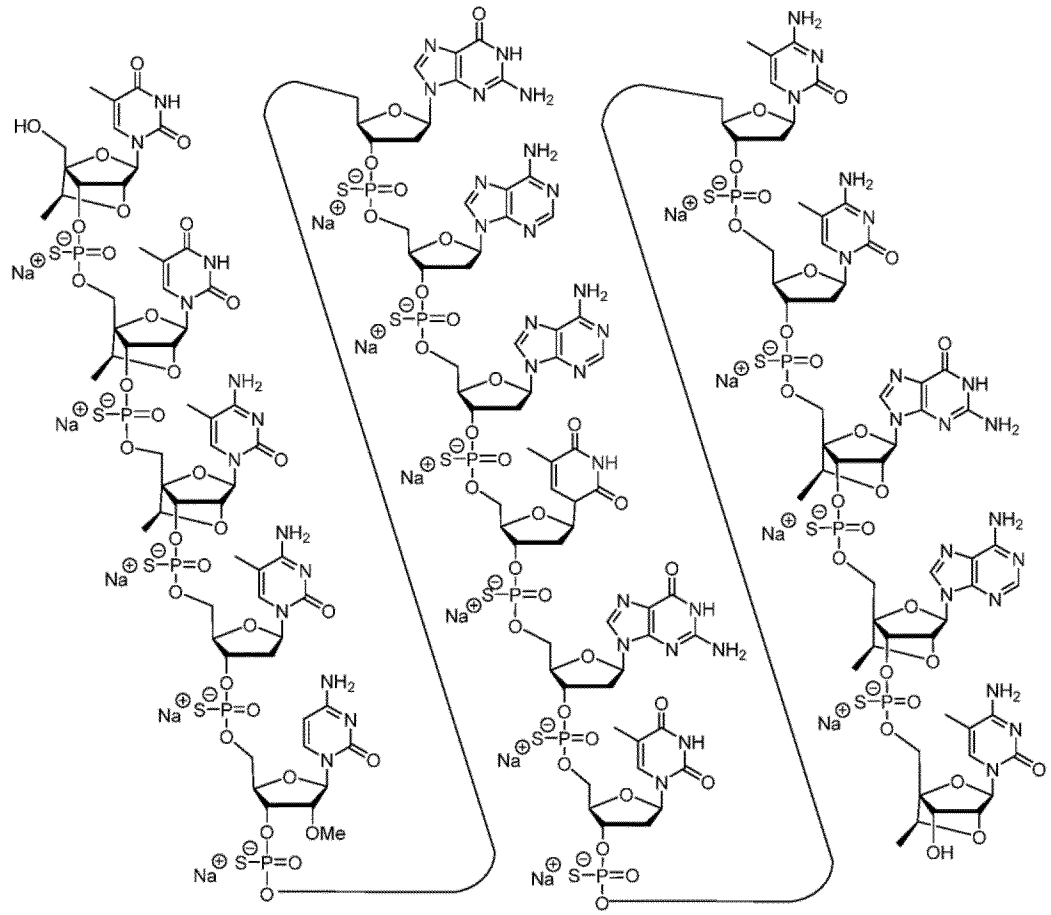

CERTIFICATE OF CORRECTION (continued)
U.S. Pat. No. 11,833,221 B2

In Columns 21 and 22, the structure should read:

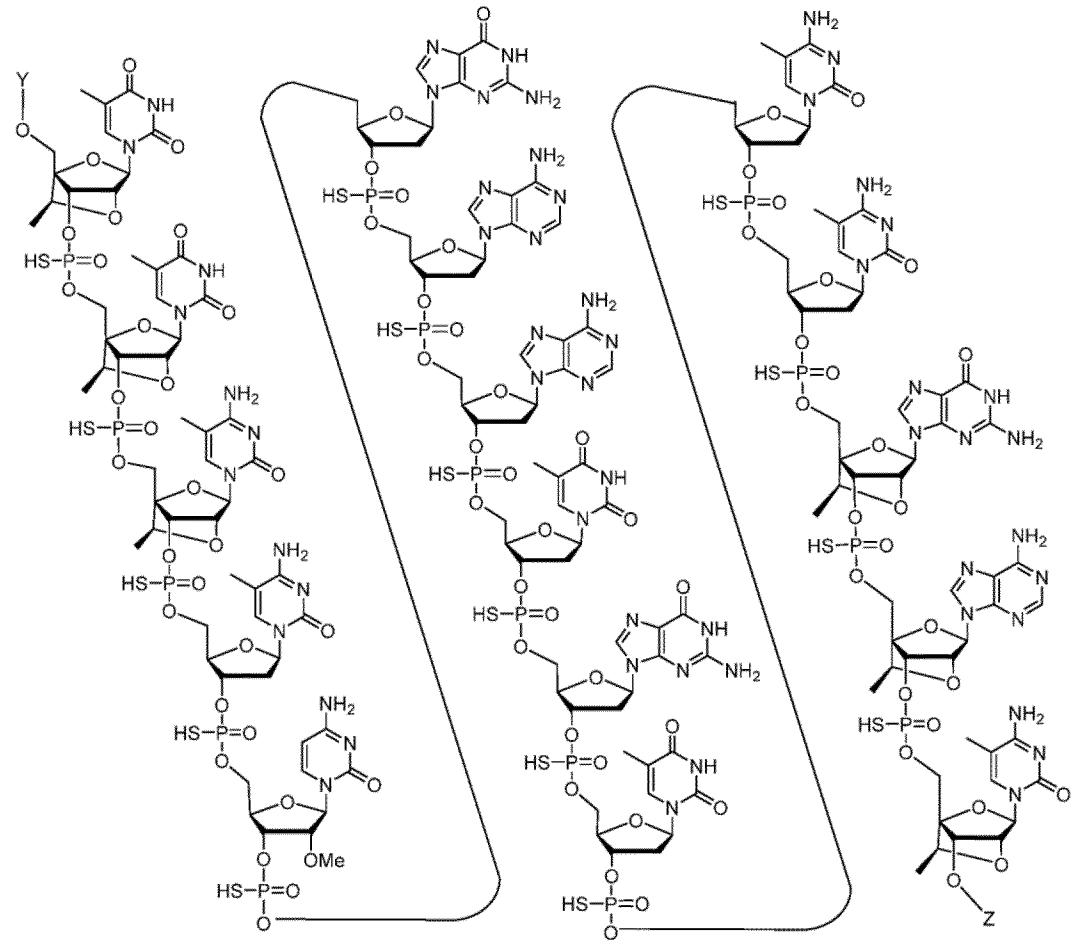

CERTIFICATE OF CORRECTION (continued)
U.S. Pat. No. 11,833,221 B2

In Columns 23 and 24, the structure should read:

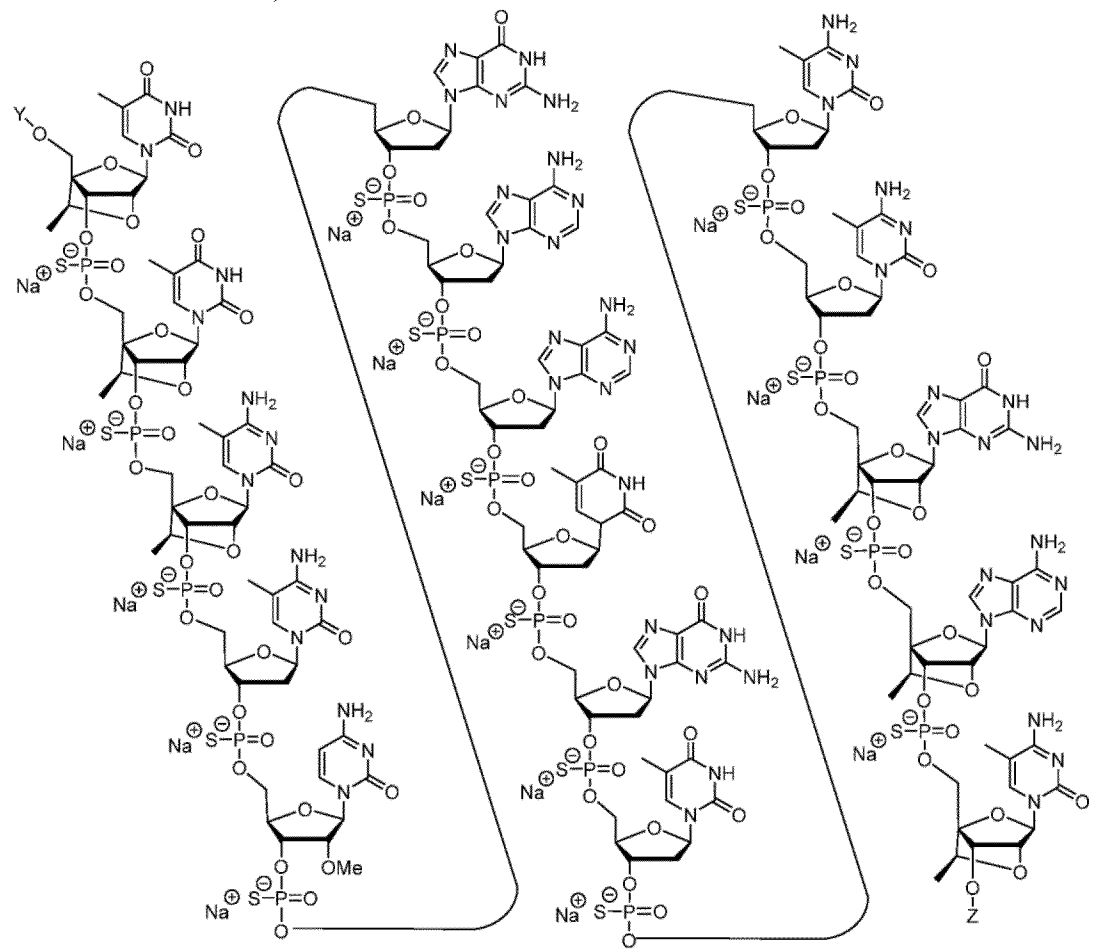

CERTIFICATE OF CORRECTION (continued)
U.S. Pat. No. 11,833,221 B2

In Columns 27 and 28, the structure should read:

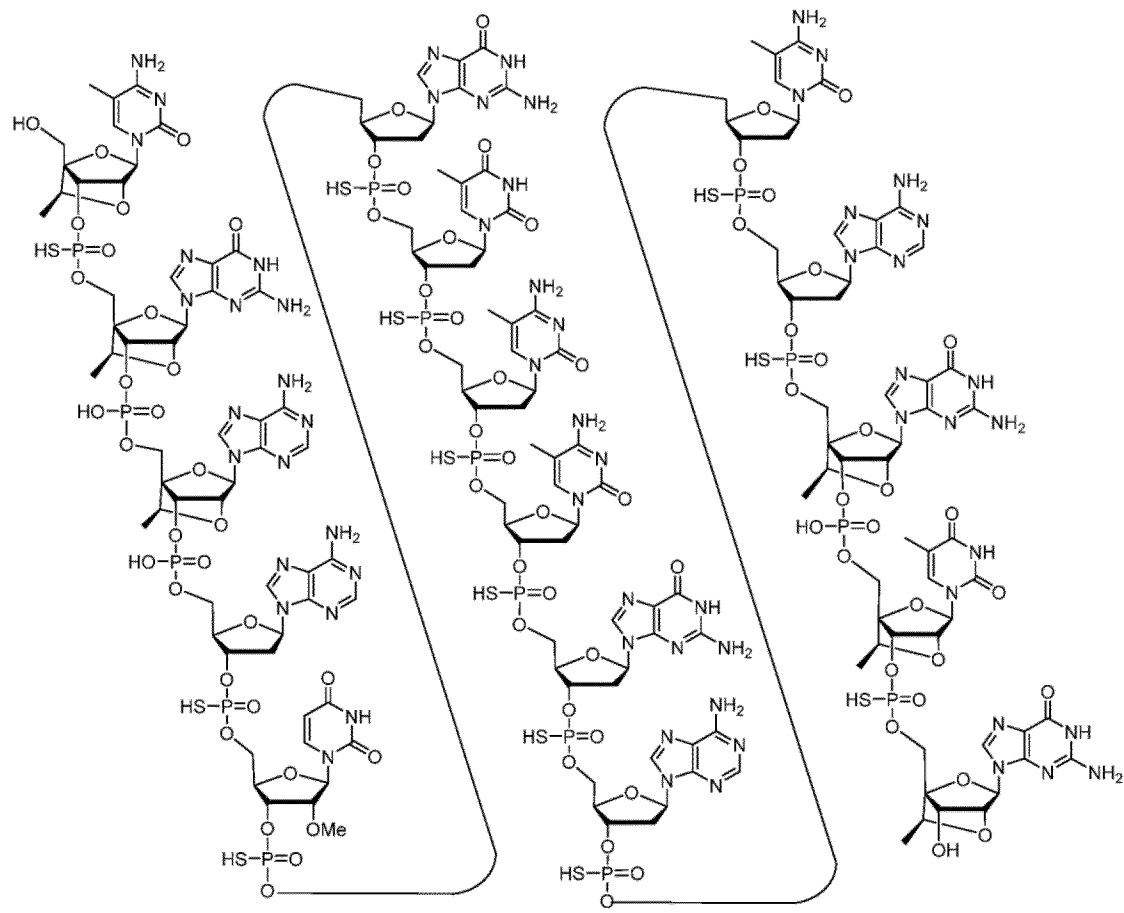

In Columns 29 and 30, the structure should read:
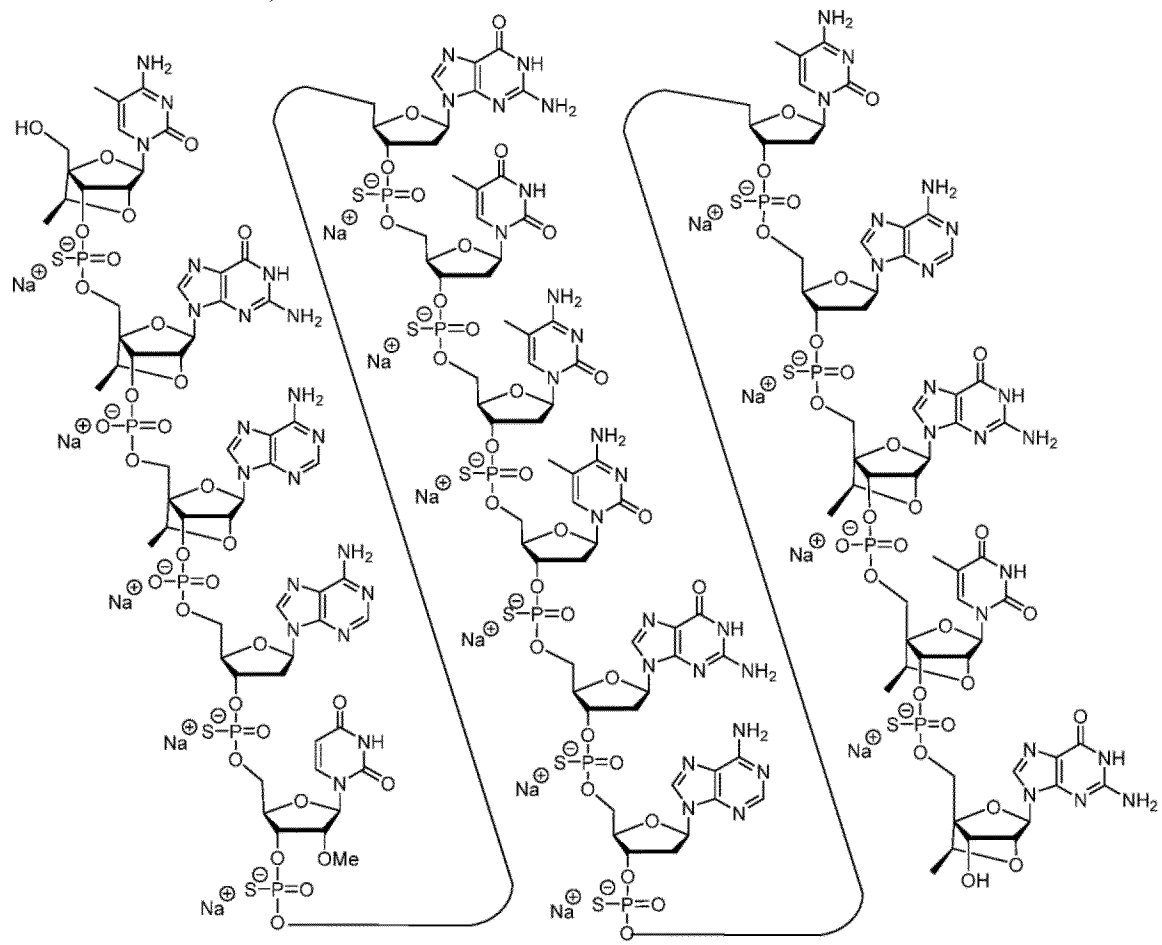

CERTIFICATE OF CORRECTION (continued)
U.S. Pat. No. 11,833,221 B2

In Columns 31 and 32, the structure should read:

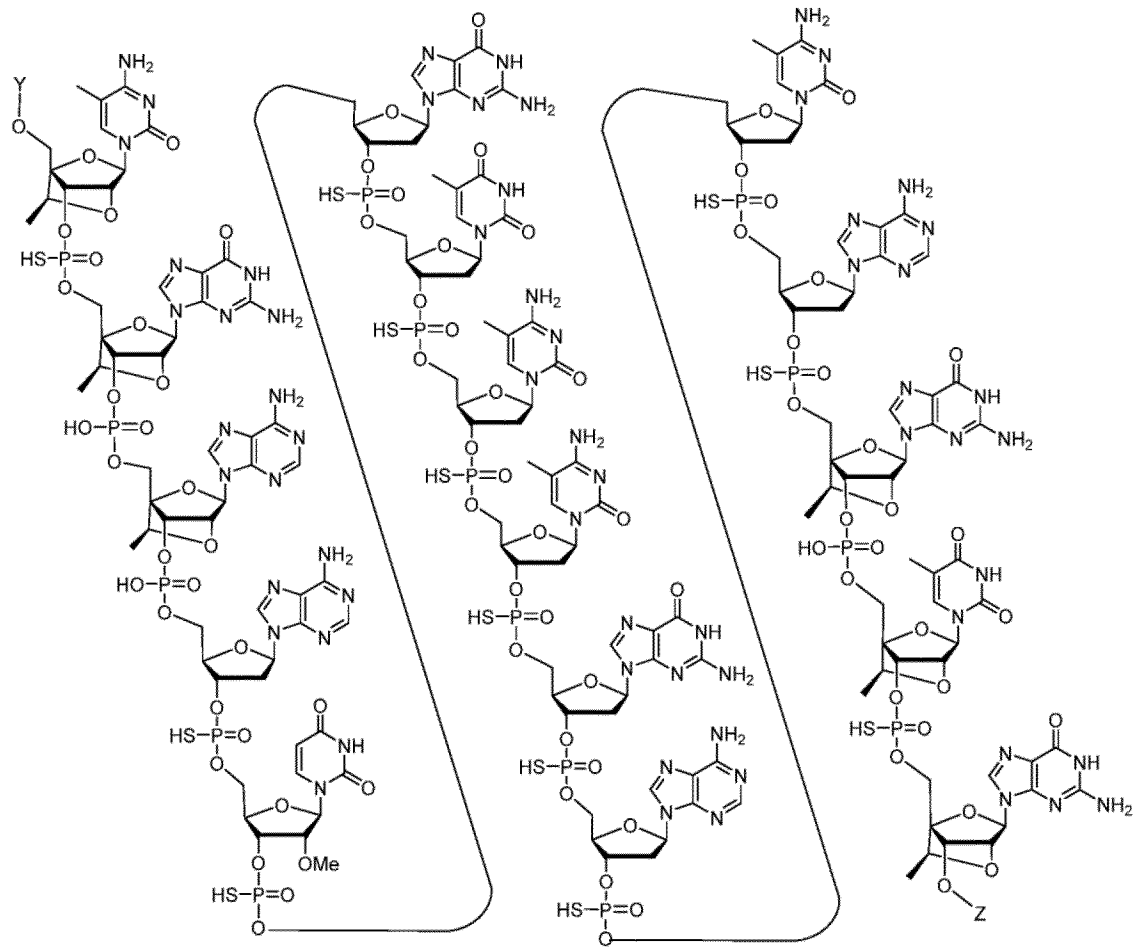

In Columns 33 and 34, the structure should read:
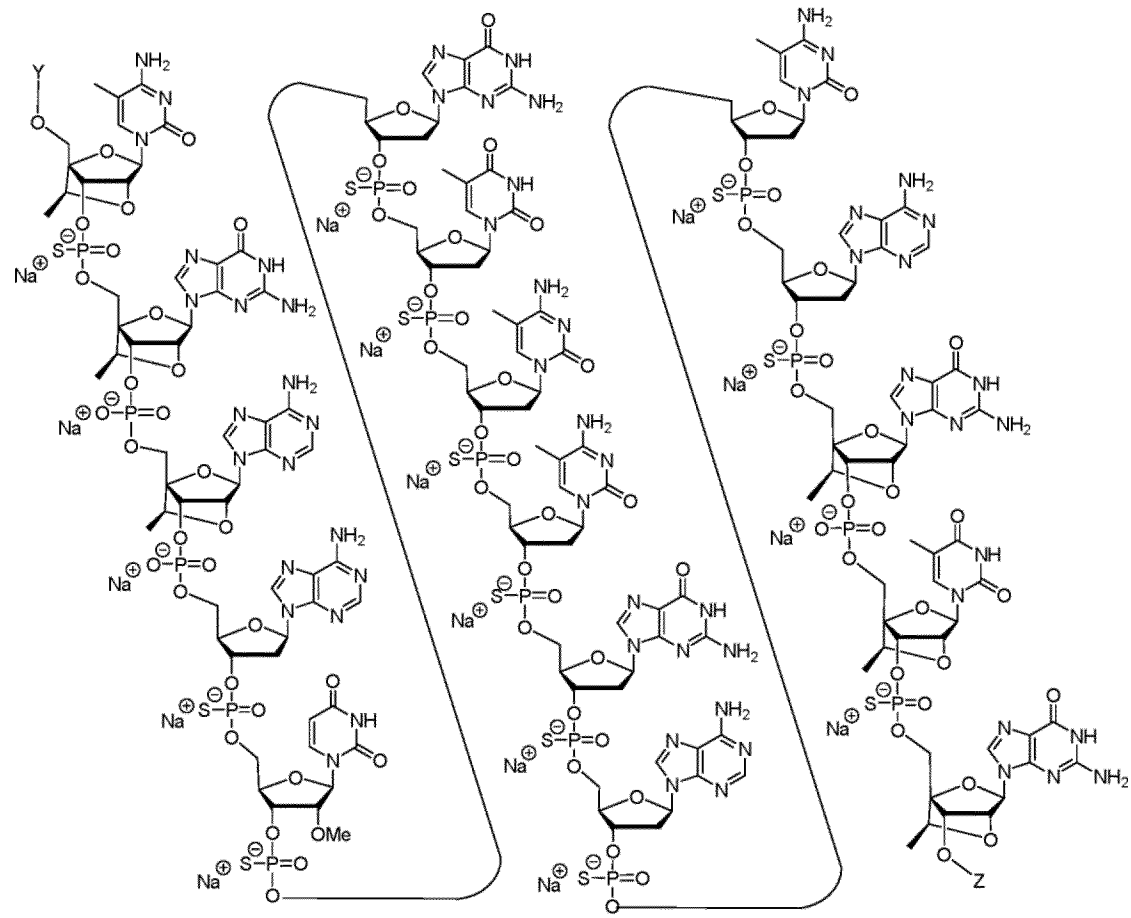

CERTIFICATE OF CORRECTION (continued)
U.S. Pat. No. 11,833,221 B2

In Columns 37 and 38, the structure should read:

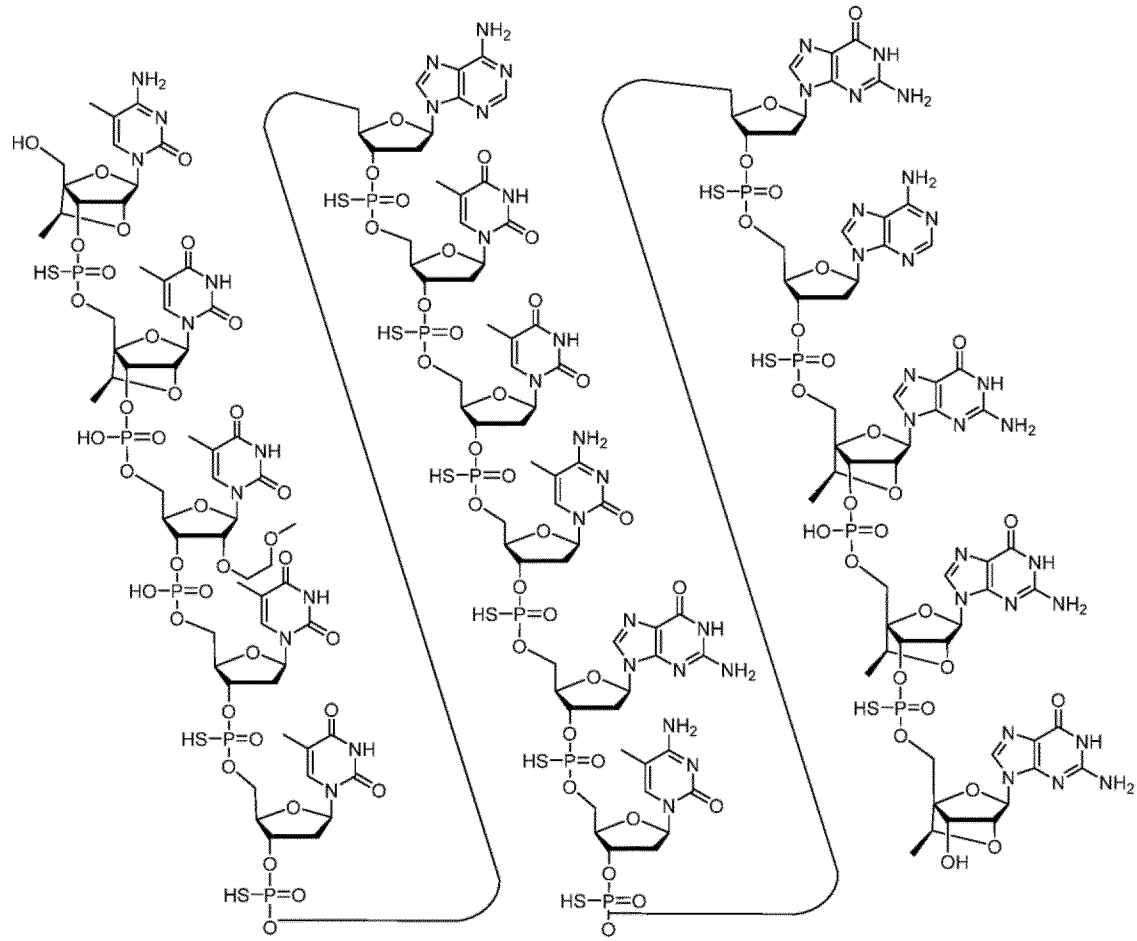

In Columns 39 and 40, the structure should read:
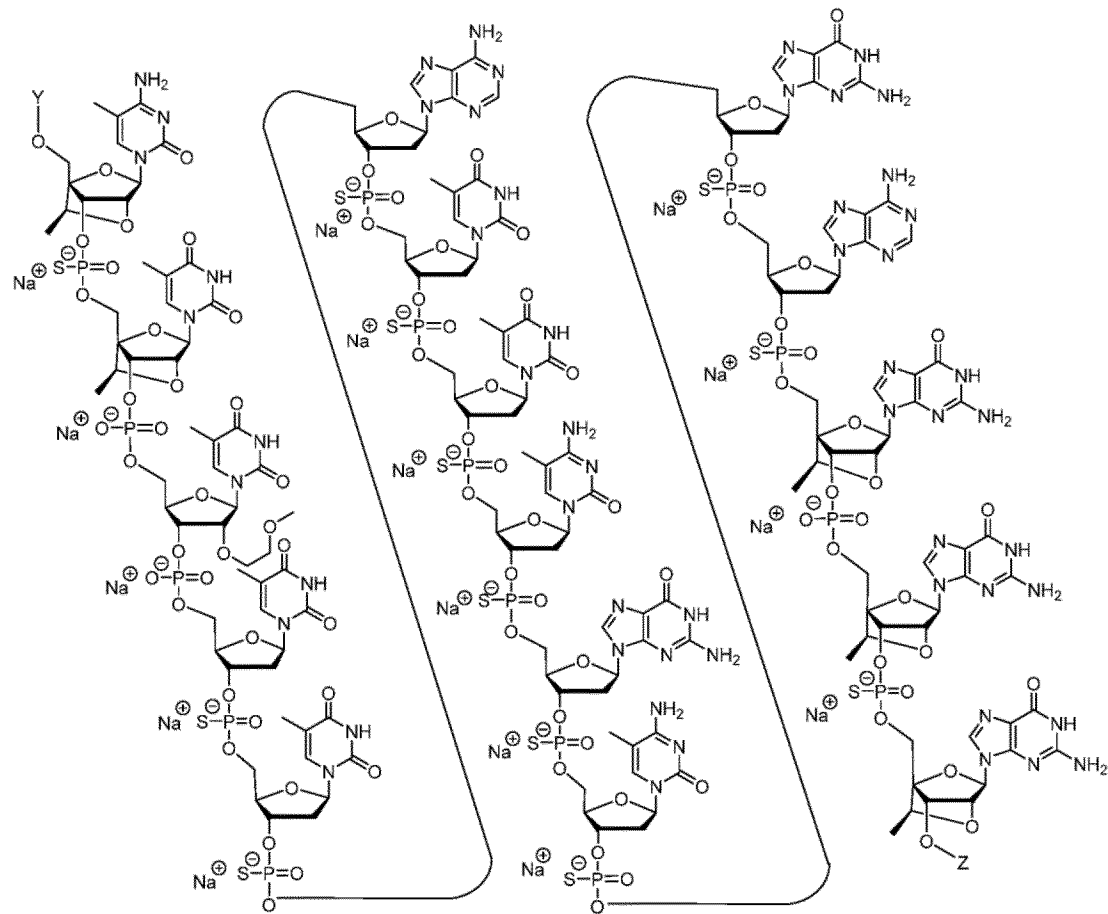

In Columns 41 and 42, the structure should read:
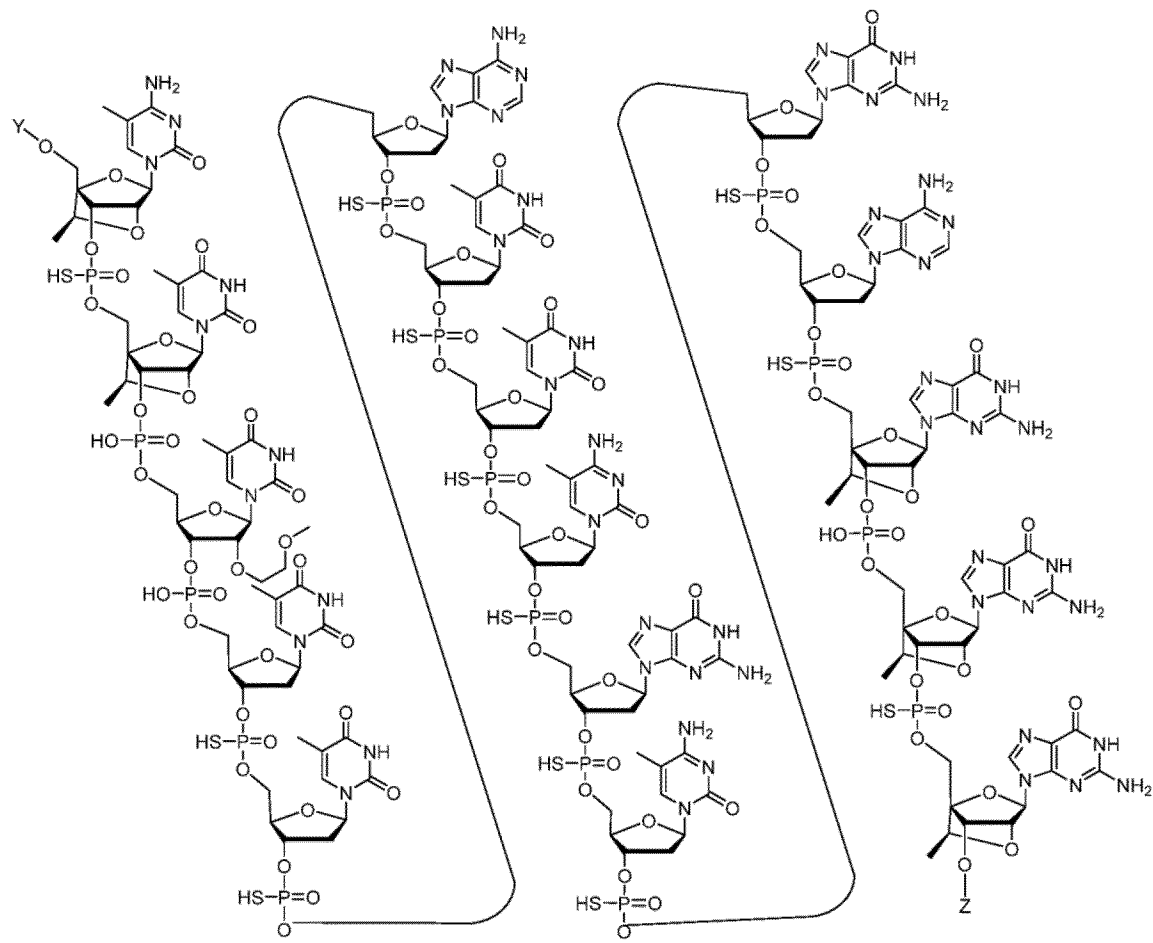
In Columns 43 and 44, the structure should read:

CERTIFICATE OF CORRECTION (continued)
U.S. Pat. No. 11,833,221 B2

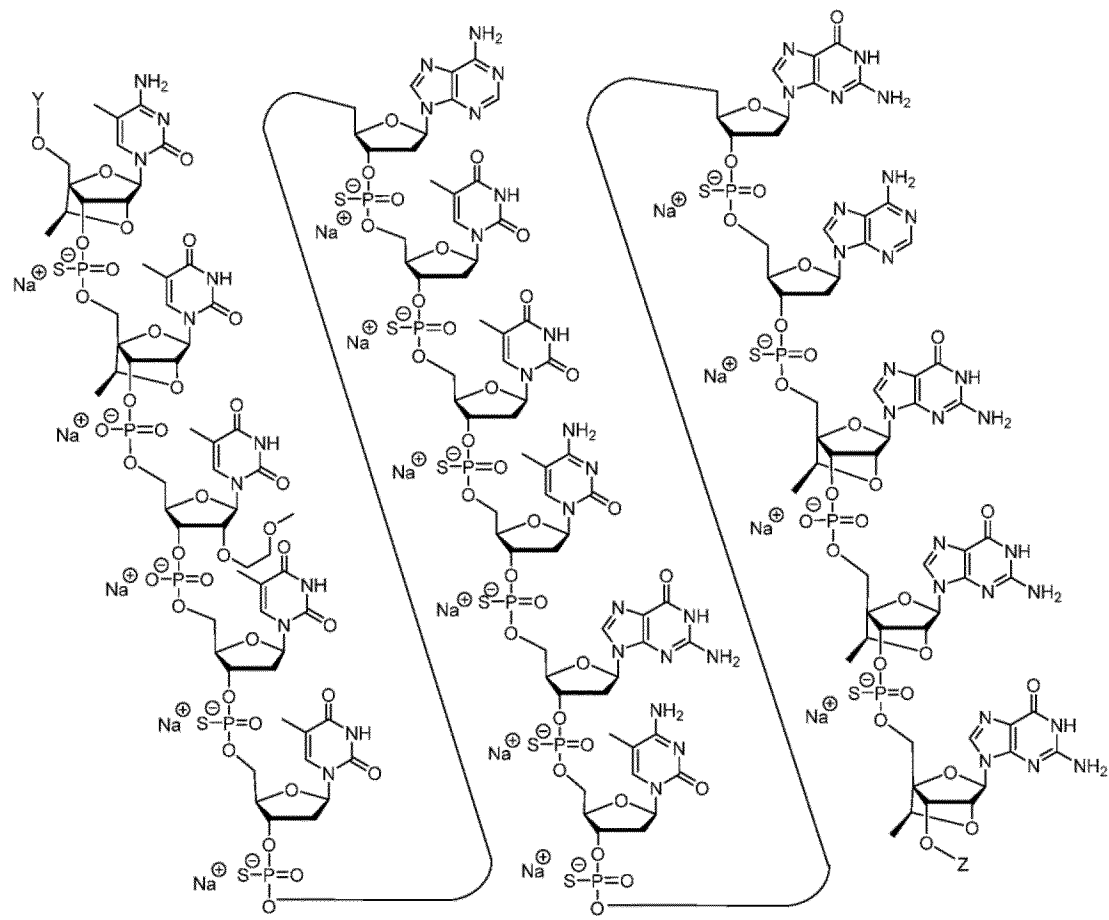

In Columns 47 and 48, the structure should read:

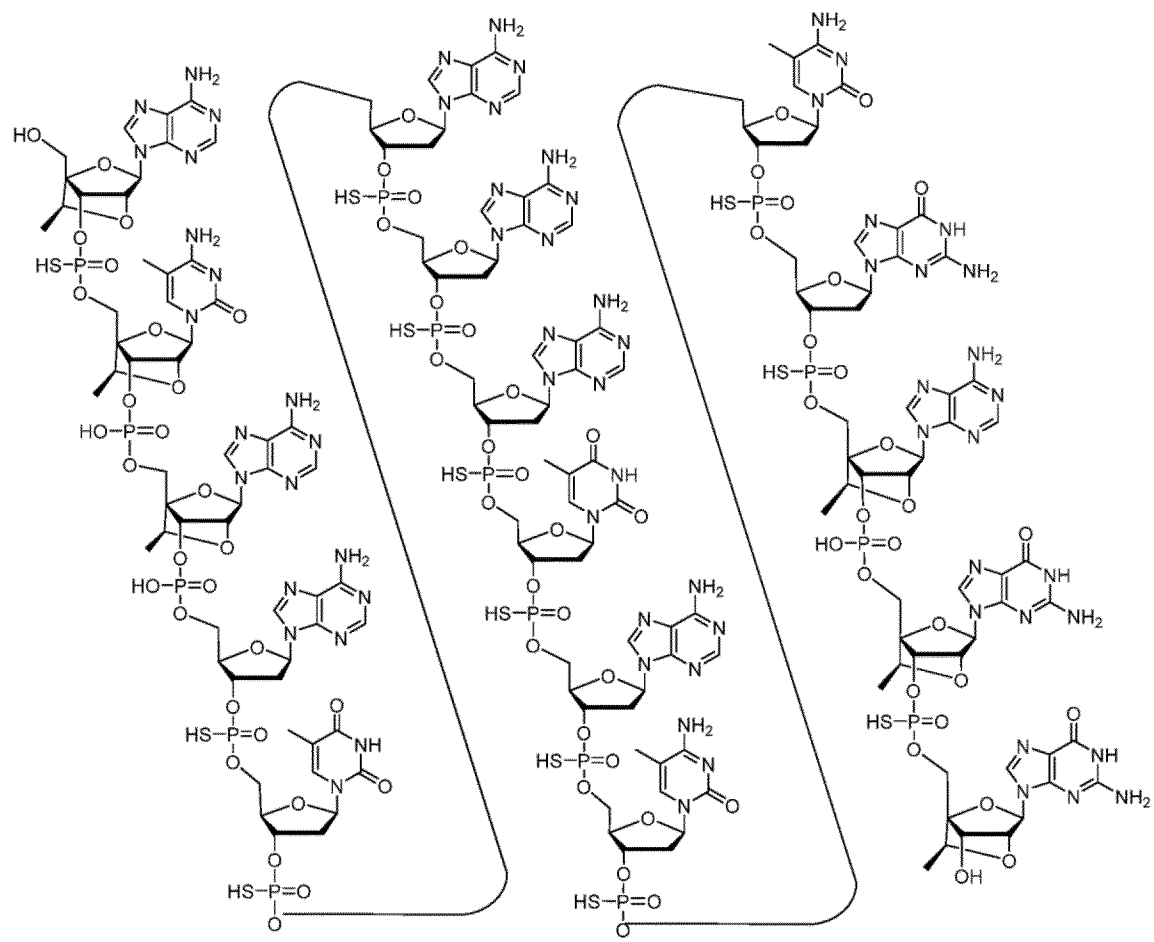
In Columns 49 and 50, the structure should read:

CERTIFICATE OF CORRECTION (continued)
U.S. Pat. No. 11,833,221 B2

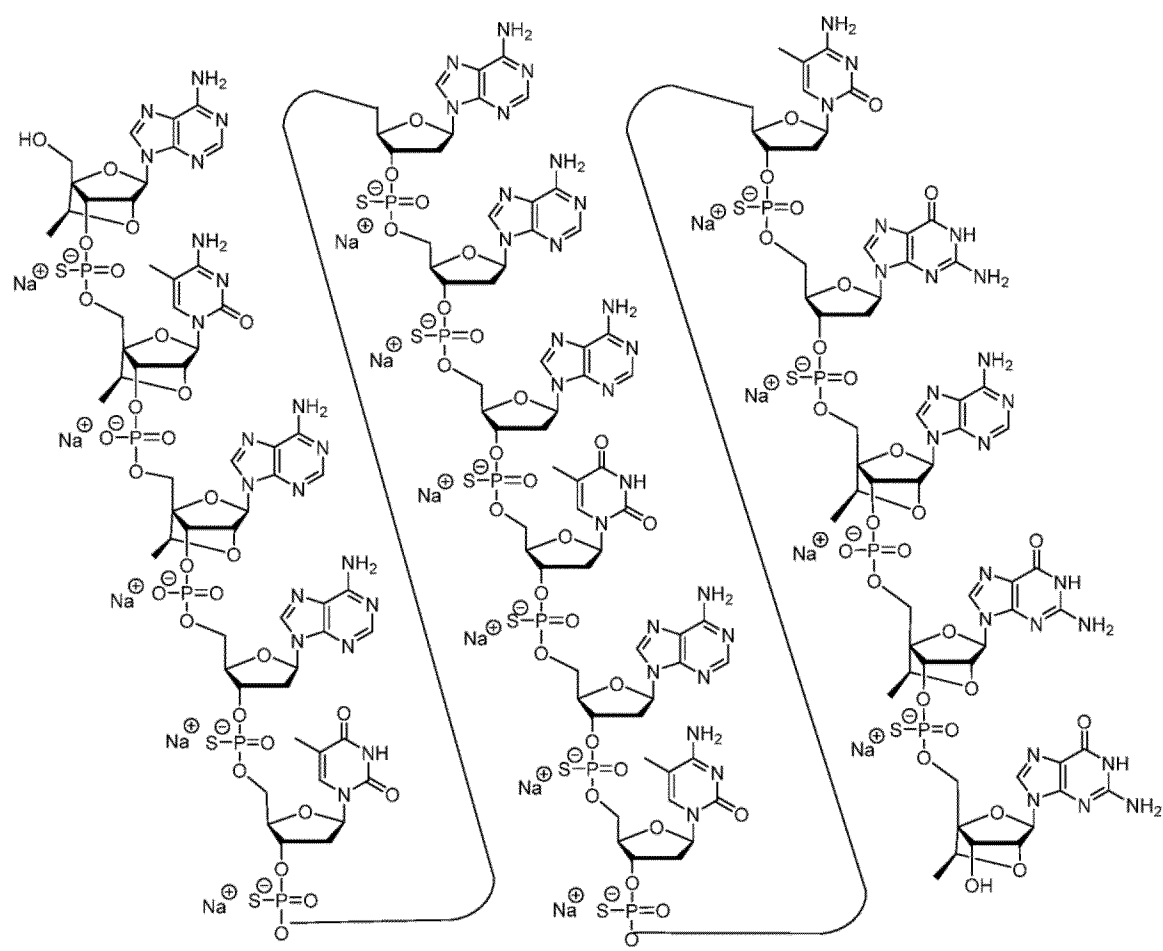

In Columns 51 and 52, the structure should read:

CERTIFICATE OF CORRECTION (continued)
U.S. Pat. No. 11,833,221 B2

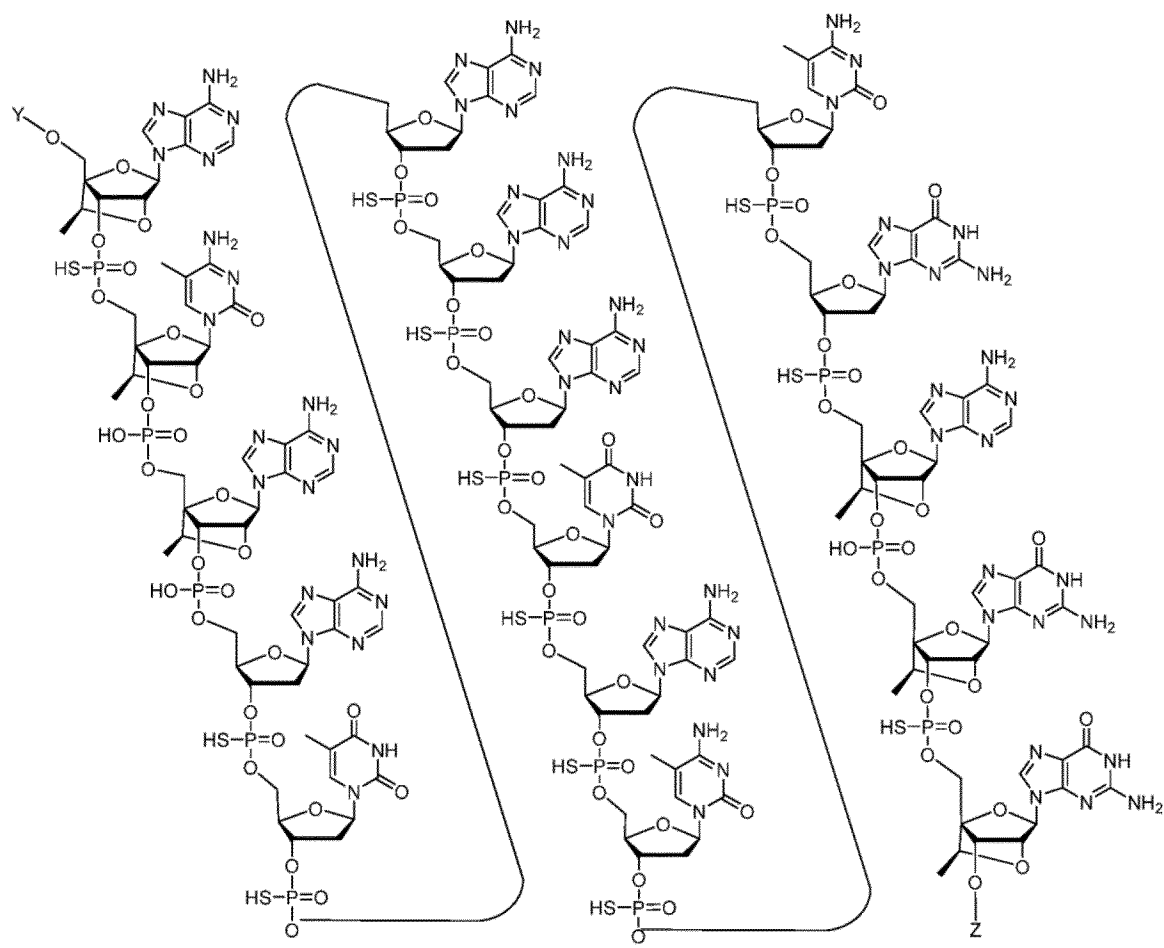

In Columns 53 and 54, the structure should read:

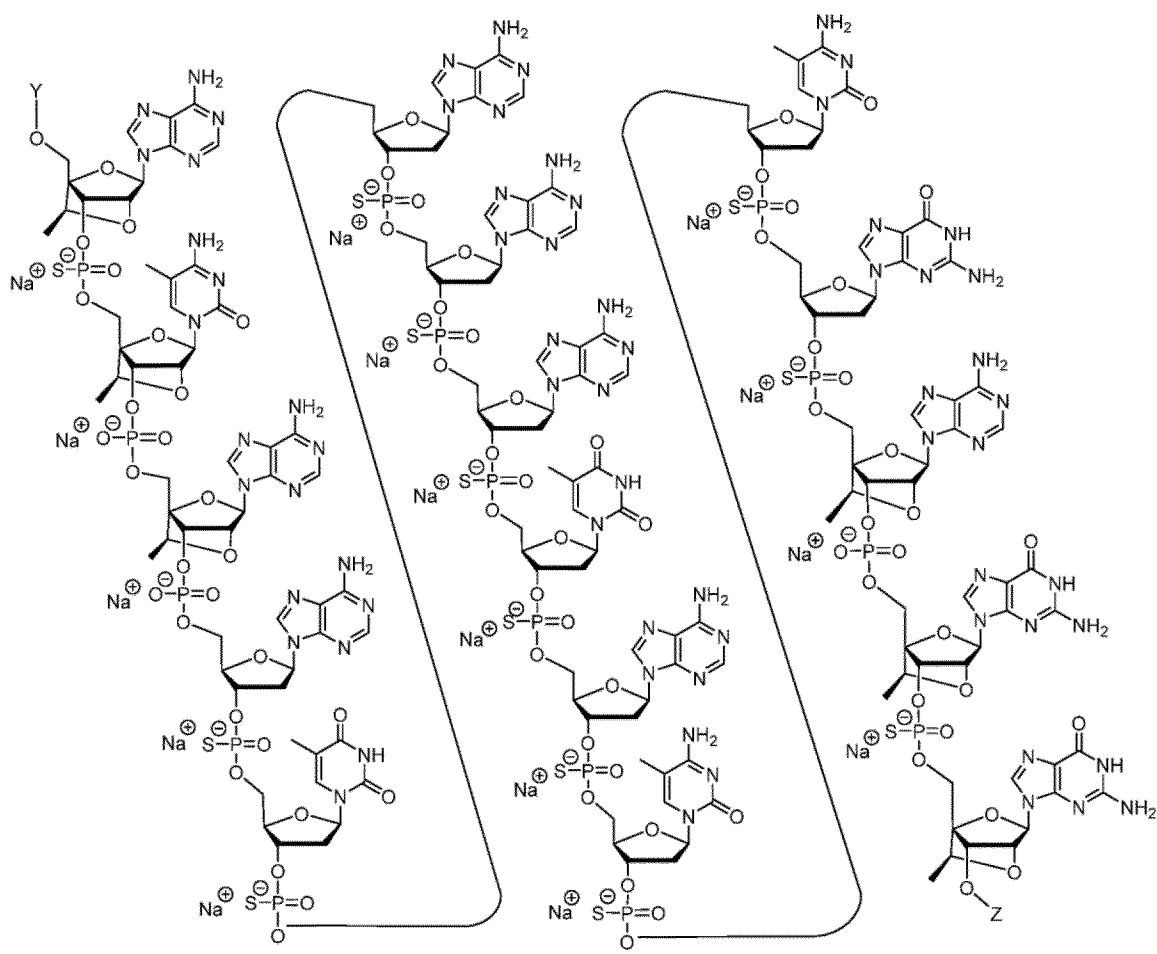
In Columns 59 and 60, the structure should read:

CERTIFICATE OF CORRECTION (continued)
U.S. Pat. No. 11,833,221 B2

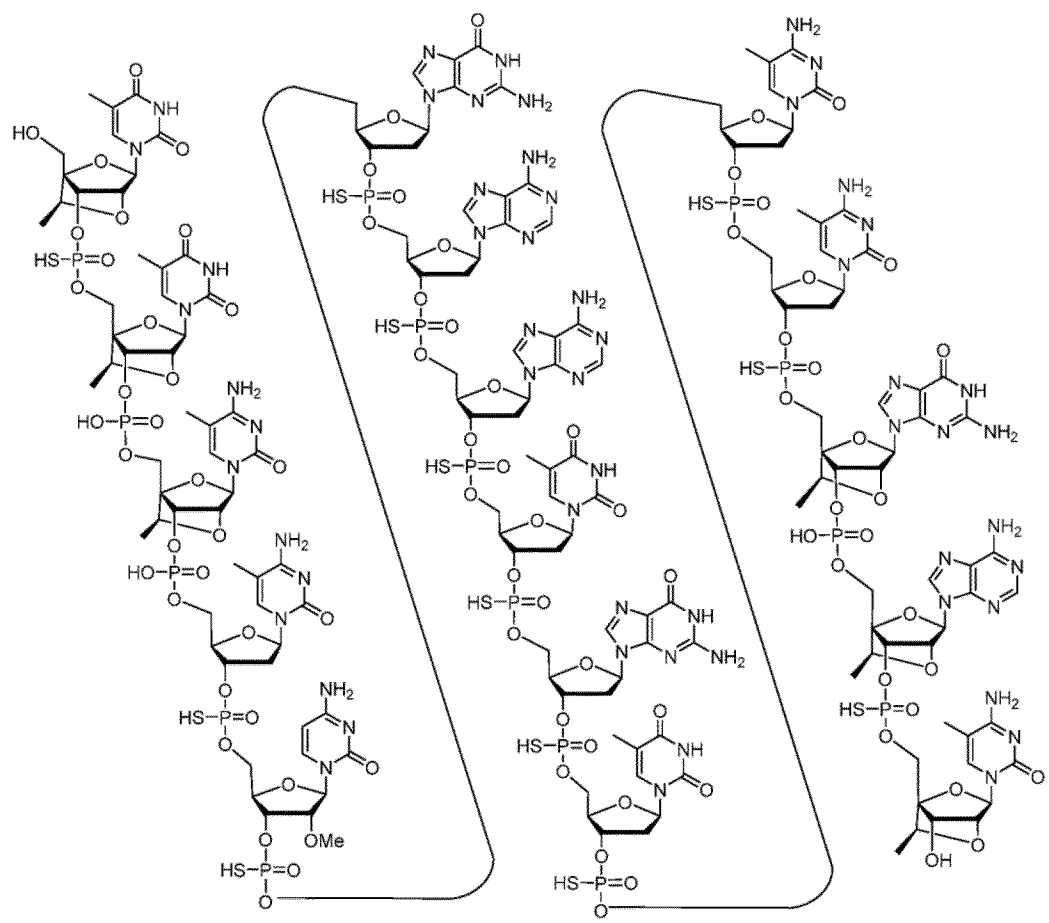

In Columns 61 and 62, the structure should read:

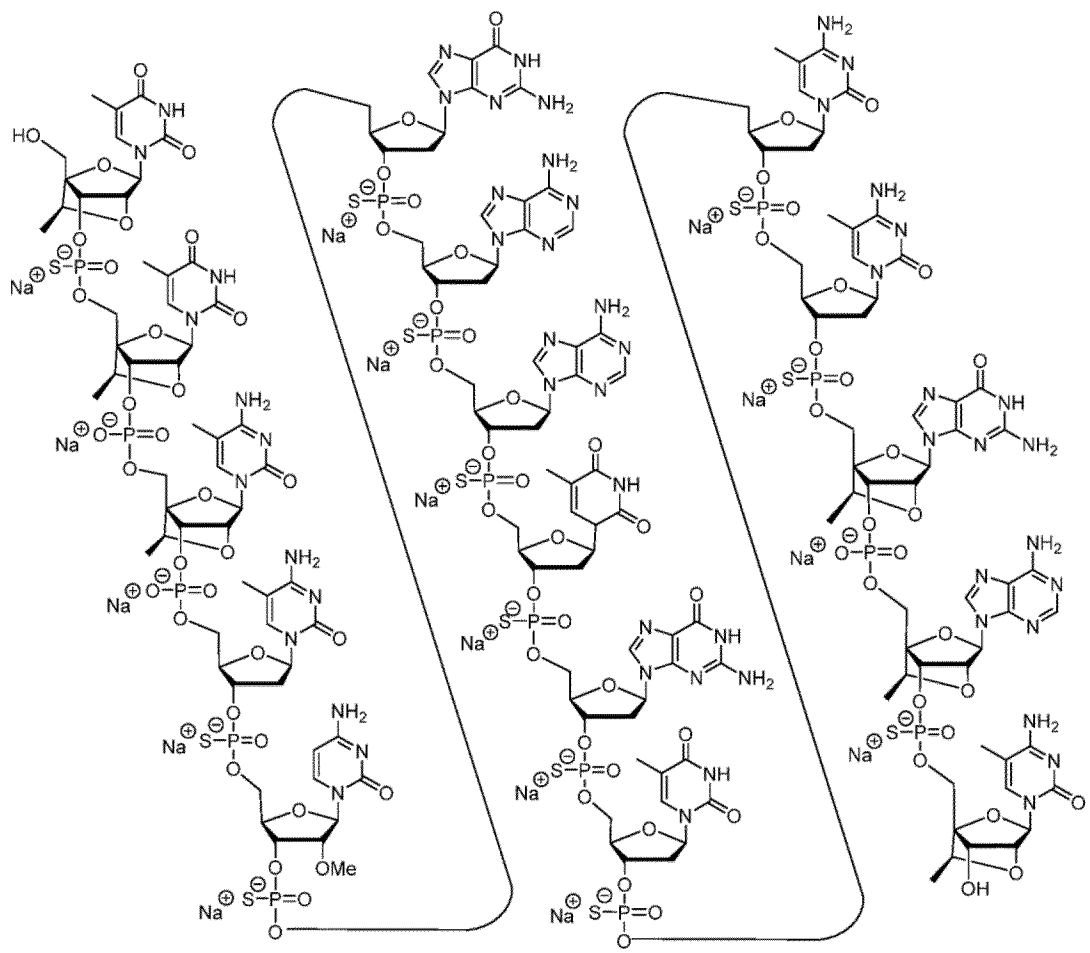
In Columns 63 and 64, the structure should read:

CERTIFICATE OF CORRECTION (continued)
U.S. Pat. No. 11,833,221 B2

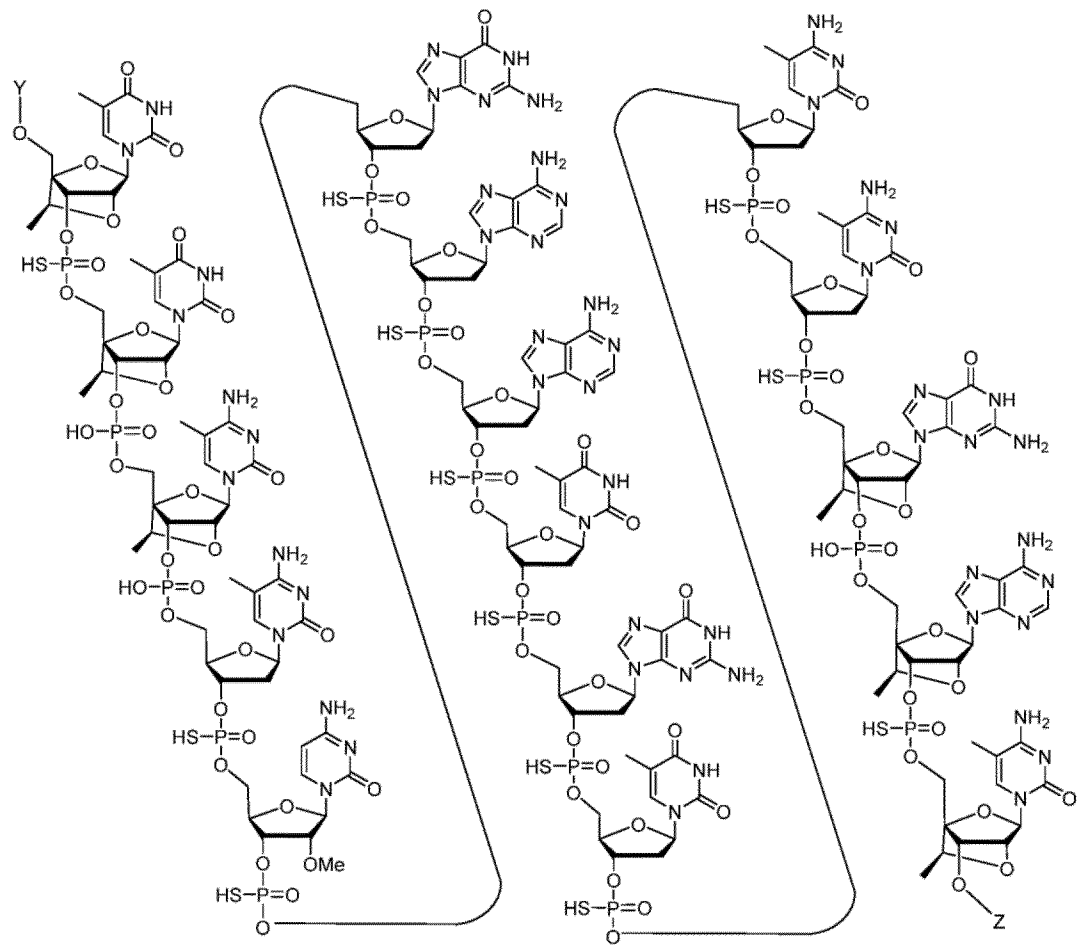

In Columns 65 and 66, the structure should read:

CERTIFICATE OF CORRECTION (continued)
U.S. Pat. No. 11,833,221 B2

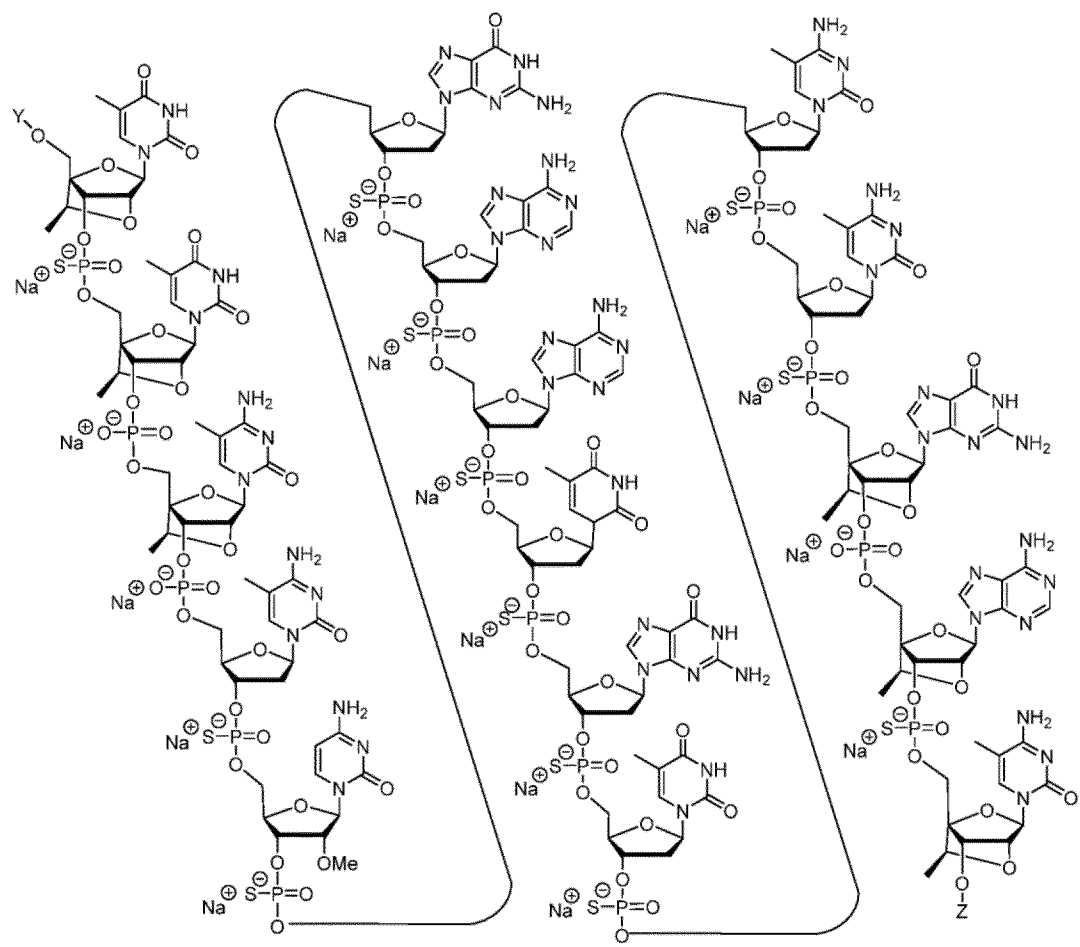

In Columns 67 and 68, the structure should read:

CERTIFICATE OF CORRECTION (continued)
U.S. Pat. No. 11,833,221 B2

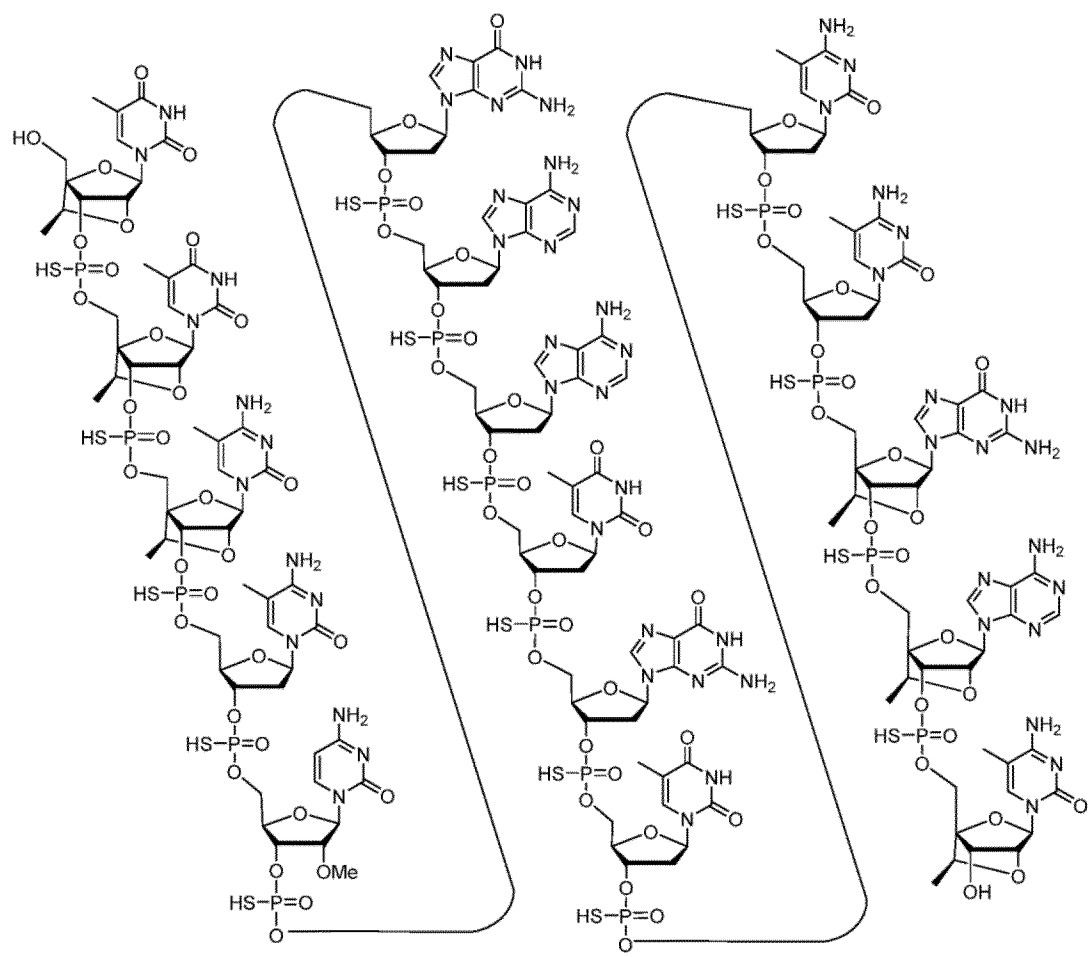

In Columns 69 and 70, the structure should read:

CERTIFICATE OF CORRECTION (continued)
U.S. Pat. No. 11,833,221 B2

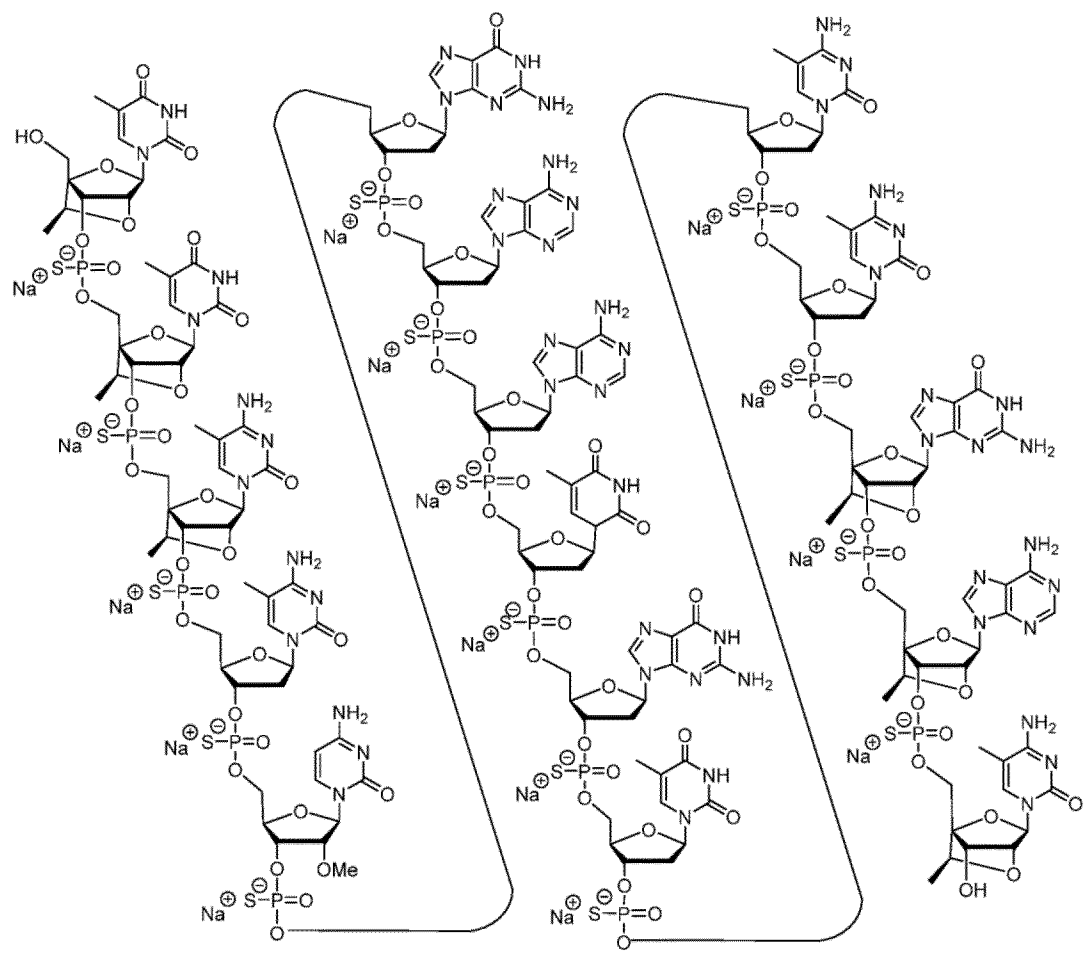

In Columns 71 and 72, the structure should read:

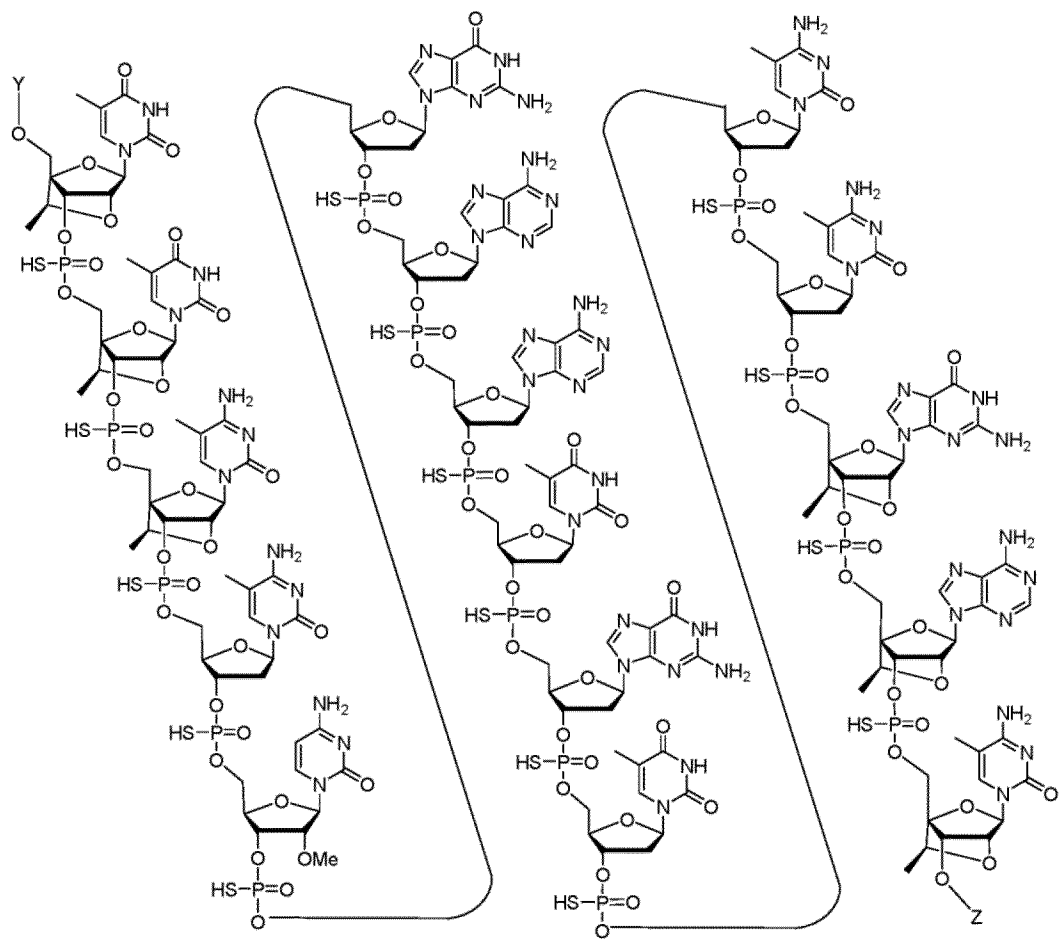
In Columns 73 and 74, the structure should read:

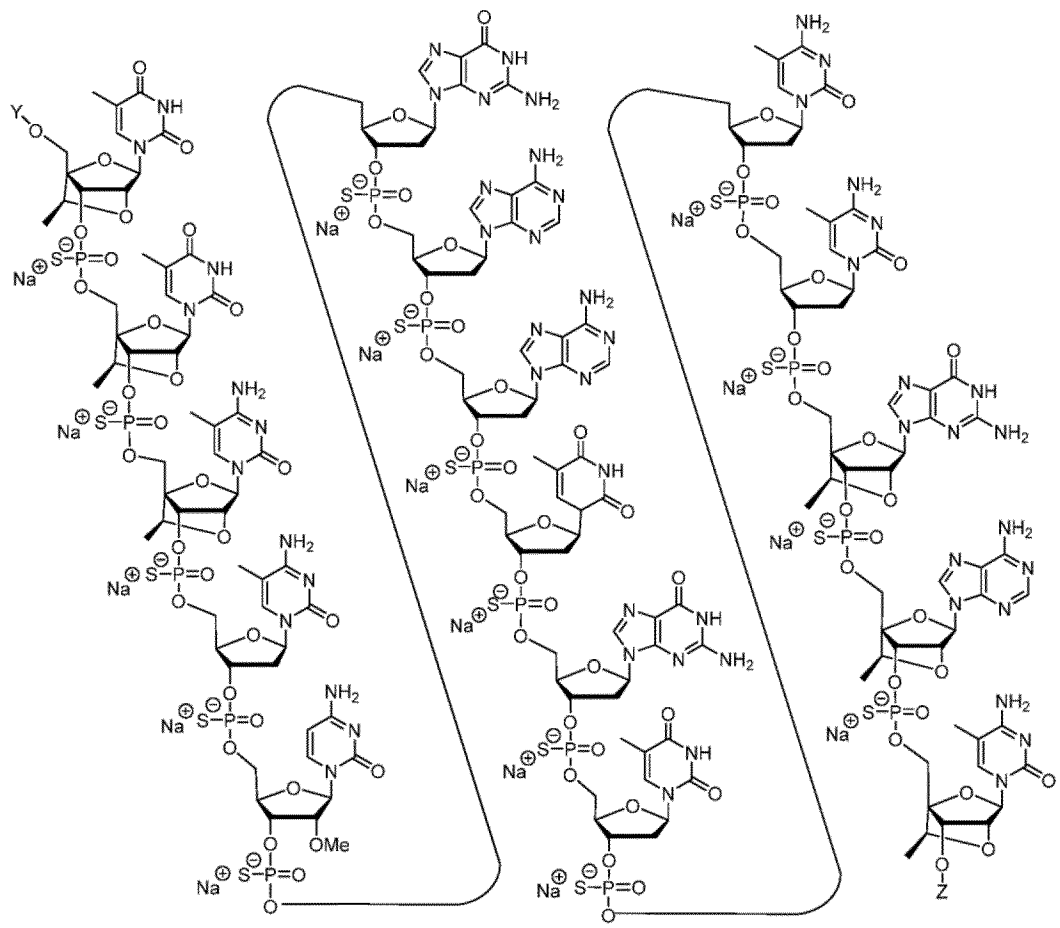
In Columns 75 and 76, the structure should read:

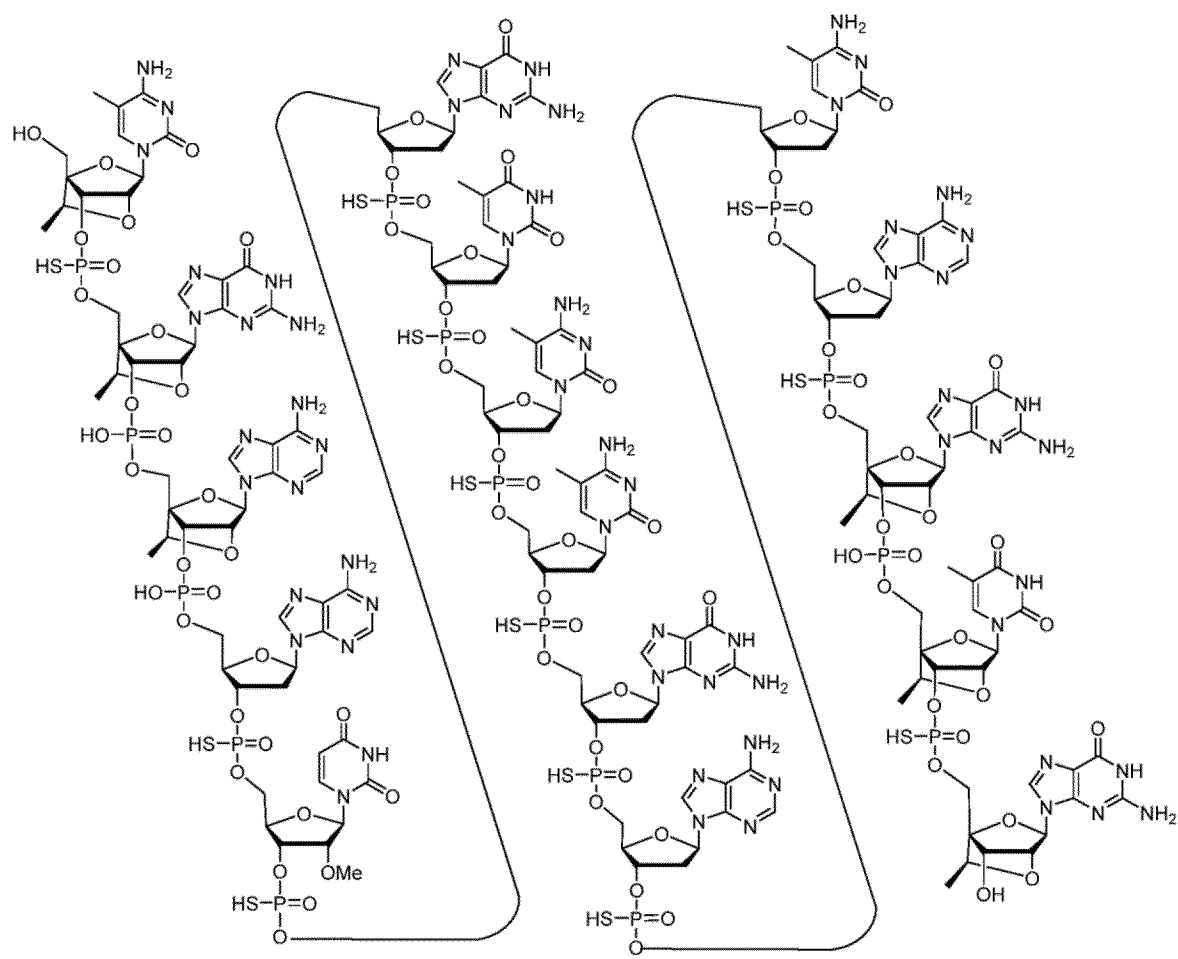
In Columns 77 and 78, the structure should read:

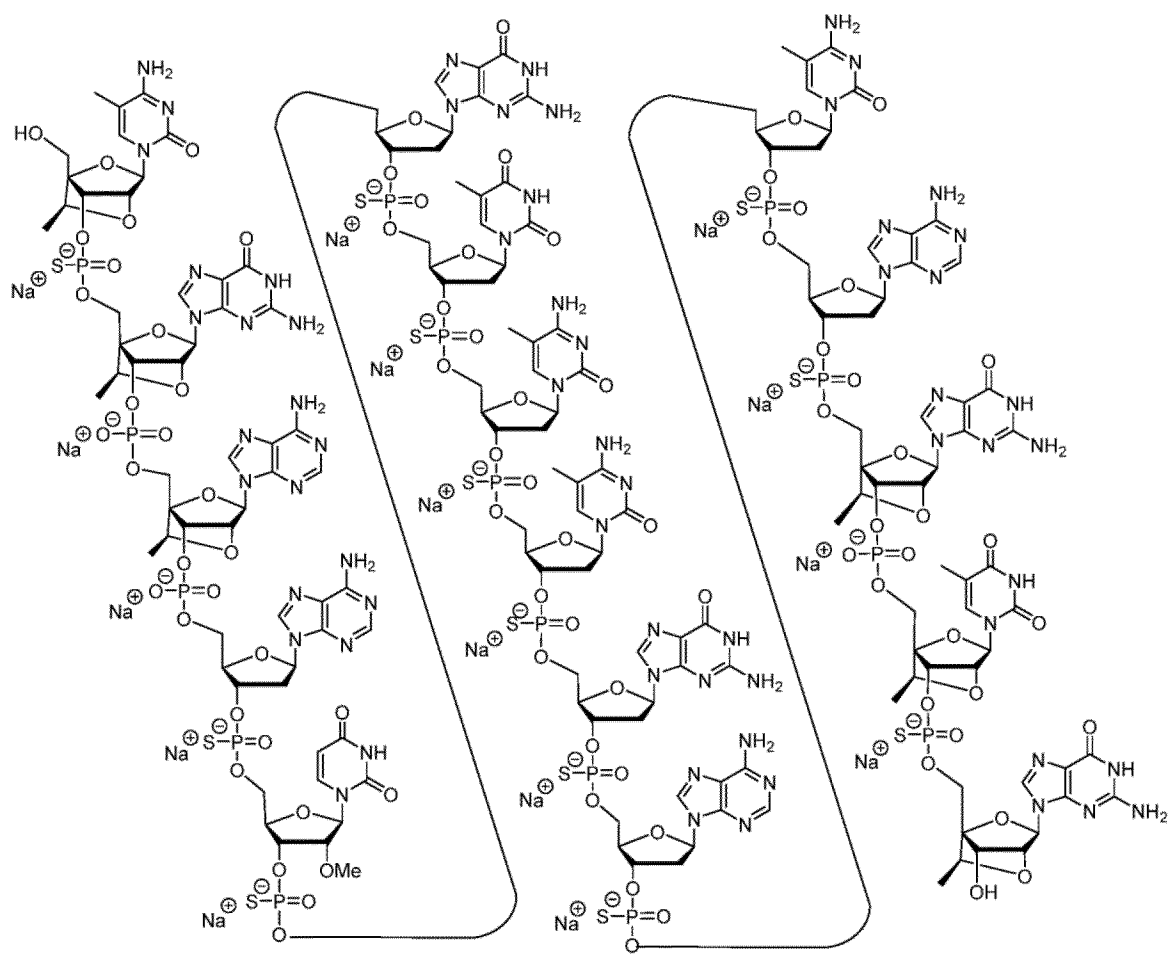
In Columns 79 and 80, the structure should read:

CERTIFICATE OF CORRECTION (continued)
U.S. Pat. No. 11,833,221 B2

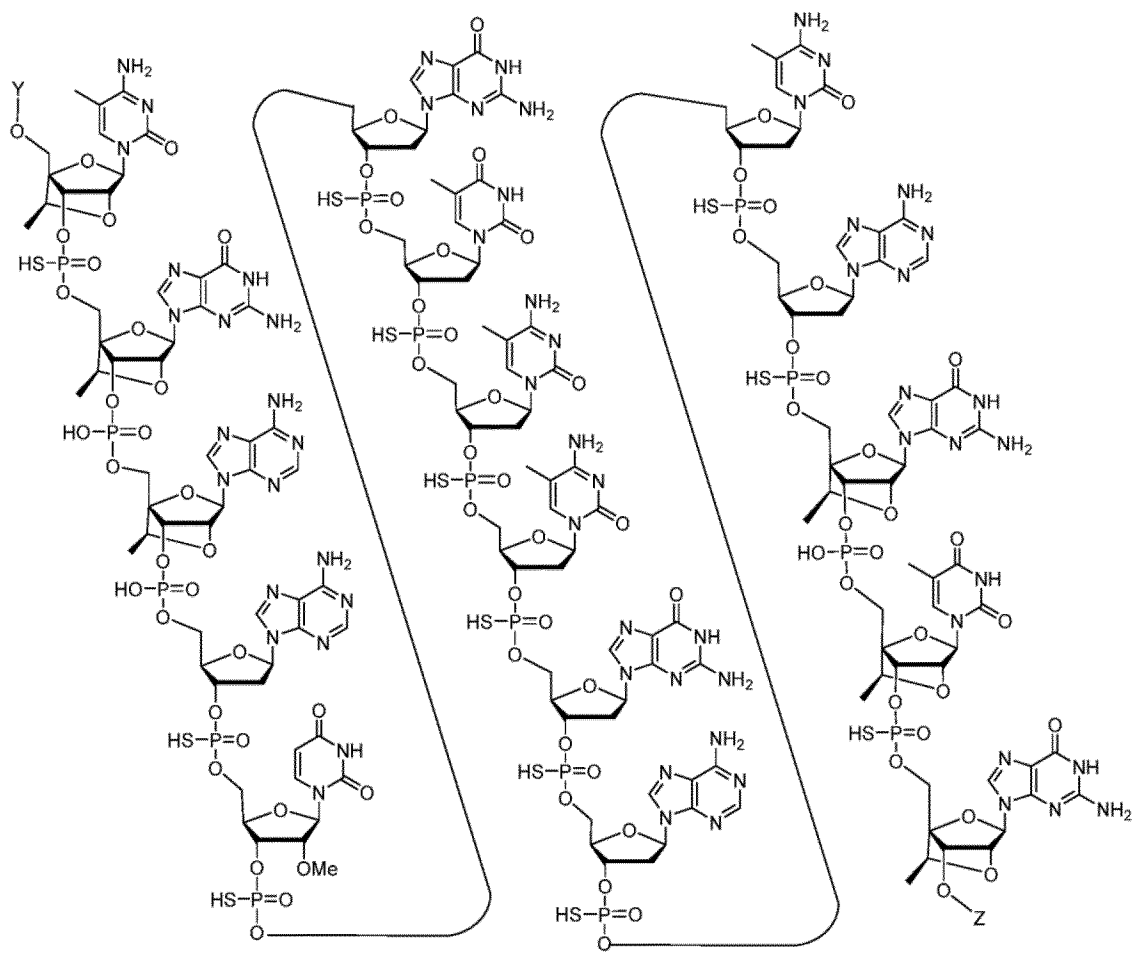

In Columns 81 and 82, the structure should read:

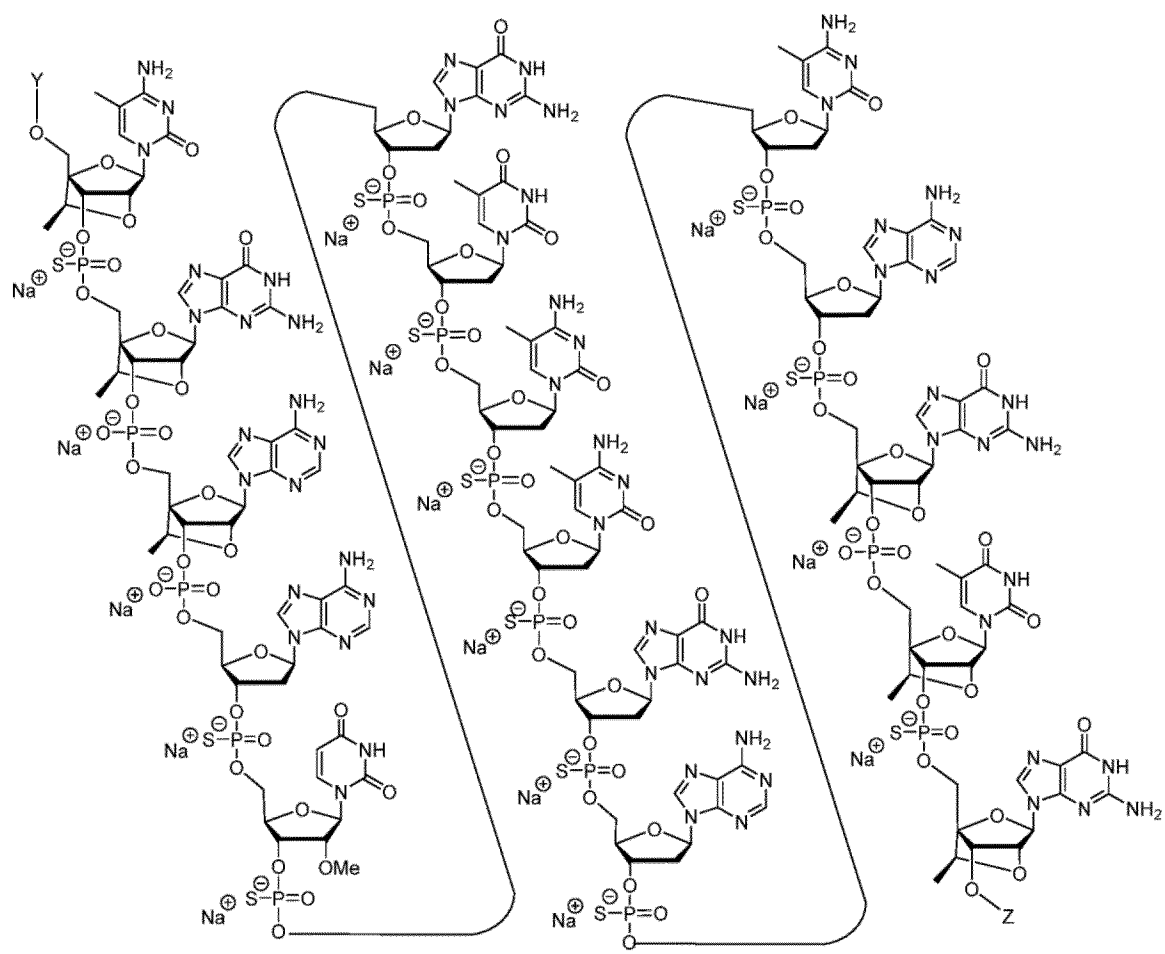

In Column 104, the structure should read:
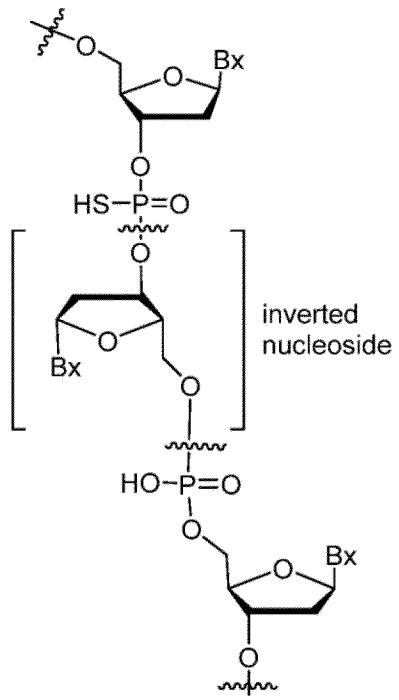

CERTIFICATE OF CORRECTION (continued)
U.S. Pat. No. 11,833,221 B2

In the Claims

In Claim 1, the structure should read:

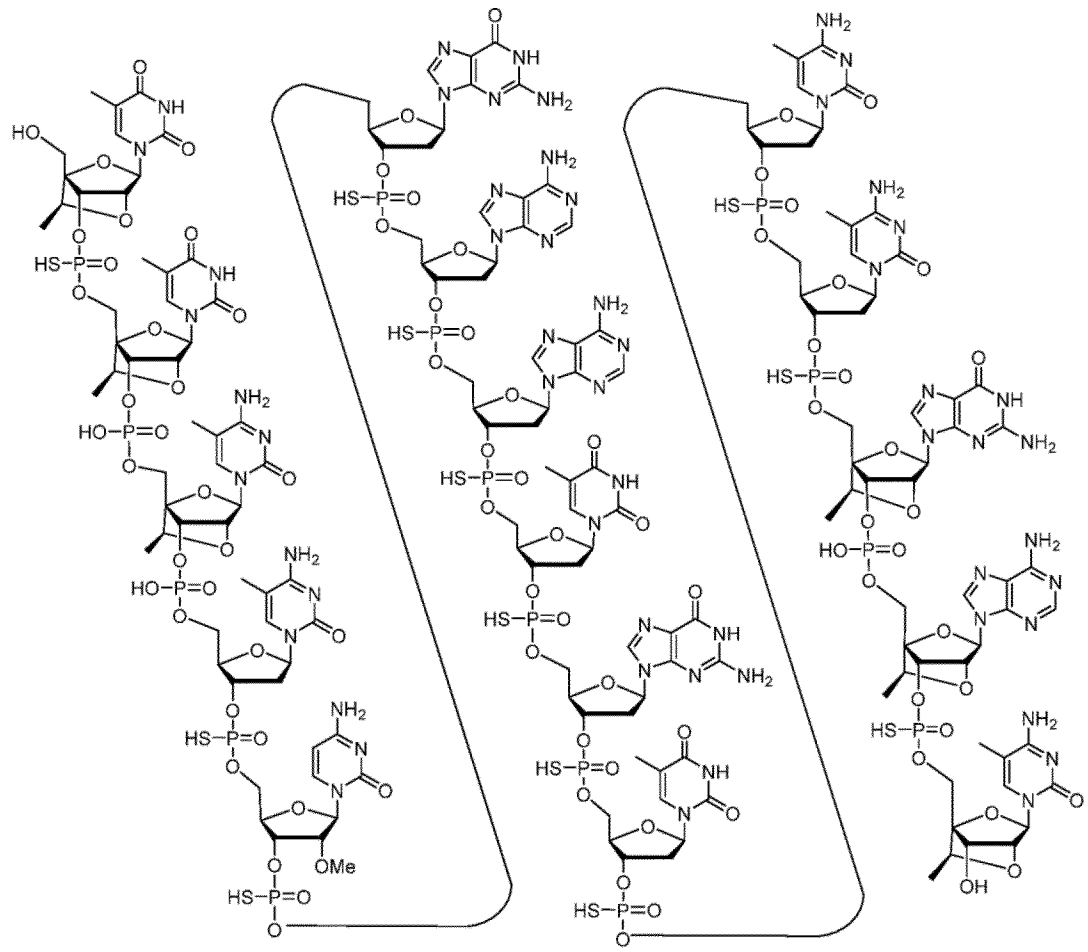

In Claim 11, the structure should read:
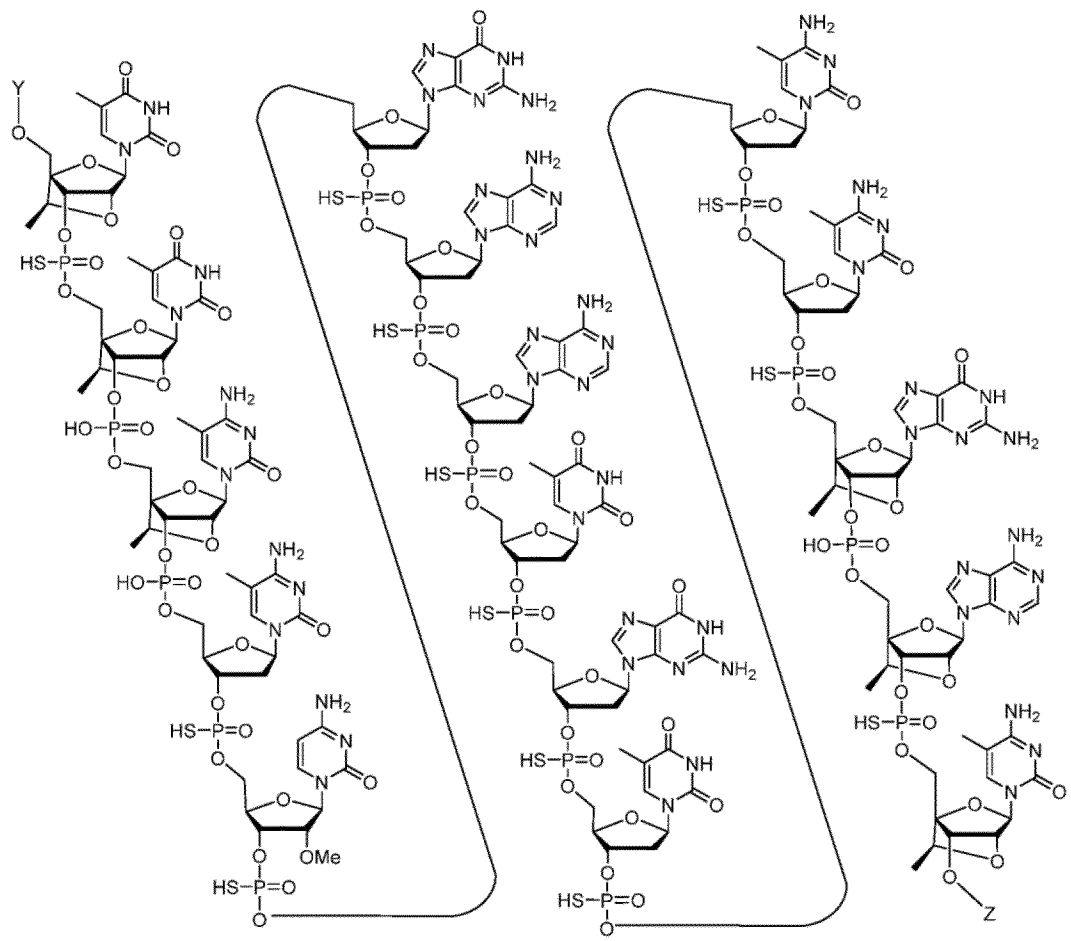

CERTIFICATE OF CORRECTION (continued)
U.S. Pat. No. 11,833,221 B2

In Claim 21, the structure should read:

SEQUENCE LISTING

```
Sequence total quantity: 37
SEQ ID NO: 1           moltype = DNA  length = 27001
FEATURE                Location/Qualifiers
source                 1..27001
                       mol_type = genomic DNA
                       organism = Homo sapiens
SEQUENCE: 1
acttgaaccc aggaggcaga ggttgcagtg agccaaaatc gtcccattgc actccagccc    60
acgtgacaag agcgagactc tgtctcaaaa aaaaaaaaaa aaaaaaaaaa agccgggtgc   120
agtggctcat gcctgtactc ccagcacttt gggaggccga ggtgggtgga tcacctgagg   180
tcaggagttc gagaccagac tggccaacat ggtgaaaccc cgtctctgag ccgagatgga   240
gccattgcac tccagcctgg gtgacagggt gagactgtct caaaaaaaac aaaaacaaaa   300
acaaaataaa acctctctac atgccaagtg aaaggtggaa gtggggtga gacagaaatc    360
tgggagacca agagacacgg ttgatgtggg ggtggggaa gggcttgggt agaggagaag   420
cttggatcag ggagaacaag gaactgagaa agaggaattc cacgtggtcg aatgcaaaag   480
acttggaggc tgtaagcggg ggcagagtga agataaatgg tacacatcta ggaagacacc   540
```

```
caggtctgtg gcctggttga ctgagtggac ggcagagcta gccctaaggt ggggatgcaa    600
gagaggtgga ggatttggtg taagacgtca atttcattgt aggattcttt tttcttctt    660
tttttttttt ttttagagag actgagtctg actctgtccc ccaggcttta gtgcagtgat    720
gtgaattcat agcagtcttg atctcctggg ctcaaacgat cctcccacct cagcctccca    780
aagtgctggg attctcggat tccaggcatg agccaccatg cccgaaccat tgtaggattt    840
ttttttttaa gtgtgagatg cccttgggac actctaggga gaaatcgtag aggccattga    900
ctacatgaga ctagaaagat ctatgatggg gctgggtggc ttcagcagac atggggagca    960
ctggctatga gtaggagctg ttgggatcag ggggagactt tgggttacga gtggatcact   1020
gggacactgg ggcaccgtgg ggatcaatac aatttggaaa tcagaggtag gttttggagg   1080
acaagtgagg ttgttgaaaa taagaaaatc atggaaatat acattggtgg ttggtggaaa   1140
atatgaagga tgtttggagt tagcattaat caatagtggg tcagaggaag tcctctgagt   1200
tgtgtgggga cacagggatt tggtgggtca ccaagggtgg ggaagaatgg tagcagatgc   1260
tgtggtcatt caggggattg aatatgtcag tgggaaacac tggaggtcag gggagtgtat   1320
attgggcgtc taaggagaga ccagggtcac ttgggggttgg ctgtgacttc atgggaaggc   1380
tggactatgg atgagggctt ctttgtcgtg ggggaaaaaa aaaaaaaaat ccctccgttg   1440
ctaggcaaac gttcccaggg cgcggttgct aaggacttga gctttctaac tggccacgcc   1500
tctttccatt gcgggctccg cccccgcagc caaccacaag tcggtcacag gctcaaaggc   1560
cgcgccacc ttctcgcccc gcccacagtc ccagccaccgt tacccgagcg accgcgggga   1620
ttcgtcccgc ctccggatct gggtgccaat cgaagaggcg ttgcccgggc gacgacccca   1680
ccttttccgg cgcggggccag cggcttccgg gaggggggccc ggctgcgggc ggcagtccgg   1740
cagtggcggg gcccggggg cgcccaagat ggcggcgggc ggcgcggagg gcggctcggg   1800
ccccggcgcc gccatggggg actgcgcgga gattaagtcg caattccgca cgcgcgaggg   1860
tttctacaag ctactcccgg gcgacgcgc cgctcgcagg tcgggtccgg cttccgccca   1920
gactccggtg ccgcctcagc caccgcagcc cccgcccggc cctgcctccg cctccggtcc   1980
cggcgctgca ggccccgcgt cgtccccgcc gcccgcaggc cccggacccg ggcccgcccct   2040
gcccgccgtg cgcctcagcc tcgtgcgcct cgggagccg gacagcgccg gggccgggga   2100
gccgccgcc acgcccgcgg ggctgggctc gggggagac cgcgtctgct tcaacttggg   2160
ccgtgagctc tatttctacc caggctgctg tcgtcgtggg agccaacggg tgagcggcct   2220
gcatcgtggg gccctgggtg ctgaaaggat ggaggttcca gagaactgat aggagggtcc   2280
ccgaattgat atgggggccct gagataggca ttctaaatgt gatggacgtt gtagggcgac   2340
agcattggag ggagtacagg attctgaaat gtgatgagga gccgcgggg tgctgggcag   2400
gcatcttgga ggtgatgggg gaaatcccct ttaccccgt tatgcgtagg agttctggga   2460
tggtgactat tggacatgat ggggtatctg agatgaggtg ggatccccg ggttctgggg   2520
tggcaggcat tctgcaggta atggggaatc atgaggtgat gcaagcccag aggtgatgga   2580
gaacccagta ttgcagcctg gaggtgtggg agagggtct tgagattgag cccaggaatg   2640
aggagaagtc tagaagtgat gggggccttg aaggtgatag gggatccaga agctgaatgg   2700
gattctagag aaaattgggg tctggaagtc atgagggtcc tggaggagat gagcgtccgg   2760
aagctgatgg gagctctcaa gggaatgaga ggccctggca ggggaatctg caggtgtgat   2820
tcaggacatc tctaaagcga tgtggtgaga accctgccg tttatggtga tcccagaaat   2880
gatgggggatc cttcggagcc cctaggtaat aaatggccct aaaatgtggg agaccgtgag   2940
gtttgacggg tcccagaact gtggcggttt agggactaca aagtgaagag aatgctagga   3000
tgttaggctt tagagtcctg gaaatttggg tgacctcaag gtttgggggt cttgaatag   3060
tgtggtacta ggtcccaagg gagttgctga ggttataga tggagtggtg aggctaaaag   3120
gaatcggagc ttaggaactg tgtggaccca gaacccgat tatgtggaca agggtgtctc   3180
tgaattagag gtgacccaac tttgggggagg cactgtggtc aagggggatc cttaccatct   3240
tttttgctac tcttgtctgt gatttgggtc cccttcccgt ctgtgttgc cccgtccttc   3300
gcaatccacc tactcacctc cccacttccc tctgggttct aaccctgctt cctcttagtg   3360
gtttccccca acctcaacat cctcttcctt ctcctcagtg gcatacacca ttaactcctt   3420
ttctcccacc cctcaagtcc attgacctca acaagccaat tgacaagcgg atctacaagg   3480
gcacccagcc cacctgccac gatttcaacc agttcactgc tgccaccgag accatctcgc   3540
tgctggtggg cttctcagcg ggtcaagtgc agtacctgga tctcatcaaa aaggacacca   3600
gcaagctgtt caatgaggag gtgattgcag cccccagagc ccccaacttc tctgccttct   3660
cacctaccca ctatatgcca ttaggatgca gctgcctgcg gaacagtgta ggcctgagag   3720
gggcaggacc agggagagat ggagaatggg gtgacagcag ctaatgacag ctgcctttac   3780
tgtaccaggg ccctgtgctg tgttaccctt gtgctgaata ctttactcct tgggttttct   3840
ttctttcttt cttctttta ttatttatt ttgagatgga gtctcaccct gtcacccagg   3900
ctggagtgca gtggcgcgat ctctgctcac tgcaagatcc acctcccggg ttcatgccat   3960
tctcctgcct cagcctcctg agtagctggg acttcaggca cctgctgcca cgcccgccta   4020
atttattgta gttttagtgg agatggggtt tcaccgtgtt agtcaggatg gtctcgatct   4080
cctgacctcg tgatctgccc acctcggcct cccaaagtgg tgggattaca ggtgtgagcc   4140
accatgcccg gttctttttt ttttttttaa ttgtaattgt aattttatt gttttaatt   4200
ttttttttct ttttaaggcg gagtctcact ctgtcgccca ggctggagtg cagtggtaca   4260
atctcgggtc actgcaacct ccgcctccca ggttcaagca attctcctgc ctcagcctcc   4320
tgagtagctg ggactacagg tgcgcactat catacctggc taatttttt ttttgagatg   4380
gagtctcgct ctgtcgccca ggctggagtg cagtggcgcg atctcggctc actgcaacct   4440
ctgcctcccg ggttcacgcc attcttcgt ctcagcctcc ccagcagctg ggactacagg   4500
cgcccagcac cacgcccagc taatttttt gtatttttag tagagacggg atttcaccgt   4560
gttagtcagg atagtctcga tctcctgacc tcgtgatctg cccgcctcgg cctcccaaag   4620
tgctgaatt aaaggcgtga gccaccacac ccggccaatt tttgtatttt tggtagagat   4680
gggtttcac catgttggcc aggctggtct caaacacctg accttgtgat ccgcccacct   4740
cggcctcccg aagtgctggg attacaggca tgagccaccg cgcccggcca ttctttgagt   4800
tttcatcaac cagtggatac agaagtgtgc tgcccatttt gcagattaga gaattgaggc   4860
tagtaaataa gtcgggactt agttgatgcc cttgctcttt gagttctggg ctctggaggc   4920
tttggattca aagccctgct gcaccattta ctcatcatgt gactttggga aggtgaccat   4980
tctctgagcc tcacttctcc tcctctgcaa aatgggattc cagttcctac cttgcaggac   5040
cgctgttgta gaatcataca tggagattgc tcagtcctgg gccaacttgg cctacgagga   5100
gataccagta aacgaccta tccgcgggca gggactgctc ttggcttctg tctcattctc   5160
tctggtccag aggaggtgtt ccataaatat tctcagaatg agtgaatggc tgaagggagt   5220
gaacggaaca gtcagtggat taaaaattca ttagctcatc cattcacaaa tagttttga   5280
```

```
gcatccgttc tgtgccaggc accgttccca gcactaggga tatcacatct cagggccctg    5340
gacaggaggc cctgcccttt tggagctttc agtctagctg gggagacaga cagttaatca    5400
agttaagtct tcgtgtgtca gcaggtgatt aaggcctgtt tagaagaagc agtgggggaag   5460
gggctgaggg aagcttggag agtttagtag ggtggtcagg aaagccctca ctaagaggtg    5520
atactgaaat aaagacctga aggaggcagg tgagaagagt tgcctgggga agggcatttt    5580
tttttttttt tttcctgaga tagggtctca ctctgtcgtc catgctggag tgcagtggta    5640
cgatcttcgt tcactgcaac ctccgcctcc caggctcaag cagtcctccc atatcagcct    5700
cctgagtagc tgggactaca tgcatgcacc accacaactg gctaactttt gtattttttg    5760
tagaggcggg gtctctttgt gttgcccaag ctggtctcga actcctgggc tcaagctatt    5820
ctcctgcttt ggcctcccaa agcgctggga ttataggcgt gagccatcac acccagccaa    5880
gaaggacatt ctgagtatcg gggccagcta ggacaaatgc aggattgcac agaagccgtg    5940
tggccagtgc agttactgag ggagagaaga tggtagatga gttccaagaa ataacggagg    6000
ggctggctca tggagagtct ggaaggtcac ggagagattt tgccttactc ttagttggaa    6060
gcctgtggag gagcctttct cattggggct cacctgagcc ctgaaaggca gaagtgacta    6120
gagtgattat ttgttcagtt ctcccaggga tgggaggcac ctcatcctgg gagagcagct    6180
ccttagttgc atacactggc tgcctgagag cattagggcc tcaggctctg gaaccctgct    6240
tgagagaggc tgcgaagtgt tcagagcagg acagtgccag gtgctggctg atacttcaca    6300
gagcatcgct gtggcggctg cagaggacag acaggcccag gcattggagc ctgaggccag    6360
tcacacagca ttgcaggctt gggggtggttg aatgggatgg tgagaggagg tcagattctg    6420
ggtgtatttt ttcttttttt tttattttga ggtggagtct cgctctgtcg cccaggctgg    6480
agtacagtgg catgatctcc cctcactgca acctccgcct cccgggttca agcaattctg    6540
cctcagcctc ctgagtagct gggactatag gcgcccgcca ccatgcctgg ctaattttttg   6600
tatttttagt agagattttg tatctctact tgtatttcac catattggct aggctggtct    6660
ggaactcctg actttgtgat ccgcctgcct cagcctccca aagtgctggg attacaggcg    6720
tgagccacca cgcccagcca cttctgggtg tattttgaag gtcgagccca caggatttgt    6780
ggaaggattg gatgaggaaa agaggggcag atgccgaggt tttttgtcta agcacctagc    6840
gggatggggg gttgtcactc atttgtccag gaattacctt caagctgcct cctgtgtgca    6900
ctgctttaaa gaatagtgaa ccaaacaaag atcgcttcct ttggggagct gccttttccgt   6960
gaagaaattt cctacttgaa gcctgacgta gtaaagatcg ggggagggtt agacagatac    7020
agtggtcccc aaccattttg gcaccaggga ctggtcttat ggaagacagt ttttccacag    7080
actgttgggg ggatggtttt gggatgaaac cgttctgcct ctgatcatca ggtgttagat    7140
tctaataagg agcgcacacc tagatccctc gcatgcatag ttcatggtgg ggttcgcact    7200
cttacgagga ttgaatggtg cgctgctccg gtaggaggct gggctcaggc tgtaatgcct    7260
gctcgcccac cactcacctc ctgctgcatg cctggttcc taacaggcca cggaccacta    7320
ctgttccatg gcccgaggt tgaggacccc gagatacagg acaattctgt ggcaagcagg     7380
actgtcccct cgccaaagat gggacatcga ggctccttgg agcaccctgt ggccaccttg    7440
cagcagcctc tgtttcccca tgtttccatg acctggtgtc catctgtctt ccccagtttg    7500
ggagcttctc tccgaggagg acctgggcct ggtgtgcac ctgctgtgtg agcggggcca     7560
tgtccaacgg ccttcttggg gacttgggt cggggagaag ttctgcctgg gttttactgc     7620
cttctcccaa ccccacactg tctccctgg cagcggttga tcgacaagac caaggtgaca     7680
tatctcgaagt ggctgcctga gtcggagagc ctgttcctgg catcacacgc cagtggccac   7740
ctgtacctgt acaacgtcag ccaccctgc gcctcggccc cgcccagta cagcctgctg      7800
aagcagggcg aggcttctc tgtctatgct gccaagagca aggcaccccg caacccgctg    7860
gccaagtggg cggtgggtga ggggcccctc aacgagttcg ccttctcgcc cgatggccgg   7920
cacctggcct gtgtgagcca ggatggctgc ctgcgcgtct tccacttcga ctccatgctc   7980
ctgcgtgggc tcatgaagag ctactttggg ggcctgctgt gtgtgtgctg gagccctgac   8040
ggccgctacg tggtgacggg tggcgaagat gacctggtca ccgtgggtc cttcaccgag    8100
ggccgcgtgg tggctcgagg ccatggccac aagtcctggg tcaacgctgt ggcctttgac   8160
ccctacacca caagggcaga ggaggcggcg acagcagccg gtgctgatgg ggagcggagc   8220
ggcgaagagg aggaggagga gccccgaggct gcgggcacag gctcggccgg gggcgccccg  8280
ctctctccac tgcccaaggc tggctccatt acttaccgct ttggctccag gggccaggac   8340
acgcagttct gcctgtggga cctcactgaa gacgtgctct acccgcaccc ccccctggcc   8400
cgcacccgca cctccctgg cacacctggc accacgccac cggccgccag cagctcgagg   8460
ggtggcgagc ctggcccagg ccccctgcct cgctcgctgt cccgctccaa cagtctcccg   8520
cacccagctc gcgggggcaa ggcgggcggc ccgggtgtgg cggcagagcc tggcacacca   8580
ttcagcattg gccgcttcgc cacgctcaca ctgcaggagg ggcggaaccg ggggcagag    8640
aaggagcaca agcgctacca cagcctgggc aacatcagcc ggggtgcag tggcggcagt    8700
ggcagtggtg gggagaagcc cagcggccct gttcccccgca gccgcctgga ccccgccaag   8760
gtgctgggca ctgcgctgtg cccgcgcatc cacgaggtgc ccctgctgga gcccttgtg    8820
tgcaagaaga tcgcccagga gcggctcaca gtcctcctgt tcctgggaga ctgcatcatc   8880
actgcctgcc aggagggcct catctgcacc tgggcccggc cggcaaggc ggtgagtggc    8940
cccacaccag cctgccgggg acctggcagg acctttcgtg ggaagaggca ggcattggca    9000
gagagaggc tttgttgctg tcacagcctc tggctccgtg gggtgagggg aagccaggga    9060
aatcttagtg tctcagtaca agacctctca gatccttaga gtgaggggt ctagccctag    9120
gcagcaggca gcagaaagag gggtgggtgt gagagcagc taggaattgg ggcatccaag    9180
gctgccgtc tgaagggcag cagatgggcc ccacatggcc aggtcttact gcctgtcact    9240
cgaaccagaa tctatttctg ttgaacatct gttttttaaa tcgtgaaact ttttgagta    9300
cttcaggcca aaactagggg cgagctcaag cctgtgggca tggctgccag cctgggtctg   9360
ggactcagga tctgagcctc cgtgaaggg cacaggctgg gaatccagga cctgggttcc    9420
agtcccactc cctctgtgac cctggacaag tcactgcccc ctctgacctc caactcatca    9480
cctcttagaa cagagcctgt aggatgggca gtggtggat gtgcttgcct cctgggtggg    9540
ctgtggcgtt gggaaggtca tagtaggcga atcaggcctg gcatcttgta agttcggagc   9600
tcgtcttggg tgtctcagct tcttaggct tggactcagt tgcccaggt cctggaggcc     9660
gtggcttggt tcctcagatc ctcagttttg gaatcgtaga gtcctgagtc ctagaactt    9720
gagagcacag tctgagtgac tcagaggcaa gagtggtggg atttggggag tctggttgag   9780
tcctaaaaga gaccccctctg tctccgtagt tcacagacga ggagaccgag gcccagacag   9840
gggaaggaag ttgcccagg tcacccagca agtcagtggt agaggtagga ctgtccctga    9900
gttctttccc cagcacctca gggtccctcc caagttagaa gggagctcca gtttcccct    9960
cccctcccac ccttacccctt accccatggt ctcactcagg atccgccaag gactttgatt  10020
```

```
attgcgtgaa agtgctgact gccaggacag gaagctagct aagatgcaag ttcccagcct   10080
agagcagtgg cctctggggg gtctagggcg gacccaaggg caaggccagg gtggcagcag   10140
ctttggggac tctgggctgg ctccctcccc ttgacactgg ctgaagccca ggtggtctct   10200
aaccCctccc atctctccct ctcatcttcc ccagggcatc tcctcccaac caggcaactc   10260
cccgagtggc acagtggtgt gaagccatgg atatcggatc ccccaaccc catgccccca   10320
gcctcctagc cataaccctc cctgctgacc tcacagatca acgtattaac aagactaacc   10380
atgatggatg gactgctcca gtcccccac ctgcacaaaa tttggggcc cccagactg    10440
gcccggacac gggcgatgta atagcccttg tggcctcagc cttgtccccc acccactgcc   10500
aagtacaatg acctcttcct ctgaaacatc agtgttaccc tcatccctgt cccagcatg    10560
tgactggtca ctcctgggga gagactcccc gcccctgcca caagagcccc aggtctgcag   10620
tgtgcccctc agttgagtgg gcagggccgg gggtggtcca gccctcgccc ggcccccacc   10680
ccagctgccc ttgctattgt ctgtgctttt gaagagtgtt aaattatgga agccctcag    10740
gttcctccct gtcccgcagg acctcttatt tatactaaag ttccctgttt tctcagcggg   10800
tctgtcccct tcggaggaga tgatgtagag gacctgtgtg tgtactctgt ggttctaggc   10860
agtccgcttt ccccagagga ggagtgcagg cctgctccca gcccagccgc tcccacccct   10920
tttcatagca ggaaaagccg gagcccaggg agggaacgga cctgcgagtc acacaactgg   10980
tgacccacac cagcggctgg agcaggaccc tcttggggag aagagcatcc tgcccgcagc   11040
cagggcccct catcaaagtc ctcggtgttt tttaaattat cagaactgcc caggaccacg   11100
tttcccaggc cctgcccagc tgggactcct cggtccttgc ctcctagttt ctcaggcctg   11160
gccctctcaa ggcccaggca ccccaggccg gttggaggcc ccgacttcca ctctggagaa   11220
ccgtccaccc tggaaagaag agctcagatt cctcttggct ctcggagccg cagggagtgt   11280
gtcttcccgc gccaccctcc accccccgaa atgtttctgt ttctaatccc agcctgggca   11340
ggaatgtggc tccccggcca ggggccaagg agctattttg gggtctcgtt tgcccaggga   11400
gggcttggct ccaccacttt cctccccag cctttgggca gcaggtcacc cctgttcagg    11460
ctctgagggt gcccctcct ggtcctgtcc tcaccacccc ttccccacct cctgggaaaa    11520
aaaaaaaaaa aaaaaaaaa agctggtata aagcagagag cctgagggct aaatttaact   11580
gtccgagtcg gaatccatct ctgagtcacc caagaagctg ccctggcctc ccgtcccctt   11640
cccaggcctc aaccccttcc tcccaccag ccccaacccc cagccctcac cccctagccc    11700
ccagttctgt agcttgtcgg gagcaagggg gtggttgcta ctgggtcact cagcctcaat   11760
tggcctgtt tcagcaatgg gcaggttctt cttgaaattc atcacacctg tggcttcctc    11820
tgtgctctac ctttttattg gggtgacagt gtgacagtc agattctcca tgcattcccc    11880
ctactctagc actgaagggt tctgaagggc cctggaagga gggagcttgg ggggctggct   11940
tgtgaggggt taaggctggg aggcgggagg ggggctggac caaggggtgg ggagaagggg   12000
aggaggcctc ggccggccgc agagagaagt ggccagagag gcccagggga cagccaggga   12060
caggcagaca tgcagccagg gctccagggc ctggacaggg gctgccaggc cctgtgacag   12120
gaggaccccg agccccggc ccggggaggg gccatggtgc tgcctgtcca acatgtcagc    12180
cgaggtgcgg ctgaggcggc tccagcagct ggtgttggac ccgggcttcc tggggctgga   12240
gcccctgctc gaccttctcc tgggcgtcca ccaggagctg ggcgcctccg aactggccca   12300
ggacaagtac gtggccgact tcttgcagtg gggtgagtgc ctaccctcgg ggctcctgca   12360
gatggggtgg gggtggggca ggagacaggt ctgggcacag aggcctggct gttggggggg   12420
caggatggca ggatgggcat ggggagatcc tcccatcctg gggctcagag tgtggacctg   12480
ggccctgggg caacatttct ctgtcctatg ccaccactct ggaggggcag agtaaggtca   12540
gcagaggcta gggtggctgt gactcagagc catggcttag gagtcacagc aggctaggct   12600
gccaacagcc tccatggcc tctctgcacc ccgcctcagg gtcagggtca gggtcatgct    12660
gggagctccc tctcctagga ccctcccccc aaaagtgggc tctatggccc tctccctgg    12720
tttcctgtgg cctgggcaa gccaggaggg ccagcatggg gcagctgcca ggggcgcagc    12780
cgacaggcag gtgttcggcg ccagcctctc cagctgcccc aacaggtgcc caggcactgg   12840
gagggcggtg actcacgcgg gccctgtggg agaaccagct ttgcagacag gcgccaccag   12900
tgcccCctcc tctgcgatcc aggagggaca actttgggtt cttctgggtg tgtctccttc   12960
ttttgtaggt tctgcaccca ccccaccccc agccccaaa gtctcggttc ctatgagccg    13020
tgtgggtcag ccaccattcc cgccacccg ggtccctgcg tcctttagtt ctcctggccc    13080
agggcctcca accttccagc tgtcccacaa aaccccttct tgcaagggct ttccagggcc   13140
tggggccagg gctggaagga ggatgcttcc gcttctgcca gctgccttgt ctgcccacct   13200
cctcccccaag cccaggactc gggctcactg gtcactggtt tctttcattc ccagcaccct   13260
gccctctgg ccctcatatg tctgccctc agtgactggt gtttggtttt tggcctgtgt    13320
gtaacaaact gtgtgtgaca cttgttttcct gtttctccgc cttcccctgc ttcctcttgt   13380
gtccatctct ttctgaccca ggcctggttc cttttccctcc tcctcccatt tcacagatgg   13440
gaaggtggag gccaagaagg gccaggccat tcagcctctg gaaaaccttt ctcccaacct   13500
cccacagccc ctaatgactc tcctggcctc cctttagtag aggatgaagt tgggttggca   13560
gggtaaactg agaccgggtg gggtaggggt ctggcgctcc cgggaggagc actccttttg   13620
tggcccgagc tgcatctcgc ggcccctccc ctgccaggcc tggggcgggg gaggggcca    13680
gggttcctgc tgccttaaaa gggctcaatg tcttggctct ctcctccctc cccgtcctc    13740
agccctggct ggttcgtccc tgctggccca ctctcccgga accccgga accctctct     13800
ttcctccaga acccactgtc tcctctcctt ccctcccccc ccataccccat ccctcctccc   13860
atcctgcctc cacttcttcc acccccggga gtccaggcctc cctgtcccc acagtccctg    13920
agccacaagc ctccaccca gctggtcccc caccaggct gccagttta acattcctag     13980
tcataggacc ttgacttctg agaggcctga ttgtcatctg taaataaggg gtaggactaa   14040
agcactcctc ctggaggact gagagatggg ctggaccgga gcacttgagt ctgggatatg   14100
tgaccatgct acctttgtct ccctgtcctg ttccttcccc cagccccaaa tccaggggttt   14160
tccaaagtgt ggttcaagaa ccacctgcat ctgaatctag aggtactgga tacaacccca   14220
cgtctgggcc gttaccagg acattctaca tgagaacgtg gggtggggc cctggctgca    14280
cctgaactgt cacctggagt cagggtgaa ggtggaagaa ctgggtctta tttccttctc    14340
cccttgttct ttagggtctg tccttctgca gactccgtta ccccacccta accatcctgc   14400
acaccctttgg gaccctctgg gccaatgcc tgtcccgcaa aggcttctc aggcatctca    14460
cctctatggg agggcatttt tggccccag aaccttacac ggtgtttatg tggggaagcc    14520
cctgggaagc agacagtcct agggtgaagc tgagaggcag agagaagggg agacagacag   14580
agggtggggc tttccccctt gtctccagtg cccttctgg tgaccctcgg ttctttccc     14640
ccaccacccc cccagcggag cccatcgtgg tgaggcttaa ggaggtccga ctgcagaggg   14700
acgacttcga gattctgaag gtgatcggac gcggggcgtt cagcgaggta agccgaaccg   14760
```

```
ggcgggagcc tgacttgact cgtggtgggc ggggcatagg ggttggggcg gggccttaga  14820
aattgatgaa tgaccgagcc ttagaaccta gggctgggct ggaggcgggg cttgggacca  14880
atgggcgtgg tgtggcaggt ggggcgggc cacggctggg tgcagaagcg ggtggagttg   14940
ggtctgggcg agccctttg ttttcccgcc gtctccactc tgtctcacta tctcgacctc   15000
aggtagcggt agtgaagatg aagcagacgg gccaggtgta gccatgaag atcatgaaca   15060
agtgggacat gctgaagagg ggcgaggtga ggggctgggc ggacgtgggg ggctttgagg  15120
atccgcgccc cgtctccggc tgcagctcct ccgggtgccc tgcaggtgtc gtgcttccgt  15180
gaggagaggg acgtgttggt gaatggggac cggcggtgga tcacgcagct gcacttcgcc  15240
ttccaggatg agaactacct ggtgagctcc gggccggggt gactaggaag agggacaaga  15300
gcccgtgctg tcactggacg aggaggtggg gagaggaagc tctaggattg ggggtgctgc  15360
ccggaaacgt ctgtgggaaa gtctgtgtgc ggtaagaggg tgtgtcaggt ggatgagggg  15420
ccttccctat ctgagacggg gatggtgtcc ttcactgccc gtttctgggg tgatctgggg  15480
gactcttata aagatgtctc tgttgcgggg ggtctcttac ctggaatggg ataggtcttc  15540
aggaattcta acggggccac tgcctaggga aggagtgtct gggacctatt ctctgggtgt  15600
tgggtggcct ctgggttctc tttcccagaa catctcaggg ggagtgaatc tgcccagtga  15660
catcccagga aagtttttt gtttgtgttt tttttgagg ggcgggggcg ggggccgcag   15720
gtggtctctg atttggcccg gcagatctct atggttatct ctgggctggg gctgcaggtc  15780
tctgcccaag gatggggtgt ctctgggagg ggttgtccca gccatccgtg atggatcagg  15840
gcctcagggg actaccaacc acccatgacg aaccccttct cagtacctgg tcatggagta  15900
ttacgtgggc ggggacctgc tgacactgct gagcaagttt ggggagcgga ttccggccga  15960
gatgcgcgc ttctacctgg cggagattgt catggccata gactcggtgc accggcttgg   16020
ctacgtgcac aggtgggtgc agcatgccg agggatgac aagcttgttc cctgccgggg    16080
ttcttggaag gtcagagccc agagaggcca gggcctggag agggaccttc ttggttgggg  16140
cccaccgggg ggtgcctggg agtagggggtc agaactgtag aagccctaca ggggcggaac  16200
ccgaggaagt ggggtcccag gtggcactgc ccggaggggc ggagcctggt gggaccacag  16260
aagggaggtt catttatccc acccttctct tttcctccgt gcagggacat caaacccgac  16320
aacatcctgc tggaccgctg tggccacatc cgcctggccg acttcggctc ttgcctcaag  16380
ctgcgggcag atgaacggt gagccagtgc cctggccaca gagcaactgg ggctgctgat   16440
gagggatgga aggcacagag tgtgggagcg ggactgatt tggaggggaa aagaggtggt   16500
gtgacccagg cttaagtgtg catctgtgtg gcggagtatt agaccaggca gaggagggg   16560
ctaagcattt ggggagtggt tggaaggagg gcccagagct ggtgggccca gagggtgagg  16620
cccaagcctc gctctgctcc ttttggtcca ggtgcggtcg ctggtggctg tgggcacccc  16680
agactacctg tcccccgaga tcctgcaggc tgtgggcggt gggcctggga caggcagcta  16740
cgggcccgag tgtgactggt gggcgctggg tgtattcgcc tatgaaatgt tctatggcca  16800
gacgcccttc tacgcggatt ccacggcgga gacctatgcc aagatcgtcc actacaaggt  16860
gagcacggcc gcagggagac ctggcctctc ccggtaggcg ctcccaggct atcgcctcct  16920
ctccctctga gcaggagcac ctctctctgc cgctggtgga cgaagggggtc cctgaggagg  16980
ctcgagactt cattcagcgg ttgctgtgtc ccccggagac acggctgggc cggggtggag  17040
caggcgactt ccggacacat cccttcttct ttggcctcga ctgggatggt ctccgggaca  17100
gcgtgccccc ctttacaccg gatttcgaag gtgccaccga cacatgcaac ttcgacttgg  17160
tggaggacgg gctcactgcc atggtgagcg ggggcgggt aggtacctgt ggcccctgct  17220
cggctgcggg aacctcccca tgctccctcc ataaagttgg agtaaggaca gtgcctacct  17280
tctgccgtcc tgaatcactc attcccaga gcacctgctc tgtgcccatc tactactgag  17340
gacccagcag tgacctagac ttacagtcca gtgggggaac acagacagt cttcagacag   17400
taaggcccca gagtgatcag ggctgagaca atggagtgca ggggtgggg gactcctgac   17460
tcagcaagga aggtcctgga gggctttctg gagtggggag ctatctgagc tgagacttgg  17520
agggatgaga agcaggagag gactcctcct cccttaggcc gtctctcttc accgtgtaac  17580
aagctgtcat ggcatgcttg ctcggctctg ggtgccctt tgctgaacaa tactgggat    17640
ccagcacgga ccagatgagc tctggtccct gccctcatcc agttgcagtc tagagaatta  17700
gagaattatg gagagtgtgg caggtgccct gaagggaagc aacaggatac aagaaaaaat  17760
gatggggcca gcacggtgg ctcacgcctg taaccccagc aatttggcag gccgaagtgg  17820
gtggattgct tgagcccagg agttcgagac cagcctgggc aatgtggtga gacccccgtc  17880
tctacaaaaa tgtttaaaa attggttggg cgtggtggcg catgcctgta tactcagcta  17940
ctagggtggc cgacgtgggc ttgagcccag gaggtcaagg ctgcagtgag ctgtgattgt  18000
gccactgcac tccagcctgg gcaacggaga gagctctgt ctcaaaaata agataaactg   18060
aaattaaaaa ataggctggg ctggccggc gtggtggctc acgcctgtaa tctcagcact   18120
ttgggaggcc gaggcgggtg gatcacgagg tcaggagatc gagaccatct ggctaacac   18180
ggtgaaaccc catctctcct aaaaatacaa aaattagcc aggcgtggtg gcgggcgcct   18240
gtagtcccag ctactcagga ggctgaggca ggagaatggc gtgaaccgg gaggcagagt   18300
ttgcagtgag ccgagatcgt gccactgcac tccagcctgg gcgacagagc gagactctgt  18360
ctcagaaaaa aaaaaaaaa aaaaaaaaa taggctggac cgcggccggg cgctgtggct   18420
catgcctgta atcccagcac tttgggagtc caaggccggt gggtcatgag atcaggagtt  18480
ttgagactag gctggccaac acggtgaaac cccgtctcta ctaaaaatac aagaaaatta  18540
gctgggtgtg tgtctcgggtg cctgtaattc cagttactgg ggaagctgag gcaggagaat  18600
tgcttgaacc tgggaggcag agtttgcagt gagccaagat catgccacta cactccagtc  18660
tgggtgacag agtgagactc tgtctcaaaa aaaaaaaaa aaaaagggt tgggcaaggt    18720
ggttcacgcc tgtaatccca gaactttggg aggctgaggc aggcagatca ctggaagtca  18780
ggagttcaag accagcctgg ccaacatggt gaaaccctgt gtctactaaa aatacaaaat  18840
ttagccaggc ttggtggcgt atgcctgtaa tgccagctac tcaggaggct gaggcaggag  18900
aatcgcttga ttgaacctgg gaggcagagt ttgcagtggg ctggggttgt gccactgcac  18960
tctaggctgg gagacagcaa gactccatct aaaaaaaaa aacagaactg ggctgggcac   19020
agtggcttat atttgtaatc ccagcacttt ggaggctga ggttgagga ctgcttgagc    19080
ccagagtttg ggactacaac agctgaggta ggcggatcac ttgaggtcag aagatggaga  19140
ccagccgcc cagcgtgcg aaaccccgtc tctaccaaaa atataaaaaa ttagccaggc    19200
gtggtagagg gcgcctgtaa tctcagctac tcaggacgct gaggcaggag aatcgcctga  19260
acctgggagg cggaggttgc agtgagctga gattgcacca ctgcactcca gcctgggtaa  19320
cagagcgaga ctccgtatca aagaaaaaga aaaagaaaa aatgctggag gggccacttt   19380
agataagccc tgagttgggg ctggtttggg gggaacatgt aagccaagat caaaaagcag  19440
tgaggggccc gccctgacga ctgctgctca catctgtgtg tcttgcgcag gagacactgt  19500
```

```
cggacattcg ggaaggtgcg ccgctagggg tccacctgcc ttttgtgggc tactcctact    19560
cctgcatggc cctcaggtaa gcactgccct ggacggcctc cagggccac gaggctgctt    19620
gagcttcctg ggtcctgctc cttggcagcc aatggagttg caggatcagt cttggaacct    19680
tactgttttg ggcccaaaga ctcctaagag gccagagttg gaggacctta aattttcaga    19740
tctatgtact tcaaaatgtt agattgaatt ttaaaacctc agagtcacag actgggcttc    19800
ccagaatctt gtaaccatta acttttacgt ctgtagtaca cagagccaca ggacttcaga    19860
acttggaaaa tatgaagttt agacttttac aatcagttgt aaaagaatgc aaattctttg    19920
aatcagccat ataacaataa ggccatttaa aagtattaat ttaggcgggc gcggtggct     19980
cacgcctgta atcctagcac tttgggaggc caaggcaggt ggatcatgag gtcaggagat    20040
cgagaccatc ctggctaaca cggtgaaacc ccgtctctac taaaaataca aaaaaattag    20100
ccgggcatgg tggcgggcgc ttgcggtccc agctacttgg gaggcgaggc aggagaatgg    20160
catgaacccg ggaggcggag cttgcagtga gccgagatca tgccactgca ctccagcctg    20220
ggcgacagag caagactccg tctcaaaaaa aaaaaaaaaa aagtatttat ttaggccggg    20280
tgtggtggct cacgcctgta attccagtgc tttgggagga tgaggtgggt ggatcacctg    20340
aggtcaggag ttcgagacca gcctgaccaa cgtggagaaa cctcatctct actaaaaaac    20400
aaaattagcc aggcgtggtg gcatatacct gtaatcccag ctactcagga ggctgaggca    20460
ggagaatcag aacccaggag ggggaggttg tggtgagctg agatcgtgcc attgcattcc    20520
agcctgggca acaagagtga aacttcatct caaaaaaaaa aaaaaaaaag tactaattta    20580
caggctgggc atggtggctc acgcttgaa tcccagcact ttgggaggct gaagtggacg     20640
gattgcttca gcccaggagt tcaagaccag cctgagcaac ataatgagac cctgtctcta    20700
caaaaaattg aaaaaatcgt gccaggcatg gtggtctgtg cctgcagtcc tagctactca    20760
ggagtctgaa gtaggagaat cacttgagcc tgggagttga ggcttcagtg agccatgata    20820
gattccagcc taggcaacaa agtgagacct ggtctcaaca aaagtattaa ttacacaaat    20880
aatgcattgc ttatcacaag taaattagaa aatacagata aggaaagga agttgatatc     20940
tcgtgagctc accagatggc agtggtccct ggctcacactg tgtactgaca catgtttaaa    21000
tagtggagaa caggtgtttt tttggttttgt ttttttcccc ttcctcatgc tactttgtct    21060
aagagaacag ttggttttct agtcagcttt tattactgaca caacattaca catactatac    21120
cttatcatta atgaactcca gcttgattct gaaccgctgc ggggcctgaa cggtgggtca    21180
ggattgaacc catcctctat tagaacccag gcgcatgtcc aggatagcta ggtcctgagc    21240
cgtgttccca caggagggac tgctgggttg gagggagcag ccacttcata ccccagggag    21300
gagctgtccc cttccacag ctgagtgggg tgtgctgacc tcaagttgcc atcttggggt     21360
cccatgccca gtcttaggac cacatctgtg gaggtggcca gagccaagca gtctcccat     21420
caggtcggcc tccctgtcct gaggccctga aagaggggt ctgcagcggt cacatgtcaa     21480
gggaggagat gagctgaccc tagaacatgg gggtctggac cccaagtccc tgcagaaggt    21540
ttagaaagag cagctcccag ggggcccaagg ccaggagagg ggcagggctt ttcctaagca    21600
gaggaggggc tattgcccta cctgggactc tgttctcttc gctctgctgc tcccttcct    21660
caaatcagga ggtcttggaa gcagctgccc ctacccacag gccagaagtt ctggttctcc    21720
accagagaat cagcattctg tctccctccc cactccctcc tcctctcccc agggacagtg    21780
aggtcccagg ccccacaccc atggaactgg aggccgagca gctgcttgag ccacacgtg     21840
aagcgcccag cctggagccc tcggtgtccc cacaggatga aacagtaagt tggtggaggg    21900
gaggggtgtcc gtcagggaca attgggagag aaaaggtgag ggcttccgg gtggcgtgca    21960
ctgtagagcc ctctagggac ttcctgaaca gaagcagaca gaaccacgg agagacgagg     22020
ttacttcaga catgggacgg tctctgtagt tacagtgggtg cattaagtaa gggtgtgtgt    22080
gttgctgggg atctgagaag tcgatctttg agctgagcgc tggtgaagga gaaacaagcc    22140
atggaaggaa aggtgccaag tggtcaggcg agagcctcca gggcaaaggc cttgggcagg    22200
tgggaatcct gatttgttcc tgaaaggtag tttggctgaa tcattcctga gaaggctgga    22260
gaggccagca ggaaacaaaa cccagcaagg cctttttgtcg tgagggcatt agggagctgg    22320
agggatttttg agcagcagag ggacataggt tgtgttagtg tttgagcacc agccctctgg    22380
tccctgtgta gatttagagg accagactca gggatggggc tgagggaggt agggaaggga    22440
gggggcttgg atcattgcag gagctatggg gattccagaa atgttgaggg gacggaggag    22500
tagggataa acaaggattc ctagcctgga accagtgcca aagtcctgag tcttccagga    22560
gccacaggca gccttaagcc tggtccccat acacaggctg aagtggcagt tccagcggct    22620
gtccctgcgg cagaggctga ggccgaggtg acgctgcggg agctccagga agccctggag    22680
gaggaggtgc tcacccggca gagcctgagc cgggagatgg aggccatccg cacggacaac    22740
cagaacttcg ccaggtcggg atcggggccg gggccgggcg cgggatgcgg gccggtggca    22800
acccttggca tccctctcg tccgcccgg acgactcac cgtccttacc tccccacagt      22860
caactacgag aggcagaggc tcggaaccgg gacctagagg cacacgtccg gcagttgcag    22920
gagcggatgg agttgctgca ggcagaggga gccacaggtg agtccctcat gtgtccctt     22980
ccccggaaga ccgggaggag gtgggcacgtc tgctccgcgg ggcgtgtata gacacctgga    23040
ggagggaagg gacccacgct ggggcacgcc gcgccaccgc cctccttcgc ccctccacgg    23100
gcctatgcc tctttcttct ccttccagct gtcacggggg tccccagtcc ccgggccacg     23160
gatccacctt cccatgtaag acccctctct ttccctgcc tcagacctgc tgcccattct     23220
gcagatcccc tccctggctc ctggtctccc cgtccagata tagggctcac cctacgtctt    23280
tgcgactta gagggcagaa gccctttatt cagccccaga tctccctccg ttcaggcctc    23340
accagattcc ctccgggatc tcccctagata acctccccaa cctcgattcc cctcgctgtc    23400
tctcgcccca ccgctgaggg ctgggctggg ctccgatcgg gtcacctgtc ccttctctct    23460
ccagctagat ggcccccccgg ccgtggctgt gggccagtgc ccgctggtgg gccaggccc    23520
catgcaccgc cgccacctgc tgctccctgc cagggtacgt ccggctgccc acgcccccct    23580
ccgccgcgct ccaccgccc cttgccaccc gcttagctgc gcatttgcgg                23640
ggctgggccc acggcaggag ggcggatctt cggcagcca atcaacacag gccgctagga    23700
agcagccaat gacgagttcg gacgggattc gaggcgtgcg agtggactaa caacagctgt    23760
aggctgttgg ggcgggggcg gggcgcaggg aagagtgcgg gccacctat gggcgtaggc     23820
ggggcgagtc ccaggagcca atcagaggcc catgccgggt gttgacctcg ccctctcccc    23880
gcaggtcctt aggcctggcc tatcgaggc gctttccctg ctctgttcg ccgttgttct     23940
gtctcgtgcc gccgccctgg gctgcattgg gttggtggcc cacgccgcc aactcaccgc     24000
agtctggcgc cgcccaggag ccgccgcgc tccctgaacc ctagaactgt cttcgactcc    24060
ggggccccgt tggaagactg agtgcccggg gcacggcaca aagccgcgc ccaccgcctg    24120
ccagttcaca accgctccga gcgtgggtct ccgcccagct ccagtcctgt gatccggcc     24180
cgccccctag cggccgggga gggaggggcc gggtccgcgg ccggcgaacg gggctcgaag    24240
```

```
ggtccttgta gccgggaatg ctgctgctgc tgctgctgct gctgctgctg ctgctgctgc   24300
tgctgctgct gctgctgctg gggggatcac agaccatttc tttctttcgg ccaggctgag   24360
gccctgacgt ggatgggcaa actgcaggcc tgggaaggca gcaagccggg ccgtccgtgt   24420
tccatcctcc acgcaccccc acctatcgtt ggttcgcaaa gtgcaaagct ttcttgtgca   24480
tgacgccctg ctctgggag cgtctggcgc gatctctgc tgcttactcg ggaaatttgc    24540
ttttgccaaa cccgcttttt cgggatccc gcgcccccct cctcacttgc gctgctctcg   24600
gagcccagc cggctccgcc cgcttcgcg gtttggatat ttattgaccct cgtcctccga    24660
ctcgctgaca ggctacagga cccccaacaa ccccaatcca cgttttggat gcactgagac   24720
cccgacattc ctcggtattt attgtctgtc cccacctagg accccaccc cgcaccctcg    24780
cgaataaaag gccctccatc tgcccaaagc tctggactcc acagtgtccg cggtttgcgt   24840
tgtgggccgg aggctccgca gcgggccaat ccggaggcgt gtggaggcgg ccgaaggtct   24900
gggaggagct agcgggatgc gaagcggccg aatcaggggtt gggggaggaa aagccacggg   24960
gcgggggcttt ggcgtccggc caataggagg gcgagcgggc cacccggagg caccgccccc  25020
gcccagctgt ggccagctg tgccaccgag cgtcgagaag aggggggctgg gctggcagcg   25080
cgcgcggcca tcctccttcc actgcgcctg cgcacgccac gcgcatccgc tcctgggacg   25140
caagctcgag aaaagttgct gcaaactttc tagcccgttc cccgccctc ctcccggcca    25200
gacccgcccc ccctgcggag ccgggaattc cgaggggcgg agcgcaggcc gagatgggga   25260
atgtggggc ctgcagagga cccttggagac ggaggcgtgc agaagctcag tctcgggggcg  25320
gaggcttcgc gcccttagtc ctcctggacg gcccgttacc ttctgcgttg tcccgatggg   25380
gaaactgagg ccctgagcca gaagcacacg ctgggggggag gcagaaagcg cggccagagg   25440
cggagggaaa acaaagggag aatcacagac agacgggagg gggacggaca cacacaaggg   25500
gacagagacc cgagtggaga gctggatctc gccttcccgg cgtggggcgg agggtcgggg   25560
agaaagaaga tcgagaagag cggggagtgg gggcgaaaag gggggacagg tgggggagga   25620
ggctgggga agcccgaggg aggaagagag ggagggagga acttcccaaa gttgcaaaac   25680
atggctacct tgcctgcgga gccgagcgcg gggccggcgg ctgggggggga ggcggtggcg   25740
gcggcgggcg cgaccgaaga ggaggaggag gaagcgcccg agtcttgca gacttttgcag   25800
gcggccgagg gtgaggcggc gcggcgcggcc gggggccgggg cggggcgcagc ggctgcggga  25860
gctgagggcc cgggatcccc gggcgtcccc gggtcgcccc ccgaggccgc ttccgaaccg   25920
cccacgggcc tccgcttctc gcccgagcag gtggcgtgcg tctgcgaggc gctgctccag   25980
gcgggccacg ccggccgctt gagccgcttc ctgggcgcac tgccccgcc cgagcgccta   26040
cgtggcagcg accggtgtt gcgcgcgcgg gccctggtgg ccttccagcg gggcgagtac   26100
gccgagctct accggctact cgagagccgc cccttcccg ccgccacca cgccttcctg    26160
caggacctct acctgcgcgc gcgctaccat gaggccgagc gggcccgcgg ccgcgcgctt   26220
ggcgcagtgg acaagtatcg actgcgcaag aagttcccgc tgcccaagac catctgggac   26280
ggcgaggaga cagtctactg cttcaaggag cgctcccgc cagcgctcaa ggcctgctac   26340
cgcggcaacc gctaccccac gccggacgag aagccgcc tggccacact caccggcctg    26400
tcgctcacgc aggtcagcaa ctggttcaag aaccggcgac agcgcgaccg gaccggggcc   26460
ggaggcggcg cgccctgcaa gaggtgaggg gcctcgggcg gcgcaagtcc agctctcccg   26520
gggacatccc gtccaccagc cctcttcccc cgtgcccact gctggggcg gcgcgccgag   26580
gtcctcggac atctcccggg accagctcac aatctcaggc gcccgcgggg cgcggggact   26640
aagtgtggac gggacaggca cccgcccggg ccctctcccc gcacgcgtct cctcttccag   26700
cggctccatt ccgagctcct tcccaaatcc catcggtgtt ggggaatcac actgcggggg   26760
gcactagagg gactgaggaa aaaggacagg gcctgtggcc actccactcc gcgtagggcc   26820
tgcctcccag ccccctttct tcactgaccg ttactcttac ccacccgccc ccacactccc   26880
tccgggcccg gacggcgtgg tccgtcttct gcctttgttg tgaaacgtga accttttccca   26940
gctccggttt ccctgtaacc caaacccttc tcctcccacc ctgagcgccg gcctctccct   27000
t                                                                  27001

SEQ ID NO: 2           moltype = DNA   length = 2874
FEATURE                Location/Qualifiers
source                 1..2874
                       mol_type = genomic DNA
                       organism = Homo sapiens
SEQUENCE: 2
aggggggctg gaccaagggg tgggagaag gggaggaggc ctcggccggc cgcagagaga     60
agtggccaga gaggcccagg ggacagccag ggacaggcag acatgcagcc agggctccag   120
ggcctggaca ggggctgcca ggccctgtga caggaggacc ccgagccccc ggcccggggga  180
ggggccatgt tgctgcctgt ccaacatgtc agccgaggtg cggctgaggc ggctccagca   240
gctggtgttg gaccccgggct tcctggggct ggagcccctg ctcgaccttc tcctgggcgt   300
ccaccaggag ctgggcgcct ccgaactggc ccaggacaag tacgtgccg acttcttgga    360
gtgggcggag cccatcgtgg tgaggcttaa ggaggtccga ctgcagaggg acgacttcga   420
gattctgaag gtgatcggac gcggggcgtt cagcgaggta gcgtagtga agatgaagca   480
gacgggccag gtgtatgcca tgaagatcat gaacaagtgg gacatgctga gaggggcga    540
ggtgtcgtgc ttccgtgagg agaggggacgt gttggtgaat gggacccgc ggtggatcac    600
gcagctgcac ttcgccttcc aggatgagaa ctacctgtac ctggtcatgg agtattacgt   660
gggcgggac ctgctgacac tgctgagcaa gtttggggag cggattccgg ccgagatggc   720
gcgcttctac ctgcggagaa ttgtcatggc catagactcg gtgcaccggc ttggctacgt   780
gcacagggac atcaaacccg acaacatcct gctggaccgc tgtggccaca tccgcctggc   840
cgacttcggc tcttgcctca agtcgcgggc agatgaaggc tggtggtcc tgttggctgt   900
gggcacccca gactacctgt ccccgagat cctgcaggct gtgggcggtg ggcctggac    960
aggcagctac gggcccagt gtgactggtg gcgctgggt gtattcgcct atgaaatgtt   1020
ctatgggcag acgcccttct acgcggattc cacggcggag acctatgcca agatcgtcca  1080
ctacaaggag cacctctctc tgccgctggt ggacgaaggg gtccctgagg aggctcgaga  1140
cttcattcag cggttgctgt gtcccccgga gaccggtgtg gagcaggcga  1200
cttccggaca catcccttct tctttggcct cgactgggat ggtctccggg acagcgtgcc  1260
ccccttaca ccggatttcg aaggtgccac cgacacatgc aacttcgact ggtgtgagga   1320
cgggctcact gccatggtga gcgggggcgg ggagacactg tcggacattc gggaaggtgc  1380
gccgctaggg gtccacctgc ctttttgtgg gctactcctac tcctgcatgg ccctcaggga   1440
cagtgaggtc ccaggcccca cacccatgga actggaggcc gagcagctgc ttgagccaca  1500
```

```
cgtgcaagcg cccagcctgg agccctcggt gtccccacag gatgaaacag ctgaagtggc   1560
agttccagcg gctgtccctg cggcagaggc tgaggccgag gtgacgctgc gggagctcca   1620
ggaagccctg gaggaggagg tgctcacccg gcagagcctg agccgggaga tggaggccat   1680
ccgcacggac aaccagaact tcgccagtca actacgcgag gcagaggctc ggaacccgga   1740
cctagaagca cacgtccggc agttgcagga gcggatggag ttgctgcagg caggggagc   1800
cacagctgtc acggggtcc ccagtccccg ggccacggat ccaccttccc atctagatgg   1860
ccccccggcc gtggctgtgg gccagtgccc gctggtgggg ccaggcccca tgcaccgccg   1920
ccacctgctg ctccctgcca gggtccctag gcctggccta tcggaggcgc tttccctgct   1980
cctgttcgcc gttgttctgt ctcgtgccgc cgccctgggc tgcattgggt tggtggccca   2040
cgccggccaa ctcaccgcag tctggccgcg cccaggaggc gcccgcgctc cctgaaccct   2100
agaactgtct tcgactccgg ggccccgttg gaagactgag tgcccggggc acggcacaga   2160
agccgcgccc accgcctgcc agttcacaac cgctccgagc gtgggtctcc gcccagctcc   2220
agtcctgtga tccgggcccg cccctagcg gccggggagg gaggggccgg gtccgcggcc   2280
ggcgaacggg gctcgaaggg tccttgtagc cgggaatgct gctgctgctg ctgctgctgc   2340
tgctgctgct gctgctgctg ctgctgctgg gggatcacag accatttctt              2400
tctttcggcc aggctgaggc cctgacgtgg atgggcaaac tgcaggcctg ggaaggcagc   2460
aagccgggcc gtccgtgttc catcctccac gcaccccac ctatcgttgg ttcgcaaagt   2520
gcaaagcttt cttgtgcatg acgccctgct ctgggggacg tctggcgcga tctctgcctg   2580
cttactcggg aaatttgctt ttgccaaacc cgctttttcg gggatcccgc gcccccctcc   2640
tcacttgcgc tgctctcgga gcccagccg gctccgcccg cttcggcggt ttggatattt   2700
attgacctcg tcctccgact cgctgacagg ctacaggacc cccaacaacc ccaatccacg   2760
ttttggatgc actgagaccc cgacattcct cggtatttat tgtctgtccc cacctaggac   2820
cccccccccc gaccctcgcg aataaaaggc cctccatctg cccaaagctc tgga         2874

SEQ ID NO: 3         moltype = DNA   length = 19000
FEATURE              Location/Qualifiers
source               1..19000
                     mol_type = genomic DNA
                     organism = Homo sapiens
SEQUENCE: 3
cagctggcgg gggcaaggcg ggcggcccgg gtgtggcggc agagcctggc acaccattca     60
gcattggccg cttcgccacg ctcacactgc aggagcggcg ggaccggggg gcagagaagg    120
agcacaagcg ctaccacagc ctgggcaaca tcagccgggg tggcagtggc ggcagtggca    180
gtggtgggga aagcccagc ggccctgttc cccgcagccg cctggaccc gccaaggtgc     240
tgggcactgc gctgtgcccg cgcatccacg aggtccccct gctggagccc cttgtgtgca    300
agagatcgc ccaggagcgg ctcacagtcc tcctgttcct ggaggactgc atcatcactg     360
cctgccagga gggcctcatc tgcacctggg cccggccggg caaggcggtg agtggcccca    420
caccagcctg ccggggacct ggcaggacct tcgtgggaa gaggcaggca ttggcagaga     480
gagggctttg ttgctgtcac agcctctggc tccgtgggt gagggaagc cagggaaatc     540
ttagtgtctc agtacaagac ctctcagatc cttagagtga gggggtctag ccctaggcag    600
caggcagcag aaagagggt gggtgtgaga gccagctagg aattgggca tccaaggctg      660
gccgtctgaa gggcagcaga tgggcccac atggccaggt cttactgcct gtcactcgaa     720
ccagaatcta tttctgttga acatctgttt tttaaatcgt aaacttttt tgagtacttc     780
aggccaaaac tagggcgag ctcaagcctg tgggcatggc tgccagcctg ggtctggac      840
tcaggatctg agcctcctgc tgaaggcaca ggctgggaat cccaggcctg ggttccagtc    900
ccactccctc tgtgaccctg acaagtcac tgcccctct gacctccaac tcatcacctc      960
ttagaacaga gcctgtagga tgggcagtgg gtggatgtgc ttgcctcctg gtggggctgt   1020
ggcgttggga aggtcatagt aggcgaatca ggcctggcat cttgtaagtt cggagctcgt   1080
cttgggtgtc tcagcttctt agggcttgga tcagttgcc cagggtcctg gaggccgtgg    1140
cttggttcct cagatcctca gttttggaat cgtagagtcc tgagtcccta gaacttgaga   1200
gcacagtctg agtgactcag aggcaagagt ggtgggattt gggagtctg gttgagtcct    1260
aaaagagacc cctctgtctc cgtagttcac agacgaggag accgaggccc agacagggga   1320
aggaagttgg cccaggtcac ccagcaagtc agtggtagag gtaggactgt ccctgagttc   1380
tttccccagc acctcaggg ccctcccaag ttagaaggga gctccagttt ccccctcccc    1440
tcccacccctt acccttaccc catggtctca ctcaggatcc gccaaggact ttgattattg   1500
cgtgaaagtg ctgactgcca ggacaggaag ctagctaaga tgcaagttcc cagcctagag   1560
cagtggcctc tgggggtgct agggcggacc aaggggcaag gccagggtgg cagcagcttt   1620
ggggactctg ggctggctcc ctcccctga cactggctga agcccaggtg gtctctaacc    1680
cctccatct ctccctctca tcttcccag ggcatctcct cccaaccagg caactccccg     1740
agtggcacag tggtgtgaag ccatgtgatat cgggcccccc caaccccatg ccccagcct   1800
cctagccata accctccctg ctgacctcac agatcaacgt attaacaaga ctaaccatga   1860
tggatggact gctccagtcc cccacctgc acaaaatttg ggggccccc agactggccc     1920
ggacacgggc gatgtaatag cccttgtggc ctcagccttg tccccaccc actgccaagt   1980
acaatgacct cttcctctga aacatcagtg ttaccctcct cctgtccccc agcatgtgac   2040
tggtcactcc tggggagaga ctccccgccc ctgccacaag agcccaggt ctgcagtgtg    2100
cccctcagtt gagtgggcag ggcggggt ggtccagccc tcgccggcc cccacccag       2160
ctgcccttgc tattgtctgt gcttttgaag agtgttaaat tatggaagcc ctcaggttc    2220
ctccctgtcc cgcaggacct cttatttata ctaaagttcc ctgttttctc agcgggtctg   2280
tccccttcgg aggagatgat gtagaggacc tgtgtgtgta tctgtggtt ctaggcagtc    2340
cgcttttccc agaggaggag tgcaggcctg ctcccagccc agcgcctccc accccttttc   2400
atagcaggaa aagccggagc ccagggaggg aacggacctg cgagtcacac aactggtgac   2460
ccacaccagc ggctggagca ggaccctctt ggggagaaga gcatcctgcc cgcagccagg   2520
gcccctcatc aaagtcctcg gtgtttttta aattatcaga actgcccagg accacgtttc   2580
ccaggcctgc cccagctggg actcctcggt ccttgcctc tagtttctca ggcctggccc    2640
tctcaaggcc caggcaccccc aggcggttg gaggccccga cttccactct ggagaaccgt   2700
ccaccctgga aagaagagct cagattcct ttggctctcg gagccgcagg gagtgtgtct    2760
tcccgcgcca cctccaccc cccgaaatgt ttctgttcct aatccagcc tgggcaggaa    2820
tgtggctccc cggccagggg ccaaggagct attttggggt ctcgtttgcc cagggagggc   2880
ttggctccac cactttcctc cccagccttt tgggcagcag gtcaccctg ttcaggctct    2940
```

```
gagggtgccc cctcctggtc ctgtcctcac caccccttcc ccacctcctg ggaaaaaaaa   3000
aaaaaaaaaa aaaaaaagct ggtataaagc agagagcctg agggctaaat ttaactgtcc   3060
gagtcggaat ccatctctga gtcacccaag aagctgccct ggcctccgt cccttccca    3120
ggcctcaacc cctttctccc acccagcccc aaccccagc cctcacccc tagccccag     3180
ttctggagct tgtcgggagc aaggggtgg ttgctactgg gtcactcagc ctcaattggc   3240
cctgtttcag caatgggcag gttcttcttg aaattcatca cacctgtggc ttcctctgtg  3300
ctctaccttt ttattggggt gacagtgtga cagctgagat tctccatgca ttccccctac  3360
tctagcactg aagggttctg aagggccctg aaggaggga gcttgggggg ctggcttgtg   3420
aggggttaag gctgggaggc gggaggggg ctggaccaag gggtggggag aagggagga    3480
ggcctcggcc ggccgcagag agaagtggcc agagaggccc aggggacagc cagggacagg  3540
cagacatgca gccagggctc cagggcctgg acaggggctg ccaggccctg tgacaggagg  3600
accccgagcc cccggcccgg ggaggggcca tggtgctgcc tgtccaacat gtcagccgag  3660
gtgcggctga ggcggctcca gcagctggtg ttggacccgg gcttcctggg gctggagccc  3720
ctgctcgacc ttctcctggg cgtccaccag gagctgggcg cctccgaact ggcccaggac  3780
aagtacgtgg ccgacttctt gcagtggggt gagtgcctac cctcgggggct cctgcagatg 3840
gggtggggggt ggggcaggag acaggtctgg gcacagaggc ctggctgttg gggggcagg   3900
atggcaggat gggcatgggg agatcctccc atcctggggc tcagagtgtg gacctgggcc  3960
ctggggcaac atttctctgt cctatgccac cactctggga gggcagagta aggtcagcag  4020
aggctagggt ggctgtgact cagagccatg gcttaggagt cacagcaggc taggctgcca  4080
acagcctccc atgcctctc tgcacccgc ctcagggtca gggtcagggt catgctggga    4140
gctccctctc ctaggaccct ccccccaaaa gtgggctcta tggccctctc cctggtttc    4200
ctgtgggctg gggcaagcca ggaggggcag catggggcag ctgcagggga cgcagccgag  4260
aggcaggtgt tcggcgccag cctctccagc tgccccaaca ggtgccagg cactgggagg    4320
gcggtgactc acgcggggccc tgtgggagaa ccagctttgc agacaggcgc caccagtgcc   4380
ccctcctctg cgatccagga gggacaactt tgggttcttc tgggtgtgtc tccttctttt  4440
gtaggttctg cacccacccc caccccccagc cccaaagtct cggttcctat gagccgttgg  4500
ggtcagccac cattcccgcc accccgggtc cctgcgtcct ttagttctcc tggcccaggg  4560
cctccaacct tccagctgtc ccacaaaacc ccttcttgca agggctttcc agggcctggg  4620
gccagggctg gaaggaggat gcttccgctt ctgccagctg ccttgtctgc ccacctcctc   4680
cccaagccca ggactcgggc tcactggtca ctggttcctt tcattccag caccctgccc   4740
ctctggccct catatgtctg gcccctcagtg actggtgttt ggttttggc ctgtgtgtaa   4800
caaactgtgt gtgacacttg tttcctgttt ctccgccttc ccctgcttcc tcttgtgtcc   4860
atctcttct gacccaggcc tggttccttt ccctcctcct cccatttcac agatgggaag   4920
gtggaggcca agaagggcca ggccattcag cctctgaaa aaccttctcc caacctccca   4980
cagcccctaa tgactctcct ggcctcctt tagtagagga tgaagttggg ttggcagggt   5040
aaactgagac cgggtggggt agggggtctgg cgctcccggg aggagcactc cttttgtggc   5100
ccgagctgca tctcgcggcc cctccctgc caggcctggg gcggggagg gggccagggt    5160
tcctgctgcc ttaaagggc tcaatgtctt ggctctctcc tccctcccc gtcctcagcc    5220
ctggctggtt cgtccctgct ggcccactct ccggaaccc ccggaaccc tctctttcc     5280
tccagaaccc actgtctcct ctccttccct cccctcccat acccatccct ctctccatcc  5340
tgcctccact tcttccaccc ccgggagtcc aggcctccct gtcccacag tccctgagcc   5400
acaagcctcc accccagctg gtcccccacc caggctgccc agtttaacat tcctagtcat  5460
aggaccttga cttctgagag gcctgattgt catctgtaaa taaggggtag gactaaagca  5520
ctcctcctgg aggactgaga gatgggctgg accggagcac ttgagtctgg gatatgtgac  5580
catgctacct ttgtctccct gtcctgttcc ttccccagc cccaaatcca gggttttcca   5640
aagtgtggtt caagaaccac ctgcatctga atctagaggt actggataca accccacgtc   5700
tgggccgtta cccaggacat tctacatgag aacgtgggg tggggcctg gctgcacctg   5760
aactgtcacc tggagtcagg gtggaaggtg gaagaactgg gtcttatttc cttctcccct   5820
tgttctttag ggtctgtcct tctgcagact ccgttacccc accctaacca tcctgcacac   5880
ccttggagcc ctctgggcca atgccctgtc ccgcaaaggg cttctcaggc atctcacctc   5940
tatggaggc cattttggc ccccagaacc ttacacgggg tttatgtggg gaagccccctg   6000
ggaagcagac agtcctaggg tgaagctgag aggcagagag aagggagac agacagaggg   6060
tggggctttc ccccttgtct ccagtgccct ttctggtgac cctcggttct tttccccac    6120
cacccccca gcggagccca tcgtggtgag gcttaaggag gtccgactgc agagggacga   6180
cttcgagatt ctgaaggtga tcggacgcgg ggcgttcagc ggggtaagcc gaaccgggcg   6240
ggagcctgac ttgactcgtg gtgggcgggg catagggggtt ggggcggggc cttagaaatt  6300
gatgaatgac cgagccttag aacctagggc tgggctggag gcggggcttg gaccaatgg    6360
gcgtggtgtg gcaggtgggg cggggccacg gctgggtgca gaagcgggtg gagttgggtc  6420
tgggcgagcc ctttgttttt cccgccgtct ccactctgtc tcactatctc gacctcaggt  6480
agcggtagtg aagatgaagc agacgggcca ggtgtatgcc atgaagatca tgaacaagtg  6540
ggacatgctg aagaggggcg aggtgagggg ctggcggac gtggggggct ttgaggatcc   6600
gcgcccgtc tccggctgca gctcctccgg gtgccctgca ggtgtcgtgc ttccgtgagg  6660
agagggacgt gttggtgaat ggggaccggc ggtggatcac gcagctgcac ttcgccttcc  6720
aggatgagaa ctaccctggtg agctccggc cgggtgact aggaagaggg acaagagccc  6780
gtgctgtcac tggacgagga ggtggggaga ggaagctcta ggattggggg tgctgccgg   6840
aaacgtctgt gggaaagtct gtgtgcggta agagggtgtg tcaggtggat gaggggcctt  6900
ccctatctga gacggggatg gtgtccttca ctgcccgttt ctgggtgat ctgggggact   6960
cttataaaga tgtctctgtt gcgggggggtc tcttacctgg aatggatag gtcttcagga  7020
attctaacgg ggccactgcc tagggaagga gtgtctggga cctattctct gggtgttgtg  7080
tggcctctgg gttctctttc ccagaacatc tcaggggaca tgaatctgcc cagtgacatc  7140
ccaggaaagt tttttttgttt gtgttttttt ttgaggggcg ggggcggggg ccgcaggtgg 7200
tctctgattt ggcccggcag atctctatgg ttatctctgg gctggggctg caggtctctg  7260
cccaaggatg gggtgtctct gggagggtt gtcccagcca tccgtgatgg atcagggcct  7320
caggggacta ccaaccaccc atgacgaacc ccttctcagt acctggtcat ggagtattac  7380
gtgggcgggg acctgctgac actgctgagc aagtttgggg agcggattcc ggccgagatg  7440
gcgcgcttct acctgcgga gattgtcatg gccatagact cggtgcaccg gcttggctac  7500
gtgcacaggt gggtgcagca tggccgaggg gatagcaagc ttgttccctg gccgggttct  7560
tggaaggtca gagcccagag aggccagggc ctggagaggg accttcttgg ttggggccca  7620
ccgggggggtg cctgggagta ggggtcagaa ctgtagaagc cctacagggg cggaacccga  7680
```

```
ggaagtgggg tcccaggtgg cactgcccgg aggggcggag cctggtggga ccacagaagg   7740
gaggttcatt tatcccaccc ttctcttttc ctccgtgcag ggacatcaaa cccgacaaca   7800
tcctgctgga ccgctgtggc cacatccgcc tggccgactt cggctcttgc ctcaagctgc   7860
gggcagatgg aacggtgagc cagtgccctg ccacagagc aactgggct gctgatgagg     7920
gatggaaggc acagagtgtg ggagcgggac tggatttgga ggggaaaaga ggtggtgtga   7980
cccaggctta agtgtgcatc tgtgtggcgg agtattagac caggcagagg gaggggctaa   8040
gcatttgggg agtggttgga aggagggccc agagctggtg ggcccagagg ggtgggccca   8100
agcctcgctc tgctcctttt ggtccaggtg cggtcgctgg tggctgtggg caccccagac   8160
tacctgtccc ccgagatcct gcaggctgtg ggcggtgggc ctgggacagg cagctacggg   8220
cccgagtgtg actggtgggc gctgggtgta ttcgcctatg aaatgttcta tgggcagacg   8280
cccttctacg cggattccac ggcggagacc tatgcaagaa tcgtccacta caaggtgagc   8340
acggccgcag ggagacctgg cctctcccgg taggcgctcc caggctatcg cctcctctcc   8400
ctctgagcag gagcacctct ctctgccgct ggtggacgaa ggggtccctg aggaggctcg   8460
agacttcatt cagcggttgc tgtgtccccc ggagacacgg ctgggccggg gtggagcagg   8520
cgacttccgg acacatccct tcttcttttgg cctcgactgg gatggtctcc gggacagcgt   8580
gcccccccttt acaccggatt tcgaaggtgc caccgcacaa tgcaacttcg acttggtgga   8640
ggacgggctc actgccatgg tgagcggggg cggggtaggt acctgtggcc cctgctcggc   8700
tgcgggaacc tccccatgct ccctccataa agttggagta aggacagtgc ctaccttctg   8760
gggtcctgaa tcactcattc cccagagcac ctgctctgtg cccatctact actgaggacc   8820
cagcagtgac ctagacttac agtccagtgg gggaacacag agcagtcttc agacagtaag   8880
gccccagagt gatcagggct gagacaatgg agtgcagggg gtgggggact cctgactcag   8940
caaggaaggt cctggagggc tttctggagt ggggagctat ctgagctgag acttggaggg   9000
atgagaagca ggagaggact cctcctcct taggccgtct ctcttcaccg tgtaacaagc    9060
tgtcatggca tgcttgctcg gctctgggtg ccctttgct gaacaatact ggggatccag     9120
cacggaccag atgagctctg gtccctgccc tcatccagtt gcagtctaga gaattagaga   9180
attatggaga gtgtggcagg tgccctgaag ggaagcaaca ggatacaaga aaaaatgga    9240
gggccaggca cggtggctca cgcctgtaac cccagcaatt tggcaggcca agtgggtgg    9300
attgcttgag cccaggagtt cgagaccagc ctgggcaatg tggtgagacc cccgtctcta   9360
caaaaatgtt ttaaaaattg gttgggcgtg gtggcgcatg cctgtatact cagctactag   9420
ggtggccgac gtgggcttga gcccaggagg tcaaggctgc agtgagctgt gattgtgcca   9480
ctgcactcca gcctgggcaa cggagagaga ctctgtctca aaaataagat aaactgaaat   9540
taaaaaatag gctgggctgg ccgggcgtgg tggctcacgc ctgtaatctc agcactttgg   9600
gaggccgagc cggtggatc acgaggtcag gagatcgaga ccatcttggc taacacggtg    9660
aaacccatc tctcctaaaa atacaaaaaa ttagccagg gtggtggcgg gcgcctgtag     9720
tcccagctac tcaggaggct gaggcaggag aatgcgtga acccgggagg cagagtttgc    9780
agtgagccga gatcgtgcca ctgcactcca gcctgggcga cagagcgaga ctctgtctca   9840
gaaaaaaaaa aaaaaaaaaa aaaaaatagg ctggaccgcg gccgggcgct gtggctcatg   9900
cctgtaatcc cagcactttg ggagtccaag gccggtgggt catgagatca ggagttttga   9960
gactaggctg gccaacacgg tgaaacccg tctctactaaa aaatacaaga aaattagctg    10020
ggtgtggtct cgggtgcctg taattccagt tactgggaa gctgaggcag gagaattgct     10080
tgaacctggg aggcagagtt tgcagtgagc caagatcatg ccactacact ccagtctggg   10140
tgacagagtg agactctgtc tcaaaaaaaa aaaaaaaaa aagggttggg caaggtggtt     10200
cacgcctgta atcccagaac tttgggaggc tgaggcaggc agatcactgg aagtcaggag   10260
ttcaagacca gcctgccaa catggtgaaa ccctgtgtct actaaaaata caaaatttag     10320
ccaggcttgg tggcgtatgc ctgtaatgcc agctactcag gaggctgagg caggagaatc   10380
gcttgattga acctgggagg cagagtttgc agtgggctgg ggttgtgcca ctgcactcta   10440
ggctgggaga cagcaagact ccatctaaaa aaaaaaaca gaactgggct gggcacagtg    10500
gcttatattt gtaatcccag cactttggga ggctgaggtt ggaggactgc ttgagcccag   10560
agtttgggac tacaacagct gaggtaggcg gatcacttga ggtcagaaga tggagaccag   10620
cctggccagc gtggcgaaac cccgtctcta ccaaaaatat aaaaaaattag ccaggcgtgg  10680
tagagggcgc ctgtaatctc agctactcag gacgctgagg caggagaatc gcctgaacct   10740
gggaggcgga ggttgcagtg agctgagatt gcaccactgc actccagcct gggtaacaga   10800
gcgagactcc gtatcaaaga aaagaaaaa agaaaaaatg ctggaggggc cactttagat    10860
aagccctgag ttggggctgg tttgggggga acatgtaagc caagatcaaa aagcagtgag    10920
gggcccgccc tgacgactgc tgctcacatc tgtgtgtctt gcgcaggaga cactgtcgga   10980
cattcgggaa ggtgcgccgc taggggtcca cctgccttt gtgggctact cctactcctg     11040
catgccctc aggtaagcac tgccctggac ggcctccagg ggccacgagg ctgcttgagc    11100
ttcctgggtc ctgctccttg gcagccaatg gagttgcagg atcagtcttg gaaccttact   11160
gttttgggcc caaagactcc taagaggcca gagttggagg accttaaatt ttcagatcta   11220
tgtacttcaa aatgttagat tgaatttaa aacctcagaa tcacagactg gccttcccag     11280
aatcttgtaa ccattaactt ttacgtctgt agtacacaga gccacaggac ttcagaactt    11340
ggaaaatatg aagtttagac ttttacaatc agttgtaaaa gaatgcaaat tctttgaatc   11400
agccatataa caataaggcc atttaaaagt attaatttag gcgggccgcg gtggctcacg   11460
cctgtaatcc tagcactttg ggaggccaag gcaggtggat catgaggtca ggagatccag    11520
accatcctgg ctaacacggt gaaacccgt ctctactaaa aatacaaaaa aattagccgg     11580
gcatggtggc gggcgcttgc ggtcccagct acttgggagg cgaggcagga aatggcatg     11640
aacccgggag gcggagcttg cagtgagccg agatcatgcc actgcactcc agcctgggcg   11700
acagagcagg actccgtctc aaaaaaaaaa aaaaaaaaagt atttatttag gccgggtgtg   11760
gtggctcacg cctgtaattc cagtgctttg ggaggtggag gtgggtggat cacctgaggt   11820
caggagttcg agaccagcct gaccaacgtg gagaaacctc atctctacta aaaaacaaaa   11880
ttagccaggc gtggtggcat atacctgtaa tcccagctac tcaggaggct gaggcaggag   11940
aatcagaacc caggaggggg aggttgtggt gagctgagat cgtgccattg cattccagcc   12000
tgggcaacaa gagtgaaact tcatctcaaa aaaaaaaaa aaaagtact aatttacagg     12060
ctgggcatgg tggctcacgc ttggaatccc agcacttttgg gaggctgaag tggacggatt   12120
gcttcagccc aggagttcaa gaccagcctg agcaacataa tgagaccctg tctctacaaa   12180
aaattgaaaa aatcgtgcca ggcatggtgg tctgtgcctg cagtcctagc tactcaggag   12240
tctgaagtag gagaatcact tgagcctgga gtttgaggct tcagtgagcc atgatagatt   12300
ccagcctagg caacaaagtg agacctggtc tcaacaaag tattaattac acaaataatg     12360
cattgcttat cacaagtaaa ttagaaaata cagataagga aaaggaagtt gatatctcgt   12420
```

```
gagctcacca gatggcagtg gtccctggct cacacgtgta ctgacacatg tttaaatagt   12480
ggagaacagg tgttttttg gtttgttttt ttcccctcc tcatgctact ttgtctaaga    12540
gaacagttgg ttttctagtc agcttttatt actggacaac attacacata ctataccta    12600
tcattaatga actccagctt gattctgaac cgctgcgggg cctgaacggt gggtcaggat   12660
tgaacccatc ctctattaga acccaggcgc atgtccagga tagctaggtc ctgagccgtg   12720
ttcccacagg agggactgct gggttggagg ggacagccac ttcataccc agggaggagc    12780
tgtccccttc ccacagctga gtggggtgtg ctgacctcaa gttgccatct tggggtccca   12840
tgcccagtct taggaccaca tctgtggagg tggccagagc caagcagtct ccccatcagg   12900
tcggcctccc tgtcctgagg ccctgagaag aggggtctgc agcggtcaca tgtcaaggga   12960
ggagatgagc tgaccctaga acatgggggt ctggacccca agtccctgca gaaggtttag   13020
aaagagcagc tcccagggc ccaaggccag gagaggggca gggcttttcc taagcagagg     13080
aggggctatt ggcctacctg ggactctgtt ctcttcgctc tgctgctccc cttcctcaaa   13140
tcaggaggtc ttggaagcag ctgccccctac ccacaggcca gaagttctgg ttctccacca  13200
gagaatcagc attctgtctc cctccccact ccctcctcct ctccccaggg acagtgaggt   13260
cccaggcccc acaccatgg aactggaggc cgagcagctg cttgagccac gtgccaagc     13320
gcccagcctg gagccctcgg tgtccccaca ggatgaaaca gtaagttggt ggaggggagg   13380
gggtccgtca gggacaattg ggagagaaaa ggtgagggct tcccgggtgg cgtgcactgt   13440
agagccctct agggacttcc tgaacagaag cagacagaaa ccacggagag acgaggttac   13500
ttcagacatg ggacggtctc tgtagttaca gtggggcatt aagtaagggt gtgtgtgttg   13560
ctggggatct gagaagtcga tctttgagct gagcgctggt gaaggagaaa caagccatgg   13620
aaggaaaggt gccaagtggt caggcgagag cctccagggc aaaggccttg ggcaggtggg   13680
aatcctgatt tgttcctgaa aggtagtttg gctgaatcat tcctgagaag gtcggagagg   13740
ccagcaggaa acaaaaccca gcaaggcctt ttgtcgtgag ggcattaggg agctggaggg   13800
attttgagca gcagagggac ataggttgtg ttagtgtttg agcaccagcc ctctggtccc   13860
tgtgtagatt tagaggacca gactcaggga tgggctgag ggaggtaggg aagggagggg    13920
gcttggatca ttgcaggagc tatgggggatt ccagaaatgt tgagggagcg gaggagtagg  13980
ggataaacaa ggattcctag cctgaaccca gtgcccaagt cctgagtctt ccaggagcca   14040
caggcagcct taagcctggt ccccatacac aggctgaagt ggcagttcca gcggctgtcc   14100
ctgcggcaga ggctgaggcc gaggtgacgc tgcgggagct ccaggaagcc ctggaggagg   14160
aggtgctcac ccggcagagc ctgagccggg agatggaggc catccgcacg gacaaccaga   14220
acttcgccag gtcgggatcg gggccgggc cggggccggg atgcgggccg gtggcaaccc    14280
ttggcatccc ctctcgtccg gcccggacgg actcaccgtc cttacctccc cacagtcaac   14340
tacgcgaggc agaggctcgg aaccgggacc tagaggcaca cgtccggcag ttgcaggagc   14400
ggatggagtt gctgcaggca gagggagcca caggtgagtc cctcatgtgt cccctttccc   14460
ggaggaccgg gaggaggtgg gccgtctgct ccgcgggacg tgtatagaca cctggaggag   14520
ggaagggacc cacgctgggg cacgccgcgc caccgccctc cttcgcccct ccacgcgccc   14580
tatgcctctt tcttctcctt ccagctgtca cgggggtccc cagtcccgg ccacggatc     14640
caccttccca tgtaagaccc ctctctttcc cctgcctcag acctgctgcc cattctgcag   14700
atcccctccc tggctcctgg tctccccgtc cagatatagg gctcaccct cgtctttgcg    14760
actttagagg gcagaagccc tttattcagc cccagatctc cctccgttca ggcctcacca   14820
gattccctcc gggatctccc tagataacct ccccaacctc gattccctc gctgtctctc    14880
gccccaccgc tgagggctgg gctgggctcc gatcgggtca cctgtcccctt ctctctccag  14940
ctagatggcc cccggccgt ggctgtgggc cagtgcccgc tggtggggcc aggcccccatg   15000
caccgccgcc acctgctgct ccctgccagg gtacgtccgg ctgccacgc ccccctccgc    15060
cgtcgcgccc cgcgctccac ccgccccttg ccacccgctt agctgcgcat ttgcggggct   15120
gggcccacgg caggagggcg gatcttcggg cagccaatca acacaggccg ctaggaagca   15180
gccaatgcga agttcggacg ggattcgagg cgtgcgagtg gactaacaac agctgtaggc   15240
tgttggggcg gggcgggc gcagggaaga gtgcgggccc acctatgggc gtaggcgggg     15300
cgagtcccag gagccaatca gaggcccatg ccgggtgttg acctcgccct ctccccgcag   15360
gtccctaggc ctggcctatc ggaggcgctt tccctgctcc tgttcgccgt tgttctgtct   15420
cgtgcgcgcg ccctgggctg cattgggttg gtggcccacg ccggccaact caccgcagtc   15480
tggcgccgcc caggagccgc ccgcgctccc tgaaccctag aactgtcttc gactccgggg   15540
ccccgttgga agactgagtg cccggggcac ggcacagaag ccgcgcccac cgcctgccag   15600
ttcacaaccg ctccgagcgt gggtctccgc ccagctccag tcctgtgatc cgggcccgcc   15660
cctagccgc cggggaggga ggggccgggt ccgcggccgg cgaacggggc tcgaagggtc    15720
cttgtagccg gaatgctgc tgctgctgct gctgctgctg ctgctgctgc tgctgctgct    15780
gctgctgctg ctgctggggg gatcacagac catttctttc tttcggccag gctgaggccc   15840
tgacgtggat gggcaaactg caggcctggg aaggcagcaa gccgggccgt ccgtgttcca   15900
tcctccacgc cccccaccct atcgttggtt cgcaaagtgc aaagctttct tgtgcatgac   15960
gccctgctct ggggagcgtc tggcgcgatc tctgcctgct tactcgggaa atttgctttt   16020
gccaaacccg ctttttcggg gatcccgcgc cccctcctc acttgcgctg ctctcggagc    16080
cccagccggc tccgcccgct tcggcggttt ggatatttat tgacctcgtc ctccgactcg   16140
ctgacaggct acaggacccc caacaacccc aatccacgtt ttggatgcac tgagacccg    16200
acattcctcg gtatttattg tctgtcccca cctaggaccc cccaccccga ccctcgcgga   16260
taaaaggccc tccatctgcc caaagctctg gactccacag tgtccgcggt ttgcgttgtg   16320
ggccggaggc tccgcagcgg gccaatccgg aggcgtgtgg aggcggccga aggtctggga   16380
ggagctagcg ggatgcgaag cggccgaatc agggttgggg gaggaaaagc cacggggcgg   16440
ggcttttggcg tccggccaat aggaggggcga gcgggccacc cggaggcacc gccccgccc  16500
agctgtggcc cagctgtgcc accgagcgtc gagaagaggg gctgggcctg gcagccgcgg   16560
cggccatcct ccttccactg cgcctgcgca cgccacgcgc atccgctcct gggacgcaag   16620
ctcgagaaaa gttgctgcaa actttctagc ccgttccccg cccctcctcc cggccagacc   16680
cgcccccct gcggagccgg gaattccgag gggcggagcc caggccgaga tgggaatgt     16740
gggggcctgc agaggaccct ggagacggag gcgtgcagaa gctcagtctc ggggcggagg   16800
cctcgcgcc ttagtcctcc tggacggccc gttaccttct gcgttgtccc gatgggggaaa   16860
ctgaggccct gagccagaag cacacgctgg gggaggcag aaagcgcggc cagaggcgga   16920
gggaaaacaa agggagaatc acagacagac gggaggggga cggacacaca aaggggaca    16980
gagacccgag tggagagctg gatctcgcct tccggcgtg gggcgcaggg tcggccagaa    17040
agaagatcga gaagagcggg gagtggggc gaaaaggggg gacaggtggg ggaggaggct    17100
ggggaaagcc cgagggagga agagaggggag gaggaactt cccaaagttg caaaacatgg   17160
```

```
ctaccttgcc tgcggagccg agcgcgggc cggcggctgg gggggaggcg gtggcggcgg    17220
cggcggcgac cgaagaggag gaggaggaag cgcgccagct cttgcagact ttgcaggcgg    17280
ccgagggtga ggcggcggcg gcggccgggg ccggggcggg cgcagcggct gcgggagctg    17340
agggcccggg atccccgggc gtccccgggt cgccccccga ggccgcttcc gaaccgccca    17400
cgggcctccg cttctcgccc gagcaggtgg cgtgcgtctg cgaggcgctg ctccaggcgg    17460
gccacgccgg ccgcttgagc cgcttcctgg gcgcactgcc cccggccgag cgcctacgtg    17520
gcagcgaccc ggtgttgcgc gcgcgggccc tggtggcctt ccagcggggc gagtacgccg    17580
agctctaccg gctactcgag agccgcccct tccccgccgc ccaccacgcc ttcctgcagg    17640
acctctacct gcgcgcgcgc taccatgagg ccgagcgggc ccgcggccgc gcgcttggcg    17700
cagtggacaa gtatcgactg cgcaagaagt tcccgctgcc caagaccatc tgggacgggg    17760
aggagacagt ctactgcttc aaggagcgct cccgcgcagc gctcaaggcc tgctaccgcg    17820
gcaaccgcta ccccacgccg gacgagaagc gccgcctggc cacactcacc ggcctgtcgc    17880
tcacgcaggt cagcaactgg ttcaagaacc ggcgacagcg cgaccggacc ggggccggag    17940
gcggcgcgcc ctgcaagagg tgaggggcct cgggcgcgcg aagtccagct ctcccgggga    18000
catcccgtcc accagccctc ttccccgtg cccactgctg gggccggcgc gccgaggtcc    18060
tcggacatct cccgggacca gctcacaatc tcaggcgccc gcggggcgcg gggactaagt    18120
gtggacggga caggcacccg cccgggccct ctccccgcac gcgtctcctc ttccagcggc    18180
tccattccga gctccttccc aaatcccatc ggtgttgggg aatcacactg cgggggcac    18240
tagagggact gaggaaaaag gacagggcct gtggccactc cactccgcgt aggggctgcc    18300
tcccagcccc ctttcttcac tgaccgttac tcttacccac ccgccccac actccctccg    18360
ggcccggacg gcgtggtccg tcttctgcct ttgttgtgaa acgtgaacct ttcccagctc    18420
cggttccct gtaacccaaa ccttctcct cccaccctga gcgccggcct ctcccttctc    18480
tgacgccccg cggggagggc accgggaact gggctggcgg ctgctgctcc ctctctccag    18540
gccactcgcc cgctttccgc ccaaccaagg aactttagg gcaacctggg agctcagcct    18600
ctggggaccc gaggccgagg tggggagag caagggcctc ttccctcccc agcgcttctc    18660
tgcagtggtg tccacgcagg gcttgcaaaa ggccctggag tttggagtgg tctcagagag    18720
gcgtcataac ccctggaatg atccaccgaa acttgggcca gggaaaggtg gggagcagc    18780
tggctggcta tgcgggaggc cccacaggct aagggacccc agctgacagc catttctccg    18840
gccagcgagt ctgatgggaa tcccacgact gaggacgagt ccagccgaag tcctgaggac    18900
ctggagagag gggcggcccc agtgtccgcc gaggccgctg cccagggctc catattcctg    18960
gcagggaccg gccctcccgc gccttgcccg gcttcctcct                         19000

SEQ ID NO: 4           moltype = DNA  length = 2933
FEATURE                Location/Qualifiers
source                 1..2933
                       mol_type = genomic DNA
                       organism = Homo sapiens
SEQUENCE: 4
agggggctg gaccaagggg tggggagaag gggaggaggc ctcggccggc cgcagagaga      60
agtggccaga gaggcccagg ggacagccag ggacaggcag acatgcagcc agggctccag    120
ggcctggaca ggggctgcca ggccctgtga caggaggacc ccgagccccc ggcccgggga    180
ggggccatgg tgctgcctgt ccaacatgtc agccgaggtg cggctgaggc ggctccagca    240
gctggttgtg gaccggggct tcctgggct ggagccctg ctcgacctc tcctgggcgt    300
ccaccaggag ctgggcgcct ccgaactggc ccaggacaag tacgtggccg acttcttgca    360
gtgggcccca aatccagggt tttccaaagt gtggttcaag aaccacctgc atctgaatct    420
agagcggagc ccatcgtggt gaggcttaag gaggtccgac tgcagaggga cgacttcgag    480
attctgaagg tgatcggacg cggggcgttc agcgaggtag cggtagtgaa gatgaagcag    540
acgggccagg tgtatgccat gaagatcatg aacaagtggg acatgctgaa gaggggcgag    600
gtgtcgtgct tccgtgagga gagggacgtg ttggtgaatg ggaccggcg gtggatcacg    660
cagctgcact tcgccttcca ggatgagaac tacctgtacc tggtcatgga gtattacgtg    720
ggcgggaacc tgctgacact gctgagcaag tttgggagc ggattccgc cgagatgcgt    780
cgcttctacc tggcggagat tgtcatggcc atagactcgg tgcaccggct tggctacgtg    840
cacagggaca tcaaacccga caacatcctg ctggaccgct gtggccacat ccgcctggcc    900
gacttcggct cttgcctcaa gctgcgggca gatggaacgg tgcggtcgct ggtggctgtg    960
ggcaccccag actacctgtc cccgagatc ctgcaggctg tgggcggtgg gcctgggaca    1020
ggcagctacg ggcccgagtg tgactggtgg gcgctgggtg tattcgccta tgaaatgttc    1080
tatggcagag cgcccttcta cgcggattcc acggcggaga cctatggcaa gatcgtccac    1140
tacaaggagc acctctctct gccgctggtg gacgaagggg tccctgagga ggctcgagac    1200
ttcattcagc ggttgctgtg tcccccggag acacggctgg gccggggtgg agcaggcgac    1260
ttccggacac atcccttctt ctttggcctc gactgggatg gtctccggga cagcgtgccc    1320
cccttttacac cggatttcga aggtgccacc gacacatgca acttcgactt ggtggaggac    1380
gggctcactg ccatggtgag cggggcggg gagacactgt cggacattcg ggaaggtgcg    1440
ccgctagggg tccacctgcc tttgtgggc tactcctact cctgcatggc cctcaggac    1500
agtgaggtcc caggcccac acccatgaa ctggaggtgg agcagctgct tgagccacac    1560
gtgcaagcgc ccagcctgga gcctcggtg tccccacagg atgaaacagc tgaagtggca    1620
gttcagcgcg ctgtccctgc ggcagaggtg gaggccgagt gacgctgcg ggagctccag    1680
gaagccctgg aggaggaggt gctcacccgg cagagcctga ccgggagat ggaggccatc    1740
cgcacggaca accagaactt cgccagtcaa ctaccgagg cagaggctcg gaaccgggac    1800
ctagaggcac acgtccggca gttgcaggag cggatggagt tgctgcaggc agagggaccg    1860
acagctgtca cggggtccc cagtccccgg gccacggatc caccttccca tctagatggc    1920
ccccccggcc tggctgtggg ccagtgcccg ctggtgggc caggcccat gcaccgccgc    1980
cacctgctgc tccctgccag ggtccctagg cctggcctat cggaggcgct ttccctgctc    2040
ctgttcgccg ttgttctgtc tcgtgccgcc gccctgggct gcattgggtt ggtggcccac    2100
gccggccaac tcaccgcagt ctggccgcgc ccaggagccg ccggcgctcc ctgaaccta    2160
gaactgtctt cgactccggg gccccgttgg aagactgagt gccgggca cggcacagaa    2220
gccgcgccca ccgcctgcca gttcacaacc gctccgagcg tgggtctccg cccagctcca    2280
gtcctgtgat ccgggcccgc ccctagcgg cggggaggg aggggccggg tccgcggccg    2340
gcgaacgggg ctcgaaggt ccttgtagcc gggaatgctg ctgctgctgc tgctgctgct    2400
gctgctgctg ctgctgctgc tgctgctgct gctgctgggg ggatcacaga ccatttcttt    2460
```

```
ctttcggcca ggctgaggcc ctgacgtgga tgggcaaact gcaggcctgg gaaggcagca    2520
agccgggccg tccgtgttcc atcctccacg caccccacc tatcgttggt tcgcaaagtg     2580
caaagctttc ttgtgcatga cgccctgctc tggggagcgt ctggcgcgat ctctgcctgc    2640
ttactcggga aatttgcttt tgccaaaccc gcttttcgg ggatcccgcg cccccctcct     2700
cacttgcgct gctctcggag cccagccgg tccgcccgc ttcggcggtt tggatattta      2760
ttgacctcgt cctccgactc gctgacaggc tacaggaccc ccaacaaccc caatccacgt    2820
tttggatgca ctgagacccc gacattcctc ggtatttatt gtctgtcccc acctaggacc   2880
cccacccccg accctcgcga ataaaaggcc ctccatctgc ccaaagctct gga            2933

SEQ ID NO: 5             moltype = DNA    length = 2859
FEATURE                  Location/Qualifiers
source                   1..2859
                         mol_type = genomic DNA
                         organism = Homo sapiens
SEQUENCE: 5
aggggggctg gaccaagggg tgggagaag gggaggaggc ctcggccggc cgcagagaga      60
agtggccaga gaggcccagg ggacagccag ggacaggcag acatgcagcc agggctccag    120
ggcctggaca ggggctgcca ggcctgtga caggaggacc ccgagccccc ggcccgggga     180
ggggccatgg tgctgcctgt ccaacatgtc agccgaggtg cggctgaggc ggctccagca   240
gctggtgttg gacccgggct tcctggggct ggagcccctg ctcgaccttc tcctgggcgt    300
ccaccaggag ctgggcgcct ccgaactggc caggacaag tacgtggccg acttcttgca     360
gtgggcggag cccatcgtgg tgaggcttaa ggaggtccga ctgcagaggg acgacttcga    420
gattctgaag gtgatcggac gcggggcgtt cagcgaggta gcggtagtga agatgaagca    480
gacgggccag gtgtatgcca tgaagatcat gaacaagtgg gacatgctga agaggggcga    540
ggtgtcgtgc ttccgtgagg agagggacgt gttggtgaat ggggaccggc ggtggatcac    600
gcagctgcac ttcgccttcc aggatgagaa ctacctgtac ctggtcatgg agtattacgt    660
gggcggggac ctgctgacac tgctgagcaa gtttggggag cggattccgg ccgagatggc    720
gcgcttctac ctgcggagaa ttgtcatggc catagactcg gtgcaccggc ttggctacgt    780
gcacagggac atcaaacccg acaacatcct gctggaccgc tgtggccaca tccgcctggc    840
cgacttcggc tcttgcctca agtcgcgggc agatgaaacg gtcggtcgc tggtggcttg     900
gggcacccca gactacctgt ccccgagat cctgcaggct gtgggcggtg ggcctgggac     960
aggcagctac gggccgagt gtgactggtg ggcgctgggt gtattcgcct atgaaatgtt    1020
ctatgggcag acgcccttct acgcggattc cacggcggag acctatggca agatcgtcca   1080
ctacaaggag cacctctctc tgccgctggt ggacgaaggg gtcccgagg aggctgcgaga  1140
cttcattcag cggttgctgt gtcccccgga gacacggctg ggccggggtg gagcaggcga   1200
cttccggaca catcccttct tctttggcct cgactgggat ggtctcccgg gacagcgtgcc  1260
cccctttaca ccggatttcg aaggtgccac cgacacatgc aacttcgact tggtgaggga   1320
cgggctcact gccatggaga cactgtcgga cattcggaa ggtgcgccgc tagggtccag    1380
cctgccttttt gtgggctact cctactcctg catgccctc agggacagtg aggtcccagg   1440
ccccacaccc atggaactgg aggccgagca gctgcttgag ccacacgtgc aagcgcccag   1500
cctggagccc tcggtgtccc cacaggatga aacagctgaa gtggcagttc agcggctgt    1560
ccctgcggca gaggctgagg ccgaggtgac gctgcggag ctccaggaag ccctggagga   1620
ggaggtgctc accccgcaga gcctgagccg ggagatggca gccatccgca ggacaaaca    1680
gaacttcgcc agtcaactac gcgaggcaga ggctcggaac cgggacctag aggcacacgt   1740
ccggcagttg caggagcgga tggagttgct gcaggcagag ggagccacag ctgtcacggg   1800
ggtccccagt ccccggggcca cggatccacc ttcccatctca gatggccccc cggccgtggc  1860
tgtggggcag tgcccgctgg tggggccagg cccatgcac cgccgcgcc tgctgctccg    1920
tgccagggtc cctaggcctg cctatcgga ggcgctttcc ctgctcctgt tcgccgttgt    1980
tctgtctcgt gccgccgccc tgggctgcat tgggttggtg gccacgccg gccaactcac    2040
cgcagtctgc cgccgcccag gagccgcccg cgctccctga accctagaac tgtcttcgac   2100
tccggggccc cgttggaaga ctgagtgccc ggggcacggc acagaagccg cgcaccgc     2160
ctgccagttc acaaccgctc cgagcgtggg tctccgccca gctccagtcc tgtgatccgg   2220
gcccgccccc tagcggccgg ggagggaggg gccgggtccg cggccggcga acggggctcg   2280
aagggtcctt gtagcgggga atgctgctgc tgctgctgct gctgctgctg ctgctgctgc   2340
tgctgctgct gctgctgctg ctgggggat cacagaccat ttcttcttt cggccaggct   2400
gaggccctga cgtggatggg caaactgcag gcctggaag gcagcaagcc gggccgtccg   2460
tgttccatcc tccacgcacc cccacctatc gttggttcgc aaagtgcaaa gctttcttgt   2520
gcatgacgcc ctgctctggg gagcgtctgg cgcgatctct gcctgcttac tcgggaaatt   2580
tgcttttgcc aaacccgctt tttcggggat cccgcgcccc cctcctcact tgcgctgctc   2640
tcggagcccc agccggctcc gcccgcttc ggcggttga tatttattga cctcgtcctc    2700
cgactcgctg acaggctaca ggaccccccaa caacccccaat ccacgttttg gatgcactga  2760
gaccccgaca ttcctcggta tttattgtct gtccccacct aggacccca ccccgaccc     2820
tcgcgaataa aaggccctcc atctgcccaa agctctgga                          2859

SEQ ID NO: 6             moltype = DNA    length = 17
FEATURE                  Location/Qualifiers
source                   1..17
                         mol_type = other DNA
                         organism = synthetic construct
SEQUENCE: 6
ctgagccggg agatgga                                                   17

SEQ ID NO: 7             moltype = DNA    length = 18
FEATURE                  Location/Qualifiers
source                   1..18
                         mol_type = other DNA
                         organism = synthetic construct
SEQUENCE: 7
ggacgtgtgc ctctaggt                                                  18
```

```
SEQ ID NO: 8            moltype = DNA  length = 24
FEATURE                 Location/Qualifiers
source                  1..24
                        mol_type = other DNA
                        organism = synthetic construct
SEQUENCE: 8
tgactggcga agttctggtt gtcc                                              24

SEQ ID NO: 9            moltype =    length =
SEQUENCE: 9
000

SEQ ID NO: 10           moltype =    length =
SEQUENCE: 10
000

SEQ ID NO: 11           moltype = DNA  length = 16
FEATURE                 Location/Qualifiers
source                  1..16
                        mol_type = other DNA
                        organism = synthetic construct
modified_base           1
                        mod_base = OTHER
                        note = cEt adenosine 3'-phosphorothioate
modified_base           2
                        mod_base = OTHER
                        note = cEt 5-methylcytidine 3'-phosphodiester
modified_base           3
                        mod_base = OTHER
                        note = cEt adenosine 3'-phosphodiester
modified_base           4
                        mod_base = OTHER
                        note = 2'-deoxyadenosine 3'-phosphorothioate
modified_base           5
                        mod_base = OTHER
                        note = 2'-deoxythymidine 3'-phosphorothioate
modified_base           6..8
                        mod_base = OTHER
                        note = 2'-deoxyadenosine 3'-phosphorothioate
modified_base           9
                        mod_base = OTHER
                        note = 2'-deoxythymidine 3'-phosphorothioate
modified_base           10
                        mod_base = OTHER
                        note = 2'-deoxyadenosine 3'-phosphorothioate
modified_base           11..12
                        mod_base = OTHER
                        note = 5-methyl-2'-deoxycytidine 3'-phosphorothioate
modified_base           13
                        mod_base = OTHER
                        note = 2'-deoxyguanosine 3'-phosphorothioate
modified_base           14
                        mod_base = OTHER
                        note = cEt adenosine 3'-phosphodiester
modified_base           15
                        mod_base = OTHER
                        note = cEt guanosine 3'-phosphorothioate
modified_base           16
                        mod_base = OTHER
                        note = cEt guanosine
SEQUENCE: 11
acaataaata ccgagg                                                       16

SEQ ID NO: 12           moltype = DNA  length = 16
FEATURE                 Location/Qualifiers
source                  1..16
                        mol_type = other DNA
                        organism = synthetic construct
modified_base           1
                        mod_base = OTHER
                        note = 2'-O-methoxyethyl thymidine 3'-phosphorothioate
modified_base           2
                        mod_base = OTHER
                        note = 2'-O-methoxyethyl 5-methylcytidine
                         3'-phosphorothioate
modified_base           3..4
                        mod_base = OTHER
                        note = cEt 5-methylcytidine 3'-phosphorothioate
```

-continued

```
modified_base        5
                     mod_base = OTHER
                     note = 2'-deoxyguanosine 3'-phosphorothioate
modified_base        6..7
                     mod_base = OTHER
                     note = 2'-deoxyadenosine 3'-phosphorothioate
modified_base        8
                     mod_base = OTHER
                     note = 2'-deoxythymidine 3'-phosphorothioate
modified_base        9
                     mod_base = OTHER
                     note = 2'-deoxyguanosine 3'-phosphorothioate
modified_base        10
                     mod_base = OTHER
                     note = 2'-deoxythymidine 3'-phosphorothioate
modified_base        11..12
                     mod_base = OTHER
                     note = 5-methyl-2'-deoxycytidine 3'-phosphorothioate
modified_base        13
                     mod_base = OTHER
                     note = cEt guanosine 3'-phosphorothioate
modified_base        14
                     mod_base = OTHER
                     note = cEt adenosine 3'-phosphorothioate
modified_base        15
                     mod_base = OTHER
                     note = 2'-O-methoxyethyl 5-methylcytidine
                      3'-phosphorothioate
modified_base        16
                     mod_base = OTHER
                     note = 2'-O-methoxyethyl adenosine
SEQUENCE: 12
tcccgaatgt ccgaca                                                       16

SEQ ID NO: 13        moltype = DNA  length = 16
FEATURE              Location/Qualifiers
source               1..16
                     mol_type = other DNA
                     organism = synthetic construct
modified_base        1
                     mod_base = OTHER
                     note = cEt thymidine 3'-phosphorothioate
modified_base        2
                     mod_base = OTHER
                     note = cEt thymidine 3'-phosphodiester
modified_base        3
                     mod_base = OTHER
                     note = cEt 5-methylcytidine 3'-phosphodiester
modified_base        4
                     mod_base = OTHER
                     note = 5-methyl-2'-deoxycytidine 3'-phosphorothioate
modified_base        5
                     mod_base = OTHER
                     note = 2'-O-methyl cytidine 3'-phosphorothioate
modified_base        6
                     mod_base = OTHER
                     note = 2'-deoxyguanosine 3'-phosphorothioate
modified_base        7..8
                     mod_base = OTHER
                     note = 2'-deoxyadenosine 3'-phosphorothioate
modified_base        9
                     mod_base = OTHER
                     note = 2'-deoxythymidine 3'-phosphorothioate
modified_base        10
                     mod_base = OTHER
                     note = 2'-deoxyguanosine 3'-phosphorothioate
modified_base        11
                     mod_base = OTHER
                     note = 2'-deoxythymidine 3'-phosphorothioate
modified_base        12..13
                     mod_base = OTHER
                     note = 5-methyl-2'-deoxycytidine 3'-phosphorothioate
modified_base        14
                     mod_base = OTHER
                     note = cEt guanosine 3'-phosphodiester
modified_base        15
                     mod_base = OTHER
                     note = cEt adenosine 3'-phosphorothioate
```

```
                          -continued modified_base             16
                          mod_base = OTHER
                          note = cEt 5-methylcytidine
SEQUENCE: 13
ttcccgaatg tccgac                                                           16

SEQ ID NO: 14             moltype = DNA   length = 16
FEATURE                   Location/Qualifiers
source                    1..16
                          mol_type = other DNA
                          organism = synthetic construct
modified_base             5
                          mod_base = OTHER
                          note = uracil
modified_base             1
                          mod_base = OTHER
                          note = cEt 5-methylcytidine 3'-phosphorothioate
modified_base             2
                          mod_base = OTHER
                          note = cEt guanosine 3'-phosphodiester
modified_base             3
                          mod_base = OTHER
                          note = cEt adenosine 3'-phosphodiester
modified_base             4
                          mod_base = OTHER
                          note = 2'-deoxyadenosine 3'-phosphorothioate
modified_base             5
                          mod_base = OTHER
                          note = 2'-O-methyl uridine 3'-phosphorothioate
modified_base             6
                          mod_base = OTHER
                          note = 2'-deoxyguanosine 3'-phosphorothioate
modified_base             7
                          mod_base = OTHER
                          note = 2'-deoxythymidine 3'-phosphorothioate
modified_base             8..9
                          mod_base = OTHER
                          note = 5-methyl-2'-deoxycytidine 3'-phosphorothioate
modified_base             10
                          mod_base = OTHER
                          note = 2'-deoxyguanosine 3'-phosphorothioate
modified_base             11
                          mod_base = OTHER
                          note = 2'-deoxyadenosine 3'-phosphorothioate
modified_base             12
                          mod_base = OTHER
                          note = 5-methyl-2'-deoxycytidine 3'-phosphorothioate
modified_base             13
                          mod_base = OTHER
                          note = 2'-deoxyadenosine 3'-phosphorothioate
modified_base             14
                          mod_base = OTHER
                          note = cEt guanosine 3'-phosphodiester
modified_base             15
                          mod_base = OTHER
                          note = cEt thymidine 3'-phosphorothioate
modified_base             16
                          mod_base = OTHER
                          note = cEt guanosine
SEQUENCE: 14
cgaatgtccg acagtg                                                           16

SEQ ID NO: 15             moltype = DNA   length = 16
FEATURE                   Location/Qualifiers
source                    1..16
                          mol_type = other DNA
                          organism = synthetic construct
modified_base             1
                          mod_base = OTHER
                          note = cEt 5-methylcytidine 3'-phosphorothioate
modified_base             2
                          mod_base = OTHER
                          note = cEt thymidine 3'-phosphodiester
modified_base             3
                          mod_base = OTHER
                          note = 2'-O-methoxyethyl thymidine 3'-phosphodiester
modified_base             4..5
                          mod_base = OTHER
                          note = 2'-deoxythymidine 3'-phosphorothioate
```

```
modified_base        6
                     mod_base = OTHER
                     note = 2'-deoxyadenosine 3'-phosphorothioate
modified_base        7..8
                     mod_base = OTHER
                     note = 2'-deoxythymidine 3'-phosphorothioate
modified_base        9
                     mod_base = OTHER
                     note = 5-methyl-2'-deoxycytidine 3'-phosphorothioate
modified_base        10
                     mod_base = OTHER
                     note = 2'-deoxyguanosine 3'-phosphorothioate
modified_base        11
                     mod_base = OTHER
                     note = 5-methyl-2'-deoxycytidine 3'-phosphorothioate
modified_base        12
                     mod_base = OTHER
                     note = 2'-deoxyguanosine 3'-phosphorothioate
modified_base        13
                     mod_base = OTHER
                     note = 2'-deoxyadenosine 3'-phosphorothioate
modified_base        14
                     mod_base = OTHER
                     note = cEt guanosine 3'-phosphodiester
modified_base        15
                     mod_base = OTHER
                     note = cEt guanosine 3'-phosphorothioate
modified_base        16
                     mod_base = OTHER
                     note = cEt guanosine
SEQUENCE: 15
cttttattcg cgaggg                                                      16

SEQ ID NO: 16        moltype = DNA  length = 19
FEATURE              Location/Qualifiers
source               1..19
                     mol_type = other DNA
                     organism = synthetic construct
SEQUENCE: 16
gaaggtgaag gtcggagtc                                                   19

SEQ ID NO: 17        moltype = DNA  length = 20
FEATURE              Location/Qualifiers
source               1..20
                     mol_type = other DNA
                     organism = synthetic construct
SEQUENCE: 17
gaagatggtg atgggatttc                                                  20

SEQ ID NO: 18        moltype = DNA  length = 20
FEATURE              Location/Qualifiers
source               1..20
                     mol_type = other DNA
                     organism = synthetic construct
SEQUENCE: 18
caagcttccc gttctcagcc                                                  20

SEQ ID NO: 19        moltype = DNA  length = 16
FEATURE              Location/Qualifiers
source               1..16
                     mol_type = other DNA
                     organism = synthetic construct
modified_base        1
                     mod_base = OTHER
                     note = cEt adenosine 3'-phosphorothioate
modified_base        2
                     mod_base = OTHER
                     note = cEt 5-methylcytidine 3'-phosphorothioate
modified_base        3
                     mod_base = OTHER
                     note = cEt adenosine 3'-phosphorothioate
modified_base        4
                     mod_base = OTHER
                     note = 2'-deoxyadenosine 3'-phosphorothioate
modified_base        5
                     mod_base = OTHER
                     note = 2'-deoxythymidine 3'-phosphorothioate
```

```
modified_base            6..8
                         mod_base = OTHER
                         note = 2'-deoxyadenosine 3'-phosphorothioate
modified_base            9
                         mod_base = OTHER
                         note = 2'-deoxythymidine 3'-phosphorothioate
modified_base            10
                         mod_base = OTHER
                         note = 2'-deoxyadenosine 3'-phosphorothioate
modified_base            11..12
                         mod_base = OTHER
                         note = 5-methyl-2'-deoxycytidine 3'-phosphorothioate
modified_base            13
                         mod_base = OTHER
                         note = 2'-deoxyguanosine 3'-phosphorothioate
modified_base            14
                         mod_base = OTHER
                         note = cEt adenosine 3'-phosphorothioate
modified_base            15
                         mod_base = OTHER
                         note = cEt guanosine 3'-phosphorothioate
modified_base            16
                         mod_base = OTHER
                         note = cEt guanosine
SEQUENCE: 19
acaataaata ccgagg                                                       16

SEQ ID NO: 20            moltype = DNA  length = 16
FEATURE                  Location/Qualifiers
source                   1..16
                         mol_type = other DNA
                         organism = synthetic construct
modified_base            1..2
                         mod_base = OTHER
                         note = cEt thymidine 3'-phosphorothioate
modified_base            3
                         mod_base = OTHER
                         note = cEt 5-methylcytidine 3'-phosphorothioate
modified_base            4
                         mod_base = OTHER
                         note = 5-methyl-2'-deoxycytidine 3'-phosphorothioate
modified_base            5
                         mod_base = OTHER
                         note = 2'-O-methyl cytidine 3'-phosphorothioate
modified_base            6
                         mod_base = OTHER
                         note = 2'-deoxyguanosine 3'-phosphorothioate
modified_base            7..8
                         mod_base = OTHER
                         note = 2'-deoxyadenosine 3'-phosphorothioate
modified_base            9
                         mod_base = OTHER
                         note = 2'-deoxythymidine 3'-phosphorothioate
modified_base            10
                         mod_base = OTHER
                         note = 2'-deoxyguanosine 3'-phosphorothioate
modified_base            11
                         mod_base = OTHER
                         note = 2'-deoxythymidine 3'-phosphorothioate
modified_base            12..13
                         mod_base = OTHER
                         note = 5-methyl-2'-deoxycytidine 3'-phosphorothioate
modified_base            14
                         mod_base = OTHER
                         note = cEt guanosine 3'-phosphorothioate
modified_base            15
                         mod_base = OTHER
                         note = cEt adenosine 3'-phosphorothioate
modified_base            16
                         mod_base = OTHER
                         note = cEt 5-methylcytidine
SEQUENCE: 20
ttcccgaatg tccgac                                                       16

SEQ ID NO: 21            moltype = DNA  length = 16
FEATURE                  Location/Qualifiers
source                   1..16
                         mol_type = other DNA
                         organism = synthetic construct
```

```
modified_base                         mod_base = OTHER
                                      note = THA-GalNAc
modified_base                         1
                                      mod_base = OTHER
                                      note = 2'-O-methoxyethyl thymidine 3'-phosphorothioate
modified_base                         2
                                      mod_base = OTHER
                                      note = 2'-O-methoxyethyl 5-methylcytidine 3'-phosphodiester
modified_base                         3
                                      mod_base = OTHER
                                      note = cEt 5-methylcytidine 3'-phosphodiester
modified_base                         4
                                      mod_base = OTHER
                                      note = cEt 5-methylcytidine 3'-phosphorothioate
modified_base                         5
                                      mod_base = OTHER
                                      note = 2'-deoxyguanosine 3'-phosphorothioate
modified_base                         6..7
                                      mod_base = OTHER
                                      note = 2'-deoxyadenosine 3'-phosphorothioate
modified_base                         8
                                      mod_base = OTHER
                                      note = 2'-deoxythymidine 3'-phosphorothioate
modified_base                         9
                                      mod_base = OTHER
                                      note = 2'-deoxyguanosine 3'-phosphorothioate
modified_base                         10
                                      mod_base = OTHER
                                      note = 2'-deoxythymidine 3'-phosphorothioate
modified_base                         11..12
                                      mod_base = OTHER
                                      note = 5-methyl-2'-deoxycytidine 3'-phosphorothioate
modified_base                         13
                                      mod_base = OTHER
                                      note = cEt guanosine 3'-phosphorothioate
modified_base                         14
                                      mod_base = OTHER
                                      note = cEt adenosine 3'-phosphodiester
modified_base                         15
                                      mod_base = OTHER
                                      note = 2'-O-methoxyethyl 5-methylcytidine
                                       3'-phosphorothioate
modified_base                         16
                                      mod_base = OTHER
                                      note = 2'-O-methoxyethyl adenosine
SEQUENCE: 21
tcccgaatgt ccgaca                                                              16

SEQ ID NO: 22                         moltype = DNA   length = 16
FEATURE                               Location/Qualifiers
source                                1..16
                                      mol_type = other DNA
                                      organism = synthetic construct
modified_base                         5
                                      mod_base = OTHER
                                      note = Uracil
modified_base                         
                                      mod_base = OTHER
                                      note = THA-GalNAc
modified_base                         1
                                      mod_base = OTHER
                                      note = cEt 5-methylcytidine 3'-phosphorothioate
modified_base                         2
                                      mod_base = OTHER
                                      note = cEt guanosine 3'-phosphodiester
modified_base                         3
                                      mod_base = OTHER
                                      note = cEt adenosine 3'-phosphodiester
modified_base                         4
                                      mod_base = OTHER
                                      note = 2'-deoxyadenosine 3'-phosphorothioate
modified_base                         5
                                      mod_base = OTHER
                                      note = 2'-O-methyl uridine 3'-phosphorothioate
modified_base                         6
                                      mod_base = OTHER
                                      note = 2'-deoxyguanosine 3'-phosphorothioate
```

```
modified_base        7
                     mod_base = OTHER
                     note = 2'-deoxythymidine 3'-phosphorothioate
modified_base        8..9
                     mod_base = OTHER
                     note = 5-methyl-2'-deoxycytidine 3'-phosphorothioate
modified_base        10
                     mod_base = OTHER
                     note = 2'-deoxyguanosine 3'-phosphorothioate
modified_base        11
                     mod_base = OTHER
                     note = 2'-deoxyadenosine 3'-phosphorothioate
modified_base        12
                     mod_base = OTHER
                     note = 5-methyl-2'-deoxycytidine 3'-phosphorothioate
modified_base        13
                     mod_base = OTHER
                     note = 2'-deoxyadenosine 3'-phosphorothioate
modified_base        14
                     mod_base = OTHER
                     note = cEt guanosine 3'-phosphodiester
modified_base        15
                     mod_base = OTHER
                     note = cEt thymidine 3'-phosphorothioate
modified_base        16
                     mod_base = OTHER
                     note = cEt guanosine
SEQUENCE: 22
cgaatgtccg acagtg                                                        16

SEQ ID NO: 23        moltype = DNA   length = 16
FEATURE              Location/Qualifiers
source               1..16
                     mol_type = other DNA
                     organism = synthetic construct
modified_base
                     mod_base = OTHER
                     note = THA-GalNAc
modified_base        1
                     mod_base = OTHER
                     note = cEt thymidine 3'-phosphorothioate
modified_base        2
                     mod_base = OTHER
                     note = cEt thymidine 3'-phosphodiester
modified_base        3
                     mod_base = OTHER
                     note = cEt 5-methylcytidine 3'-phosphodiester
modified_base        4
                     mod_base = OTHER
                     note = 5-methyl-2'-deoxycytidine 3'-phosphorothioate
modified_base        5
                     mod_base = OTHER
                     note = 2'-O-methyl cytidine 3'-phosphorothioate
modified_base        6
                     mod_base = OTHER
                     note = 2'-deoxyguanosine 3'-phosphorothioate
modified_base        7..8
                     mod_base = OTHER
                     note = 2'-deoxyadenosine 3'-phosphorothioate
modified_base        9
                     mod_base = OTHER
                     note = 2'-deoxythymidine 3'-phosphorothioate
modified_base        10
                     mod_base = OTHER
                     note = 2'-deoxyguanosine 3'-phosphorothioate
modified_base        11
                     mod_base = OTHER
                     note = 2'-deoxythymidine 3'-phosphorothioate
modified_base        12..13
                     mod_base = OTHER
                     note = 5-methyl-2'-deoxycytidine 3'-phosphorothioate
modified_base        14
                     mod_base = OTHER
                     note = cEt guanosine 3'-phosphodiester
modified_base        15
                     mod_base = OTHER
                     note = cEt adenosine 3'-phosphorothioate
```

```
modified_base            16
                         mod_base = OTHER
                         note = cEt 5-methylcytidine
SEQUENCE: 23
ttcccgaatg tccgac                                                            16

SEQ ID NO: 24            moltype = DNA  length = 16
FEATURE                  Location/Qualifiers
source                   1..16
                         mol_type = other DNA
                         organism = synthetic construct
modified_base
                         mod_base = OTHER
                         note = THA-GalNAc
modified_base            1
                         mod_base = OTHER
                         note = cEt 5-methylcytidine 3'-phosphorothioate
modified_base            2
                         mod_base = OTHER
                         note = cEt thymidine 3'-phosphodiester
modified_base            3
                         mod_base = OTHER
                         note = 2'-O-methoxyethyl thymidine 3'-phosphodiester
modified_base            4..5
                         mod_base = OTHER
                         note = 2'-deoxythymidine 3'-phosphorothioate
modified_base            6
                         mod_base = OTHER
                         note = 2'-deoxyadenosine 3'-phosphorothioate
modified_base            7..8
                         mod_base = OTHER
                         note = 2'-deoxythymidine 3'-phosphorothioate
modified_base            9
                         mod_base = OTHER
                         note = 5-methyl-2'-deoxycytidine 3'-phosphorothioate
modified_base            10
                         mod_base = OTHER
                         note = 2'-deoxyguanosine 3'-phosphorothioate
modified_base            11
                         mod_base = OTHER
                         note = 5-methyl-2'-deoxycytidine 3'-phosphorothioate
modified_base            12
                         mod_base = OTHER
                         note = 2'-deoxyguanosine 3'-phosphorothioate
modified_base            13
                         mod_base = OTHER
                         note = 2'-deoxyadenosine 3'-phosphorothioate
modified_base            14
                         mod_base = OTHER
                         note = cEt guanosine 3'-phosphodiester
modified_base            15
                         mod_base = OTHER
                         note = cEt guanosine 3'-phosphorothioate
modified_base            16
                         mod_base = OTHER
                         note = cEt guanosine
SEQUENCE: 24
cttttattcg cgaggg                                                            16

SEQ ID NO: 25            moltype = DNA  length = 16
FEATURE                  Location/Qualifiers
source                   1..16
                         mol_type = other DNA
                         organism = synthetic construct
modified_base
                         mod_base = OTHER
                         note = THA-GalNAc
modified_base            1
                         mod_base = OTHER
                         note = 2'-O-methoxyethyl thymidine 3'-phosphorothioate
modified_base            2
                         mod_base = OTHER
                         note = 2'-O-methoxyethyl 5-methylcytidine
                          3'-phosphorothioate
```

```
                       -continued modified_base          3..4
                       mod_base = OTHER
                       note = cEt 5-methylcytidine 3'-phosphorothioate
modified_base          5
                       mod_base = OTHER
                       note = 2'-deoxyguanosine 3'-phosphorothioate
modified_base          6..7
                       mod_base = OTHER
                       note = 2'-deoxyadenosine 3'-phosphorothioate
modified_base          8
                       mod_base = OTHER
                       note = 2'-deoxythymidine 3'-phosphorothioate
modified_base          9
                       mod_base = OTHER
                       note = 2'-deoxyguanosine 3'-phosphorothioate
modified_base          10
                       mod_base = OTHER
                       note = 2'-deoxythymidine 3'-phosphorothioate
modified_base          11..12
                       mod_base = OTHER
                       note = 5-methyl-2'-deoxycytidine 3'-phosphorothioate
modified_base          13
                       mod_base = OTHER
                       note = cEt guanosine 3'-phosphorothioate
modified_base          14
                       mod_base = OTHER
                       note = cEt adenosine 3'-phosphorothioate
modified_base          15
                       mod_base = OTHER
                       note = 2'-O-methoxyethyl 5-methylcytidine
                        3'-phosphorothioate
modified_base          16
                       mod_base = OTHER
                       note = 2'-O-methoxyethyl adenosine
SEQUENCE: 25
tcccgaatgt ccgaca                                                         16

SEQ ID NO: 26          moltype = DNA  length = 16
FEATURE                Location/Qualifiers
source                 1..16
                       mol_type = other DNA
                       organism = synthetic construct
modified_base
                       mod_base = OTHER
                       note = THA-GalNAc
modified_base          1..2
                       mod_base = OTHER
                       note = cEt thymidine 3'-phosphorothioate
modified_base          3
                       mod_base = OTHER
                       note = cEt 5-methylcytidine 3'-phosphorothioate
modified_base          4
                       mod_base = OTHER
                       note = 5-methyl-2'-deoxycytidine 3'-phosphorothioate
modified_base          5
                       mod_base = OTHER
                       note = 2'-O-methyl cytidine 3'-phosphorothioate
modified_base          6
                       mod_base = OTHER
                       note = 2'-deoxyguanosine 3'-phosphorothioate
modified_base          7..8
                       mod_base = OTHER
                       note = 2'-deoxyadenosine 3'-phosphorothioate
modified_base          9
                       mod_base = OTHER
                       note = 2'-deoxythymidine 3'-phosphorothioate
modified_base          10
                       mod_base = OTHER
                       note = 2'-deoxyguanosine 3'-phosphorothioate
modified_base          11
                       mod_base = OTHER
                       note = 2'-deoxythymidine 3'-phosphorothioate
modified_base          12..13
                       mod_base = OTHER
                       note = 5-methyl-2'-deoxycytidine 3'-phosphorothioate
modified_base          14
                       mod_base = OTHER
                       note = cEt guanosine 3'-phosphorothioate
```

```
modified_base       15
                    mod_base = OTHER
                    note = cEt adenosine 3'-phosphorothioate
modified_base       16
                    mod_base = OTHER
                    note = cEt 5-methylcytidine
SEQUENCE: 26
ttcccgaatg tccgac                                                              16

SEQ ID NO: 27       moltype = DNA  length = 16
FEATURE             Location/Qualifiers
source              1..16
                    mol_type = other DNA
                    organism = synthetic construct
modified_base
                    mod_base = OTHER
                    note = THA-GalNAc
modified_base       1
                    mod_base = OTHER
                    note = cEt adenosine 3'-phosphorothioate
modified_base       2
                    mod_base = OTHER
                    note = cEt 5-methylcytidine 3'-phosphodiester
modified_base       3
                    mod_base = OTHER
                    note = cEt adenosine 3'-phosphodiester
modified_base       4
                    mod_base = OTHER
                    note = 2'-deoxyadenosine 3'-phosphorothioate
modified_base       5
                    mod_base = OTHER
                    note = 2'-deoxythymidine 3'-phosphorothioate
modified_base       6..8
                    mod_base = OTHER
                    note = 2'-deoxyadenosine 3'-phosphorothioate
modified_base       9
                    mod_base = OTHER
                    note = 2'-deoxythymidine 3'-phosphorothioate
modified_base       10
                    mod_base = OTHER
                    note = 2'-deoxyadenosine 3'-phosphorothioate
modified_base       11..12
                    mod_base = OTHER
                    note = 5-methyl-2'-deoxycytidine 3'-phosphorothioate
modified_base       13
                    mod_base = OTHER
                    note = 2'-deoxyguanosine 3'-phosphorothioate
modified_base       14
                    mod_base = OTHER
                    note = cEt adenosine 3'-phosphodiester
modified_base       15
                    mod_base = OTHER
                    note = cEt guanosine 3'-phosphorothioate
modified_base       16
                    mod_base = OTHER
                    note = cEt guanosine
SEQUENCE: 27
acaataaata ccgagg                                                              16

SEQ ID NO: 28       moltype = DNA  length = 16
FEATURE             Location/Qualifiers
source              1..16
                    mol_type = other DNA
                    organism = synthetic construct
modified_base
                    mod_base = OTHER
                    note = 5'-conjugate or a Hydrogen
modified_base       1..2
                    mod_base = OTHER
                    note = cEt thymidine 3'-phosphorothioate
modified_base       3
                    mod_base = OTHER
                    note = cEt 5-methylcytidine 3'-phosphorothioate
modified_base       4
                    mod_base = OTHER
                    note = 5-methyl-2'-deoxycytidine 3'-phosphorothioate
modified_base       5
                    mod_base = OTHER
                    note = 2'-O-methyl cytidine 3'-phosphorothioate
```

| | |
|---|---|
| modified_base | 6<br>mod_base = OTHER<br>note = 2'-deoxyguanosine 3'-phosphorothioate |
| modified_base | 7..8<br>mod_base = OTHER<br>note = 2'-deoxyadenosine 3'-phosphorothioate |
| modified_base | 9<br>mod_base = OTHER<br>note = 2'-deoxythymidine 3'-phosphorothioate |
| modified_base | 10<br>mod_base = OTHER<br>note = 2'-deoxyguanosine 3'-phosphorothioate |
| modified_base | 11<br>mod_base = OTHER<br>note = 2'-deoxythymidine 3'-phosphorothioate |
| modified_base | 12..13<br>mod_base = OTHER<br>note = 5-methyl-2'-deoxycytidine 3'-phosphorothioate |
| modified_base | 14<br>mod_base = OTHER<br>note = cEt guanosine 3'-phosphorothioate |
| modified_base | 15<br>mod_base = OTHER<br>note = cEt adenosine 3'-phosphorothioate |
| modified_base | 16<br>mod_base = OTHER<br>note = cEt 5-methylcytidine |
| modified_base | 16<br>mod_base = OTHER<br>note = 3'-conjugate or a Hydrogen |
| SEQUENCE: 28 | |
| ttcccgaatg tccgac | 16 |
| SEQ ID NO: 29<br>FEATURE<br>source | moltype = DNA  length = 16<br>Location/Qualifiers<br>1..16<br>mol_type = other DNA<br>organism = synthetic construct |
| modified_base | 5<br>mod_base = OTHER<br>note = Uracil |
| modified_base | <br>mod_base = OTHER<br>note = 5'-conjugate or a Hydrogen |
| modified_base | 1<br>mod_base = OTHER<br>note = cEt 5-methylcytidine 3'-phosphorothioate |
| modified_base | 2<br>mod_base = OTHER<br>note = cEt guanosine 3'-phosphodiester |
| modified_base | 3<br>mod_base = OTHER<br>note = cEt adenosine 3'-phosphodiester |
| modified_base | 4<br>mod_base = OTHER<br>note = 2'-deoxyadenosine 3'-phosphorothioate |
| modified_base | 5<br>mod_base = OTHER<br>note = 2'-O-methyl uridine 3'-phosphorothioate |
| modified_base | 6<br>mod_base = OTHER<br>note = 2'-deoxyguanosine 3'-phosphorothioate |
| modified_base | 7<br>mod_base = OTHER<br>note = 2'-deoxythymidine 3'-phosphorothioate |
| modified_base | 8..9<br>mod_base = OTHER<br>note = 5-methyl-2'-deoxycytidine 3'-phosphorothioate |
| modified_base | 10<br>mod_base = OTHER<br>note = 2'-deoxyguanosine 3'-phosphorothioate |
| modified_base | 11<br>mod_base = OTHER<br>note = 2'-deoxyadenosine 3'-phosphorothioate |
| modified_base | 12<br>mod_base = OTHER<br>note = 5-methyl-2'-deoxycytidine 3'-phosphorothioate |

-continued

```
modified_base               13
                            mod_base = OTHER
                            note = 2'-deoxyadenosine 3'-phosphorothioate
modified_base               14
                            mod_base = OTHER
                            note = cEt guanosine 3'-phosphodiester
modified_base               15
                            mod_base = OTHER
                            note = cEt thymidine 3'-phosphorothioate
modified_base               16
                            mod_base = OTHER
                            note = cEt guanosine
modified_base               16
                            mod_base = OTHER
                            note = 3'-conjugate or a Hydrogen
SEQUENCE: 29
cgaatgtccg acagtg                                                        16

SEQ ID NO: 30               moltype = DNA  length = 16
FEATURE                     Location/Qualifiers
source                      1..16
                            mol_type = other DNA
                            organism = synthetic construct
modified_base
                            mod_base = OTHER
                            note = 5'-conjugate or a Hydrogen
modified_base               1
                            mod_base = OTHER
                            note = cEt thymidine 3'-phosphorothioate
modified_base               2
                            mod_base = OTHER
                            note = cEt thymidine 3'-phosphodiester
modified_base               3
                            mod_base = OTHER
                            note = cEt 5-methylcytidine 3'-phosphodiester
modified_base               4
                            mod_base = OTHER
                            note = 5-methyl-2'-deoxycytidine 3'-phosphorothioate
modified_base               5
                            mod_base = OTHER
                            note = 2'-O-methyl cytidine 3'-phosphorothioate
modified_base               6
                            mod_base = OTHER
                            note = 2'-deoxyguanosine 3'-phosphorothioate
modified_base               7..8
                            mod_base = OTHER
                            note = 2'-deoxyadenosine 3'-phosphorothioate
modified_base               9
                            mod_base = OTHER
                            note = 2'-deoxythymidine 3'-phosphorothioate
modified_base               10
                            mod_base = OTHER
                            note = 2'-deoxyguanosine 3'-phosphorothioate
modified_base               11
                            mod_base = OTHER
                            note = 2'-deoxythymidine 3'-phosphorothioate
modified_base               12..13
                            mod_base = OTHER
                            note = 5-methyl-2'-deoxycytidine 3'-phosphorothioate
modified_base               14
                            mod_base = OTHER
                            note = cEt guanosine 3'-phosphodiester
modified_base               15
                            mod_base = OTHER
                            note = cEt adenosine 3'-phosphorothioate
modified_base               16
                            mod_base = OTHER
                            note = cEt 5-methylcytidine
modified_base               16
                            mod_base = OTHER
                            note = 3'-conjugate or a Hydrogen
SEQUENCE: 30
ttcccgaatg tccgac                                                        16

SEQ ID NO: 31               moltype = DNA  length = 16
FEATURE                     Location/Qualifiers
source                      1..16
                            mol_type = other DNA
                            organism = synthetic construct
```

| | | |
|---|---|---|
| modified_base | | |
| | mod_base | = OTHER |
| | note | = 5'-conjugate or a Hydrogen |
| modified_base | 1 | |
| | mod_base | = OTHER |
| | note | = cEt 5-methylcytidine 3'-phosphorothioate |
| modified_base | 2 | |
| | mod_base | = OTHER |
| | note | = cEt thymidine 3'-phosphodiester |
| modified_base | 3 | |
| | mod_base | = OTHER |
| | note | = 2'-O-methoxyethyl thymidine 3'-phosphodiester |
| modified_base | 4..5 | |
| | mod_base | = OTHER |
| | note | = 2'-deoxythymidine 3'-phosphorothioate |
| modified_base | 6 | |
| | mod_base | = OTHER |
| | note | = 2'-deoxyadenosine 3'-phosphorothioate |
| modified_base | 7..8 | |
| | mod_base | = OTHER |
| | note | = 2'-deoxythymidine 3'-phosphorothioate |
| modified_base | 9 | |
| | mod_base | = OTHER |
| | note | = 5-methyl-2'-deoxycytidine 3'-phosphorothioate |
| modified_base | 10 | |
| | mod_base | = OTHER |
| | note | = 2'-deoxyguanosine 3'-phosphorothioate |
| modified_base | 11 | |
| | mod_base | = OTHER |
| | note | = 5-methyl-2'-deoxycytidine 3'-phosphorothioate |
| modified_base | 12 | |
| | mod_base | = OTHER |
| | note | = 2'-deoxyguanosine 3'-phosphorothioate |
| modified_base | 13 | |
| | mod_base | = OTHER |
| | note | = 2'-deoxyadenosine 3'-phosphorothioate |
| modified_base | 14 | |
| | mod_base | = OTHER |
| | note | = cEt guanosine 3'-phosphodiester |
| modified_base | 15 | |
| | mod_base | = OTHER |
| | note | = cEt guanosine 3'-phosphorothioate |
| modified_base | 16 | |
| | mod_base | = OTHER |
| | note | = cEt guanosine |
| modified_base | 16 | |
| | mod_base | = OTHER |
| | note | = 3'-conjugate or a Hydrogen |
| SEQUENCE: 31 | | |
| cttttattcg cgaggg | | 16 |
| | | |
| SEQ ID NO: 32 | moltype = DNA  length = 16 | |
| FEATURE | Location/Qualifiers | |
| source | 1..16 | |
| | mol_type | = other DNA |
| | organism | = synthetic construct |
| modified_base | | |
| | mod_base | = OTHER |
| | note | = 5'-conjugate or a Hydrogen |
| modified_base | 1 | |
| | mod_base | = OTHER |
| | note | = cEt adenosine 3'-phosphorothioate |
| modified_base | 2 | |
| | mod_base | = OTHER |
| | note | = cEt 5-methylcytidine 3'-phosphodiester |
| modified_base | 3 | |
| | mod_base | = OTHER |
| | note | = cEt adenosine 3'-phosphodiester |
| modified_base | 4 | |
| | mod_base | = OTHER |
| | note | = 2'-deoxyadenosine 3'-phosphorothioate |
| modified_base | 5 | |
| | mod_base | = OTHER |
| | note | = 2'-deoxythymidine 3'-phosphorothioate |
| modified_base | 6..8 | |
| | mod_base | = OTHER |
| | note | = 2'-deoxyadenosine 3'-phosphorothioate |
| modified_base | 9 | |
| | mod_base | = OTHER |

```
                        note = 2'-deoxythymidine 3'-phosphorothioate
modified_base           10
                        mod_base = OTHER
                        note = 2'-deoxyadenosine 3'-phosphorothioate
modified_base           11..12
                        mod_base = OTHER
                        note = 5-methyl-2'-deoxycytidine 3'-phosphorothioate
modified_base           13
                        mod_base = OTHER
                        note = 2'-deoxyguanosine 3'-phosphorothioate
modified_base           14
                        mod_base = OTHER
                        note = cEt adenosine 3'-phosphodiester
modified_base           15
                        mod_base = OTHER
                        note = cEt guanosine 3'-phosphorothioate
modified_base           16
                        mod_base = OTHER
                        note = cEt guanosine
modified_base           16
                        mod_base = OTHER
                        note = 3'-conjugate or a Hydrogen
SEQUENCE: 32
acaataaata ccgagg                                                           16

SEQ ID NO: 33           moltype = DNA  length = 16
FEATURE                 Location/Qualifiers
source                  1..16
                        mol_type = other DNA
                        organism = synthetic construct
SEQUENCE: 33
acaataaata ccgagg                                                           16

SEQ ID NO: 34           moltype = DNA  length = 16
FEATURE                 Location/Qualifiers
source                  1..16
                        mol_type = other DNA
                        organism = synthetic construct
SEQUENCE: 34
tcccgaatgt ccgaca                                                           16

SEQ ID NO: 35           moltype = DNA  length = 16
FEATURE                 Location/Qualifiers
source                  1..16
                        mol_type = other DNA
                        organism = synthetic construct
SEQUENCE: 35
ttcccgaatg tccgac                                                           16

SEQ ID NO: 36           moltype = DNA  length = 16
FEATURE                 Location/Qualifiers
source                  1..16
                        mol_type = other DNA
                        organism = synthetic construct
modified_base           5
                        mod_base = OTHER
                        note = Uracil
SEQUENCE: 36
cgaatgtccg acagtg                                                           16

SEQ ID NO: 37           moltype = DNA  length = 16
FEATURE                 Location/Qualifiers
source                  1..16
                        mol_type = other DNA
                        organism = synthetic construct
SEQUENCE: 37
cttttattcg cgaggg                                                           16
```